(12) United States Patent
Foster et al.

(10) Patent No.: US 10,975,363 B2
(45) Date of Patent: Apr. 13, 2021

(54) MATERIALS AND METHODS FOR BIOSYNTHETIC MANUFACTURE AND UTILIZATION OF SYNTHETIC POLYPEPTIDES, AND PRODUCTS THEREFROM

(71) Applicant: INV NYLON CHEMICALS AMERICAS, LLC, Wilmington, DE (US)

(72) Inventors: Alexander Brett Foster, Yarm (GB); Arghya Barman, Wilton (GB); Jonathan Kennedy, North Yorkshire (GB); Paul S. Pearlman, Thornton, PA (US)

(73) Assignee: INV Nylon Chemicals Americas, LLC, Wilmington, DE (US)

( * ) Notice: Subject to any disclaimer, the term of this patent is extended or adjusted under 35 U.S.C. 154(b) by 0 days.

(21) Appl. No.: 16/372,072

(22) Filed: Apr. 1, 2019

(65) Prior Publication Data

US 2019/0359957 A1   Nov. 28, 2019

Related U.S. Application Data

(60) Provisional application No. 62/650,629, filed on Mar. 30, 2018.

(51) Int. Cl.
| | | |
|---|---|---|
| *C12N 9/16* | (2006.01) | |
| *C12P 7/40* | (2006.01) | |
| *C12P 7/44* | (2006.01) | |
| *C12P 13/00* | (2006.01) | |

(52) U.S. Cl.
CPC ............ *C12N 9/16* (2013.01); *C12P 7/40* (2013.01); *C12P 7/44* (2013.01); *C12P 13/005* (2013.01); *C12Y 301/02014* (2013.01)

(58) Field of Classification Search
CPC ... C12N 9/16; C12N 15/70; C12P 7/40; C12P 7/44; C12P 13/005; C12Y 301/02014
See application file for complete search history.

(56) References Cited

U.S. PATENT DOCUMENTS

| | | | |
|---|---|---|---|
| 4,554,101 | A | 11/1985 | Hopp |
| 7,384,783 | B2 | 6/2008 | Kunas et al. |
| 9,580,733 | B2 | 2/2017 | Botes et al. |
| 9,637,764 | B2 | 5/2017 | Botes et al. |
| 9,862,973 | B2 | 1/2018 | Botes et al. |
| 9,920,339 | B2 | 3/2018 | Botes et al. |
| 10,072,150 | B2 | 9/2018 | Botes et al. |
| 10,196,657 | B2 | 2/2019 | Botes et al. |
| 2007/0264688 | A1 | 11/2007 | Venter et al. |
| 2007/0269862 | A1 | 11/2007 | Glass et al. |
| 2012/0003706 | A1 | 1/2012 | Hickey |
| 2012/0064622 | A1 | 3/2012 | Fischer et al. |
| 2013/0065285 | A1 | 3/2013 | Sefton |
| 2013/0323714 | A1 | 12/2013 | Cheng et al. |
| 2015/0315599 | A1 | 11/2015 | Shetty et al. |
| 2017/0218406 | A1 | 8/2017 | Conradie et al. |
| 2018/0023103 | A1 | 1/2018 | Foster et al. |
| 2018/0023104 | A1 | 1/2018 | Cartman et al. |
| 2019/0300838 | A1 | 10/2019 | Smith et al. |
| 2019/0300839 | A1 | 10/2019 | Smith et al. |
| 2019/0316072 | A1 | 10/2019 | Smith et al. |
| 2019/0338320 | A1 | 11/2019 | Foster et al. |

FOREIGN PATENT DOCUMENTS

| | | |
|---|---|---|
| EP | 0995490 A2 | 4/2000 |
| EP | 1728853 A1 | 12/2006 |
| EP | 1938892 A1 | 7/2008 |
| EP | 3399015 A1 | 11/2018 |
| JP | S49124358 A | 11/1974 |
| WO | 2008094282 A1 | 8/2008 |
| WO | 2010003007 A2 | 1/2010 |
| WO | 2010069313 A1 | 6/2010 |
| WO | 2013090769 A2 | 6/2013 |
| WO | 2013152051 A2 | 10/2013 |
| WO | 2013186340 A1 | 12/2013 |
| WO | 2014093505 A2 | 6/2014 |
| WO | 2014105793 A1 | 7/2014 |
| WO | 2014105797 A2 | 7/2014 |
| WO | 2015195654 A1 | 12/2015 |
| WO | 2017115855 A1 | 7/2017 |
| WO | 2017165244 A1 | 9/2017 |
| WO | 2018022633 A1 | 2/2018 |
| WO | 2018106549 A1 | 6/2018 |
| WO | 2018022595 A1 | 12/2018 |
| WO | 2019191761 A1 | 10/2019 |
| WO | 2019191763 A1 | 10/2019 |
| WO | 2019191767 A1 | 10/2019 |
| WO | 2019191770 A1 | 10/2019 |
| WO | 2019191772 A1 | 10/2019 |

(Continued)

OTHER PUBLICATIONS

Lucas et al., GenBank accession No. ACU95033, Aug. 26, 2009.*
Witkowski et al. (Biochemistry 38:11643-11650, 1999.*
Tang et al. (Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Lin, S., et al., "Biotin Synthesis Beings by Hijacking the Fatty Acid Synthesis Pathway," Nature Chemical Biology, vol 6, No. 9, Sep. 2010, pp. 682-688.
Ishizuka, H., et al., "Putrescine Oxidase of Micrococcus Rubens: Primary Structure and *Escherichia Coli*", Journal of General Microbiology, vol. 139, 1993, pp. 425-432.

(Continued)

*Primary Examiner* — Delia M Ramirez

(57) ABSTRACT

Provided herein are novel, synthetic polypeptides having, for example, acyl-acyl carrier protein (ACP) thioesterase (TE) activity, including polypeptides that convert pimeloyl-ACP to pimelic acid. In some aspects, the synthetic polypeptides have advantageous enzymatic activity and/or improved substrate specificity relative to a wild type acyl-ACP TE.

16 Claims, 5 Drawing Sheets

Specification includes a Sequence Listing.

(56) References Cited

FOREIGN PATENT DOCUMENTS

| WO | 2019213108 A1 | 11/2019 |
|---|---|---|
| WO | 2019213118 A1 | 11/2019 |

OTHER PUBLICATIONS

Devereaux, J., et al., "A comprehensive set of sequence analysis programs for the VAX", Nucleic Acids Research, vol. 12, Issue 1, Part 1, Jan. 11, 1984, pp. 387-395.
Kyte, J., et al., "A simple method for displaying the hydropathic character of a protein", Journal of Molecular Biology, vol. 157, No. 1, May 5, 1982, pp. 105-132.
Smith, T.F., et al., "Comparison of biosequences", Advances in Applied Mathematics, vol. 2, Issue 4, Dec. 1981, pp. 482-489.
Needleman, S.B., et al., "A general method applicable to the search for similarities in the amino acid sequence of two proteins", Journal of Molecular Biology, vol. 48, Issue 3, Mar. 1970, pp. 443-453.
Pearson, W.R., et al., "Improved tools for biological sequence comparison", Proceedings of the National Academy of Science of the United States of America, vol. 85, Issue 8, Apr. 1988, pp. 2444-2448.
Meyers, et al., "Optimal alignments in linear space", Computer Applications in the Biosciences, vol. 4, 1988, pp. 11-17.
Shulman, A.I., et al. "Structural determinants of allosteric ligand activation in RXR heterodimers," Cell, vol. 116, Issue 3, Feb. 6, 2004, pp. 417-429.
International Search Report and Written Opinion dated Jul. 29, 2019, for International Application No. PCT/US2019/025211, 19 pages.
Nguyen, C., et al., "Trapping the dynamic acyl carrier protein in fatty acid biosynthesis", Nature, vol. 505, No. 7483, Dec. 22, 2013, pp. 427-431.
Feng, Y., "Tuning of acyl-ACP thioesterase activity directed for tailored fatty acid synthesis," Applied Microbiology and Biotechnology, vol. 102, No. 7, Feb. 22, 2018, pp. 3173-3182.
Haushalter, R.W., "Production of Odd-Carbon Dicarboxylic Acids in *Escherichia coli* Using an Engineered Biotin-catty Acid Biosynthetic Pathway", Journal of the American Chemical Society, vol. 139, No. 13, Mar. 2017, pp. 4615-4618.
Beld, J., "Evolution of acyl-ACP thioesterases and [beta]-ketoacyl-ACP synthases revealed by protein-protein interactions", Journal of Applied Phycology, vol. 26. No. 4, Nov. 22, 2013, pp. 1619-1629.
Ziesack, M., et al., "Chimeric Fatty Acyl-Acyl Carrier Protein Thioesterases Provide Mechanistic Insight into Enzyme Specificity and Expression", Applied and Environmental Microbiology, vol. 84, No. 10, Mar. 16, 2018, pp. 1-12.
Manandhar, M., et al., "Pimelic acid, the first precursor of the Bacillus subtilis biotin synthesis pathway. exists as the free acid and is assembled by fatty acid synthesis: Bacillus subtilis biotin synthesis", Molecular Microbiology, vol. 104, No. 4, Mar. 3, 2017, pp. 595-607.
Zeph et al., "Gram-Negative Versus Gram-Positive (Actinomycete) Nonobligate Bacterial Predators of Bacteria in. Soil", Applied Environmental Microbiology, vol. 52, No. 4, Oct. 1986, pp. 819-823.
International Application Serial No. PCT/US2019/029956, Written Opinion dated Aug. 13, 2019, 13 pgs.
Abayomi, Oluwanbe Johnson., et al. "An engineered constitutive promoter set with broad activity range for Cupriavidus necator H16", Acs Synthetic Biology, vol. 7, (Jun. 27, 2018), XP002792846, pp. 1918-1928.
Hun-Suk, Song, et al., "Enhanced isobutanol production from acetate by combinatorial overexpression of acetyl-CoA synthetase and anaplerotic enzymes in engineered *Escherichia coli*", Biotechnology and Bioengineering, vol. 115, (May 2, 2018), XP002792879, pp. 1971-1978.
Janina, Kluge, et al., "Inducible promoters and functional genomic approaches for the genetic engineering of filamentous fungi", Applied Microbiology and Biotechnology, vol. 102, (Jun. 2, 2018), XP036546152, pp. 6357-6372.

U.S. Appl. No. 16/399,155, Non Final Office Action dated Jul. 15, 2019, 19 pgs.
International Application Serial No. PCT/US2019/029973, International Search Report dated Jul. 23, 2019, 4 pgs.
International Application Serial No. PCT/US2019/029973, Written Opinion dated Jul. 23, 2019, 10 pgs.
Martin, Koller, "A review on established and emerging fermentation schemes for microbial production of polyhydroxyalkanoate (PHA) biopolyesters", Fermentation, vol. 4, (Apr. 23, 2018), XP002792757, pp. 1-30.
Gabriela, Montiel-Jarillo, et al., "Enrichment of a mixed microbial culture for polyhydroxyalkanoates production: Effect of pH and N And P concentrations", Science of the Total Environment, vol. 583, XP029914697, Apr. 1, 2017, pp. 300-307.
Fernando, Silva, et al., "Impact of nitrogen feeding regulation on polyhydroxyalkanoates production by mixed microbial cultures", New Biotechnology, vol. 37, XP029943712, 2017, pp. 90-98.
Justyna, Mozejko-Ciesielska, et al., "Bacterial polyhydroxyalkanoates: Still fabulous ?", Microbiological Research, vol. 192, XP029740446, Nov. 2016, pp. 271-282.
Jiachao, Zhu, et al., "Factors for promoting polyhydroxyalkanoate (PHA) synthesis in bio-nutrient-removal and recovery system", 4th International Conference on Environmental Systems Research (ICESR 2017) Conference paper, KP002792821, pp. 1-4.
Kianoush, Khosravi-Darani, et al., "Simulation of bioreactors for poly(3-hydroxybutyrate) production from natural gas", Iranian Journal of Chemistry and Chemical Engineering, vol. 39, XP002792822, 2018, 1-24.
International Application Serial No. PCT/US2019/025202, International Search Report dated Jul. 30, 2019, 4 pgs.
International Application Serial No. PCT/US2019/025202, Written Opinion dated Jul. 30, 2019, 10 pgs.
Jessup, M Shively., et al., "Something From Almost Nothing: Carbon Dioxide Fixation in Chemoautotrophs", Annu. Rev. Microbiol., vol. 52, 1998, pp. 191-230.
Girdhar, Amandeep, et al., "Process Parameters for Influencing Polyhydroxyalkanoate Producing Bacterial Factories: an Overview", Journal of Petroleum & Environmental Biotechnolog, vol. 4, No. 5, 2013, 8 pgs.
International Application Serial No. PCT/US2019/025194, International Search Report dated Aug. 22, 2019, 7 pgs.
International Application Serial No. PCT/US2019/025194, Written Opinion dated Aug. 22, 2019, 13 pgs.
Tanaka, K, et al., "Production of Poly (D-3-HydrOxybutyrate) From CO2, H2, and O2 by High Cell Density Autotropic Cultivation of Alcaligenes Eutrophus", Biotechnology and Bioengineering, Wiley, vol. 45, No. 3, (Feb. 5, 1995), KP000489583, pp. 268-275 (Abstract only).
International Application Serial No. PCT/US2019/025218, International Search Report dated Sep. 5, 2019, 8 pgs.
International Application Serial No. PCT/US2019/025218, Written Opinion dated Sep. 5, 2019, 9 pgs.
Chae, Tong Un., et al., "Metabolic engineering of *Escherichia coli* for the production of four-, five-and six-carbon lactams", Metabolic Engineering, Academic Press, US, vol. 41, 2017, pp. 82-91.
U.S. Appl. No. 16/399,155, Response filed Oct. 15, 2019 to Non-Final Office Action dated Jul. 15, 2019, 12 pgs.
International Application Serial No. PCT/US2019/025194, Invitation to Pay Additional Fees dated Jul. 1, 2019, 14 pgs.
International Application Serial No. PCT/US2019/025218, Invitation to Pay Additional Fees dated Jun. 25, 2019, 8 pgs.
Atlic, et al., "Continuous Production of Poly([R]-3-Hydroxybutyrate) by Cupriavidus Necator in a Multistage Bioreactor cascade", Appl Microbial Biotechnology, vol. 91, Apr. 19, 2011, pp. 295-304.
Byrd, et al., "Bacterial Control of Agromyces Ramosus in Soil", Canadian Journal of Microbiology, vol. 31, No. 12, 1985, pp. 1157-1163 (Abstract Only).
Eggers, et al., "Impact of Ralstonia Eutropha's Poly(3-Hydroxybutyrate) (PHB) Depolymerases and Phasins on PHB Storage in Recombinant *Escherichia Coli*", Applied and Environmental Microbiology, vol. 80, No. 24, Dec. 2014, pp. 7702-7709.
Horvat, et al., "Mathematical Modelling and Process Optimization of a Continuous 5-Stage Bioreactor Cascade for Production of

(56) References Cited

OTHER PUBLICATIONS

Poly[-(R)-3-Hydroxybutyrate] by Cupriavidus Necator", Bioprocess Biosyst Eng, vol. 36, 2013, pp. 1235-1250.

Koller, et al., "Potential and Prospects of Continuous Polyhydroxyalkanoate (PHA) Production", Bioengineering, 2015, pp. 94-121.

Kunasundari, et al. "Revisiting the Single Cell Protein Application of Cupriavidus Necator H16 and Recovering Bioplastic Granules Simultaneously", Plos One, vol. 8, No. 10, Oct. 2013, 15 pgs.

Makkar, et al., "Cupriavidus Necator Gen. Nov., Sp. Nov.: A Nonobligate Bacterial Predator of Bacteria in Soil", International Journal of Systematic Bacteriology, vol. 37, No. 4, Oct. 1987, pp. 323-326.

Raberg, et al., "A Closer Look on the Polyhydroxybutyrate-(PHB-) Negative Phenotype of Ralstonia Eutropha PHB-4", Plos One, vol. 9, No. 5, May 2014, pp. 1-11.

Russell, "The Energy Spilling Reactions of Bacteria and Other Organisms", Journal of Molecular Microbiology Biotechnology, vol. 13, No. 1, 2007, pp. 1-11.

Sillman, et aL, "Isolation of Nonobligate Bacterial Predators of Bacteria from Soil", Canadian Journal of Microbiology, vol. 32, No. 9, 1986, pp. 760-762.

Database UniProt [Online] Jun. 11, 2014 (Jun. 11, 2014), "RecName: Full=Thiopurine S-methyltransferase {EC0:0000256IHAMAPRule: MF 00812, EC0:0000256ISAAS:SAAS0089691O}; EC=2.1.1.67 {EC0:0000256IHAMAP-Rule:MF 00812, EC0:0000256I SAAS-:SAAS0089691 O}; AltName: Full= Thiopurine methyltransferase {ECO:0000256IHAMAP-Rule:MF 00812};", retrieved from EBI accession No. UNIPROT:AOA009ZVV4 Database accession No. AOAOO9ZVV4.

Database UniProt [Online] Mar. 15, 2017 (Mar. 15, 2017), "RecName: Full=Thiopurine S-methyltransferase {EC0:0000256IHAMAPRule: MF 00812, EC0:0000256ISAAS:SAAS0089691 O}; EC=2.1.1.67 {EC0:00002561HAMAP-00812, EC0:0000256I SAAS:SAAS0089691 O}; AltName: Full= Thiopurine methyltransferase {ECO:00002561HAMAP-Rule:MF 00812};", retrieved from EBI accession No. UNIPROT:AOA1 L8MA47 Database accession No. A0A1L8MA47.

Database UniProt [Online] Jul. 24, 2013 (Jul. 24, 2013), "SubName: Full=Acyl-ACP thioesterase {EC0:00003131. EMBLCDD77481.1 };", retrieved from EBI accession No. UNIPROT:R7CHF5 Database accession No. R7CHF5.

International Preliminary Report on Patentability for PCT application No. PCT/US2019/025211, dated Oct. 15, 2020, 13 pages.

\* cited by examiner

| Score | Pos. 1 | Residue | Pos. 2 | Residue |
|---|---|---|---|---|
| 1 | 33 | Asp | 128 | Tyr |
| 0.83 | 59 | Val | 90 | Phe |
| 0.77 | 40 | Glu | 111 | Trp |
| 0.77 | 36 | Gly | 128 | Tyr |
| 0.74 | 32 | Gln | 40 | Glu |

SEQUENCE LISTING

```
<160> NUMBER OF SEQ ID NOS: 172

<210> SEQ ID NO 1
<211> LENGTH: 245
<212> TYPE: PRT
<213> ORGANISM: Eggerthella sp.

<400> SEQUENCE: 1

Met Thr Ile Gly Tyr Glu Gln Thr Tyr Gln Leu Arg Thr Gly Asp Phe
1               5                   10                  15

Asp Arg Tyr Ala His Leu Leu Pro Ser Ser Ile Leu Asp Val Phe Gln
            20                  25                  30

Asp Val Ala Gly Val Asn Ala Glu Gln Val Pro Gly Met Thr Trp Lys
        35                  40                  45

Glu Leu Thr Asp Ala Gly Leu Phe Trp Val Val Thr Arg Ile Lys Tyr
    50                  55                  60

Glu Val Ile Glu Thr Pro His Leu His Glu Gln Val Ile Ala Arg Thr
65                  70                  75                  80

Trp Pro Leu Ala Pro Thr Arg Leu Gly Phe Gln Arg Glu Tyr Thr Met
                85                  90                  95

Arg Lys Leu Asp Gly Thr Pro Leu Val Lys Cys Ser Ser Asp Trp Ile
            100                 105                 110

Leu Met Asp Tyr Lys Thr Arg Ser Phe Ala Ser Ala Arg Asp Phe Tyr
        115                 120                 125

Asn Gly Pro Gln Asp Phe Ser Glu Glu Lys Val Phe Glu Lys Lys Leu
    130                 135                 140

Arg Lys Ile Lys Thr Phe Glu Pro Glu Asp Thr Gly Glu Thr Phe Gln
145                 150                 155                 160

Val His Phe Val Asp Ile Asp Ile Asn Gly His Val Asn Asn Ser Lys
                165                 170                 175

Tyr Pro Asn Phe Val Met Asn Ser Leu Asp Leu Gly Glu Asp Glu Thr
            180                 185                 190

Ile Lys Thr Phe Gln Ile Asp Tyr Arg His Glu Leu Arg Ala Gly Ser
        195                 200                 205

Thr Val Arg Ile His Ser Lys Arg Asp Gly Asn Val Ile Thr Ser Met
    210                 215                 220

Gly Ile Ser Thr Glu Gly Asp Thr Ala Gly Glu Cys Met Phe Ala Thr
225                 230                 235                 240

Gln Ile Glu Leu Ala
                245

<210> SEQ ID NO 2
<211> LENGTH: 24
<212> TYPE: PRT
<213> ORGANISM: Erwinia carotovora
```

```
<400> SEQUENCE: 2

Met Lys Tyr Leu Leu Pro Thr Ala Ala Ala Gly Leu Leu Leu Ala
1               5                  10                  15

Ala Gln Pro Ala Met Ala Met Gly
            20

<210> SEQ ID NO 3
<211> LENGTH: 200
<212> TYPE: PRT
<213> ORGANISM: Vibrio mimicus

<400> SEQUENCE: 3

Met Ile Arg Leu Leu Ser Leu Val Leu Phe Phe Cys Leu Ser Ala Ala
1               5                  10                  15

Ser Gln Ala Ser Glu Lys Leu Leu Val Leu Gly Asp Ser Leu Ser Ala
            20                  25                  30

Gly Tyr Gln Met Pro Ile Glu Lys Ser Trp Pro Ser Leu Leu Pro Asp
        35                  40                  45

Ala Leu Leu Glu His Gly Gln Asp Val Thr Val Ile Asn Gly Ser Ile
    50                  55                  60

Ser Gly Asp Thr Thr Gly Asn Gly Leu Ala Arg Leu Pro Gln Leu Leu
65                  70                  75                  80

Asp Gln His Thr Pro Asp Leu Val Leu Ile Glu Leu Gly Ala Asn Asp
                85                  90                  95

Gly Leu Arg Gly Phe Pro Pro Lys Val Ile Thr Ser Asn Leu Ser Lys
            100                 105                 110

Met Ile Ser Leu Ile Lys Asp Ser Gly Ala Asn Val Val Met Met Gln
        115                 120                 125

Ile Arg Val Pro Pro Asn Tyr Gly Lys Arg Tyr Ser Asp Met Phe Tyr
    130                 135                 140

Asp Ile Tyr Pro Lys Leu Ala Glu His Gln Gln Val Gln Leu Met Pro
145                 150                 155                 160

Phe Phe Leu Glu His Val Ile Thr Lys Pro Glu Trp Met Met Asp Asp
                165                 170                 175

Gly Leu His Pro Lys Pro Glu Ala Gln Pro Trp Ile Ala Glu Phe Val
            180                 185                 190

Ala Gln Glu Leu Val Lys His Leu
        195                 200

<210> SEQ ID NO 4
<211> LENGTH: 211
<212> TYPE: PRT
<213> ORGANISM: Sedimenticola thiotaurini

<400> SEQUENCE: 4

Met Lys Lys Leu Phe Leu Leu Ile Phe Ala Met Ser Asn Val Pro
1               5                  10                  15

Ala Ala Glu Pro Val Ile Leu Val Leu Gly Asp Ser Leu Ser Ala Ala
            20                  25                  30

Tyr Gly Ile Glu Arg Ser Arg Gly Trp Val Ser Leu Leu Gln Ser Arg
        35                  40                  45

Leu Gln Gln Ala Gly Tyr Pro His Arg Val Val Asn Ala Ser Ile Ser
    50                  55                  60

Gly Asp Thr Thr Ala Gly Gly Leu Ala Arg Leu Pro Arg Ala Leu Glu
65                  70                  75                  80

Gln Phe Gln Pro Asp Ile Leu Ile Ile Glu Leu Gly Gly Asn Asp Gly
```

```
                    85                  90                  95

Leu Arg Gly Leu Gly Asn Arg Gln Thr Arg Asp His Leu Asp Gln Met
                100                 105                 110

Ile Thr Leu Ala Arg Ala Ser His Ser Arg Pro Leu Leu Leu Gly Met
            115                 120                 125

Met Leu Pro Pro Asn Phe Gly Lys Ala Phe Thr Glu Lys Phe Leu Gln
        130                 135                 140

Ile Tyr Arg Asp Leu Ala Glu Gln Arg Asn Val Pro Leu Val Pro Phe
145                 150                 155                 160

Phe Leu Ala Gly Val Ala Asp Arg Pro Glu Trp Met Gln Ser Asp Gly
                165                 170                 175

Ile His Pro Thr Ala Glu Gly Gln Pro Leu Met Leu Glu His Val Trp
            180                 185                 190

Glu Gln Leu Gln Pro Met Leu Glu Glu Thr Ser Val His Ser Asp Lys
        195                 200                 205

Ser Leu Lys
    210

<210> SEQ ID NO 5
<211> LENGTH: 247
<212> TYPE: PRT
<213> ORGANISM: Bacteroides finegoldii

<400> SEQUENCE: 5

Met Ser Glu Ser Asn Lys Ile Gly Thr Tyr Lys Phe Val Ala Glu Pro
1               5                   10                  15

Phe His Val Asp Phe Asn Gly Arg Leu Thr Met Gly Val Leu Gly Asn
                20                  25                  30

His Leu Leu Asn Cys Ala Gly Phe His Ala Ser Asp Arg Gly Phe Gly
            35                  40                  45

Ile Ala Ser Leu Asn Glu Asp Asn Tyr Thr Trp Val Leu Ser Arg Leu
        50                  55                  60

Ala Ile Glu Leu Asp Glu Met Pro Tyr Gln Tyr Glu Asp Phe Ser Val
65                  70                  75                  80

Gln Thr Trp Val Glu Asn Val Tyr Arg Leu Phe Thr Asp Arg Asn Phe
                85                  90                  95

Ala Ile Met Asn Lys Glu Gly Lys Lys Ile Gly Tyr Ala Arg Ser Val
                100                 105                 110

Trp Ala Met Ile Ser Leu Asn Thr Arg Lys Pro Ala Asp Leu Leu Ala
            115                 120                 125

Leu His Gly Gly Ser Ile Val Asp Tyr Ile Cys Asp Glu Pro Cys Pro
        130                 135                 140

Ile Glu Lys Pro Ser Arg Ile Lys Val Thr Asn Thr Gln Pro Leu Ala
145                 150                 155                 160

Thr Leu Thr Ala Lys Tyr Ser Asp Ile Asp Ile Asn Gly His Val Asn
                165                 170                 175

Ser Ile Arg Tyr Ile Glu His Ile Leu Asp Leu Phe Pro Ile Asp Leu
            180                 185                 190

Tyr Lys Thr Lys Arg Ile Arg Arg Phe Glu Met Ala Tyr Val Ala Glu
        195                 200                 205

Ser Tyr Phe Gly Asp Glu Leu Thr Phe Phe Cys Asp Glu Ala Asn Glu
    210                 215                 220

Asn Glu Phe His Val Glu Val Lys Lys Asn Gly Ser Glu Val Val Cys
225                 230                 235                 240
```

Arg Ser Lys Val Ile Phe Glu
            245

<210> SEQ ID NO 6
<211> LENGTH: 206
<212> TYPE: PRT
<213> ORGANISM: Pseudoalteromonas sp.

<400> SEQUENCE: 6

Met Ser Ala Ser Ile Leu Arg Val Phe Ile Val Leu Leu Val Thr
1               5                   10                  15

Lys Pro Leu Phe Ala Trp Ala Asp Asn Gln Ile Leu Val Leu Gly Asp
            20                  25                  30

Ser Leu Ser Ala Ala Tyr Gly Leu Lys Gln His Gln Gly Trp Val Gln
            35                  40                  45

Leu Leu Gln Asp Thr Tyr Glu Gln Gln Asn Thr Pro Thr Thr Leu Ile
        50                  55                  60

Asn Ala Ser Ile Ser Gly Glu Thr Thr Gly Gly Ala Leu Arg Arg Leu
65                  70                  75                  80

Asp Ala Ile Leu Lys Glu His Thr Pro Thr His Val Leu Ile Glu Leu
                85                  90                  95

Gly Gly Asn Asp Gly Leu Arg Gly Phe Pro Val Thr Lys Met Lys Ala
            100                 105                 110

Asn Leu His Ala Leu Ile Asp Lys Ser Arg Glu Ala Gly Ala Glu Val
            115                 120                 125

Ala Leu Met Gln Ile Arg Ile Pro Pro Asn Tyr Gly Arg Arg Tyr Thr
        130                 135                 140

Glu Leu Phe Glu Gln Ser Phe Val Asp Val Ala Lys Glu Lys Gln Val
145                 150                 155                 160

Thr Leu Met Pro Phe Phe Val Glu Gln Val Ala Thr Asn Gly Glu Leu
                165                 170                 175

Met Gln Asn Asp Asn Ile His Pro Asn Ala Glu Ala Gln Pro Ile Leu
            180                 185                 190

Arg Asp Ile Met Lys Thr Gln Ile Ser Asn Trp Leu Thr Lys
        195                 200                 205

<210> SEQ ID NO 7
<211> LENGTH: 233
<212> TYPE: PRT
<213> ORGANISM: Unknown
<220> FEATURE:
<223> OTHER INFORMATION: Description of Unknown:
      marine sediment metagenome sequence

<400> SEQUENCE: 7

Met Thr Val Lys Ala Leu Thr Thr Arg Leu Pro Ala Pro Gly Pro Gln
1               5                   10                  15

Val Arg Tyr Phe Ser Ala Leu Arg Ser Ala Val Leu Cys Val Phe Leu
            20                  25                  30

Leu Ala Ala Gly Phe Cys Ala Ser Thr Ser Ala Glu Ser Asp Asp Gly
            35                  40                  45

Val Leu Leu Val Phe Gly Asp Ser Leu Ser Ala Ala Tyr Arg Met Asp
        50                  55                  60

Glu Arg Asp Gly Trp Val Ala Leu Leu Gln Gln Gln Leu Arg Glu Glu
65                  70                  75                  80

Ser Thr Ala Leu Gln Val Val Asn Gly Ser Val Ser Gly Glu Thr Thr
                85                  90                  95

```
Ala Gly Gly Leu Ala Arg Leu Pro Ala Met Leu Asp Ala His Gln Pro
            100                 105                 110

Asp Ile Val Met Leu Glu Leu Gly Gly Asn Asp Gly Leu Arg Gly Leu
        115                 120                 125

Pro Val Thr Ser Ile Arg Gln Asn Leu Glu Arg Met Ile Gln Met Ser
    130                 135                 140

Gln Gln Ala Gly Ala Arg Val Ile Leu Ala Gly Ile Gln Ile Pro Pro
145                 150                 155                 160

Asn Tyr Gly Pro Arg Tyr Thr Ala Pro Phe Tyr Ala Gln Tyr Gln Glu
                165                 170                 175

Leu Ala Asp Glu Tyr Gly Leu Val Leu Ile Pro Phe Leu Leu Glu Gly
            180                 185                 190

Ile Ala Asp Asn Pro Ala Leu Met Gln Asp Gly Ile His Pro Thr
        195                 200                 205

Ala Ala Ala Gln Pro Met Ile Val Asp Thr Val Trp Pro Val Leu Gln
    210                 215                 220

Gly Val Leu Thr Ala Thr Asp Arg Pro
225                 230

<210> SEQ ID NO 8
<211> LENGTH: 200
<212> TYPE: PRT
<213> ORGANISM: Vibrio mytili

<400> SEQUENCE: 8

Met Ile Arg Leu Leu Ser Leu Phe Leu Phe Phe Ser Leu Ser Thr Leu
1               5                   10                  15

Ala His Ala Asn Glu Lys Leu Leu Val Leu Gly Asp Ser Leu Ser Ala
            20                  25                  30

Gly Tyr Gln Met Pro Ile Glu Lys Ser Trp Pro Ser Leu Leu Ser Asn
        35                  40                  45

Ala Leu Leu Glu His Asp Gln Asp Val Thr Val Ile Asn Gly Ser Ile
    50                  55                  60

Ser Gly Asp Thr Thr Gly Asn Gly Leu Ala Arg Leu Pro Gln Leu Leu
65                  70                  75                  80

Asp Gln His Thr Pro Asp Phe Val Ile Leu Glu Leu Gly Ala Asn Asp
                85                  90                  95

Gly Leu Arg Gly Phe Pro Pro Lys Leu Ile Thr Ala Asn Leu Ser Lys
            100                 105                 110

Met Ile Thr Met Ile Lys Asn Ser Gly Ala Lys Val Phe Met Met Gln
        115                 120                 125

Ile Arg Val Pro Pro Asn Tyr Gly Lys Arg Tyr Ser Asp Met Phe Tyr
    130                 135                 140

Asp Ile Tyr Pro Lys Leu Ala Glu His Gln Val Thr Leu Leu Pro
145                 150                 155                 160

Phe Phe Leu Glu His Val Val Thr Lys Pro Glu Trp Met Met Asp Asp
                165                 170                 175

Gly Leu His Pro Lys Pro Glu Ala Gln Pro Trp Ile Ala Glu Phe Val
            180                 185                 190

Ala Gln Glu Leu Ile Lys His Leu
        195                 200

<210> SEQ ID NO 9
<211> LENGTH: 202
<212> TYPE: PRT
<213> ORGANISM: Vibrio shilonii
```

<400> SEQUENCE: 9

| | | | | | | | | | | | | | | |
|---|---|---|---|---|---|---|---|---|---|---|---|---|---|---|
|Met|Ile|Arg|Gln|Leu|Ser|Tyr|Phe|Val|Leu|Ile|Val|Ile|Ser|Leu|Ala|
|1| | | |5| | | | |10| | | | |15| |
|Ser|Phe|His|Ala|Lys|Ala|Ala|Thr|Leu|Leu|Ile|Leu|Gly|Asp|Ser|Leu|
| | | |20| | | | |25| | | | |30| | |
|Ser|Ala|Gly|Tyr|Asn|Met|Arg|Ala|Glu|Gln|Ser|Trp|Pro|Thr|Met|Leu|
| | | | |35| | | | |40| | | | |45| |
|Ser|Asp|Glu|Leu|Ser|Ser|Gly|Asp|Glu|Pro|Met|Lys|Val|Ile|Asn|Gly|
| |50| | | | |55| | | | |60| | | | |
|Ser|Val|Ser|Gly|Asp|Thr|Thr|Ser|Asn|Gly|Leu|Ala|Lys|Leu|Pro|Gly|
|65| | | | |70| | | | |75| | | | |80|
|Leu|Leu|Lys|Gln|His|Ser|Pro|Asp|Tyr|Val|Leu|Ile|Glu|Leu|Gly|Ala|
| | | | |85| | | | |90| | | | |95| |
|Asn|Asp|Gly|Leu|Arg|Gly|Phe|Gln|Pro|Ser|Ile|Ile|Lys|Asn|Asn|Leu|
| | | |100| | | | |105| | | | |110| | |
|Ala|Ser|Leu|Ile|Glu|Met|Ser|Gln|Gln|Ala|Gly|Ser|Lys|Val|Leu|Leu|
| | | | |115| | | | |120| | | | |125| |
|Met|Gln|Ile|Arg|Ile|Pro|Pro|Asn|Tyr|Gly|Lys|Arg|Tyr|Ala|Ser|Met|
| |130| | | | |135| | | | |140| | | | |
|Phe|Glu|Gly|Ile|Tyr|Pro|Ala|Leu|Ala|Gln|Glu|Ser|Gly|Val|Pro|Leu|
|145| | | | |150| | | | |155| | | | |160|
|Leu|Pro|Phe|Phe|Leu|Glu|Gln|Val|Ile|Ile|Lys|Pro|Glu|Trp|Met|Met|
| | | | |165| | | | |170| | | | |175| |
|Glu|Asp|Gly|Leu|His|Pro|Lys|Pro|Glu|Ala|Gln|Pro|Phe|Ile|Ala|Gln|
| | | |180| | | | |185| | | | |190| | |
|Phe|Val|Ala|Glu|Ser|Met|Gln|Pro|His|Leu| | | | | | |
| | | | |195| | | | |200| | | | | | |

<210> SEQ ID NO 10
<211> LENGTH: 201
<212> TYPE: PRT
<213> ORGANISM: Pseudomonas fluorescens

<400> SEQUENCE: 10

| | | | | | | | | | | | | | | |
|---|---|---|---|---|---|---|---|---|---|---|---|---|---|---|---|
|Met|Arg|Val|Trp|Phe|Leu|Ser|Ala|Gly|Leu|Ala|Leu|Met|Cys|Met|Ala|
|1| | | |5| | | | |10| | | | |15| |
|Gln|Asn|Ala|Ala|Ala|Gly|Thr|Val|Leu|Ile|Val|Gly|Asp|Ser|Ile|Ser|
| | | |20| | | | |25| | | | |30| | |
|Ala|Gly|Phe|Gly|Leu|Asp|Thr|Arg|Leu|Gly|Trp|Val|Ser|Leu|Leu|Glu|
| | | | |35| | | | |40| | | | |45| |
|Gln|Arg|Leu|Glu|Gln|Glu|Gly|Phe|Asp|Asp|Lys|Val|Val|Asn|Ala|Ser|
| |50| | | | |55| | | | |60| | | | |
|Ile|Ser|Gly|Asp|Thr|Ser|Ala|Gly|Gly|Gln|Ala|Arg|Leu|Pro|Ala|Leu|
|65| | | | |70| | | | |75| | | | |80|
|Leu|Ala|Glu|His|Lys|Pro|Asp|Leu|Val|Ile|Leu|Glu|Leu|Gly|Gly|Asn|
| | | | |85| | | | |90| | | | |95| |
|Asp|Gly|Leu|Arg|Gly|Met|Pro|Pro|Thr|Gln|Leu|Gln|Gln|Asn|Leu|Ala|
| | | |100| | | | |105| | | | |110| | |
|Ala|Met|Ile|Asp|Ser|Ser|Arg|Gln|Ser|Gly|Ala|Lys|Val|Leu|Leu|Leu|
| | | | |115| | | | |120| | | | |125| |
|Gly|Met|Gln|Leu|Pro|Pro|Asn|Tyr|Gly|Lys|Arg|Tyr|Thr|Asp|Ala|Phe|
| |130| | | | |135| | | | |140| | | | |
|Ala|Glu|Val|Tyr|Gly|Lys|Leu|Ala|Asp|Asp|Lys|Lys|Ile|Pro|Leu|Val|
|145| | | | |150| | | | |155| | | | |160|

Pro Phe Phe Leu Asp Gly Val Gly Gly His Pro Asp Leu Met Gln Ala
              165                 170                 175

Asp Gly Leu His Pro Ala Ala Gly Ala Gln Gly Lys Leu Leu Glu Asn
          180                 185                 190

Val Trp Pro Thr Leu Lys Pro Leu Leu
          195                 200

<210> SEQ ID NO 11
<211> LENGTH: 260
<212> TYPE: PRT
<213> ORGANISM: Thalassospira xiamenensis

<400> SEQUENCE: 11

Met Thr Ile Gln Trp Asp Glu Ile Ala Lys Pro Ala Leu Pro Ala Asn
1               5                   10                  15

Cys Gly Trp Arg Gly Thr Tyr Arg Val Arg Tyr Ser Glu Ile Gly Asp
            20                  25                  30

Asn Gly Leu Ala Met Leu Pro Ala Leu Ala Asp Tyr Met Gln Asp Ala
        35                  40                  45

Ala Gly Trp Gly Ala Arg Ile Leu Lys Leu Ala Tyr Asp Asp Thr Val
    50                  55                  60

Asp Lys Gly Met Ala Trp Val Leu Ala Arg Met Val Ile His Val Arg
65                  70                  75                  80

Arg Tyr Pro Gly Asn Gly Glu Asp Ile Ile Val Glu Thr Trp Pro Ser
                85                  90                  95

Gly Val Ala Arg Arg Val Ala Thr Arg Asp Phe Arg Leu Ile Asp Ser
            100                 105                 110

Ser Gly Asp Val Ile Ala Val Ala Gln Ser Phe Trp Val Met Phe Asp
        115                 120                 125

Leu Leu Glu Arg Arg Ala Ala Ser Trp Pro Asp Trp Ile Glu Glu Arg
130                 135                 140

Leu Pro Lys Pro Pro Gly Pro Lys Leu Ile Glu Pro Pro Phe Arg Pro
145                 150                 155                 160

Pro Phe Thr Thr Asp Pro Leu Pro Glu Ile Asp Ser Ile Lys Ala Arg
                165                 170                 175

Pro Ser Asp Leu Asp Leu Tyr Gly His Val Asn Asn Val Arg Leu Met
            180                 185                 190

Gln Trp Val Leu Gly Ala Thr Gly Ala Asp Ser Lys Pro Asp Phe His
        195                 200                 205

Pro Glu Ser Ile Asp Ile Gln Phe Arg Thr Glu Cys Arg Val Gln Glu
    210                 215                 220

Arg Val Thr Val Arg Gln Lys Asp Gly Phe Ala Ala Ile Thr Arg Asp
225                 230                 235                 240

Gly Asp Gly Val Asp Leu Val Arg Ala His Val Val Pro Lys Asn Arg
                245                 250                 255

Thr Ala Leu Ala
        260

<210> SEQ ID NO 12
<211> LENGTH: 201
<212> TYPE: PRT
<213> ORGANISM: Pseudomonas stutzeri

<400> SEQUENCE: 12

Met Arg Arg Trp Leu Lys Cys Gly Ala Leu Ala Leu Leu Cys Trp Thr
1               5                   10                  15

```
Gln Gly Ala Leu Ala Gly Thr Val Leu Val Gly Asp Ser Ile Ser
            20                  25                  30

Ala Ala Phe Gly Leu Glu Thr Ser Gln Gly Trp Val His Leu Leu Gln
35                      40                  45

Glu Arg Leu Val Glu Gly Asp Glu Ser Trp Arg Val Val Asn Ala Ser
50                      55                  60

Ile Ser Gly Asp Thr Thr Ala Gly Gly Leu Ala Arg Leu Asp Pro Leu
65                  70                  75                  80

Leu Glu Glu His Thr Pro Glu Val Val Ile Leu Glu Leu Gly Gly Asn
                85                  90                  95

Asp Gly Leu Arg Gly Gln Ser Pro Val Gln Leu Lys Gln Asn Leu Ala
            100                 105                 110

Asp Met Ile Asp Arg Ser Arg Glu Ala Gly Ala Glu Val Leu Leu Leu
        115                 120                 125

Gly Met Arg Met Pro Pro Asn Leu Gly Gln Arg Tyr Thr Arg Ala Phe
130                 135                 140

Ala Asp Ala Phe Asp Ser Leu Ala Gln Glu Lys Ser Val Ala Tyr Val
145                 150                 155                 160

Pro Phe Leu Leu Glu Gly Val Gly Gly Val Ala Gly Met Met Gln Ala
                165                 170                 175

Asp Gly Ile His Pro Thr Ala Glu Ala Gln Ser Gln Leu Leu Glu Thr
            180                 185                 190

Val Trp Pro Ala Leu Glu Pro Leu Leu
        195                 200

<210> SEQ ID NO 13
<211> LENGTH: 248
<212> TYPE: PRT
<213> ORGANISM: Halobacteriovorax marinus

<400> SEQUENCE: 13

Met Lys Ser Pro Val Phe Lys Lys Tyr Gln Val Ser Ile Ser Asn
1               5                   10                  15

Val Asn Ile Asn Lys Arg Leu Gly Leu Phe Gly Leu Leu Gly Tyr Leu
            20                  25                  30

Gln Asp Ile Ala Thr Leu His Ala Glu Ile Ala Gly Phe Gly Leu Asp
        35                  40                  45

Glu Met Ile Ser Ser Asn Ser Phe Trp Val Leu Val Arg Gln Glu Ile
50                  55                  60

Arg Met Asn Lys Phe Pro Lys Trp Asn Asp Glu Ile Glu Ile Gln Thr
65                  70                  75                  80

Trp Ser Arg Thr Pro Gln Gly Met Tyr Ala Phe Arg Glu Phe Glu Phe
                85                  90                  95

Phe Leu Asn Asp Glu Lys Val Gly Ser Cys Ser Thr Ala Trp Met Ile
            100                 105                 110

Leu Ser Gly Asp Thr Arg Arg Ile Lys Lys Pro Asp Phe Pro Ile Glu
        115                 120                 125

Lys Ile Asn Pro Arg Leu Asp Ser Leu Asp Tyr Cys Ala Glu Arg
130                 135                 140

Ile Lys Val Leu Asp Asn Phe Glu Leu Val Asn Glu Ile Lys Val Arg
145                 150                 155                 160

Ile Ser Asp Leu Asp Leu Asn Met His Val Asn Asn Thr Lys Tyr Thr
                165                 170                 175

Gln Trp Val Leu Asp Ser Ile Pro Ile Glu Leu His Lys Ser Ala Lys
```

```
                      180                 185                 190
Leu Arg Asn Tyr Gln Ile Asn Phe Leu Lys Glu Ala His Leu Gly Asp
                195                 200                 205

Glu Ile Asp Ile Tyr Arg Ala Ser Ser Ala Lys Asp Glu Ser Ala His
            210                 215                 220

Asp Thr Gln Phe Lys Gly Ile Arg Arg Ser Asp Gln Ser Thr Ile Phe
225                 230                 235                 240

Tyr Val Asn Ile Ile Ala Asp Thr
                245

<210> SEQ ID NO 14
<211> LENGTH: 250
<212> TYPE: PRT
<213> ORGANISM: Bacillus coagulans

<400> SEQUENCE: 14

Met Ala Asn Gly Ser Ser Leu Tyr Lys Gly Gln Tyr His Ile Glu Leu
1               5                   10                  15

Arg Asp Val Asp Phe Thr Lys Lys Leu Lys Leu Ser Ala Leu Phe Ser
                20                  25                  30

Leu Phe Gln Asp Ile Ala Ser Leu Ala Ala Glu Asp Leu Gly Tyr Gly
            35                  40                  45

Ile Glu Thr Leu Glu Lys Lys Tyr Lys Val Ala Trp Ile Leu Thr Arg
50                  55                  60

Ile Arg Val Asp Ile Leu Arg His Pro Thr Trp Asp Glu Asn Ile Thr
65                  70                  75                  80

Ile Glu Thr Trp Pro Leu Gln Pro Ser Lys Ile Asp Phe Asp Arg Asp
                85                  90                  95

Phe Leu Val Lys Asp His Thr Gly Ala Val Ile Lys Ala Ala Ser
            100                 105                 110

Lys Trp Val Val Met Gly Leu Asn Asp Arg Lys Ile Lys Arg Thr Glu
            115                 120                 125

Ser Ile Asn Ile His Tyr Pro Glu Asn Arg Thr Glu Arg Ala Ile Glu
            130                 135                 140

Gly Lys Phe Gly Lys Phe Lys Asp Phe Gly Leu Glu Pro Ala Tyr
145                 150                 155                 160

Gln Lys Val Ile Gly Tyr Ser Asp Ile Asp Phe Asn Gly His Leu Asn
                165                 170                 175

Asn Ser Lys Tyr Val Asp Tyr Ile Met Asp Cys Phe Leu Pro Asp Phe
                180                 185                 190

His Lys Arg His Pro Ile His Thr Ile Glu Ile Asn Phe Asn Gln Glu
                195                 200                 205

Ala Leu Pro Gly Asp Ser Ile Thr Leu Tyr Lys Asp Ile Ser Lys Met
            210                 215                 220

Asp Glu His Glu Leu Tyr Val Glu Gly Val Asn Gln Thr Asp His His
225                 230                 235                 240

Thr Ile Phe Lys Ser His Ile Thr Ile His
                245                 250

<210> SEQ ID NO 15
<211> LENGTH: 200
<212> TYPE: PRT
<213> ORGANISM: Ferrimonas balearica

<400> SEQUENCE: 15

Met Val Arg Arg Ser Leu Leu Ile Leu Met Leu Cys Leu Tyr Gln Pro
```

```
                1               5                      10                      15
            Gly Ala Trp Ala Asp Gln Pro Ser Ile Leu Ile Leu Gly Asp Ser Leu
                        20                      25                      30
            Ser Ala Ser Tyr Gly Met Ser Glu Ala Glu Gly Trp Val Lys Lys Leu
                        35                      40                      45
            Gln Gln Asn Leu Pro Asp Ala Gln Ile Ile Asn Ala Ser Val Ser Gly
                        50                      55                      60
            Glu Thr Ser Gly Gly Leu Arg Arg Leu Pro Gly Leu Leu Gln Gln
            65                      70                      75                      80
            His Gln Pro Asp Trp Val Phe Val Glu Leu Gly Gly Asn Asp Gly Leu
                                85                      90                      95
            Arg Gly Phe Gln Pro Thr Ile Thr Glu Asn Asn Ile Glu Gln Leu Ile
                        100                     105                     110
            Thr Leu Ser Lys Ala Ser Gly Ala Gln Val Leu Leu Ser Glu Val Met
                        115                     120                     125
            Val Pro Pro Asn Tyr Gly Arg Arg Tyr Ala Glu Arg Phe Gln Gln Ile
                        130                     135                     140
            Tyr His Gly Leu Ala Lys Glu His Glu Val Glu Leu Val Pro Phe Phe
            145                     150                     155                     160
            Met Thr Glu Ile Ala Thr Asp Pro Asn Leu Met Gln Ala Asp Gly Ile
                                165                     170                     175
            His Pro Asn Arg Glu Ala Gln Gly Arg Ile Ala Ala Phe Leu Leu Pro
                        180                     185                     190
            Trp Phe Glu Gln Ala Ile Ala Glu
                        195                     200

<210> SEQ ID NO 16
<211> LENGTH: 196
<212> TYPE: PRT
<213> ORGANISM: Pseudomonas sp.

<400> SEQUENCE: 16

Met Ser Ala Gly Leu Ala Leu Met Cys Met Ala Gln Gly Ala Ala Ala
            1               5                       10                      15
            Gly Thr Val Leu Ile Val Gly Asp Ser Ile Ser Ala Ala Phe Gly Leu
                        20                      25                      30
            Asp Thr Arg Glu Gly Trp Val Ala Leu Leu Glu Gln Arg Leu Lys Arg
                        35                      40                      45
            Glu Gly Phe Asp Ala Lys Val Val Asn Ala Ser Ile Ser Gly Asp Thr
                        50                      55                      60
            Ser Ala Gly Gly Gln Ala Arg Leu Pro Ala Leu Leu Ala Glu His Lys
            65                      70                      75                      80
            Pro Glu Leu Val Val Leu Glu Leu Gly Gly Asn Asp Gly Leu Arg Gly
                                85                      90                      95
            Gln Leu Pro Thr Gln Leu Gln Gln Asn Leu Ala Ser Met Ile Asp Lys
                        100                     105                     110
            Ser Arg Ala Ala Gly Ala Lys Val Leu Leu Gly Met Arg Leu Pro
                        115                     120                     125
            Pro Asn Tyr Gly Lys Arg Tyr Asn Glu Ala Phe Ala Lys Val Tyr Glu
                        130                     135                     140
            Asn Leu Ala Thr Glu Lys Gln Val Pro Leu Val Pro Phe Phe Leu Glu
            145                     150                     155                     160
            Gly Val Gly Gly Val Pro Glu Leu Met Gln Ala Asp Gly Ile His Pro
                                165                     170                     175
```

Gly Gln Gly Ala Gln Ala Arg Leu Leu Glu Asn Ala Trp Pro Gln Leu
            180                 185                 190

Lys Pro Leu Leu
        195

<210> SEQ ID NO 17
<211> LENGTH: 246
<212> TYPE: PRT
<213> ORGANISM: Cellulosilyticum lentocellum

<400> SEQUENCE: 17

Met Ser Arg Leu Lys Glu Asn Tyr Gln Val Asp Phe Asp Val Val Asp
1               5                   10                  15

Phe Thr Gly Lys Leu Ser Ile Asn Gly Leu Cys Ser Tyr Met Gln Thr
            20                  25                  30

Val Ala Ala Lys His Ala Thr Lys Leu Gly Ile Asn Phe Tyr Lys Asn
        35                  40                  45

Gly Glu Lys Pro Thr Tyr Tyr Trp Ile Leu Ser Arg Val Lys Tyr Glu
    50                  55                  60

Ile Asp Thr Tyr Pro Arg Trp Glu Asp Leu Val Ser Leu Glu Thr Tyr
65                  70                  75                  80

Pro Gly Gly Tyr Glu Lys Leu Phe Ala Val Arg Leu Phe Asp Leu Thr
                85                  90                  95

Asp Glu Lys Gly Glu Leu Ile Gly Arg Ile Thr Gly Asp Tyr Leu Leu
            100                 105                 110

Met Asp Ala Glu Lys Gly Arg Pro Val Arg Ile Lys Gly Ala Thr Gly
        115                 120                 125

Pro Leu Ser Val Leu Asp Phe Pro Tyr Glu Gly Arg Lys Ile Asp Lys
    130                 135                 140

Ile Glu Val Pro Glu Val Val Leu Arg Glu Gln Ile Arg Lys Ala Tyr
145                 150                 155                 160

Tyr Ser Glu Leu Asp Leu Asn Gly His Met Asn Asn Ala His Tyr Ile
                165                 170                 175

Arg Trp Thr Val Asp Met Leu Pro Leu Glu Val Leu Lys Glu Asn Glu
            180                 185                 190

Ile Val Ser Leu Gln Ile Asn Tyr Asn Ala Ser Ile Thr Tyr Gly Val
        195                 200                 205

Glu Thr Lys Leu Ile Ile Gly Lys Asn Glu Ala Gly Asn Tyr Leu Val
    210                 215                 220

Ala Gly Asn Ser Leu Asp Asp Ser Val Asn Tyr Phe Thr Ser Glu Ile
225                 230                 235                 240

Ile Leu Arg Lys Asn Lys
                245

<210> SEQ ID NO 18
<211> LENGTH: 201
<212> TYPE: PRT
<213> ORGANISM: Pseudomonas putida

<400> SEQUENCE: 18

Met Arg Val Trp Leu Leu Ser Ala Gly Leu Ala Leu Leu Cys Met Ala
1               5                   10                  15

Gln Asn Ala Ala Ala Gly Thr Val Leu Ile Val Gly Asp Ser Ile Ser
            20                  25                  30

Ala Ala Phe Gly Leu Asp Thr Arg Gln Gly Trp Val Ala Leu Leu Glu
        35                  40                  45

```
Lys Arg Leu Lys Asp Glu Gly Phe Asp Asp Lys Val Ile Asn Ala Ser
 50                  55                  60

Ile Ser Gly Asp Thr Ser Ala Gly Gly Gln Ala Arg Leu Pro Ala Leu
 65                  70                  75                  80

Leu Ser Ala His Lys Pro Ser Leu Val Val Leu Glu Leu Gly Gly Asn
                 85                  90                  95

Asp Gly Leu Arg Gly Gln Leu Pro Ala Gln Leu Gln Gln Asn Leu Ala
                100                 105                 110

Ser Met Ile Asp Lys Ser Arg Ala Gly Ala Lys Val Leu Leu Leu
                115                 120                 125

Gly Met Gln Leu Pro Pro Asn Tyr Gly Ala Arg Tyr Thr Lys Ala Phe
        130                 135                 140

Ala Gln Val Tyr Ser Asp Leu Ala Val Gln Lys Asn Val Pro Leu Val
145                 150                 155                 160

Pro Phe Phe Leu Glu Gly Val Gly Gly His Pro Glu Leu Met Gln Ala
                165                 170                 175

Asp Gly Ile His Pro Ala Gln Gly Ala Gln Gly Arg Leu Leu Glu Asn
                180                 185                 190

Ala Trp Pro Ala Ile Lys Pro Leu Leu
        195                 200

<210> SEQ ID NO 19
<211> LENGTH: 201
<212> TYPE: PRT
<213> ORGANISM: Pseudomonas pseudoalcaligenes

<400> SEQUENCE: 19

Met Arg Ala Trp Leu Leu Gly Gly Cys Leu Ser Leu Leu Leu Leu Ala
  1               5                  10                  15

Gln Glu Ala Met Ala Gly Thr Val Leu Val Val Gly Asp Ser Ile Ser
                 20                  25                  30

Ala Ala Leu Gly Leu Glu Ser Ser Gln Gly Trp Val Ser Leu Leu Glu
             35                  40                  45

Lys Arg Leu Val Glu Lys Gly Tyr Asp Lys Gln Val Val Asn Ala Ser
 50                  55                  60

Ile Ser Gly Asp Thr Ser Ala Gly Gly Leu Ser Arg Leu Pro Ala Leu
 65                  70                  75                  80

Leu Ala Glu His Lys Pro Glu Leu Val Ile Ile Glu Leu Gly Gly Asn
                 85                  90                  95

Asp Gly Leu Arg Gly Gln Pro Pro Ala Gln Leu Gln Gln Asn Leu Ala
                100                 105                 110

Gly Met Ile Asp Ser Ser Arg Ala Gln Gly Ala Ala Val Leu Leu Leu
                115                 120                 125

Gly Met Arg Leu Pro Pro Asn Tyr Gly Ala Arg Tyr Thr Ser Ala Phe
        130                 135                 140

Ala Lys Val Tyr Ser Asp Leu Ala Glu Gln Lys Gln Val Pro Leu Val
145                 150                 155                 160

Pro Phe Phe Leu Glu Gly Val Gly Gly Val Pro Glu Leu Met Gln Pro
                165                 170                 175

Asp Gly Ile His Pro Gln Ala Asn Ala Gln Pro Arg Leu Leu Glu Asn
                180                 185                 190

Val Trp Pro Thr Leu Glu Pro Leu Leu
        195                 200

<210> SEQ ID NO 20
```

```
<211> LENGTH: 201
<212> TYPE: PRT
<213> ORGANISM: Pseudomonas fluorescens

<400> SEQUENCE: 20
```

Met Arg Val Trp Phe Leu Ser Ala Gly Leu Ala Leu Met Cys Met Ala
1               5                   10                  15

Gln Asn Ala Ala Ala Gly Thr Val Leu Ile Val Gly Asp Ser Ile Ser
            20                  25                  30

Ala Ala Phe Gly Leu Asp Thr Arg Gln Gly Trp Val Ser Leu Leu Glu
        35                  40                  45

Gln Arg Leu Lys Ala Glu Gly Phe Asp Asp Lys Val Val Asn Ala Ser
    50                  55                  60

Ile Ser Gly Asp Thr Ser Ala Gly Gly Gln Ala Arg Leu Pro Ala Leu
65                  70                  75                  80

Leu Ala Ala His Lys Pro Asp Leu Val Ile Leu Glu Leu Gly Gly Asn
                85                  90                  95

Asp Gly Leu Arg Gly Gln Pro Pro Thr Gln Leu Gln Gln Asn Leu Ala
            100                 105                 110

Ala Met Ile Asp Ser Ala Arg Ala Ser Gly Ala Lys Val Leu Leu Leu
        115                 120                 125

Gly Met Gln Leu Pro Pro Asn Tyr Gly Arg Arg Tyr Thr Glu Ala Phe
    130                 135                 140

Ala Arg Val Tyr Ser Thr Val Ala Glu Glu Lys Val Pro Leu Val
145                 150                 155                 160

Pro Phe Phe Leu Lys Asp Val Gly Gly Ile Pro Thr Met Met Gln Gly
                165                 170                 175

Asp Gly Leu His Pro Ser Val Ala Ala Gln Gly Gln Leu Leu Glu Asn
            180                 185                 190

Val Trp Pro Thr Leu Lys Pro Leu Leu
    195                 200

```
<210> SEQ ID NO 21
<211> LENGTH: 215
<212> TYPE: PRT
<213> ORGANISM: Alteromonas australica

<400> SEQUENCE: 21
```

Met Phe Tyr Ser Leu Arg Asn Ile Ala Phe Val Phe Leu Leu Leu Ile
1               5                   10                  15

Pro Thr Phe Ala Gln Ser Asp Gln His Asp Ser Asp Glu Lys Glu Pro
            20                  25                  30

Asn Ala Lys Leu Leu Ile Leu Gly Asp Ser Leu Ser Ala Ala Tyr Gly
        35                  40                  45

Leu Arg Gln Glu Glu Gly Trp Val Ser Leu Leu Gln Asn Thr Trp Arg
    50                  55                  60

Asp Glu Asn Ile Pro Ile Asp Ile Val Asn Ala Val Ser Gly Glu
65                  70                  75                  80

Thr Thr Asp Gly Gly Leu Ala Arg Leu Pro Arg Leu Leu Thr Gln His
                85                  90                  95

Gln Pro Ser His Val Leu Ile Glu Leu Gly Gly Asn Asp Gly Leu Gln
            100                 105                 110

Gly His Asn Val Lys Lys Ile Arg Ser Asn Leu Val Ala Leu Val Lys
        115                 120                 125

Ile Ala Gln Ser Ala Asp Ala Lys Val Phe Leu Gln Asp Met Gln Ile
    130                 135                 140

```
Pro Thr Asn Tyr Gly Lys Arg Tyr Thr Asn Met Phe Gly Glu Ser Phe
145                 150                 155                 160

Asp Arg Val Gly Glu Glu Leu Asn Val Pro Val Ile Pro Phe Phe Leu
            165                 170                 175

Gln Asn Ile Ala Leu Asp Thr Ser Leu Met Gln Arg Asp Gly Ile His
        180                 185                 190

Pro Asn Ala Glu Ala Gln Ala Leu Ile Ala Glu Phe Met His Arg Gln
        195                 200                 205

Leu Met Pro Leu Phe Asp Asn
        210                 215

<210> SEQ ID NO 22
<211> LENGTH: 244
<212> TYPE: PRT
<213> ORGANISM: Cecembia lonarensis

<400> SEQUENCE: 22

Met Lys Glu Ser Ser Asn Lys Pro Phe Gln Phe Gln Lys Thr Phe Glu
1               5                   10                  15

Ile Leu Ser Phe Gln Ile Asp Pro Ser Gly Lys Leu Arg Trp Ala Ala
            20                  25                  30

Leu Ala Asp Leu Leu Gln Glu Val Ala Trp Lys His Ala Asp Ser Arg
        35                  40                  45

Glu Phe Gly Gln Val Leu Phe Asp Lys Gly Phe Met Trp Val Leu Ser
    50                  55                  60

Arg Phe Asp Ile Gln Val His Ala Met Pro Ser Trp Gly Glu Thr Ile
65                  70                  75                  80

His Ile Glu Thr Ala Gly Arg Gly Ile Asn Lys Leu Phe Ala Leu Arg
                85                  90                  95

Glu Phe Arg Val Thr Asp Ser Ser Gly Thr Val Leu Ala Thr Ala Met
            100                 105                 110

Ser Ala Trp Leu Leu Asp Ile Lys Thr Lys Arg Pro Gln Arg Pro
        115                 120                 125

Ser Leu Val Leu Pro Ser Glu Leu Phe Glu Thr Glu Pro Ser Asp Tyr
    130                 135                 140

Ala Pro Pro Glu Lys Ile Ser Val Pro Glu Lys Gly His Thr Gly Lys
145                 150                 155                 160

Thr Phe His Val Asn His Ser Asp Leu Asp Met Asn Asn His Val Asn
                165                 170                 175

Asn Val Ser Tyr Ile Arg Trp Ile Glu Asp Phe Cys Leu Glu Gln Gly
            180                 185                 190

Phe Thr Phe Asp Lys Ile Ser Ile Asn Tyr Leu Asn Glu Ala Leu Leu
        195                 200                 205

Gly Glu Asn Ile Glu Ile Leu Phe Ser Leu Asp Ala Gln Lys Met Leu
    210                 215                 220

Val Ser Gly Arg Ser Gly Glu Arg Asp Val Phe Thr Ser Trp Val Glu
225                 230                 235                 240

Lys Leu Asn Gly

<210> SEQ ID NO 23
<211> LENGTH: 217
<212> TYPE: PRT
<213> ORGANISM: Spongiibacter sp.

<400> SEQUENCE: 23
```

```
Met Thr His Phe Ile Gln Phe Leu Pro Gly Arg Ile Ser Pro Arg Arg
1               5                   10                  15

Ala Leu Ala Leu Leu Val Leu Leu Gln Gly Ala Leu Pro Arg
            20                  25                  30

Ile Val Leu Ala Asp Thr Ile Leu Leu Gly Asp Ser Leu Ser Ala
            35                  40                  45

Ala Tyr Lys Ile Pro Val Glu Ser Ser Trp Pro Ala Leu Leu Gln Asp
    50                  55                  60

Ser Ile Asp Glu Glu His Ser Leu Lys Asn Ala Ser Val Ser Gly Glu
65                  70                  75                  80

Thr Thr Ala Gly Gly Leu Ala Arg Leu Pro Ala Leu Leu Ala Lys Asn
                85                  90                  95

Asn Thr Asp Ile Leu Ile Ile Glu Leu Gly Gly Asn Asp Gly Leu Arg
                100                 105                 110

Gly Tyr Pro Leu Val Arg Ile Arg Glu Asn Ile Glu Lys Met Ile Lys
            115                 120                 125

Leu Gly Gln Lys Lys Gly Ala Lys Val Val Leu Leu Gly Met His Ile
    130                 135                 140

Pro Pro Asn Tyr Gly Arg Arg Tyr Ala Asp Gly Phe His Asn Ile Tyr
145                 150                 155                 160

Leu Ser Leu Ala Glu Glu Asn Asn Thr Ala Leu Leu Pro Phe Leu Leu
                165                 170                 175

Asp Gly Val Ala Lys Gln Pro Arg Leu Met Gln Gly Asp Gly Ile His
                180                 185                 190

Pro Thr Ala Glu Ala Gln Pro Ile Ile Leu Gln Asn Val Leu Ser Val
            195                 200                 205

Leu Arg Pro Leu Leu Asp Ser Thr Asn
    210                 215

<210> SEQ ID NO 24
<211> LENGTH: 194
<212> TYPE: PRT
<213> ORGANISM: Brenneria sp.

<400> SEQUENCE: 24

Met Ala Ala Asp Thr Leu Leu Ile Leu Gly Asp Ser Leu Ser Ala Gly
1               5                   10                  15

Tyr Arg Met Pro Ala Ala Ser Ala Trp Pro Ala Leu Leu Asp Gln Lys
            20                  25                  30

Trp Gln Thr Arg Pro Asp Gly Val Lys Val Val Asn Ala Ser Ile Ser
            35                  40                  45

Gly Asp Thr Ala Gly Gln Gly Leu Ala Arg Leu Pro Ala Leu Leu Lys
    50                  55                  60

Gln His Gln Pro Arg Trp Val Leu Ile Glu Leu Gly Gly Asn Asp Gly
65                  70                  75                  80

Leu Arg Gly Phe Pro Pro Asn Asn Ile Glu Gln Asp Leu Ser Lys Ile
                85                  90                  95

Ile Thr Leu Val Glu Gln Ala Gln Ala Gln Pro Leu Leu Met Gln Ile
                100                 105                 110

Arg Leu Pro Thr Asn Tyr Gly Arg Arg Tyr Asn Glu Ser Phe Ser Asp
            115                 120                 125

Val Tyr Pro Arg Leu Ala Lys Gln Phe Ser Ile Pro Leu Val Pro Phe
    130                 135                 140

Phe Met Glu Gln Val Tyr Leu Lys Pro Glu Trp Ile Leu Glu Asp Gly
145                 150                 155                 160
```

Ile His Pro Ala Arg Asp Ala Gln Pro Phe Ile Ala Asp Trp Met Ala
            165                 170                 175

Gln Gln Leu Glu Ser Leu Tyr Pro Ile Asp Phe Glu Leu Gln Glu Gly
            180                 185                 190

Gly Asn

<210> SEQ ID NO 25
<211> LENGTH: 245
<212> TYPE: PRT
<213> ORGANISM: Flavobacterium frigoris

<400> SEQUENCE: 25

Met Pro Ile Ala Ser Asn Phe Thr Ser Val Leu Ser Lys Asp Trp Glu
1               5                   10                  15

Ile Asn Phe Thr Gln Cys Met Pro Asn Gly Tyr Leu Lys Tyr Thr Asp
            20                  25                  30

Leu Cys Asn Ile Leu Gln Leu Thr Ala Ala His Ser Asp Met Gly
        35                  40                  45

Gly Ile Ser Phe Ser Asp Met Gln Glu Phe Asn Gln Ala Trp Val Leu
    50                  55                  60

Ser Arg Met Arg Val Glu Ile Ala Ala Leu Pro Lys Trp Arg Asp Ile
65                  70                  75                  80

Val Thr Val Lys Thr Trp Ile Asn Thr Leu Glu Asn Ser Arg Ser Val
                85                  90                  95

Arg Ala Leu Glu Met Tyr Val Asn Gly Glu Lys Ile Val Gly Ser Glu
            100                 105                 110

Thr Phe Trp Ala Val Phe Asn Thr Glu Arg Arg Pro Glu Gly Leu
        115                 120                 125

Ala Leu Pro Tyr Glu His Phe Glu Leu Tyr Pro Glu Leu Lys Ala Thr
    130                 135                 140

Lys Glu Ser Phe Ser Lys Ile Asn Ile Asn Ser Glu Lys Glu Asp Val
145                 150                 155                 160

Phe Glu Lys Ser Ile Tyr Leu Ser Asp Leu Asp Ile Val Asn His Val
                165                 170                 175

Asn Asn Val Lys Tyr Leu Glu Trp Cys Leu Asp His Leu Glu Val Asp
            180                 185                 190

Leu Ile Leu Ser Gln Lys Ile Arg Ser Phe Glu Met Asn Phe Leu Lys
    195                 200                 205

Glu Leu Ser Leu Tyr Asp Lys Val Ile Ile His Glu Asn Tyr Ser Glu
    210                 215                 220

Asp Ser Ile Leu Phe Ser Ile Thr Lys Glu Asn Lys Asn Cys Tyr Ala
225                 230                 235                 240

Leu Gln Leu Asn Leu
            245

<210> SEQ ID NO 26
<211> LENGTH: 200
<212> TYPE: PRT
<213> ORGANISM: Oceanimonas sp.

<400> SEQUENCE: 26

Met Leu Arg Ile Leu Val Leu Leu Cys Leu Val Ser Pro Thr Val
1               5                   10                  15

Leu Ala Asp Thr Leu Leu Ile Leu Gly Asp Ser Leu Ser Ala Gly Tyr
            20                  25                  30

```
Arg Met Arg Ser Asp Gln Ala Trp Pro His Leu Leu Ala Glu Gln Trp
         35                  40                  45

Arg Arg Glu Gly Arg Gln Val Thr Val Ile Asn Ala Ser Val Ser Gly
 50                  55                  60

Asp Thr Thr Gln Gly Gly Leu Gln Arg Leu Pro Pro Leu Leu Gln Arg
65                  70                  75                  80

His Gln Pro Ser Leu Val Leu Glu Leu Gly Gly Asn Asp Gly Leu
             85                  90                  95

Arg Gly Leu Pro Pro Gly Leu Ile Glu Arg Asn Leu Glu Arg Leu Ile
            100                 105                 110

Ala Leu Ala Gly Asp Ala Gly Ala Arg Val Ile Leu Thr Asp Ile Gln
        115                 120                 125

Leu Pro Pro Asn Tyr Gly Arg Arg Tyr Leu Gln Gln Phe Glu Gln Val
    130                 135                 140

Phe Ser Arg Leu Ala Ser Gln His Gln Leu Pro Leu Leu Pro Phe Phe
145                 150                 155                 160

Val Ala Pro Leu Met Gly Glu Gln Gly Met Met Met Asp Asp Gly Ile
                165                 170                 175

His Pro Thr Val Lys Ala Gln Pro Leu Ile Ala Arg Gln Val Gly Glu
            180                 185                 190

Phe Leu Thr Pro Tyr Leu Thr Pro
        195                 200

<210> SEQ ID NO 27
<211> LENGTH: 209
<212> TYPE: PRT
<213> ORGANISM: Shimwellia blattae

<400> SEQUENCE: 27

Met Met His Phe Lys Asn Met Leu Arg Trp His Leu Pro Phe Leu Leu
1               5                   10                  15

Leu Val Leu Leu Met Cys Arg Thr Ala Ala Ala Asp Thr Leu Leu Val
            20                  25                  30

Leu Gly Asp Ser Leu Ser Ala Gly Tyr Arg Met Pro Ala Glu Glu Ala
        35                  40                  45

Trp Pro Ala Leu Leu Asp Lys Gln Trp Glu Lys Arg Gln Ile Arg Val
    50                  55                  60

Ile Asn Ala Ser Ile Ser Gly Asp Thr Ala Ala Gln Gly Leu Ala Arg
65                  70                  75                  80

Leu Pro Thr Leu Leu Ala Glu His Lys Pro Arg Trp Val Val Ile Glu
                85                  90                  95

Leu Gly Gly Asn Asp Gly Leu Arg Gly Phe Pro Pro Ala Gly Ile Ala
            100                 105                 110

Ala Thr Leu Ser Gln Ile Ile Ser Gln Val Lys Ala Ala Arg Ala Arg
        115                 120                 125

Pro Ile Leu Val Gln Ile His Leu Pro Ala Asn Tyr Gly Arg Arg Tyr
    130                 135                 140

Asn Glu Ser Phe Gly Ala Ile Tyr Ala Thr Leu Ala Ala Ser Asn Asp
145                 150                 155                 160

Ile Pro Leu Leu Pro Phe Phe Met Glu Glu Val Tyr Leu Lys Pro Gln
                165                 170                 175

Trp Met Gln Asp Asp Gly Ile His Pro Asn Ala Ser Ala Gln Pro Phe
            180                 185                 190

Ile Ala Asp Trp Met Ala Gln His Leu Asn Pro Leu Val Asn His Asp
        195                 200                 205
```

Ser

<210> SEQ ID NO 28
<211> LENGTH: 268
<212> TYPE: PRT
<213> ORGANISM: Pseudodesulfovibrio piezophilus

<400> SEQUENCE: 28

```
Met Val Ser Leu His Pro Phe Pro Ser Gln Leu His Lys Ile Val Met
1               5                   10                  15

Thr Thr Asn Ile Asp Leu Ala Phe Glu His Leu Tyr Pro Val Gln Ser
            20                  25                  30

Tyr Glu Pro Arg Met Asp Gly Arg Ile Ala Ile Pro Ser Val Cys Asn
        35                  40                  45

Tyr Leu Gln Asp Ile Ala Ser Arg His Ala Asp Thr Leu Gly Phe Gly
    50                  55                  60

Tyr His Asp Leu Glu Lys Cys Gly His Phe Trp Met Leu Ala Arg Leu
65                  70                  75                  80

His Val Thr Met Glu Arg Leu Pro Arg Phe Gly Glu Ser Cys Arg Ile
                85                  90                  95

Glu Thr Trp Pro Ser Gly Asn Glu Arg Leu Val Ala Leu Arg Asp Phe
            100                 105                 110

Leu Leu His Asp Glu Lys Gly Leu Ile Gly Lys Ala Thr Thr Ser Trp
        115                 120                 125

Val Thr Val Asn Thr Thr Thr His Lys Pro Asp Asn Pro Glu Thr Val
    130                 135                 140

Leu Asn Arg Arg Phe Ile Pro Lys Arg Asp Arg Ala Thr Ile Phe Pro
145                 150                 155                 160

Thr Lys Ala Ile Lys Arg Leu Lys Gly Gly Glu His Asp Ile Arg Leu
                165                 170                 175

Val Ala Arg Arg Ser Asp Met Asp Ile Asn Asn His Val Asn Asn Val
            180                 185                 190

His Tyr Val Glu Phe Cys Leu Glu Ala Ile Pro Arg Ser Trp Glu Glu
        195                 200                 205

Lys Asn Arg Cys Leu Gly Ile Asp Ile Gln Phe Arg Ser Glu Ser His
    210                 215                 220

Ala Gly Asp Glu Tyr Val Ser Ala Cys Ala Pro Ala Asp Pro Asp Gly
225                 230                 235                 240

Pro His Ala Thr Phe Leu His Ser Leu Thr Arg Leu Ser Asp Gly Arg
                245                 250                 255

Glu Val Val Arg Met Arg Ser Trp Trp Ile Gln Ala
            260                 265
```

<210> SEQ ID NO 29
<211> LENGTH: 201
<212> TYPE: PRT
<213> ORGANISM: Pseudomonas sp.

<400> SEQUENCE: 29

```
Met Arg Val Trp Phe Leu Ser Ala Gly Leu Ala Leu Cys Met Ala
1               5                   10                  15

Gln Asn Ala Ala Ala Gly Thr Val Leu Ile Val Gly Asp Ser Ile Ser
            20                  25                  30

Ala Gly Phe Gly Leu Asp Thr Arg Glu Gly Trp Val Ser Leu Leu Glu
        35                  40                  45
```

Gln Arg Leu Lys Arg Glu Gly Phe Asp Asp Lys Val Asn Ala Ser
    50              55                  60

Ile Ser Gly Asp Thr Ser Ala Gly Gly Arg Ala Arg Leu Pro Ala Leu
65              70                  75                  80

Leu Ala Glu His Lys Pro Glu Leu Val Ile Leu Glu Leu Gly Gly Asn
                85                  90                  95

Asp Gly Leu Arg Gly Met Leu Pro Thr Gln Leu Gln Gln Asn Leu Ala
            100                 105                 110

Ala Met Ile Asn Ser Ser Lys Ala Ser Gly Ala Lys Val Leu Leu Leu
            115                 120                 125

Gly Met Gln Leu Pro Pro Asn Tyr Gly Ala Arg Tyr Asn Lys Val Phe
130                 135                 140

Ala Glu Ala Phe Ser Asn Val Ala Ala Glu Lys Lys Ile Pro Leu Val
145                 150                 155                 160

Pro Phe Phe Leu Glu Gly Val Gly Gly His Pro Glu Leu Met Gln Ser
                165                 170                 175

Asp Gly Leu His Pro Ala Ala Gly Ala Gln Asp Lys Leu Leu Glu Asn
            180                 185                 190

Val Trp Pro Thr Leu Lys Pro Leu Leu
            195                 200

<210> SEQ ID NO 30
<211> LENGTH: 218
<212> TYPE: PRT
<213> ORGANISM: Pantoea sp.

<400> SEQUENCE: 30

Met Leu Ser Leu Thr Asp Gly Leu Ser Lys Met Met Asn Phe Asn Asn
1               5                   10                  15

Val Phe Arg Trp His Tyr Ser Phe Leu Leu Leu Leu Leu Leu Leu Val
            20                  25                  30

Ser Arg Leu Ala Ala Ala Asp Thr Leu Leu Val Leu Gly Asp Ser Leu
            35                  40                  45

Ser Ala Gly Tyr Arg Met Ser Ala Asn Val Ala Trp Pro Tyr Leu Leu
50                  55                  60

Asp Lys Glu Trp Gln Gln Gln Pro Lys Val Ile Asn Ala Ser Ile Ser
65              70                  75                  80

Gly Asp Thr Ala Gly Gln Gly Leu Ala Arg Leu Pro Ala Leu Leu Lys
                85                  90                  95

Gln His Gln Pro Arg Trp Val Leu Ile Glu Leu Gly Gly Asn Asp Gly
            100                 105                 110

Leu Arg Gly Phe Pro Pro Gln Asn Ile Ala Gln Asp Leu Ser Lys Ile
            115                 120                 125

Ile Asp Asp Val Lys Ala Ala Asn Ala Gln Pro Leu Leu Met Gln Ile
            130                 135                 140

Arg Leu Pro Ala Asn Tyr Gly Arg Arg Tyr Thr Gln Ala Phe Ser Ala
145                 150                 155                 160

Ile Tyr Pro Gln Leu Ala Gln Gln Tyr Asn Ile Pro Leu Val Pro Phe
                165                 170                 175

Phe Met Glu Gln Val Tyr Leu Lys Pro Glu Trp Met Gln Gln Asp Gly
            180                 185                 190

Ile His Pro Asn Pro Asp Ala Gln Pro Phe Ile Ala Ser Val Met Ala
            195                 200                 205

Lys Glu Leu Ala Pro Leu Val Lys His Asp
210                 215

<210> SEQ ID NO 31
<211> LENGTH: 247
<212> TYPE: PRT
<213> ORGANISM: Bacteriovorax sp.

<400> SEQUENCE: 31

Met Lys Asp Lys Val Phe Lys Lys Thr Tyr Gln Val Ser Ile Asn Ser
1               5                   10                  15

Val Asn Ile Asn Lys Lys Leu Gly Leu Phe Gly Ile Leu Gly Tyr Leu
            20                  25                  30

Gln Asp Ile Ala Thr Val His Ala Glu Val Met Gly Phe Gly Leu Glu
        35                  40                  45

Asp Met Ile Arg Asp Gln Ser Phe Trp Val Leu Val Arg Gln Lys Leu
    50                  55                  60

Arg Met Thr Lys Phe Pro Val Trp Asn Glu Ser Val Glu Ile Gln Thr
65                  70                  75                  80

Trp Ser Arg Pro Pro Glu Gly Met Tyr Ala Phe Arg Glu Phe Glu Ile
                85                  90                  95

Phe Leu Asp Gly Glu Lys Ile Gly Asp Cys Ser Thr Val Trp Met Ile
            100                 105                 110

Leu Asp Gly Val Thr Arg Lys Val Lys Lys Pro Asp Phe Ser Met Glu
        115                 120                 125

Arg Ile Asn Pro Arg Thr Asp Tyr His Leu Asp Tyr Ile Ala His Lys
    130                 135                 140

Val Glu Val Arg Asp Asn Phe Glu Lys Val Asn Thr Ile Thr Val Arg
145                 150                 155                 160

Asn Ser Asp Leu Asp Leu Asn Met His Val Asn Asn Thr Lys Tyr Ser
                165                 170                 175

Gln Trp Ile Leu Asp Ser Ile Pro Ile Glu Leu His Lys Thr Ala Thr
            180                 185                 190

Leu Asn Glu Phe Glu Ile Asn Phe Met Ala Glu Thr His Leu Gly Asp
        195                 200                 205

Glu Ile Asp Ile Tyr Arg Ala Arg Asn Val Gly Glu Phe Lys His
    210                 215                 220

Asp Ile Thr Tyr Lys Gly Val Arg His Ser Asp Gly Lys Thr Cys Phe
225                 230                 235                 240

Leu Ala Lys Leu Leu Ala Asp
            245

<210> SEQ ID NO 32
<211> LENGTH: 198
<212> TYPE: PRT
<213> ORGANISM: Azotobacter chroococcum

<400> SEQUENCE: 32

Met Leu Gly Gly Ala Leu Ala Ser Leu Leu Phe Trp Ala Gln Gly Ala
1               5                   10                  15

Leu Ala Gly Thr Val Leu Val Val Gly Asp Ser Ile Ser Ala Ala Leu
            20                  25                  30

Gly Val Glu Thr Ser Gln Gly Trp Val Ala Leu Leu Glu Arg Arg Leu
        35                  40                  45

Val Asp Gln Gly Leu Thr His Arg Val Val Asn Ala Ser Ile Ser Gly
    50                  55                  60

Asp Thr Ser Ala Gly Gly Leu Ala Arg Leu Pro Thr Leu Leu Ala Thr
65                  70                  75                  80

```
His Arg Pro Glu Leu Val Ile Ile Glu Leu Gly Gly Asn Asp Gly Leu
                 85                  90                  95

Arg Gly Gln Pro Pro Gln Leu Gln Gln Asn Leu Ala Ala Met Ile
            100                 105                 110

Asp Ser Ser His Ser Ser Gly Ala Gln Val Val Leu Leu Gly Met Gln
            115                 120                 125

Leu Pro Pro Asn Tyr Gly Pro Arg Tyr Asn Gln Ala Phe Ser Arg Val
        130                 135                 140

Tyr Ala Thr Leu Ala Glu Glu Lys Gln Val Pro Leu Val Pro Phe Phe
145                 150                 155                 160

Leu Asp Gly Val Gly Val Pro Gly Met Met Gln Ala Asp Gly Ile
                165                 170                 175

His Pro Thr Ala Lys Ala Gln Pro Lys Met Leu Asp Asn Leu Trp Pro
            180                 185                 190

Thr Leu Glu Pro Leu Leu
        195
```

<210> SEQ ID NO 33
<211> LENGTH: 208
<212> TYPE: PRT
<213> ORGANISM: Citrobacter rodentium

<400> SEQUENCE: 33

```
Met Val Asn Phe Asn Asn Val Phe Arg Trp His Leu Pro Phe Leu Phe
1               5                   10                  15

Leu Ile Leu Phe Thr Cys Arg Ser Val Ala Ala Asp Thr Leu Leu Ile
            20                  25                  30

Leu Gly Asp Ser Leu Ser Ala Gly Tyr Arg Met Ser Ala Ser Ala Ala
        35                  40                  45

Trp Pro Ala Leu Leu Asn Asp Lys Trp His Ser Lys Thr Thr Ile Val
50                  55                  60

Asn Ala Ser Ile Ser Gly Asp Thr Ser Gly Gln Ala Leu Ala Arg Leu
65                  70                  75                  80

Pro Ala Leu Leu Lys Gln His Gln Pro Arg Trp Val Leu Val Glu Leu
                85                  90                  95

Gly Gly Asn Asp Gly Leu Arg Gly Phe Ser Pro Ala Gln Thr Glu Gln
            100                 105                 110

Thr Leu Arg Thr Ile Leu Gln Asn Val Lys Ala Ala Ser Ala Glu Pro
        115                 120                 125

Leu Leu Met Gln Ile Arg Leu Pro Ala Asn Tyr Gly Arg Arg Tyr Asn
    130                 135                 140

Glu Thr Phe Ser Ala Ile Tyr Pro Lys Leu Ala Ser Glu Phe Asp Ile
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gly Pro Phe Ile
            180                 185                 190

Ala Asp Trp Met Ala Lys Gln Leu Ser Pro Leu Val Lys Tyr Glu Ser
        195                 200                 205
```

<210> SEQ ID NO 34
<211> LENGTH: 205
<212> TYPE: PRT
<213> ORGANISM: Pseudomonas sp.

<400> SEQUENCE: 34

```
Met Arg Ser Trp Leu Lys Gly Val Leu Leu Val Met Trp Ala
1               5                   10                  15

Gln Gly Ala Leu Ala Gly Thr Val Leu Val Gly Asp Ser Ile Ser
            20                  25                  30

Ala Ala Phe Gly Leu Glu Thr Ser Gln Gly Trp Val His Leu Leu Gln
        35                  40                  45

Gln Arg Leu Ala Glu Gln Ala Arg Pro Arg Ser Val Val Asn Ala Ser
50                  55                  60

Ile Ser Gly Asp Thr Ser Ala Gly Gly Leu Ala Arg Leu Pro Thr Leu
65                  70                  75                  80

Leu Ala Glu His Arg Pro Glu Val Val Ile Leu Glu Leu Gly Gly Asn
                85                  90                  95

Asp Gly Leu Arg Gly Gln Ser Pro Ala Gln Leu Lys Gln Asn Leu Ala
            100                 105                 110

Ala Met Ile Glu Gln Ser Gln Gln Ala Asp Ala Lys Val Leu Leu Leu
        115                 120                 125

Gly Met Arg Leu Pro Pro Asn Tyr Gly Arg Arg Tyr Thr Glu Ala Phe
130                 135                 140

Ala Arg Val Tyr His Glu Leu Ala Asp Glu Arg Asp Val Ala Leu Val
145                 150                 155                 160

Pro Phe Val Leu Glu Gly Val Ala Gly Glu Pro Gly Met Met Gln Gly
                165                 170                 175

Asp Gly Val His Pro Thr Ala Ser Ala Gln Ala Gln Leu Leu Glu Asn
            180                 185                 190

Val Trp Pro Ala Leu Ala Pro Leu Leu Ala Pro Gln Arg
        195                 200                 205

<210> SEQ ID NO 35
<211> LENGTH: 247
<212> TYPE: PRT
<213> ORGANISM: Sediminispirochaeta smaragdinae

<400> SEQUENCE: 35

Met Lys Gln Val Ser Arg Tyr Thr Thr Glu His Thr Val Met Tyr Ser
1               5                   10                  15

Glu Thr Asp Ala Arg Gly Val Leu Ser Leu Pro Ser Phe Phe Ala Leu
            20                  25                  30

Phe Gln Glu Ala Ala Leu Leu His Ala Glu Glu Leu Gly Phe Gly Glu
        35                  40                  45

Thr Tyr Ser Lys Gln Glu Asn Leu Met Trp Val Leu Ser Arg Leu Leu
    50                  55                  60

Leu Glu Ile Asp Ala Phe Pro Lys His Arg Asp Arg Ile Arg Leu Ser
65                  70                  75                  80

Thr Trp Pro Lys Gln Pro Gln Gly Pro Phe Ala Ile Arg Asp Tyr Ile
                85                  90                  95

Leu Glu Ser Glu Glu Gly Thr Val Cys Ala Arg Ala Thr Ser Ser Trp
            100                 105                 110

Leu Leu Leu Lys Leu Asp Thr Met Arg Pro Ile Arg Pro Gln Thr Ile
        115                 120                 125

Phe Ala Asn Leu Ser Met Glu Gly Ile Gly Leu Ala Val Glu Gly Thr
130                 135                 140

Ala Pro Lys Ile Ser Glu Ile Asp Asn Asp Ser Lys Gln Glu Met Glu
145                 150                 155                 160

Val Thr Ala Arg Tyr Ser Asp Leu Asp Gln Asn Asn His Val Asn Asn
```

```
                        165                 170                 175
Thr Arg Tyr Val Arg Trp Phe Leu Asp Cys Tyr Thr Pro Glu Glu Ile
                    180                 185                 190

Thr Thr Ser Gly Asn Leu His Phe Ala Ile Asn Tyr Leu Gln Ala Ala
                195                 200                 205

Ser Tyr Ser Asp Lys Leu Leu Leu Arg Arg Tyr Asp Thr Glu Ser Asp
            210                 215                 220

Ser Ser Val Tyr Gly Tyr Leu Glu Asp Gly Thr Pro Ser Phe Ser Ala
225                 230                 235                 240

Arg Ile Glu Arg Lys Ser Asp
                245

<210> SEQ ID NO 36
<211> LENGTH: 253
<212> TYPE: PRT
<213> ORGANISM: Clostridium thermocellum

<400> SEQUENCE: 36

Met Gln Lys Lys Arg Phe Ser Lys Lys Tyr Glu Val His Tyr Tyr Glu
1               5                   10                  15

Ile Asn Ser Met Gln Glu Ala Thr Leu Leu Ser Leu Leu Asn Tyr Met
                20                  25                  30

Glu Asp Cys Ala Ile Ser His Ser Thr Ser Ala Gly Tyr Gly Val Asn
            35                  40                  45

Glu Leu Leu Ala Ala Asp Ala Gly Trp Val Leu Tyr Arg Trp Leu Ile
        50                  55                  60

Lys Ile Asp Arg Leu Pro Lys Leu Gly Glu Thr Ile Thr Val Gln Thr
65                  70                  75                  80

Trp Ala Ser Ser Phe Glu Arg Phe Tyr Gly Asn Arg Glu Phe Ile Val
                85                  90                  95

Leu Asp Gly Arg Asp Asn Pro Ile Val Lys Ala Ser Ser Val Trp Ile
            100                 105                 110

Tyr Phe Asn Ile Lys Lys Arg Lys Pro Met Arg Ile Pro Leu Glu Met
        115                 120                 125

Gly Asp Ala Tyr Gly Ile Asp Glu Thr Arg Ala Leu Glu Glu Pro Phe
    130                 135                 140

Thr Asp Phe Asp Phe Asp Phe Glu Pro Lys Val Ile Glu Glu Phe Thr
145                 150                 155                 160

Val Lys Arg Ser Asp Ile Asp Thr Asn Ser His Val Asn Asn Lys Lys
                165                 170                 175

Tyr Val Asp Trp Ile Met Glu Thr Val Pro Gln Gln Ile Tyr Asp Asn
            180                 185                 190

Tyr Lys Val Thr Ser Leu Gln Ile Ile Tyr Lys Lys Glu Ser Ser Leu
        195                 200                 205

Gly Ser Gly Ile Lys Ala Gly Cys Val Ile Asp Glu Gln Asn Thr Asp
    210                 215                 220

Asn Pro Arg Leu Leu His Lys Ile Trp Asp Lys Asn Thr Gly Leu Glu
225                 230                 235                 240

Leu Val Ser Ala Glu Thr Ile Trp Gln Lys Ile Gln Ser
                245                 250

<210> SEQ ID NO 37
<211> LENGTH: 204
<212> TYPE: PRT
<213> ORGANISM: Gammaproteobacteria bacterium
```

```
<400> SEQUENCE: 37

Met Leu Leu Ile Ile Leu Leu Ser Cys Tyr Phe Gly Thr Phe Ser Ser
1               5                   10                  15

Ala Ser Leu Ala Asn Thr Ile Leu Val Leu Gly Asp Ser Ile Ser Ala
                20                  25                  30

Ala Tyr Arg Ile Pro Val Glu Ser Gly Trp Val Ser Leu Leu Gln Glu
            35                  40                  45

Arg Leu Asp Glu His Arg Pro Gly His Tyr Thr Val Val Asn Ala Ser
        50                  55                  60

Ile Ser Gly Asp Thr Thr Ala Gly Ala Leu Asn Arg Leu Pro Pro Leu
65                  70                  75                  80

Leu Glu Lys His Arg Pro Asp Gln Val Ile Val Glu Leu Gly Gly Asn
                85                  90                  95

Asp Gly Leu Arg Gly Leu Pro Leu Lys Gly Met Arg Asp Asn Leu Gln
            100                 105                 110

Ala Ile Ile Asp Leu Ser Arg Gln Gln Gly Ala Asp Val Val Leu Val
        115                 120                 125

Ser Ile Asp Leu Pro Thr Ser Tyr Gly Ser His Phe Asn Gln Arg Phe
130                 135                 140

Thr Gln Val Tyr Asp Glu Leu Glu Ser Asn Lys Leu Pro Arg Val
145                 150                 155                 160

Ser Leu Gly Phe Lys Leu Leu Asn Asp Arg Asn Leu Ile Gln Glu Asp
                165                 170                 175

Gly Ile His Pro Thr Glu Glu Ala Gln Pro Leu Leu Leu Asp Val Val
            180                 185                 190

Trp Pro Leu Ile Ala Pro Gly Val Glu Arg Glu Gly
            195                 200

<210> SEQ ID NO 38
<211> LENGTH: 249
<212> TYPE: PRT
<213> ORGANISM: Terrisporobacter othiniensis

<400> SEQUENCE: 38

Met Glu Arg Val Phe Thr Lys Glu Tyr Glu Val Thr Tyr Arg Asp Thr
1               5                   10                  15

Asp Ala Arg Gly Glu Cys Phe Leu Thr Ser Tyr Met Asn Phe Met Ala
                20                  25                  30

Asp Cys Gly Leu Ser Gln Asp Glu Lys Tyr Gly Phe Val Ile Ala Asp
            35                  40                  45

Met Val Lys Glu Asn His Thr Trp Met Leu Val Asp Tyr Glu Ile Thr
        50                  55                  60

Ile Tyr Lys Tyr Val Lys Tyr Lys Glu Lys Leu Arg Ala Ile Thr Tyr
65                  70                  75                  80

Ile Glu Gly Met Asn Lys Phe Tyr Ala Val Arg Tyr Phe Lys Ile Tyr
                85                  90                  95

Asn Asp Lys Asp Asp Leu Ile Leu Glu Gly Lys Thr Leu Val Ile Leu
            100                 105                 110

Val Asp Ser Lys Lys Arg Arg Pro Leu Ser Ile Pro Asp Glu His Tyr
        115                 120                 125

Lys Ala Tyr Gly Val Glu Glu Lys Thr Pro Thr Ile Gly Arg Asn Lys
    130                 135                 140

Leu Lys Leu Ser Lys Cys Lys Asn Val Asp Tyr Lys Lys Glu Phe Asn
145                 150                 155                 160
```

Val Arg Tyr Ser Asp Ile Asp Leu Asn Leu His Val Gly Asn Val Thr
                165                 170                 175

Tyr Leu Gly Trp Ile Leu Glu Thr Ile Pro Phe Glu Ile Met Thr Asp
            180                 185                 190

Tyr Lys Ile Tyr Ser Val Lys Ile Lys Tyr Gln Lys Glu Leu Thr Tyr
        195                 200                 205

Gly Asp Lys Val Ser Val Lys Thr Glu Met Glu Tyr Asn Asp Asn
    210                 215                 220

Ile Ser Ala Tyr His Glu Ile Ile Asn Glu Ser Glu Val Val Ala
225                 230                 235                 240

Leu Leu Glu Thr His Trp Asn Glu Ile
                245

<210> SEQ ID NO 39
<211> LENGTH: 199
<212> TYPE: PRT
<213> ORGANISM: Shewanella baltica

<400> SEQUENCE: 39

Met Ala Lys Thr Leu Gly Ala Phe Ile Leu Leu Ser Val Leu Thr Val
1               5                   10                  15

Thr Pro Ala His Ala Ala Lys Val Leu Ile Leu Gly Asp Ser Leu Gly
                20                  25                  30

Ala Ser Tyr Gly Met Ala Glu Gln Ser Gly Trp Val Ala Leu Leu Gln
            35                  40                  45

Lys Asn Leu Pro Glu His Gln Phe Thr Asn Gly Ser Val Ser Gly Glu
        50                  55                  60

Thr Thr Ala Gly Gly Leu Arg Arg Leu Pro Ala Leu Leu Asp Ser Val
65                  70                  75                  80

Ala Pro Asp Leu Val Val Glu Leu Gly Gly Asn Asp Gly Leu Arg
                85                  90                  95

Gly Phe Pro Pro Thr Gln Leu Glu Asn Asn Leu Ile Gln Ile Ile Thr
            100                 105                 110

Leu Ala Lys Asp Ser Gly Ala Lys Val Leu Leu Thr Glu Ile Met Val
        115                 120                 125

Pro Pro Asn Tyr Gly Pro Arg Tyr Thr Gln Lys Phe Thr Gln Val Tyr
    130                 135                 140

Gln Asp Ile Ser Lys Thr Gln Asp Ile Val Leu Ile Pro Phe Phe Met
145                 150                 155                 160

Gln Asp Ile Ala Pro His Pro Glu Leu Met Gln Arg Asp Gly Ile His
                165                 170                 175

Pro Asn Glu Lys Ala Gln Ala Gln Ile Ala Thr Trp Met Gln Pro Trp
            180                 185                 190

Ile Glu Asp Ala Leu Thr Gln
        195

<210> SEQ ID NO 40
<211> LENGTH: 197
<212> TYPE: PRT
<213> ORGANISM: Shewanella loihica

<400> SEQUENCE: 40

Met Gln Ala Ala Cys Leu Leu Val Phe Phe Leu Ile Pro Gln Ala His
1               5                   10                  15

Ala Asn Pro Ile Leu Ile Leu Gly Asp Ser Leu Ser Ala Ser Tyr Gly
                20                  25                  30

```
Met Glu Gln Asp Lys Gly Trp Val His Leu Leu Gln Gln Ser Pro
            35                  40                  45
Glu Val Thr Ile Ile Asn Gly Ser Val Ser Gly Glu Thr Ser Ala Gly
 50                  55                  60
Gly Leu Arg Arg Leu Pro Ala Leu Leu Asp Ser Thr Lys Ala Lys Arg
 65                  70                  75                  80
Val Phe Ile Glu Leu Gly Gly Asn Asp Gly Leu Arg Gly Phe Ser Pro
                 85                  90                  95
Lys Gln Leu Lys Asn Asn Leu Thr Lys Met Ile Leu Leu Ala Lys Asp
            100                 105                 110
Ser Gly Ala Glu Val Leu Leu Ser Glu Val Met Val Pro Pro Asn Tyr
            115                 120                 125
Gly Pro Arg Tyr Ala Lys Gln Phe Thr Gln Val Tyr Gln Glu Leu Ser
130                 135                 140
Ser Glu Gln Gly Val Thr Leu Val Pro Phe Phe Met Thr Glu Ile Ala
145                 150                 155                 160
Ile His Pro Glu Leu Met Gln Ala Asp Gly Ile His Pro Asn Glu Gln
                165                 170                 175
Ala Gln Pro Gln Ile Val Ser Phe Ile Arg Pro Trp Leu Ile Asp Thr
            180                 185                 190
Gln Gln Pro Ser Glu
            195

<210> SEQ ID NO 41
<211> LENGTH: 246
<212> TYPE: PRT
<213> ORGANISM: Lactobacillus brevis

<400> SEQUENCE: 41

Met Ala Ala Asn Glu Phe Ser Glu Thr His Arg Val Val Tyr Tyr Glu
  1               5                  10                  15
Ala Asp Asp Thr Gly Gln Leu Thr Leu Ala Met Leu Ile Asn Leu Phe
                 20                  25                  30
Val Leu Val Ser Glu Asp Gln Asn Asp Ala Leu Gly Leu Ser Thr Ala
             35                  40                  45
Phe Val Gln Ser His Gly Val Gly Trp Val Val Thr Gln Tyr His Leu
 50                  55                  60
His Ile Asp Glu Leu Pro Arg Thr Gly Ala Gln Val Thr Ile Lys Thr
 65                  70                  75                  80
Arg Ala Thr Ala Tyr Asn Arg Tyr Phe Ala Tyr Arg Glu Tyr Trp Leu
                 85                  90                  95
Leu Asp Asp Ala Gly Gln Val Leu Ala Tyr Gly Glu Gly Ile Trp Val
            100                 105                 110
Thr Met Ser Tyr Ala Thr Arg Lys Ile Thr Thr Ile Pro Ala Glu Val
            115                 120                 125
Met Ala Pro Tyr His Ser Glu Glu Gln Thr Arg Leu Pro Arg Leu Pro
130                 135                 140
Arg Pro Asp His Phe Asp Glu Ala Val Asn Gln Thr Leu Lys Pro Tyr
145                 150                 155                 160
Thr Val Arg Tyr Phe Asp Ile Asp Gly Asn Gly His Val Asn Asn Ala
                165                 170                 175
His Tyr Phe Asp Trp Met Leu Asp Val Leu Pro Ala Thr Phe Leu Arg
            180                 185                 190
Ala His His Pro Thr Asp Val Lys Ile Arg Phe Glu Asn Glu Val Gln
            195                 200                 205
```

-continued

```
Tyr Gly His Gln Val Thr Ser Glu Leu Ser Gln Ala Ala Ala Leu Thr
            210                 215                 220
Thr Gln His Met Ile Lys Val Gly Asp Leu Thr Ala Val Lys Ala Thr
225                 230                 235                 240
Ile Gln Trp Asp Asn Arg
                245

<210> SEQ ID NO 42
<211> LENGTH: 248
<212> TYPE: PRT
<213> ORGANISM: Bacteroidales bacterium

<400> SEQUENCE: 42

Met Val Pro Leu Lys His Val His His Leu Lys Ala Lys Ser Tyr His
1               5                   10                  15

Ile Asn Arg Phe Gly Glu Val Ser Thr Pro Phe Leu Phe Trp Tyr Met
                20                  25                  30

Gln Glu Ile Ala Trp Glu His Ala His Lys Leu Gly Phe Gly Phe Glu
            35                  40                  45

His Leu Lys Glu Asp Gln Leu Phe Trp Val Leu Ser Arg Leu Leu Val
        50                  55                  60

Lys Ile Asp His Arg Pro Arg Trp Thr Asp Glu Phe Thr Leu Glu Thr
65                  70                  75                  80

Trp Ser Arg Gly Thr Asp Gly Phe Phe Ala Tyr Arg Asp Tyr Arg Phe
                85                  90                  95

Leu Asp Gln Asn Gly Asn Glu Phe Ile Lys Ala Thr Ser Ser Trp Leu
            100                 105                 110

Val Leu Asp Leu Glu Ser Arg Arg Ile Gln Arg Leu Ser Gln Phe Lys
        115                 120                 125

Asn Phe Pro Val Tyr Gln Glu Ser Val Leu Gly Asn Asn Ala Gly Lys
130                 135                 140

Val Asp Thr Pro Glu Thr Leu Gly Asp Leu Ser Phe Phe Pro Val Leu
145                 150                 155                 160

Phe Asn Glu Ile Asp Ile Asn Gln His Phe Asn Thr Gly Arg Tyr Leu
                165                 170                 175

Glu Arg Ile Asn Asn Ser Tyr Ser Phe Asp Phe His Glu Asn His Thr
            180                 185                 190

Leu Ser Glu Leu Glu Val Asn Phe Ile Lys Glu Gly Met Ala Asp Asp
        195                 200                 205

Ser Leu Ala Val Cys Gln Gln Arg Leu Ser Gly Glu His Leu Cys
    210                 215                 220

Ser Val Ile Arg Gln Arg Asp Gly Ser Glu Leu Ile Lys Ala Arg Leu
225                 230                 235                 240

Val Trp Glu Gln Lys Lys Lys Ile
                245

<210> SEQ ID NO 43
<211> LENGTH: 217
<212> TYPE: PRT
<213> ORGANISM: Halorhodospira halophila

<400> SEQUENCE: 43

Met Ala Gly Ser Ser Cys Phe Ser Leu Ser Leu Arg Arg Ala Leu Cys
1               5                   10                  15

Ala Ala Ala Leu Ala Leu Leu Leu Gly Pro Ser Ala Ala Thr Ala Glu
                20                  25                  30
```

Arg Pro Thr Ile Leu Ile Phe Gly Asp Ser Leu Ser Thr Ala Tyr Gly
                35                  40                  45

Phe Asp Arg Asp Glu Ala Trp Pro Val Leu Leu Glu Ala Arg Leu Asp
 50                  55                  60

Glu Ala Asp Arg Pro His Arg Val Ala Asn Val Ser Arg Ser Gly Glu
 65                  70                  75                  80

Thr Thr Ser Gly Gly Thr Arg Arg Leu Pro Asp Ala Leu Glu Glu His
                85                  90                  95

Glu Pro Glu Ile Val Leu Leu Gln Leu Gly Gly Asn Asp Gly Leu Arg
                100                 105                 110

Gly Gln Pro Pro Glu Arg Ile Arg Ser Asn Leu Gln Gln Met Ile Glu
            115                 120                 125

Gln Ala Arg Ala Val Asp Ser Arg Val Leu Leu Ile Gly Ile Arg Ile
        130                 135                 140

Pro Pro Asn Tyr Gly Arg Thr Tyr Thr Glu Gln Phe Ala Ala Ile Tyr
145                 150                 155                 160

Pro Glu Leu Ala Asp Glu Gln Asp Val Pro Val Ile Pro Phe Leu Leu
                165                 170                 175

Glu Gly Val Trp Asp Arg Asp Gly Met Met Gln Asp Asp Gly Val His
                180                 185                 190

Pro Thr Ala Lys Ala Gln Pro Glu Ile Ala Glu Thr Val Trp Glu Thr
            195                 200                 205

Leu Arg Glu Met Leu Asp Gly Pro Ser
        210                 215

<210> SEQ ID NO 44
<211> LENGTH: 154
<212> TYPE: PRT
<213> ORGANISM: Haemophilus influenzae

<400> SEQUENCE: 44

Met Ser Ala Asn Phe Thr Asp Lys Asn Gly Arg Gln Ser Lys Gly Val
 1               5                  10                  15

Leu Leu Leu Arg Thr Leu Ala Met Pro Ser Asp Thr Asn Ala Asn Gly
                20                  25                  30

Asp Ile Phe Gly Gly Trp Ile Met Ser Gln Met Asp Met Gly Gly Ala
                35                  40                  45

Ile Leu Ala Lys Glu Ile Ala His Gly Arg Val Val Thr Val Ala Val
         50                 55                  60

Glu Ser Met Asn Phe Ile Lys Pro Ile Ser Val Gly Asp Val Val Cys
 65                 70                  75                  80

Cys Tyr Gly Gln Cys Leu Lys Val Gly Arg Ser Ser Ile Lys Ile Lys
                85                  90                  95

Val Glu Val Trp Val Lys Lys Val Ala Ser Glu Pro Ile Gly Glu Arg
            100                 105                 110

Tyr Cys Val Thr Asp Ala Val Phe Thr Phe Val Ala Val Asp Asn Asn
            115                 120                 125

Gly Arg Ser Arg Thr Ile Pro Arg Glu Asn Asn Gln Glu Leu Glu Lys
        130                 135                 140

Ala Leu Ala Leu Ile Ser Glu Gln Pro Leu
145                 150

<210> SEQ ID NO 45
<211> LENGTH: 241
<212> TYPE: PRT

-continued

<213> ORGANISM: Eubacterium rectale

<400> SEQUENCE: 45

Met Ala Phe Ser Phe Asp Ser Arg Ile Arg Tyr Ser Glu Val Asp Ser
1               5                   10                  15

Ser Cys Arg Leu Ser Leu Thr Gly Leu Thr Asn Tyr Phe Gln Asp Cys
            20                  25                  30

Ser Val Phe His Ser Gln Ser His Asp Val Gly Ile Arg Phe Leu Ala
        35                  40                  45

Asp Asn His Ile Ala Trp Val Leu Ser Ser Trp Gln Ile Cys Ile Asn
    50                  55                  60

Arg Leu Pro Leu Leu Asn Glu Gln Val Lys Ile Ser Thr Trp Ala Tyr
65                  70                  75                  80

Gly Met Lys Ala Phe Tyr Gly Tyr Arg Asn Phe Thr Leu Glu Asp Ala
                85                  90                  95

Gly Gly Ser Thr Leu Ala Tyr Ala Asn Ser Val Trp Val Leu Val Asp
            100                 105                 110

Thr Arg Thr Gly Arg Pro Val Lys Val Pro Gln Glu Phe Ala Asp Thr
        115                 120                 125

Tyr Gly Leu Glu Pro Gln Leu Glu Met Glu Cys Ala Lys Arg Lys Leu
    130                 135                 140

His Ile Pro Asp Asp Met Glu Lys Lys Gly Glu Ile Glu Val Pro Gln
145                 150                 155                 160

Phe Phe Ile Asp Ser Asn His His Met Asn Asn Glu Lys Tyr Val Met
                165                 170                 175

Leu Ala Gln Gln Leu Leu Pro Asn Asp Phe Glu Ile Ser Glu Leu Arg
            180                 185                 190

Val Glu Tyr Arg Lys Glu Ala Lys Leu Gly Asp Thr Val Ile Ser Tyr
        195                 200                 205

Val Lys Tyr Thr Ser Lys Ser Val Thr Val Leu Ala Asp Thr Asp
    210                 215                 220

Lys Lys Pro Tyr Ser Val Val Glu Phe Leu Ser Lys Pro Val Pro Gly
225                 230                 235                 240

Lys

<210> SEQ ID NO 46
<211> LENGTH: 502
<212> TYPE: PRT
<213> ORGANISM: Oryza sativa

<400> SEQUENCE: 46

Met Ala Ala Thr Arg Ser Thr Ala Thr Ala Ala Leu Ala Leu Ser Arg
1               5                   10                  15

Thr Leu Ala Arg Arg Pro Ala Ala Ser Ser Ser Arg Arg Ile Ser
            20                  25                  30

Leu Glu Leu Ser Ala Pro Arg Gly Thr Asn Pro Phe Gln Ser Ala Ala
        35                  40                  45

Phe Ser Ser Thr Thr Thr Gly Asp Pro Pro Pro Thr Met Asp Ser
    50                  55                  60

Pro Ile Lys Val Val Ser His Ile Gly Gly Ser Gly Asp Gly Gly
65                  70                  75                  80

Gly Gly Ala Ile Asp Ala Gly Arg Ser Ala Arg Lys Pro Leu Ser Leu
                85                  90                  95

Trp Pro Gly Met Tyr His Ser Pro Val Thr Asn Ala Leu Trp Glu Ala
            100                 105                 110

Arg Ser Ser Ile Phe Glu Arg Met Ile Asp Ala Gly Ala Ala Gly Lys
            115                 120                 125

Gln Gln Gln Gln Pro Gln Thr Glu Leu Leu Thr Lys Thr Pro Ala
    130                 135                 140

Gly Ser Arg Thr Ser Ile Val Tyr Lys Phe Ala Thr Asp Asp Ile Leu
145                 150                 155                 160

Arg Glu Gln Tyr Arg Asp Pro Trp Asn Glu Val Arg Ile Gly Lys Leu
                165                 170                 175

Leu Glu Asp Leu Asp Ala Leu Ala Gly Thr Ile Ala Val Lys His Cys
            180                 185                 190

Ser Asp Glu Asp Ser Thr Thr Arg Pro Leu Leu Leu Val Thr Ala Ser
            195                 200                 205

Val Asp Lys Met Glu Leu Lys Lys Pro Ile Cys Val Asp Thr Asp Leu
            210                 215                 220

Lys Ile Ala Gly Ala Val Thr Tyr Val Gly Arg Ser Ser Ile Asp Ile
225                 230                 235                 240

Gln Ile Glu Val Thr Gln Val Asp Gln Asp Ser Asp Met Gln Ser Asp
                245                 250                 255

Pro Ile Ala Leu Thr Ala Asn Phe Thr Phe Val Ala Arg Asp Ser Met
            260                 265                 270

Thr Gly Lys Ser Ala Pro Val Asn Arg Leu Ser Pro Glu Thr Glu Lys
            275                 280                 285

Glu Lys Gln Leu Phe Ala Glu Arg Glu Ala Arg Asp Lys Leu Arg Lys
            290                 295                 300

Arg Lys Arg Glu Glu Gln Lys Gly Val Phe Glu Asn Gly Ile Asn Lys
305                 310                 315                 320

Leu His Val Glu Ala Glu Arg Leu Asn Ser Leu Leu Ala Glu Gly Arg
            325                 330                 335

Val Phe Ser Asp Leu Pro Ala Leu Ala Asp Arg Asp Ser Ile Leu Leu
            340                 345                 350

Lys Asp Thr Arg Leu Glu Asn Ser Leu Ile Cys Gln Pro Gln Gln Arg
            355                 360                 365

Asn Leu His Gly Arg Ile Phe Gly Gly Phe Leu Met Arg Ala Phe
            370                 375                 380

Glu Leu Ala Phe Ser Thr Ala Tyr Ala Phe Val Gly Gln Arg Pro Cys
385                 390                 395                 400

Phe Leu Glu Val Asp His Val Asp Phe Leu Lys Pro Val Asp Val Gly
            405                 410                 415

Asp Phe Leu Arg Phe Lys Ser Cys Val Leu Tyr Thr Gln Leu Asp Asn
            420                 425                 430

Ala Glu Gln Pro Leu Val Asn Val Glu Val Val Ala His Val Thr Arg
            435                 440                 445

Pro Glu Leu Arg Lys Ser Glu Val Ser Asn Thr Phe His Phe Thr Phe
            450                 455                 460

Thr Val Cys Ser Asp Ala Leu Lys Asn Gly Leu Lys Ile Arg His Val
465                 470                 475                 480

Val Pro Ser Thr Glu Glu Ala Arg Arg Ile Leu Glu Arg Met Asp
            485                 490                 495

Ala Glu Gly Leu Phe Asp
            500

<210> SEQ ID NO 47
<211> LENGTH: 204

<212> TYPE: PRT
<213> ORGANISM: Marinomonas fungiae

<400> SEQUENCE: 47

Met Met Ser Lys Val Cys Val Val Leu Leu Cys Phe Leu Ser Leu Leu
1               5                   10                  15

Thr Asn Ala His Ala Asn Thr Leu Leu Val Phe Gly Asp Ser Leu Ser
                20                  25                  30

Ala Ala Tyr Asn Leu Arg Gln Gln Gly Trp Val Ser Leu Leu Ser
            35                  40                  45

Gln Gln Leu Asn Arg Ser His Pro Asp Val Asn Val Asn Ala Ser
50                  55                  60

Ile Ser Gly Glu Thr Thr Gln Gly Gly Leu Ser Arg Leu Pro Lys Leu
65                  70                  75                  80

Leu Glu Thr His Gln Pro Lys Trp Val Val Leu Glu Leu Gly Ala Asn
                85                  90                  95

Asp Gly Leu Arg Gly Tyr Pro Leu Asn Gln Met Lys Gln Asn Leu Ala
            100                 105                 110

His Met Ile Asp Gln Ser Gln Gln Thr Gly Ala Lys Val Leu Leu Val
        115                 120                 125

Gly Asn His Leu Pro Ser Asn Tyr Gly Arg Thr Tyr Thr Thr Gln Phe
130                 135                 140

Phe Asn Val Tyr Ser Glu Leu Ala Lys Glu Tyr Gln Leu Ala Tyr Val
145                 150                 155                 160

Pro Phe Met Leu Glu Asn Val Ala Leu Asp Ser Thr Leu Met Gln Asn
                165                 170                 175

Asp Gly Leu His Pro Asn Ala Asp Gly Gln Pro Val Val Leu Glu Asn
            180                 185                 190

Ile Ala Pro Thr Leu Leu Pro Leu Leu Asn Leu Pro
        195                 200

<210> SEQ ID NO 48
<211> LENGTH: 199
<212> TYPE: PRT
<213> ORGANISM: Shewanella putrefaciens

<400> SEQUENCE: 48

Met Ala Lys Thr Leu Gly Ala Phe Ile Leu Leu Ser Met Leu Met Ala
1               5                   10                  15

Thr Pro Val His Ala Ala Lys Val Leu Ile Leu Gly Asp Ser Leu Gly
                20                  25                  30

Ala Ser Tyr Gly Met Ser Glu Gln Leu Gly Trp Val Ala Met Leu Gln
            35                  40                  45

Lys Asn Leu Pro Glu His Gln Phe Ile Asn Gly Ser Val Ser Gly Glu
50                  55                  60

Thr Thr Ala Gly Gly Leu Arg Arg Leu Pro Ala Leu Leu Asp Ser Val
65                  70                  75                  80

Ser Pro Asp Leu Val Val Glu Leu Gly Asn Asp Gly Leu Arg
                85                  90                  95

Gly Phe Pro Pro Thr Gln Leu Glu Asn Asn Leu Ile Gln Ile Thr
            100                 105                 110

Leu Ala Gln Lys Ser Gly Ala Lys Val Leu Leu Thr Glu Ile Met Val
        115                 120                 125

Pro Pro Asn Tyr Gly Pro Arg Tyr Thr Gln Lys Phe Thr Gln Val Tyr
130                 135                 140

Gln Asp Ile Ser Lys Thr Gln Asn Ile Glu Leu Ile Pro Phe Phe Met
145                 150                 155                 160

Gln Glu Ile Ala Pro Tyr Pro Asp Leu Met Gln Arg Asp Gly Ile His
            165                 170                 175

Pro Asn Glu Lys Ala Gln Ala Lys Ile Ala Ala Trp Met Gln Pro Trp
        180                 185                 190

Ile Glu Lys Ala Leu Asn Gln
        195

<210> SEQ ID NO 49
<211> LENGTH: 203
<212> TYPE: PRT
<213> ORGANISM: Aeromonas veronii

<400> SEQUENCE: 49

Met Val Arg Ile Leu Phe Ala Leu Phe Val Gly Leu Gly Ser Leu Leu
1               5                   10                  15

Ser Ser Ala Gln Ala Gln Thr Leu Leu Val Leu Gly Asp Ser Leu Ser
            20                  25                  30

Ala Gly Tyr Gln Met Gln Val Glu Gln Ser Trp Pro Ala Leu Leu Asn
        35                  40                  45

Gln Lys Trp Gln Glu Glu Gly Ser Lys His Thr Leu Leu Asn Ala Ser
    50                  55                  60

Ile Ser Gly Glu Thr Thr Gln Gly Ala Leu Ala Arg Leu Pro Ala Leu
65                  70                  75                  80

Leu Lys Glu His Lys Pro Asp Trp Leu Leu Ile Glu Leu Gly Gly Asn
                85                  90                  95

Asp Gly Leu Arg Gly Phe Ala Pro Thr Ile Thr Arg Gln Asn Leu Ala
            100                 105                 110

Ser Met Ile Ala Leu Ala Lys Gln Gln Thr Arg Val Val Leu Thr
        115                 120                 125

Gln Ile Gln Leu Pro Arg Asn Tyr Gly Ala Arg Tyr Leu Arg Gln Phe
    130                 135                 140

Glu Gln Ile Phe Pro Glu Leu Ala Gln Ala Asn Asp Leu Pro Leu Leu
145                 150                 155                 160

Pro Phe Phe Met Asp Asp Ile Ala Leu Arg Pro Glu Leu Met Met Asn
                165                 170                 175

Asp Gly Ile His Pro Thr Pro Ala Ala Gln Pro Gln Ile Arg Asp Lys
            180                 185                 190

Val Ala Arg Phe Met Glu Pro Leu Leu Ser Gln
        195                 200

<210> SEQ ID NO 50
<211> LENGTH: 292
<212> TYPE: PRT
<213> ORGANISM: Selaginella moellendorffii

<400> SEQUENCE: 50

Asp Thr Leu Lys Gln Gly Arg Leu Val Glu Arg Val Tyr Arg Gln
1               5                   10                  15

Thr Phe Val Val Arg Ser Tyr Glu Val Gly Pro Asp Lys Thr Ala Thr
            20                  25                  30

Leu Asp Thr Phe Leu Asn Leu Phe Gln Glu Thr Ala Leu Asn His Val
        35                  40                  45

Leu Ile Ser Gly Leu Ala Gly Asn Gly Phe Gly Thr Thr His Glu Met
    50                  55                  60

```
Ile Arg Asn Asn Leu Ile Trp Val Val Thr Arg Met Gln Val Gln Val
 65                  70                  75                  80

Glu Arg Tyr Pro Ala Trp Gly Asn Ala Leu Glu Ile Asp Thr Trp Val
                 85                  90                  95

Gly Ala Ser Gly Lys Asn Gly Met Arg Arg Asp Trp Leu Val Arg Asp
            100                 105                 110

Tyr Lys Thr Gly Ser Ile Leu Ala Arg Ala Thr Ser Thr Trp Val Met
        115                 120                 125

Met His Lys Asp Thr Arg Arg Leu Ser Lys Met Pro Asp Leu Val Arg
130                 135                 140

Ala Glu Ile Ser Pro Trp Phe Leu Ser Arg Thr Ala Phe Ile Pro Glu
145                 150                 155                 160

Glu Ser Cys Ser Lys Ile Glu Lys Leu Asp Asn Ser Asn Thr Arg Tyr
            165                 170                 175

Ile Arg Ser Asn Leu Thr Pro Arg His Ser Asp Leu Asp Met Asn Gln
        180                 185                 190

His Val Asn Asn Val Lys Tyr Leu Thr Trp Met Met Glu Ser Leu Pro
    195                 200                 205

Gln Asn Ile Leu Glu Ser His His Leu Val Gly Ile Thr Leu Glu Tyr
210                 215                 220

Arg Arg Glu Cys Ser Lys Ser Asp Met Val Glu Ser Leu Thr His Pro
225                 230                 235                 240

Glu Arg Gly Gly His Leu Ala Ile Asn Gly Ala Ala Ala Ala Ala Ala
            245                 250                 255

Ala Ala Ala Ala Ala Pro Pro Ser Gln Leu Asp Phe Ile His Leu Leu
        260                 265                 270

Arg Met Gln Thr Gly Gly Ser Glu Ile Val Arg Ala Arg Thr Ser Trp
275                 280                 285

Lys Ser Arg His
    290

<210> SEQ ID NO 51
<211> LENGTH: 207
<212> TYPE: PRT
<213> ORGANISM: Trabulsiella guamensis

<400> SEQUENCE: 51

Met Asp Phe Lys Tyr Ile Phe Arg Trp His Leu Pro Phe Leu Leu Leu
1               5                   10                  15

Val Leu Phe Ala Phe Arg Ala Ala Ala Asp Thr Val Leu Val Leu
            20                  25                  30

Gly Asp Ser Leu Ser Ala Gly Tyr Arg Met Ala Ala Asn Ala Ala Trp
        35                  40                  45

Pro Ala Leu Leu Asn Glu Lys Trp Gln Pro Gln Thr Arg Val Ile Asn
    50                  55                  60

Ala Ser Ile Ser Gly Asp Thr Ala Gln Gln Gly Leu Ala Arg Leu Pro
65                  70                  75                  80

Ala Leu Leu Lys Gln His Gln Pro Asp Trp Val Leu Val Glu Leu Gly
            85                  90                  95

Gly Asn Asp Gly Leu Arg Gly Phe Gln Pro Gln Thr Glu Gln Thr
            100                 105                 110

Leu Arg Thr Ile Leu Gln Asp Ile Lys Ala Ala Asn Ala Arg Pro Val
        115                 120                 125

Leu Met Gln Ile Arg Leu Pro Ala Asn Tyr Gly Arg Arg Tyr Asn Glu
130                 135                 140
```

```
Ala Phe Ser Ala Ile Tyr Pro Lys Leu Ala Gly Glu Phe Ser Val Pro
145                 150                 155                 160

Leu Leu Pro Phe Phe Met Glu Glu Val Tyr Leu Lys Pro Gln Trp Met
            165                 170                 175

Gln Asp Asp Gly Ile His Pro Asn Arg Asp Ala Gln Pro Phe Ile Ala
            180                 185                 190

Asp Trp Met Ala Ala Arg Leu Ala Pro Leu Val Asn His Asp Ser
        195                 200                 205

<210> SEQ ID NO 52
<211> LENGTH: 242
<212> TYPE: PRT
<213> ORGANISM: Weeksella virosa

<400> SEQUENCE: 52

Met Asn Pro Val Asp Tyr Tyr Thr Glu Lys Phe Tyr Ile Asp Tyr Ser
1               5                   10                  15

Arg Val Tyr Pro Asn Arg Lys Ile Lys Tyr Pro Glu Leu Ala Asn Ile
            20                  25                  30

Leu Gln Ile Thr Ala Ala Asn His Ala Asp Phe Cys Gly Leu Gly Phe
        35                  40                  45

Asp Asp Leu Gln His Asn Lys Gln Ala Trp Val Met Asn Arg Ile Arg
50                  55                  60

Ile Glu Ile Asp Thr Leu Pro Glu Leu Asn Asp Glu Val Thr Ile Asp
65                  70                  75                  80

Thr Trp Leu Glu Leu Leu Arg Val Pro Lys Ser Ile Arg Asn Leu Glu
                85                  90                  95

Ile Lys Lys Glu Gly Lys Lys Leu Val Gly Val Ser Ser Leu Trp Ala
            100                 105                 110

Val Phe Asn Thr Glu Arg Arg Pro Glu Ala Leu Lys Ile Asp Ala
        115                 120                 125

Asp His Leu Lys Ile Phe Thr Asp Leu His Ala Thr Ser Leu Glu Asn
    130                 135                 140

Asn Lys Ile Glu Thr Pro Glu Ser Phe Gln Lys Val Ala Glu Tyr Gln
145                 150                 155                 160

Val Lys Leu Ser Asp Leu Asp Val Val Asn His Val Asn Asn Ile Gln
                165                 170                 175

Tyr Leu Thr Trp Cys Leu Asp Thr Leu Ser Lys Glu Val Leu Glu
            180                 185                 190

Arg Ser Ile Ala Val Leu Glu Met Asn Phe Leu Lys Glu Leu Ser Tyr
        195                 200                 205

Gln Lys Ile Ile His Ile Glu Gln Tyr Arg Gln Glu His Glu Leu Tyr
    210                 215                 220

Leu Arg Ile Arg Asp Glu Gln Phe Ile Tyr Phe Val Ala Arg Ile Thr
225                 230                 235                 240

Tyr Gln

<210> SEQ ID NO 53
<211> LENGTH: 207
<212> TYPE: PRT
<213> ORGANISM: Pseudoalteromonas haloplanktis

<400> SEQUENCE: 53

Met Thr His Ser Ile Leu Arg Leu Val Phe Ile Leu Phe Leu Val Ile
1               5                   10                  15
```

Lys Pro Leu Ser Ala Ala Ala Asp Asn Thr Ile Leu Ile Leu Gly Asp
                20                  25                  30

Ser Leu Ser Ala Ala Tyr Gly Leu Gln Gln Glu Glu Gly Trp Val Lys
            35                  40                  45

Leu Leu Gln Asp Lys Tyr Asp Asp Glu Gln Ala Asp Ile Glu Leu Ile
        50                  55                  60

Asn Ala Ser Ile Ser Gly Glu Thr Ser Gly Gly Ala Leu Arg Arg Leu
65                  70                  75                  80

Asp Ala Leu Leu Glu Gln Tyr Glu Pro Thr His Val Leu Ile Glu Leu
                85                  90                  95

Gly Ala Asn Asp Gly Leu Arg Gly Phe Pro Val Lys Lys Met Gln Thr
            100                 105                 110

Asn Leu Thr Ser Leu Ile Gln Lys Ser Gln Ala Ala Asn Ala Met Thr
        115                 120                 125

Ala Leu Met Glu Ile Tyr Ile Pro Pro Asn Tyr Gly Pro Arg Tyr Ser
    130                 135                 140

Lys Met Phe Thr Asp Thr Phe Ser Arg Val Ser Glu Glu Thr Asn Ala
145                 150                 155                 160

His Leu Met Asn Phe Phe Met Leu Asp Ile Ala Ser Gln Ser Asp Leu
                165                 170                 175

Met Gln Asn Asp Ser Leu His Pro Asn Lys Lys Ala Gln Pro Leu Ile
            180                 185                 190

Arg Asp Glu Met Tyr Asp Ser Ile Lys Lys Trp Leu Asn Lys Asp
        195                 200                 205

<210> SEQ ID NO 54
<211> LENGTH: 208
<212> TYPE: PRT
<213> ORGANISM: Escherichia coli

<400> SEQUENCE: 54

Met Met Asn Phe Asn Asn Val Phe Arg Trp His Leu Pro Phe Leu Phe
1               5                   10                  15

Leu Val Leu Leu Thr Phe Arg Ala Ala Ala Ala Asp Thr Leu Leu Ile
                20                  25                  30

Leu Gly Asp Ser Leu Ser Ala Gly Tyr Arg Met Ser Ala Ser Ala Ala
            35                  40                  45

Trp Pro Ala Leu Leu Asn Asp Lys Trp Gln Ser Lys Thr Ser Val Val
        50                  55                  60

Asn Ala Ser Ile Ser Gly Asp Thr Ser Gln Gln Gly Leu Ala Arg Leu
65                  70                  75                  80

Pro Ala Leu Leu Lys Gln His Gln Pro Arg Trp Val Leu Val Glu Leu
                85                  90                  95

Gly Gly Asn Asp Gly Leu Arg Gly Phe Gln Pro Gln Gln Thr Glu Gln
            100                 105                 110

Thr Leu Arg Gln Ile Leu Gln Asp Val Lys Ala Ala Asn Ala Glu Pro
        115                 120                 125

Leu Leu Met Gln Ile Arg Leu Pro Ala Asn Tyr Gly Arg Arg Tyr Asn
    130                 135                 140

Glu Ala Phe Ser Ala Ile Tyr Pro Lys Leu Ala Lys Glu Phe Asp Val
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gln Pro Phe Ile
            180                 185                 190

Ala Asp Trp Met Ala Lys Gln Leu Gln Pro Leu Val Asn His Asp Ser
        195                 200                 205

<210> SEQ ID NO 55
<211> LENGTH: 245
<212> TYPE: PRT
<213> ORGANISM: Lactobacillus mellis

<400> SEQUENCE: 55

Met Gly Gln Gln Tyr Gln Glu Thr Lys Val Ile Pro Phe Tyr Ser Thr
1               5                   10                  15

Asn Ala Thr Ser Glu Ile Asn Ile Ser Ala Leu Phe Asn Glu Met Leu
            20                  25                  30

Leu Val Ser Glu His Gln Leu His Ala Val Gly Ile Asp Ser Gln Gln
        35                  40                  45

Met Val Ala Gln Gly Ile Gly Trp Val Val Thr Lys Tyr His Leu Glu
    50                  55                  60

Ile Lys Arg Leu Pro Arg Ile Asn Glu Lys Val Thr Ile Val Thr Glu
65                  70                  75                  80

Ala Asn Ser Tyr Asn Lys Phe Phe Cys Tyr Arg Thr Phe Thr Leu Tyr
                85                  90                  95

Asp Ser Gln Gly Gln Gln Leu Leu His Leu Leu Ser Asn Trp Val Met
            100                 105                 110

Met Asp Ile Lys Lys Arg Ser Met Ile Glu Val Ile Pro Glu Thr Met
        115                 120                 125

Ala Lys Ile Gly Cys Glu Tyr Ser Thr Asp Ile Trp Arg Phe Pro Arg
    130                 135                 140

Ile Gln Arg Phe Lys Tyr Ser Gln Ser Pro Gln Ile Tyr Arg Thr Arg
145                 150                 155                 160

Phe Phe Asp Ile Asp Val Asn Gly His Val Asn Asn Ser Ile Tyr Leu
                165                 170                 175

Asp Trp Met Leu Asp Ser Leu Gly Lys Asp Phe Leu Met Gln His Gln
            180                 185                 190

Leu Gln Thr Leu Asp Ile Lys Tyr Asp Arg Glu Val Ala Tyr Gly Gln
        195                 200                 205

Ser Val Gln Ser Phe Val Gln Leu Glu Asp Asn Leu Ile Ser His His
    210                 215                 220

Gln Ile Leu Thr Asp Asn Lys Val Asn Ala Gln Ala Gln Met Gln Trp
225                 230                 235                 240

Gln Gln Arg Gln Lys
                245

<210> SEQ ID NO 56
<211> LENGTH: 244
<212> TYPE: PRT
<213> ORGANISM: Lactobacillus johnsonii

<400> SEQUENCE: 56

Met Glu Lys Ile Phe Lys Glu Glu His Gln Val Ser Tyr Gly Asp Cys
1               5                   10                  15

Asp Glu Thr Gly Lys Ile Gln Leu Pro His Leu Ile Glu His Phe Met
            20                  25                  30

Gln Val Ser Asn Asp Gln Leu Thr Ala Gly Gly Ala Gly Ile His Asp
        35                  40                  45

Leu Leu Lys Gln Asn Leu Gly Trp Val Val Glu Tyr His Leu Asp
    50                  55                  60

```
Ile Asp Arg Leu Pro Glu Ala Gly Glu Lys Ile Thr Val Thr Thr Asn
 65                  70                  75                  80

Gly Ser Gly Tyr Asn Arg Phe Phe Glu Tyr Arg Asp Phe Gly Ile Ile
                 85                  90                  95

Asp Ser Thr Asn Lys Lys Ile Val Gly Val Lys Ser Gln Trp Val Ile
                100                 105                 110

Leu Asp Leu Lys Asn Arg Lys Ile Thr Glu Ala Asp Asp Gln Met Met
            115                 120                 125

Gln Lys Phe Gly Asn Pro Tyr Leu Lys His Met Pro Arg Phe Lys Arg
130             135                 140

Leu Arg Pro Leu Lys Glu Tyr Arg Ser Ser Lys Lys Tyr Thr Val Arg
145                 150                 155                 160

Tyr Tyr Asp Leu Asp Thr Asn His His Leu Thr Asn Ser Ile Tyr Phe
                165                 170                 175

Asp Trp Met Ile Asp Thr Leu Pro Arg Glu Phe Leu Asn Ser His Thr
                180                 185                 190

Val Lys Ser Ile Asp Ile Ser Phe Lys Lys Glu Val Gln Tyr Gly Asp
            195                 200                 205

Gln Ala Leu Ala Glu Val Glu Leu Asp Gln Asp Thr Leu Thr Ser Tyr
210                 215                 220

His Leu Ile Ser Asn Gln Gly Glu Ala Ser Ala Leu Ala Glu Ile Asn
225                 230                 235                 240

Trp Lys Glu Asn

<210> SEQ ID NO 57
<211> LENGTH: 251
<212> TYPE: PRT
<213> ORGANISM: Thermovirga lienii

<400> SEQUENCE: 57

Met Tyr Glu His Asn Phe Arg Ile Ser Tyr Ser Gln Ala Gly Ala Leu
 1               5                  10                  15

Gly Arg Leu Lys Leu Thr Gly Ala Met Asn Leu Cys Gln Asp Ile Ala
                20                  25                  30

Asp Asp His Ala Glu Arg Val Gly Val Ser Val Ala Asp Leu Leu Lys
                35                  40                  45

Gln Ser Lys Thr Trp Val Leu His Arg Phe Lys Met Thr Ile Gln Thr
 50                  55                  60

Met Pro Gln Arg Gly Asp Leu Val Thr Ile Lys Thr Trp Tyr Arg Pro
 65                  70                  75                  80

Glu Lys Asn Leu Tyr Ser Leu Arg Asn Phe Glu Met Leu Asp Cys Asn
                 85                  90                  95

Gly Lys Lys Leu Leu Ser Val Gln Thr Ser Trp Val Val Val Asp Met
                100                 105                 110

Asn Arg Gly Arg Pro Leu Arg Leu Asp Arg Val Met Pro Glu Ala Tyr
            115                 120                 125

Asp Lys Asn Lys Asp Glu Asn Leu Glu Val Ser Phe Gln Glu Leu Leu
130                 135                 140

Leu Pro Glu Lys Val Asp Val Lys Lys Thr Ile Gln Val Ala Val Thr
145                 150                 155                 160

Asp Leu Asp Met Asn Phe His Val Asn Asn Val His Tyr Leu Arg Trp
                165                 170                 175

Ala Leu Asp Thr Ile Pro Val Glu Ile Leu Lys Glu Tyr Lys Pro Lys
                180                 185                 190
```

Gly Val Glu Ile Ala Phe Lys Arg Pro Ala Phe Tyr Gly Asp Ser Val
                195                 200                 205

Ile Ser Glu Val Gly Ile Asp Lys Asn Ser Cys Ser Ile Leu Cys Arg
210                 215                 220

His His Ile Tyr Gly Glu Lys Asp Gly Gln Ser Met Ala Val Ile Ser
225                 230                 235                 240

Thr Glu Trp Glu Lys Ile Ser Arg Glu Arg
                245                 250

<210> SEQ ID NO 58
<211> LENGTH: 245
<212> TYPE: PRT
<213> ORGANISM: Cryptobacterium curtum

<400> SEQUENCE: 58

Met Thr Ile Ser Ala Ser Leu Phe Leu Glu Lys Asp Tyr Arg Leu Arg
1               5                   10                  15

Thr Gly Asp Phe Asp Arg Tyr Arg Leu His Pro Thr Ala Val Leu
                20                  25                  30

Asp Leu Phe Gln Asp Ile Gly Gly Leu Gln Ala Glu Met Met Gly Ile
            35                  40                  45

Gly Tyr Asp Ala Met Ala Ala Gln Asp Val Phe Trp Ala Val Val Arg
50                  55                  60

Thr Ala Tyr Gln Val Glu His Thr Pro Ala Glu His Glu Val Val Lys
65                  70                  75                  80

Val Ser Thr Trp Pro His Ser Pro Ser Arg Tyr Ser Phe Gln Arg Asp
                85                  90                  95

Tyr Ala Leu Arg Ser Thr Asp Gly Ser Leu Leu Val Arg Gly Thr Ser
                100                 105                 110

Glu Trp Val Leu Met Asp Met Asn Thr Arg Ser Leu Thr Ser Val Leu
            115                 120                 125

Asp Tyr Tyr His Gly Ser Leu Asp Phe Ile Asp Glu Arg Met Phe Ala
            130                 135                 140

Lys Lys Leu Arg Lys Ile Arg Asp Phe Thr Glu Glu Gly Ser Gly Leu
145                 150                 155                 160

Ser Ile Thr Pro Arg Tyr Ser Asp Val Asp Gln Asn Gly His Val Asn
                165                 170                 175

Asn Ala Arg Tyr Ala Ser Phe Val Leu Asp Ala Leu Asp Pro Ser Ala
                180                 185                 190

Ala Gly Ser Ile Ala Ser Phe Gln Ile Asp Phe Arg His Glu Val Ile
                195                 200                 205

Glu Gly Thr Pro Leu Val Val Phe Thr Gln Val Glu Gly Lys Asp Ile
                210                 215                 220

Gln Ala Lys Gly Leu Asp Ser Asn Gly Glu Ile Lys Phe Ala Cys Lys
225                 230                 235                 240

Ile Thr Ala Gln Ala
                245

<210> SEQ ID NO 59
<211> LENGTH: 247
<212> TYPE: PRT
<213> ORGANISM: Treponema primitia

<400> SEQUENCE: 59

Met Asp Val Trp Lys Glu Ser Tyr Pro Val Gly Phe Thr Ala Val Asp
1               5                   10                  15

```
Glu Ser Glu Gly Leu Thr Leu Ala Ala Ala Phe Asp Tyr Phe Gln Glu
            20                  25                  30

Ala Ala Arg Arg His Ala Glu Val Leu Gly Val Gly Gln Glu Pro Met
        35                  40                  45

Val Gln Ala Gly Gln Gly Trp Val Leu Ser Arg Ile Ser Val Leu Val
 50                  55                  60

Glu Arg Arg Pro Arg Gln Gly Glu Leu Ile Thr Val Ser Thr Trp Pro
 65                  70                  75                  80

Arg Gly Trp Glu Lys Leu Phe Ala Leu Arg Asp Phe Asp Ile Arg Asp
                85                  90                  95

Glu Ser Asp Lys Pro Ile Val Arg Ala Arg Ser Cys Trp Leu Ile Val
            100                 105                 110

Asn Ile Glu Lys Arg Arg Pro Leu Arg Pro Gln Ala Thr Met Glu Lys
        115                 120                 125

Leu Pro Leu Asn Glu Gly Arg Asp Ala Leu Pro Gly Gly Val Gly
    130                 135                 140

Leu Ala Pro Leu Glu Asn Leu Leu Lys Ala Gly Asp Arg Val Ala Ala
145                 150                 155                 160

Tyr Ser Asp Ile Asp Tyr Asn Gly His Val Asn Asn Ala Arg Tyr Val
                165                 170                 175

Gln Trp Val Gln Asp Ile Ala Asp Pro Thr Ala Leu Val Gln Ala Lys
            180                 185                 190

Thr Leu Arg Leu Asp Ile Asn Tyr Leu Ser Glu Val Lys Ile His Glu
        195                 200                 205

Pro Ile Glu Leu Trp Thr Glu Pro Leu Pro Ala Glu Ser Asp Ala Val
    210                 215                 220

Tyr Thr Leu Gly Val Glu Gly Arg Arg Asn Gly Gly Ala Val Phe Arg
225                 230                 235                 240

Ala Glu Leu Arg Ile Lys Asp
                245

<210> SEQ ID NO 60
<211> LENGTH: 254
<212> TYPE: PRT
<213> ORGANISM: Lactobacillus ruminis

<400> SEQUENCE: 60

Met Glu Ser Lys Gly Phe Ser Glu Lys His Arg Val Thr Tyr Tyr Glu
1               5                   10                  15

Thr Asp Met Asn Gly Thr Val Gly Leu Gly Arg Leu Val Asp Leu Met
            20                  25                  30

Met Leu Ser Cys Asn Asp Gln Ser Asp Ala Val Gly Leu Ser Ser Glu
        35                  40                  45

Lys Val Asn Gln Met Gly Leu Gly Trp Ile Val Thr Gln Asn Met Ile
    50                  55                  60

Asp Ile Lys Arg Leu Pro Arg Arg Asn Glu Thr Ile Tyr Ile Thr Thr
 65                  70                  75                  80

His Ala Lys Ser Tyr Asn Arg Tyr Phe Cys Tyr Arg Asp Phe Trp Ile
                85                  90                  95

His Asp Ile Arg Lys Gln Glu Leu Ala His Met His Thr Val Phe Ala
            100                 105                 110

Leu Met Asp Gln Asn Glu Arg Lys Ile Val Arg Ile Pro Glu Asn Leu
        115                 120                 125

Ile Glu Pro Tyr His Ser Glu Tyr Ala Thr Lys Ile Glu Arg Leu Pro
```

```
            130                 135                 140
Leu Pro Lys Glu Leu Glu Arg Ile Asp Arg Gln Lys Glu Tyr Glu Val
145                 150                 155                 160

Arg Phe Trp Asp Ile Asp Ile Asn Gln His Val Asn Asn Val His Tyr
                165                 170                 175

Phe Glu Trp Met Leu Asp Ala Leu Asp Leu Asp Phe Leu Ile Lys Tyr
            180                 185                 190

Gln Pro Val Ser Met Asn Ile Glu Tyr Lys Lys Glu Ile Arg Tyr Gly
        195                 200                 205

Gln Lys Ala Val Ser Gln Ala Gln Ile Thr Met Thr Gly Val Glu Thr
    210                 215                 220

Val Thr Thr Phe His Glu Ile Lys Val Asn Asp Glu Leu Ser Cys Arg
225                 230                 235                 240

Ala Val Cys Asp Trp Lys Leu Arg Lys Glu Glu Trp Ile Met
                245                 250

<210> SEQ ID NO 61
<211> LENGTH: 241
<212> TYPE: PRT
<213> ORGANISM: Lactococcus raffinolactis

<400> SEQUENCE: 61

Met Leu Thr Tyr Lys Lys Tyr Thr Val Pro Tyr Tyr Glu Thr Asp
1               5                   10                  15

Ala Asn Gly Asn Met Lys Leu Pro Ser Leu Phe Asn Ile Ala Leu Gln
                20                  25                  30

Leu Ser Gly Glu Gln Ser His Ser Leu Gly Ile Ser Asp Asp Trp Leu
            35                  40                  45

Lys Glu Thr Tyr Asn Tyr Ala Trp Val Val Glu Tyr Asp Val Thr
50                  55                  60

Ile Gln Arg Leu Pro Arg Phe Ser Glu Ile Ile Thr Met Ser Thr Phe
65                  70                  75                  80

Ala Lys Ser Tyr Asn Lys Phe Phe Cys Tyr Arg Asp Phe Val Phe Tyr
                85                  90                  95

Ala Glu Asn Gly Asp Thr Leu Leu Thr Ile Asn Ser Thr Phe Val Leu
            100                 105                 110

Ile Asp Thr Thr Ser Arg Lys Val Ala His Val Glu Asp Asp Ile Val
        115                 120                 125

Ala Pro Tyr Gln Ser Glu Lys Ile Ser Lys Ile Val Arg Gly His Lys
    130                 135                 140

Ser Thr Ala Leu Ser Asp Thr Pro Leu Glu Lys Ser Tyr His Val Arg
145                 150                 155                 160

Phe Asn Asp Ile Asp Gln Asn Gly His Val Asn Asn Ser Lys Tyr Phe
                165                 170                 175

Asp Trp Met Thr Asp Val Leu Gly Tyr Asp Phe Leu Ser Ser His Val
            180                 185                 190

Pro Ser Arg Ile His Leu Lys Tyr Ser Lys Glu Val Leu Tyr Gly Ala
        195                 200                 205

Thr Val Thr Ser Arg Val Asp Leu Val Gly Val Gln Ser Phe His Glu
    210                 215                 220

Ile Val Ser Glu Gly Lys His Ala Gln Ala Glu Met Thr Trp Arg Glu
225                 230                 235                 240

Lys
```

<210> SEQ ID NO 62
<211> LENGTH: 265
<212> TYPE: PRT
<213> ORGANISM: Aerococcus viridans

<400> SEQUENCE: 62

Met Ile Asn Ile Arg His Tyr Gln Gly Gly Lys Arg Met Gly Leu Leu
1               5                   10                  15

Tyr Gln Glu Ser Val Lys Val Arg His Tyr His Cys Asn Ala Leu Gly
            20                  25                  30

Glu Met Thr Leu Pro Ala Ile Leu Asp Ile Met Leu Ile Ala Ser Asn
        35                  40                  45

Asn Gln Glu Ala Thr Ile Pro Glu Ala Lys Glu Gly Phe Arg Gln Glu
    50                  55                  60

Gly Trp Ala Trp Ile Ile Thr Gln Asn Gln Ile Asp Ile Asn Arg Leu
65                  70                  75                  80

Pro Arg Tyr Asp Glu Asp Ile Ile Ala Glu Thr Glu Ala Thr Thr Tyr
                85                  90                  95

Asn Lys Phe Phe Ser Lys Arg His Tyr Ala Leu Lys Thr Arg Asp Gly
            100                 105                 110

Leu Val Leu Ala Gln Ala Glu Thr Thr Phe Ala Leu Ile Asp Leu Asn
        115                 120                 125

Gln Arg Ser Ile Val Arg Ile Pro Glu Ile Val Ala Glu Trp Tyr Gln
    130                 135                 140

Val Glu Lys Glu Glu Arg Pro Ser Arg Arg Lys Arg Leu Asn Lys Glu
145                 150                 155                 160

Ile Ala Val Glu Ser Lys Leu Asp Arg Phe Glu Val Lys Phe Leu Asp
                165                 170                 175

Ile Asp Leu Asn Asn His Val Asn Asn Thr Ile Tyr Leu Arg Trp Ile
            180                 185                 190

Thr Asn Ser Leu Gly Met Glu Trp Phe Glu Lys Tyr Thr Pro Thr Ser
        195                 200                 205

Phe Thr Val Ala Tyr Glu Lys Glu Met Tyr Leu His Gln Glu Gly Ala
    210                 215                 220

Val His Ser Asp Ile Ser Thr Val Ser Glu Asp Leu Lys Ser Gly Asp
225                 230                 235                 240

Thr Phe Asn Ser Gln His Val Ile Asp Ser Glu Asp Lys Ala His Cys
                245                 250                 255

Leu Thr Glu Ile Thr Trp Gln Val Lys
            260                 265

<210> SEQ ID NO 63
<211> LENGTH: 250
<212> TYPE: PRT
<213> ORGANISM: Clostridiales bacterium

<400> SEQUENCE: 63

Met Pro Gly Phe Val Tyr Glu Lys Glu Tyr Glu Ile His Tyr Tyr Glu
1               5                   10                  15

Ile Asp Tyr Lys Arg Arg Ala Leu Ile Thr Ser Leu Val Asp Phe Phe
            20                  25                  30

Gly Asp Ile Ala Thr Val Gln Ser Glu Gln Leu Gly Ile Gly Ile Glu
        35                  40                  45

Tyr Leu Lys Glu Asn Asn Leu Ala Trp Val Leu Tyr Lys Trp Asn Ile
    50                  55                  60

Asp Val Val Lys Tyr Pro Leu His Gly Glu Lys Ile Ile Val Lys Thr

```
                65                  70                  75                  80
Cys Pro Tyr Ser Met Lys Lys Phe Tyr Ala Tyr Arg Thr Phe Glu Val
                        85                  90                  95
Leu Asn Ser Glu Gly Glu Val Ile Ala Thr Ala Asp Ser Ile Trp Phe
                100                 105                 110
Leu Ile Asn Ile Glu Arg Arg Pro Val Arg Ile Asn Glu Asp Val
            115                 120                 125
Tyr Arg Leu Tyr Gly Leu Asp Tyr Asn Asp Gln Asn Thr Leu Glu Ile
            130                 135                 140
Glu Asp Ile Lys Lys Pro Asp Lys Ala Asp Leu Glu Lys Ile Phe Asn
145                 150                 155                 160
Val Arg Tyr Ser Asp Ile Asp Thr Asn Gln His Val Asn Asn Ala Lys
                165                 170                 175
Tyr Ile Ala Trp Ala Ile Glu Thr Val Pro Met Glu Val Val Leu Asn
                180                 185                 190
Tyr Thr Ile Lys Asn Leu Lys Val Ile Tyr Glu Lys Glu Thr Thr Tyr
                195                 200                 205
Gly Glu Ile Val Lys Val Ile Thr Glu Ile Ile His Asn Asp Asn Thr
            210                 215                 220
Val Ile Cys Ile His Lys Ile Ile Asp Lys Glu Glu Lys Glu Leu Thr
225                 230                 235                 240
Leu Ile Lys Thr Thr Trp Glu Lys Asn Phe
                245                 250

<210> SEQ ID NO 64
<211> LENGTH: 250
<212> TYPE: PRT
<213> ORGANISM: Clostridium novyi

<400> SEQUENCE: 64

Met Ser Gly Ile Ile Thr Glu Lys Gln Tyr Glu Ile His Tyr Tyr Glu
1               5                   10                  15
Ala His Leu Lys Gln Gln Ala Thr Ile Thr Asn Ile Ile Asp Phe Phe
                20                  25                  30
Thr Asp Val Ser Thr Phe Gln Ser Glu Glu Leu Gly Val Gly Ile Asn
            35                  40                  45
Tyr Met Met Glu Asn Asn Met Ala Trp Ile Leu Tyr Lys Trp Asp Ile
        50                  55                  60
Asn Val Glu Arg Tyr Pro Arg Tyr Arg Glu Lys Ile Leu Ala Val Thr
65                  70                  75                  80
Glu Pro Tyr Ser Ile Lys Lys Phe Tyr Ala Tyr Arg Lys Phe Tyr Ile
                85                  90                  95
Leu Asp Glu Asn Arg Asn Ile Ile Ala Ser Ala Lys Ser Thr Trp Leu
                100                 105                 110
Leu Ile Asp Thr Lys Lys Arg Arg Pro Leu Arg Ile Ser Lys Glu Met
            115                 120                 125
Val Lys Ala Phe Gly Leu Glu Asn Lys Glu Glu Thr Leu Glu Ile Glu
            130                 135                 140
Asn Val His Lys Leu Pro Glu Glu Asn Thr Glu Ile Asn Phe Lys Val
145                 150                 155                 160
Arg Tyr Ser Asp Ile Asp Thr Asn Gly His Val Asn Asn Glu Lys Tyr
                165                 170                 175
Val Ala Trp Met Ile Glu Ser Ile Pro Arg Asp Ile Ile Leu Asn Tyr
            180                 185                 190
```

```
Thr Leu Lys Asn Thr Lys Ile Thr Tyr Lys Lys Glu Thr Met Tyr Gly
            195                 200                 205

Glu Ser Ile Lys Val Ile Thr Gly Lys Ile Lys Glu Asp Glu Asp Lys
        210                 215                 220

Val Lys Phe Val His Asn Ile Leu Arg Glu Asn Gly Glu Leu Leu Thr
225                 230                 235                 240

Glu Gly Glu Thr Leu Trp Glu Lys Asn Lys
                245                 250

<210> SEQ ID NO 65
<211> LENGTH: 136
<212> TYPE: PRT
<213> ORGANISM: Haemophilus influenzae

<400> SEQUENCE: 65

Met Leu Asp Asn Gly Phe Ser Phe Pro Val Arg Val Tyr Tyr Glu Asp
1               5                   10                  15

Thr Asp Ala Gly Gly Val Val Tyr His Ala Arg Tyr Leu His Phe Phe
            20                  25                  30

Glu Arg Ala Arg Thr Glu Tyr Leu Arg Thr Leu Asn Phe Thr Gln Gln
        35                  40                  45

Thr Leu Leu Glu Glu Gln Gln Leu Ala Phe Val Val Lys Thr Leu Ala
    50                  55                  60

Ile Asp Tyr Cys Val Ala Ala Lys Leu Asp Asp Leu Leu Met Val Glu
65                  70                  75                  80

Thr Glu Val Ser Glu Val Lys Gly Ala Thr Ile Leu Phe Glu Gln Arg
                85                  90                  95

Leu Met Arg Asn Thr Leu Met Leu Ser Lys Ala Thr Val Lys Val Ala
            100                 105                 110

Cys Val Asp Leu Gly Lys Met Lys Pro Val Ala Phe Pro Lys Glu Val
        115                 120                 125

Lys Ala Ala Phe His His Leu Lys
    130                 135

<210> SEQ ID NO 66
<211> LENGTH: 245
<212> TYPE: PRT
<213> ORGANISM: Streptococcus infantis

<400> SEQUENCE: 66

Met Gly Leu Thr Tyr Gln Met Lys Met Lys Ile Pro Phe Asp Met Ala
1               5                   10                  15

Asp Met Asn Gly His Ile Lys Leu Pro Asp Val Ile Leu Leu Ser Leu
            20                  25                  30

Gln Val Ser Gly Met Gln Ser Ile Asn Leu Gly Val Ser Asp Lys Asp
        35                  40                  45

Val Leu Glu Gln Tyr Asn Leu Val Trp Ile Ile Thr Asp Tyr Asp Ile
    50                  55                  60

Asp Val Val Arg Leu Pro Gln Phe Asp Glu Glu Ile Thr Ile Glu Thr
65                  70                  75                  80

Glu Ala Leu Thr Tyr Asn Arg Leu Phe Cys Tyr Arg Arg Phe Thr Ile
                85                  90                  95

Tyr Asp Glu Asp Gly Gln Glu Ile Ile Arg Met Val Ala Thr Phe Val
            100                 105                 110

Leu Met Asp Arg Asp Ser Arg Lys Val His Pro Val Val Pro Glu Ile
        115                 120                 125
```

```
Val Ala Pro Tyr Gln Ser Glu Phe Ser Lys Lys Leu Val Arg Gly Pro
    130                 135                 140

Lys Tyr Thr Glu Leu Glu Asn Ala Ile Asn Lys Asp Tyr His Val Arg
145                 150                 155                 160

Phe Tyr Asp Leu Asp Met Asn Gly His Val Asn Asn Ser Lys Tyr Leu
                165                 170                 175

Asp Trp Ile Phe Glu Val Met Gly Ala Asp Phe Leu Thr Asn His Ile
                180                 185                 190

Pro Lys Lys Ile Asn Leu Lys Tyr Val Lys Glu Val Arg Pro Gly Gly
                195                 200                 205

Met Ile Thr Ser Ser Tyr Glu Leu Asn Gln Leu Glu Ser Asn His Gln
    210                 215                 220

Val Thr Ser Asp Gly Asp Ile Asn Ala Gln Ala Lys Ile Ile Trp Gln
225                 230                 235                 240

Glu Ile Asn Thr Asp
                245

<210> SEQ ID NO 67
<211> LENGTH: 245
<212> TYPE: PRT
<213> ORGANISM: Mesotoga prima

<400> SEQUENCE: 67

Met Lys Pro Val Ile Thr Lys Glu Val Tyr Lys Val Arg Tyr Tyr Glu
1               5                   10                  15

Leu Asp Cys His Trp Lys Ala Ser Val Ser Thr Leu Met Asp Tyr Phe
                20                  25                  30

Asn Asp Ile Val Thr Leu Gln Thr Val Glu Ile Gly His Gly Val Asp
                35                  40                  45

Ile Met Ser Lys Gly Glu Tyr Ala Trp Leu Leu Leu Arg Trp Asp Val
    50                  55                  60

Asn Val Asn Arg Tyr Pro Asp Tyr Met Glu Asn Val Val Val Gln Thr
65                  70                  75                  80

Ile Pro Tyr Ser Met Asp Arg Phe Tyr Ala Tyr Arg Arg Phe Glu Ile
                85                  90                  95

Phe Asp Arg Ser Asp Asn Leu Ile Val Asp Ala Asn Ser Gln Trp Ile
                100                 105                 110

Leu Ile Asp Gln Arg Lys Arg Arg Pro Ile Arg Ile Gly Asp Gln Phe
                115                 120                 125

Tyr Ala Leu Tyr Gly Ile Asp Ser Asp Phe His Gln Pro Leu Ser Phe
    130                 135                 140

Pro Gln Val Asn Asp Asn Asp Ser Tyr Gly Glu Glu Ile Thr Phe Arg
145                 150                 155                 160

Val Arg Ser Ser Asp Leu Asp Thr Asn Gly His Ser Asn Asn Val Ser
                165                 170                 175

Tyr Val Arg Trp Ile Met Glu Thr Val Pro Asp Glu Phe Ala Lys Arg
                180                 185                 190

Ser Leu Arg Arg Leu Thr Ile Glu Tyr Lys Arg Glu Ser Arg Glu Gly
                195                 200                 205

Asp Glu Ile Ser Val Glu Ser Val Phe Glu Asn Gly Asp Glu Phe Ala
    210                 215                 220

Glu Gly Lys His Lys Ile Ile Ser Ser Gly Arg Val Leu Ser Leu Ala
225                 230                 235                 240

Arg Thr Glu Trp Lys
                245
```

<210> SEQ ID NO 68
<211> LENGTH: 244
<212> TYPE: PRT
<213> ORGANISM: Bacteroides sp.

<400> SEQUENCE: 68

Met Gly Lys Tyr Cys Glu Lys Asp Ile Ile Thr Cys Tyr Arg Ser Asp
1               5                   10                  15

Ser His His Lys Met Arg Ser Glu Ala Phe Leu Asp Phe Ala Gln Gln
                20                  25                  30

Leu Ala Val Lys Gly Ala Gln Leu Leu Ser Phe Asn Asp Thr Ala Leu
            35                  40                  45

Ser Gln Leu Gly Cys Ile Trp Val Leu Ala Arg Met His Val Arg Phe
        50                  55                  60

Glu Arg Asp Val Ala Phe Asp Glu Lys Val Asp Leu Ser Thr Trp His
65                  70                  75                  80

Lys Gly Gln Ser Gly Leu Tyr Phe Leu Arg Asp Tyr Gln Leu Cys Asp
                85                  90                  95

Arg His Gly Ala Ala Val Asn Ala Thr Ser Ser Trp Ile Val Met Asn
            100                 105                 110

Ala Glu Thr Arg His Ile Ser Arg Asp Glu Lys Val Leu Glu Leu Leu
        115                 120                 125

Ser Val Gly Pro Gln Ser Glu Asp His Ala Ile Lys Glu Ala Ser Pro
    130                 135                 140

Lys Ile Thr Val Pro Lys Asp Cys Thr Leu Glu Val Ile Gly Glu His
145                 150                 155                 160

Thr Val Arg Tyr Ser Asp Val Asp Tyr Asn Asn His Ala Asn Asn Val
                165                 170                 175

Lys Tyr Thr Val Trp Ala Leu Asp His Leu Pro Asp Asn Ile Ala Met
            180                 185                 190

Thr Arg Arg Leu Lys Glu Leu Ser Ile Asn Phe Asn Lys Glu Thr Leu
        195                 200                 205

Leu Gly Glu Thr Val Thr Leu Tyr His Cys Ile Thr Pro Glu Gly Glu
    210                 215                 220

His Ile Val Glu Gly Arg Ser Gly Asp Ile Gln Val Phe Ile Glu Lys
225                 230                 235                 240

Leu Leu Phe Glu

<210> SEQ ID NO 69
<211> LENGTH: 246
<212> TYPE: PRT
<213> ORGANISM: Eubacterium limosum

<400> SEQUENCE: 69

Met Gly Ile Ile Tyr Glu Lys Lys Gln Lys Ile Asn Gly Tyr Glu Cys
1               5                   10                  15

Thr Tyr Asn Tyr Gln Leu Gln Pro Thr Ala Ala Leu Asn Tyr Phe Gln
                20                  25                  30

Gln Thr Ser Gln Glu Gln Ser Glu Gln Leu Gly Val Gly Pro Glu Val
            35                  40                  45

Leu Asp Glu Met Gly Leu Ala Trp Phe Leu Val Lys Tyr Lys Leu Gln
        50                  55                  60

Phe His Glu Tyr Pro Lys Phe Asn Asp Glu Val Met Val Glu Thr Glu
65                  70                  75                  80

```
Ala Ile Ala Phe Asp Lys Phe Ala Ala His Arg Arg Phe Ala Ile Lys
                85                  90                  95

Ser Leu Asp Gly Arg Met Met Val Glu Gly Asp Thr Glu Trp Met Leu
            100                 105                 110

Gln Asn Arg Lys Glu Asn Arg Leu Glu Arg Leu Ser Asn Val Pro Glu
        115                 120                 125

Leu Asp Val Tyr Glu Ser Gly His Glu Asn His Phe Lys Leu Lys Arg
    130                 135                 140

Val Ala Lys Val Glu Glu Trp Thr Glu Ser Lys Asn Phe Gln Val Arg
145                 150                 155                 160

Tyr Leu Asp Ile Asp Phe Asn Ser His Val Asn His Val Lys Tyr Leu
                165                 170                 175

Ala Trp Ala Leu Glu Thr Leu Pro Leu Glu Lys Val Lys Ala Gly Glu
            180                 185                 190

Ile Glu Thr Ala Lys Ile Ile Tyr Lys Asn Gln Gly Phe Tyr Gly Asp
        195                 200                 205

Met Ile Thr Val Lys Ser Ala Glu Ile Asp Glu Asn Thr Tyr Arg Met
    210                 215                 220

Asp Ile Glu Asn Gln Glu Gly Ile Leu Leu Cys Gln Ile Glu Met Thr
225                 230                 235                 240

Met Arg Ile Arg Glu Asp
                245

<210> SEQ ID NO 70
<211> LENGTH: 249
<212> TYPE: PRT
<213> ORGANISM: Tepidanaerobacter acetatoxydans

<400> SEQUENCE: 70

Met Ser Gly Ser Asn Ile Leu Glu Lys Glu Tyr Arg Ile His Tyr Tyr
1               5                   10                  15

Glu Val Asn Ala Lys Gly Arg Val Leu Ile Ala Ser Leu Met Arg Tyr
            20                  25                  30

Phe Asp Asp Ile Ala Thr Gln Gln Ser Arg Glu Leu Gly Val Gly Ile
        35                  40                  45

Asn Tyr Leu Lys Glu His Asn Val Ala Trp Met Leu Tyr Gln Trp Asp
    50                  55                  60

Ile Lys Ile Asn Lys Tyr Pro Arg Tyr Gly Glu Thr Ile Lys Val Arg
65                  70                  75                  80

Thr Ala Pro Tyr Ser Phe Arg Lys Phe Tyr Ala Tyr Arg Trp Phe Asp
                85                  90                  95

Val Leu Asn Lys Asp Gly Glu Thr Leu Val Asn Ala Asn Ser Val Trp
            100                 105                 110

Leu Phe Val Asp Thr Asp Lys Arg Arg Pro Leu Lys Ile Pro Asp Val
        115                 120                 125

Met Tyr Glu Ala Tyr Gln Val Thr Ser Asp Glu Pro Leu Glu Ile Gly
    130                 135                 140

Glu Ile Thr Glu Leu Ser Ser Cys Asp Ile Glu Lys Lys Phe Gln Val
145                 150                 155                 160

Arg Tyr Ser Asp Ile Asp Thr Asn Ser His Val Asn Asn Val Val Tyr
                165                 170                 175

Val Thr Trp Ala Leu Glu Ala Leu Pro Tyr Asp Ile Ile Ser Asn Tyr
            180                 185                 190

Glu Leu Arg Asn Leu Lys Val Thr Tyr Lys Gln Glu Thr Thr Tyr Gly
        195                 200                 205
```

```
Met Ile Ile Arg Ser Gln Ala Gln Val Ile Lys Ser Asp Asp Glu Val
    210                 215                 220

Ile Thr Arg His Ser Ile Leu Ser Glu Glu Gly Lys Lys Leu Cys Leu
225                 230                 235                 240

Leu Glu Gly Arg Trp Ile Lys Asn Ser
                245

<210> SEQ ID NO 71
<211> LENGTH: 252
<212> TYPE: PRT
<213> ORGANISM: Thermincola potens

<400> SEQUENCE: 71

Met Glu Pro Tyr Gln Thr Ser Ile Pro Val His Tyr Tyr Glu Ile Asn
1               5                   10                  15

Asn His Arg Gln Ala Ser Pro Val Ala Ile Leu Asn Tyr Leu Glu Glu
            20                  25                  30

Ala Ala Ile Arg His Ser Glu Ser Val Gly Trp Gly Ile Glu Lys Leu
        35                  40                  45

Leu Ala Asn Ser Arg Gly Trp Leu Leu Thr Arg Trp Ser Leu His Met
    50                  55                  60

Gln Lys Tyr Pro Gln Trp Gly Glu Thr Val Asn Ile Glu Thr Trp Pro
65                  70                  75                  80

Tyr Lys Phe Glu Arg Phe Tyr Ala Thr Arg Glu Phe Arg Ile Ser Asp
                85                  90                  95

Arg Glu Gly Arg Val Leu Gly Ala Ala Thr Thr Leu Trp Val Phe Phe
            100                 105                 110

Asp Leu Arg Arg Lys Arg Pro Val Arg Ile Pro Pro Asp Ile Tyr Asp
        115                 120                 125

Ala Tyr Gly Thr Gly Ala Glu Arg Met Val Ala Asp Glu Phe Ala Asp
    130                 135                 140

Leu Pro Val Val Asp Glu Pro Glu Ile Lys Leu Glu Phe Arg Val Arg
145                 150                 155                 160

Leu Ser Asp Ile Asp Thr Asn Asp His Val Asn Asn Thr Lys Tyr Val
                165                 170                 175

Glu Trp Leu Leu Glu Thr Val Pro Leu Ser Val His Asn Gly Phe Leu
            180                 185                 190

Leu Ser Ser Val Glu Ile Ala Tyr Lys Lys Glu Thr Ser Tyr Gly Ser
        195                 200                 205

Thr Val Leu Cys Gly Ile Lys Glu Thr Glu Ala Gly Glu Arg Gln Thr
    210                 215                 220

Thr Phe Leu His Ile Ile Leu Asp Lys Asp Ser Gly Thr Glu Leu Ala
225                 230                 235                 240

Arg Ala Arg Thr Val Trp Gln Lys Arg Ser Lys Ile
                245                 250

<210> SEQ ID NO 72
<211> LENGTH: 252
<212> TYPE: PRT
<213> ORGANISM: Clostridium perfringens

<400> SEQUENCE: 72

Met Ser Glu Asn Lys Phe Met Lys Lys Tyr Asp Val Leu Tyr Tyr Asp
1               5                   10                  15

Ser Asp Val Asn Glu Asn Ile Arg Met Val Pro Leu Met Lys Ile Phe
            20                  25                  30
```

Gly Asp Val Ser Ala Ile His Glu Glu Leu Ala Tyr Glu Gly Ile
         35                  40                  45

Lys Tyr Leu Lys Asp His Glu Leu Ser Trp Ile Ile Tyr Ser Tyr Ser
 50                  55                  60

Ile Asp Ile Lys Lys Pro Ile Pro Tyr Lys Ser Ser Ile Asn Val Glu
 65                  70                  75                  80

Thr Tyr Leu Glu Gly Ile Lys Lys Phe Tyr Ala Cys Arg Val Tyr Lys
                 85                  90                  95

Val Tyr Asn Glu Lys Asn Glu Leu Val Ala Glu Gly Lys Ile Ile Phe
             100                 105                 110

Leu Leu Ile Asp Leu Glu Lys Arg Arg Ala Val Arg Ile Pro Lys Glu
         115                 120                 125

Tyr Cys Glu Leu Ile Asn Met Ser Asp Thr Gly Glu Val Glu Leu Lys
     130                 135                 140

Ser Thr Lys Val Glu Lys Leu Ile Arg Glu Asp Leu Glu Ser Asn Ile
145                 150                 155                 160

Ser Val Arg Arg Ser Asp Ile Asp Phe Asn Lys His Val Asn Asn Thr
                165                 170                 175

Lys Tyr Leu Glu Trp Thr Met Glu Ala Thr Pro Glu Cys Ile Leu Asp
            180                 185                 190

Glu Tyr Ser Leu Ile Ser Ala Lys Ile Lys Tyr Glu Lys Glu Val Arg
        195                 200                 205

Leu Gly Asp Asp Val Asn Ile Ile Cys Gln Trp Asp Glu Ile Glu Glu
    210                 215                 220

Gly Tyr Lys Cys Leu Tyr Lys Ile Val Asn Asn Arg Leu Gly Glu Val
225                 230                 235                 240

Ser Ala Ser Ile Glu Thr Ile Trp Lys Lys Glu Phe
                245                 250

<210> SEQ ID NO 73
<211> LENGTH: 141
<212> TYPE: PRT
<213> ORGANISM: Solanum lycopersicum

<400> SEQUENCE: 73

Met Ala Glu Phe His Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
                20                  25                  30

His Gly Arg His Glu Leu Leu Glu Arg Ile Gly Ile Ser Ala Asp Glu
         35                  40                  45

Val Ala Arg Ser Gly Asp Ala Leu Ala Leu Thr Glu Leu Ser Leu Lys
 50                  55                  60

Tyr Leu Ala Pro Leu Arg Ser Gly Asp Arg Phe Val Val Lys Ala Arg
 65                  70                  75                  80

Ile Ser Asp Ser Ser Ala Ala Arg Leu Phe Phe Glu His Phe Ile Phe
                 85                  90                  95

Lys Leu Pro Asp Gln Glu Pro Ile Leu Glu Ala Arg Gly Ile Ala Val
             100                 105                 110

Trp Leu Asn Lys Ser Tyr Arg Pro Val Arg Ile Pro Ala Glu Phe Arg
         115                 120                 125

Ser Lys Phe Val Gln Phe Leu Arg Gln Glu Ala Ser Asn
     130                 135                 140

<210> SEQ ID NO 74
<211> LENGTH: 247
<212> TYPE: PRT
<213> ORGANISM: Roseburia intestinalis

<400> SEQUENCE: 74

Met Tyr Ser Phe Ser Asn Arg Val Arg Tyr Ser Glu Val Asn Ser Glu
1               5                   10                  15

Lys Glu Leu Thr Leu Pro Ser Leu Leu Asp Tyr Leu Gln Asp Cys Cys
                20                  25                  30

Thr Phe Glu Ser Glu Asp Phe Gly Val Gly Val Asp Tyr Leu Ala Lys
            35                  40                  45

Glu Gln Val Ala Trp Ile Leu Ser Ser Trp Glu Ile Lys Val Tyr Arg
    50                  55                  60

Tyr Pro Gln Met Gly Gln His Ile Lys Val Ser Thr Trp Pro Tyr Ala
65                  70                  75                  80

Phe Arg Gly Phe Tyr Gly Tyr Arg Asn Phe Cys Ile Glu Gly Glu Asp
                85                  90                  95

Gly Glu Ile Phe Ala Glu Ala Asn Ser Val Trp Val Phe Met Asp Thr
            100                 105                 110

Glu Lys Met Arg Pro Ala Arg Val Ser Glu Arg Met Gln Glu Val Tyr
    115                 120                 125

Ile Pro Glu Ile Arg Asp Glu Ile Pro Gly Glu Trp Ala Asp Arg Lys
130                 135                 140

Ile Ser Leu Pro Asp Glu Ala Val Gln Lys Ser Val Glu Lys Glu Pro
145                 150                 155                 160

Val Arg Val Ser Arg Phe Tyr Ile Asp Thr Asn His His Met Asn Asn
                165                 170                 175

Gly Lys Tyr Ile Leu Val Ala Glu Glu Tyr Leu Pro Gly Gln Val Phe
            180                 185                 190

Val Cys Gly Leu Arg Ala Glu Tyr Arg Lys Ala Ala Met Leu Gly Asp
    195                 200                 205

Met Leu Tyr Pro Val Val Thr Ile Glu Glu Lys Gln Ile Thr Val Thr
210                 215                 220

Leu Ala Asp Glu Lys Gly Ala Ser Tyr Ala Ile Ile Cys Phe Gln Ile
225                 230                 235                 240

Gln Lys Lys Glu Arg Gln Ser
                245

<210> SEQ ID NO 75
<211> LENGTH: 241
<212> TYPE: PRT
<213> ORGANISM: Coraliomargarita sp.

<400> SEQUENCE: 75

Met Leu Asp Asn Ile His Arg Thr Ser Tyr Lys Val Arg Ile Ser Asp
1               5                   10                  15

Ala Asp Gln Asn Gly Thr Leu Lys Cys Asn Ala Leu Leu Gln Met Leu
                20                  25                  30

Gln Glu Ala Ala Thr Glu His Ala Thr Ile Leu Gly Val Asp Phe Lys
            35                  40                  45

Ala Leu Lys Pro Leu Asn Leu Gly Trp Ala Val Ser Lys Phe Val Ile
    50                  55                  60

Asp Val Lys Arg Leu Pro Gln Trp Gly Glu Arg Ile Asn Val Thr Thr
65                  70                  75                  80

Trp Ala Ser Asp Lys Glu Arg Val Ala Thr Tyr Arg Glu Phe Val Val

```
                 85                  90                  95
Thr Asp Ser Ser Gly Thr Glu Leu Val Ser Ala Arg Ser Gln Trp Val
            100                 105                 110

Leu Phe Asp Thr Arg Glu Arg Lys Ile Ala Lys Met Glu Lys Ile Gln
        115                 120                 125

Asp Trp Ser Arg Leu Glu Asn Lys Tyr Ala Asn Ala Ser Asn Phe Glu
    130                 135                 140

Pro Leu Lys Gln Pro Lys Thr Thr Ser Ser Ala Ile Cys Ala Ala
145                 150                 155                 160

Arg Asn Asp Asp Ile Asp Leu Asn Met His Val Asn Asn Ala Val Tyr
                165                 170                 175

Leu Ile Trp Ala Ala Glu Ser Leu Pro Gln Asn Phe Thr Ser Val Pro
            180                 185                 190

Lys Gln Ile Arg Ile Asn Phe Leu Glu Glu Val Met Pro His Thr Asn
        195                 200                 205

Val Glu Val Leu Cys His Ile Asp Gly Lys Asn Ser Tyr His Thr Leu
    210                 215                 220

Ile Asn Met Asn Thr Asn Arg Glu Cys Ala Arg Ile Asn Ile Phe Trp
225                 230                 235                 240

Gln

<210> SEQ ID NO 76
<211> LENGTH: 247
<212> TYPE: PRT
<213> ORGANISM: Weissella confusa

<400> SEQUENCE: 76

Met Ala Glu Val Tyr Ser Met Gln His Glu Val Leu Tyr Tyr Glu Ala
1               5                   10                  15

Asp Val Thr Gly Lys Leu Ser Leu Pro Met Ile Phe Asn Leu Ala Val
            20                  25                  30

Leu Ser Ser Thr Gln Gln Ser Val Asp Leu Gly Val Gly Pro Asp Tyr
        35                  40                  45

Ala His Ala Asn Gly Val Gly Trp Ile Ile Leu Gln His Val Val Asp
    50                  55                  60

Ile Lys Arg Arg Pro Lys Ile Gly Glu Lys Val Ala Leu Glu Thr Leu
65                  70                  75                  80

Ala Lys Glu Phe Asn Pro Phe Phe Ala Lys Arg Leu Tyr Arg Ile Val
                85                  90                  95

Asp Glu Ala Gly Asn Glu Leu Val Ser Ile Asp Ala Leu Tyr Ala Met
            100                 105                 110

Ile Asp Met Glu Lys Arg Lys Met Ala Arg Ile Pro Gln Glu Met Val
        115                 120                 125

Asp Ala Tyr Ala Pro Glu Arg Val Lys Lys Ile Pro Arg Gln Pro Glu
    130                 135                 140

Pro Asp His Met Ile Gly Asp Ile Pro Val Asp Val Asp Gln Gln Tyr
145                 150                 155                 160

Ala Val Arg Tyr Leu Asp Ile Asp Ser Asn Arg His Val Asn Asn Ser
                165                 170                 175

Lys Tyr Phe Asp Trp Met Gln Asp Val Leu Gly Pro Ala Phe Leu Glu
            180                 185                 190

Ala His Glu Pro Thr His Leu Asn Ile Lys Tyr Glu His Glu Ile Leu
        195                 200                 205

Leu Gly Asp Thr Val Arg Ser Glu Ala Gln Ile Met Glu Asp Lys Thr
```

```
                210                 215                 220
Ile His Arg Ile Trp Ser Gly Asp Thr Leu Ser Ala Glu Ala His Ile
225                 230                 235                 240

Asp Trp Thr Lys Ser Glu Asn
                245

<210> SEQ ID NO 77
<211> LENGTH: 257
<212> TYPE: PRT
<213> ORGANISM: Peptoanaerobacter stomatis

<400> SEQUENCE: 77

Met Leu Lys Thr Tyr Ser Glu Asn Tyr Ile Val Asp Phe Arg Asp Val
1               5                   10                  15

Asp Arg Tyr Tyr Asp Ile Lys Ile Pro Gln Leu Leu Glu Ile Met Gly
                20                  25                  30

Thr Val Ser Thr Lys His Thr Asn Glu Leu Gly Phe Asp Pro Phe Tyr
            35                  40                  45

Leu Ile Arg Gln Gly Leu Ala Trp Ile Leu Tyr Glu Trp Lys Val Asp
        50                  55                  60

Ile Glu Lys Thr Lys Leu Tyr Ala Gln Thr Ile Lys Ile Glu Thr Phe
65                  70                  75                  80

Ala Val Asp Arg Lys Gly Met Tyr Phe Ile Arg Tyr Phe Gly Ile Tyr
                85                  90                  95

Asp Lys Asp Asp Lys Leu Ile Gly Arg Ala Ala Ala Lys Trp Val Val
                100                 105                 110

Ile Asn Thr Thr Gln Arg Lys Ile Val Lys Leu Pro Gln Glu Ile Leu
            115                 120                 125

Glu Ala Ala Lys Ile Asn Ile Glu Glu Leu Asn Glu Asn Gln Lys Tyr
        130                 135                 140

Ile Tyr Asp Met Pro Glu Lys Pro Leu Arg Leu Glu Lys Arg Gln Asp
145                 150                 155                 160

Asp Phe Ile Gln Thr Ile Phe Pro Ile Arg Phe Tyr Asp Ile Asp Ser
                165                 170                 175

Asn His His Ala Asn Asn Val Lys Tyr Val Asp Trp Ala Ile Glu Ser
                180                 185                 190

Leu His Gln His Glu Asp Phe Leu Lys Lys Tyr Lys Val Ser His Leu
            195                 200                 205

Ser Ile Thr Tyr Lys Lys Glu Thr Gly Glu Asp Gly Asp Ile Ile Cys
        210                 215                 220

Lys Thr Tyr Ile Asp Asn Leu Arg Thr Tyr His Glu Ile Tyr Ser Ser
225                 230                 235                 240

Asp Asn Ser Leu Leu Thr Val Leu Glu Phe Lys Trp Ala Glu Arg Pro
                245                 250                 255

Gln

<210> SEQ ID NO 78
<211> LENGTH: 249
<212> TYPE: PRT
<213> ORGANISM: Clostridium intestinale

<400> SEQUENCE: 78

Met Gly Arg Val Phe Glu Lys Gln Tyr Glu Ile Asn Tyr Tyr Asn Leu
1               5                   10                  15

Asp Asn Ser Leu Lys Cys Lys Ile Thr Ser Ile Leu Asp Phe Phe Cys
                20                  25                  30
```

```
Asp Ile Gly Met Gln Ser Glu Glu Leu Gly Val Gly Val Asp Ser
            35                  40                  45

Leu Thr Gly Arg Asn Leu Thr Trp Val Phe Tyr Lys Tyr Asn Ile Asn
 50                  55                  60

Met Lys Arg Tyr Pro Arg Tyr Gly Glu Lys Ile Arg Ile Ile Thr Asp
 65                  70                  75                  80

Pro Ile Gly Phe Lys Lys Phe Tyr Ala Phe Arg Asp Tyr Thr Ile Leu
                 85                  90                  95

Asp Glu Gly Asn Lys Val Ile Gly Glu Gly Lys Ser Leu Phe Phe Leu
                100                 105                 110

Ile Asp Leu Ala Lys Arg Arg Pro Thr Arg Ile Pro Arg Asp Leu Tyr
            115                 120                 125

Glu Ala Tyr Gly Cys Ala Asp Glu Ile Lys Asp Asn Pro Thr Ile Val
130                 135                 140

Asp Pro Glu Lys Leu Glu Glu Gln Tyr Phe Arg Glu Phe Tyr Val
145                 150                 155                 160

Arg Arg Ser Asp Ile Asp Ser Asn Lys His Val Asn Asn Thr Lys Tyr
                165                 170                 175

Val Glu Trp Ala Leu Glu Val Ile Pro Asp Glu Ile Val Asp Glu Tyr
            180                 185                 190

Glu Leu Asp Asn Ile Ser Ile Val Tyr Ser Lys Glu Ile Thr Tyr Gly
            195                 200                 205

His Met Val Lys Thr Lys Cys Ser Val His Asn Glu Asp Asn Gly Ile
210                 215                 220

Ile Lys Ile Arg His Leu Ile Gln Asp Asp Val Gly Arg Asp Ile Thr
225                 230                 235                 240

Leu Ile Asn Thr Phe Trp Arg Lys Asn
                245

<210> SEQ ID NO 79
<211> LENGTH: 255
<212> TYPE: PRT
<213> ORGANISM: Desulfotomaculum nigrificans

<400> SEQUENCE: 79

Met Leu Asn Arg Lys Tyr Arg Lys Glu Phe Glu Val His Tyr Tyr Glu
 1               5                  10                  15

Ile Asn Gln Phe Glu Glu Ala Thr Pro Val Ala Val Leu Asn Tyr Leu
                20                  25                  30

Glu Glu Thr Ala Val Ala His Ser Glu Ser Val Gly Val Gly Ile Ser
            35                  40                  45

Lys Leu Lys Ser Gln Gly Val Ala Trp Met Leu Asn Arg Trp His Ile
 50                  55                  60

Lys Met Glu Lys Tyr Pro Leu Trp Asn Glu Lys Ile Val Ile Glu Thr
 65                  70                  75                  80

Trp Pro Ser Arg Phe Glu Arg Pro Tyr Ala Thr Arg Glu Phe Asn Ile
                 85                  90                  95

Arg Asp Ser Tyr Asp His Ile Ile Gly Arg Ala Ser Ser Leu Trp Val
                100                 105                 110

Phe Leu Asn Ile Glu Lys Lys Arg Pro Leu Arg Ile Pro Asp Lys Ile
            115                 120                 125

Lys Asp Ala Tyr Gly Thr Asp Pro His Arg Ala Ile Asp Glu Pro Phe
130                 135                 140

Gly Glu Leu Tyr Asn Leu Asp Asp Ser Val Glu Lys Lys Glu Phe Arg
```

```
            145                 150                 155                 160
Val Arg Arg Ser Asp Ile Asp Thr Asn Asn His Val Asn Asn Ala Lys
                165                 170                 175
Tyr Val Asp Trp Val Leu Glu Thr Ile Pro Ala Glu Ile Tyr His Asn
                180                 185                 190
Tyr Thr Leu Ala Ser Leu Glu Val Leu Tyr Arg Lys Glu Val Ala Phe
                195                 200                 205
Gly Ala Thr Ile Trp Ala Gly Cys Gln Gly Ile Gly Lys Gly Leu Asn
                210                 215                 220
Pro Val Tyr Ala His Ser Ile Met Asn Gln Asp Gly Asn Leu Ala Leu
225                 230                 235                 240
Ala Arg Thr Met Trp Gln Arg Arg Asn Lys Asn Leu His Thr Asn
                245                 250                 255

<210> SEQ ID NO 80
<211> LENGTH: 255
<212> TYPE: PRT
<213> ORGANISM: Anaeromyxobacter sp.

<400> SEQUENCE: 80

Met Glu Lys His Arg Gln Thr Phe Gly Val His Thr Tyr Glu Val Asp
1               5                   10                  15
Ala Phe Gly Thr Val Ala Ile Ala Ala Leu Ser Gly Tyr Leu Gln Glu
                20                  25                  30
Val Ala Gly Gln His Ala Ala Ala Leu Gly Val Gly Leu Glu Val Leu
                35                  40                  45
Met Pro Arg Gly Leu Thr Trp Val Leu Ala Arg Gln Arg Ile Glu Asn
                50                  55                  60
Pro Val Pro Ile Val Leu Gly Asp Arg Leu Glu Ile Glu Thr Trp Pro
65                  70                  75                  80
Ala Gly Ile Asp Arg Leu Ala Ala Leu Arg Asp Phe Val Val Arg Arg
                85                  90                  95
Ala Asp Gly Thr Glu Val Ala Arg Ala Thr Thr Gln Trp Phe Val Leu
                100                 105                 110
Asp Leu Glu Ser Arg Arg Pro Val Lys Pro Ala Glu Val Leu Asp Pro
                115                 120                 125
Arg Phe Gln Arg Glu Leu Leu Pro Pro Ile Leu Pro Leu Ala Pro Gly
                130                 135                 140
Lys Leu Pro Glu Leu Arg Ser Trp Glu Phe Gln Lys Arg Phe His Val
145                 150                 155                 160
Arg Tyr Gly Asp Ile Asp Val Asn Met His Val Thr Asn Thr Ser Tyr
                165                 170                 175
Pro Thr Trp Ala Gln Glu Val Val Pro Arg Glu Val Phe Arg Gly Gln
                180                 185                 190
Arg Leu Ala Ser Val Glu Val His Phe Leu Ala Glu Ala His Tyr Gly
                195                 200                 205
Ser Ala Ile Leu Ser Arg Leu Ala Ser Thr Gly Glu Gly Ala Phe Ala
                210                 215                 220
His Ala Ile Val Arg Glu Glu Asp Glu Lys Glu Leu Ala Arg Leu Ala
225                 230                 235                 240
Thr Arg Trp Val Pro Arg Ala Ala Pro Ala Val Pro Gly Ala Arg
                245                 250                 255

<210> SEQ ID NO 81
<211> LENGTH: 266
```

<212> TYPE: PRT
<213> ORGANISM: Treponema caldarium

<400> SEQUENCE: 81

| | | | | | | | | | | | | | | |
|---|---|---|---|---|---|---|---|---|---|---|---|---|---|---|
| Met | Lys | Ala | Leu | Trp | Thr | Glu | Gln | Phe | Thr | Val | Arg | Thr | Trp | Asp | Val |
| 1 | | | | 5 | | | | | 10 | | | | | 15 | |
| Asp | Arg | Asn | Asn | Arg | Leu | Ser | Pro | Ser | Ser | Leu | Phe | Asn | Tyr | Phe | Gln |
| | | | 20 | | | | | 25 | | | | | 30 | | |
| Glu | Val | Ala | Gly | Asn | His | Ala | Thr | Glu | Leu | Gly | Val | Gly | Lys | Asp | Ala |
| | | 35 | | | | | 40 | | | | | 45 | | | |
| Leu | Leu | Arg | Gly | Asn | Gln | Ala | Trp | Ile | Leu | Ser | Arg | Met | Thr | Thr | Leu |
| | 50 | | | | | 55 | | | | | 60 | | | | |
| Leu | Tyr | Arg | Arg | Pro | Gly | Trp | Gly | Glu | Thr | Ile | Thr | Val | Arg | Thr | Trp |
| 65 | | | | | 70 | | | | | 75 | | | | | 80 |
| Pro | Arg | Gly | Thr | Glu | Lys | Leu | Phe | Ala | Ile | Arg | Asp | Tyr | Asp | Ile | Ile |
| | | | | 85 | | | | | 90 | | | | | 95 | |
| Asp | Gly | Phe | Gly | Ser | Thr | Ile | Ala | Gln | Gly | Arg | Ser | Ala | Trp | Leu | Leu |
| | | | 100 | | | | | 105 | | | | | 110 | | |
| Val | Asp | Val | Glu | Lys | Leu | Arg | Pro | Leu | Arg | Pro | Gln | Ser | Leu | Thr | Glu |
| | | 115 | | | | | 120 | | | | | 125 | | | |
| Asn | Leu | Pro | Thr | Asn | Thr | Asp | Met | Pro | Ala | Ile | Pro | Asp | Gly | Ala | Gln |
| | 130 | | | | | 135 | | | | | 140 | | | | |
| Ala | Leu | Thr | Ala | Leu | Pro | Glu | Leu | Gln | Ala | Ala | Gly | Thr | Arg | Thr | Ala |
| 145 | | | | | 150 | | | | | 155 | | | | | 160 |
| Ala | Tyr | Ser | Asp | Ile | Asp | Tyr | Asn | Gly | His | Val | Asn | Asn | Ala | Arg | Tyr |
| | | | | 165 | | | | | 170 | | | | | 175 | |
| Ile | Glu | Trp | Ile | Gln | Asp | Ile | Leu | Asp | Ala | Ser | Ile | Leu | Glu | Gln | Thr |
| | | | 180 | | | | | 185 | | | | | 190 | | |
| Asn | His | Phe | Arg | Ile | Asp | Ile | Asn | Tyr | Leu | Ala | Glu | Ile | Arg | Pro | Gln |
| | | 195 | | | | | 200 | | | | | 205 | | | |
| Glu | Thr | Ile | Ser | Leu | Trp | Lys | Glu | Pro | Leu | Pro | Asn | Gln | Asp | Ala | Gly |
| | 210 | | | | | 215 | | | | | 220 | | | | |
| Thr | Glu | Glu | His | Ala | Gly | Glu | Arg | Pro | Pro | Phe | Thr | Pro | Phe | Glu | Val |
| 225 | | | | | 230 | | | | | 235 | | | | | 240 |
| Thr | Glu | Leu | Trp | Ala | Phe | Glu | Gly | Lys | His | Ile | Asp | Ser | Gly | Gln | Ser |
| | | | | 245 | | | | | 250 | | | | | 255 | |
| Ser | Phe | Arg | Ala | Glu | Leu | Arg | Cys | Gly | Ala | | | | | | |
| | | | 260 | | | | | 265 | | | | | | | |

<210> SEQ ID NO 82
<211> LENGTH: 239
<212> TYPE: PRT
<213> ORGANISM: Lactobacillus iners

<400> SEQUENCE: 82

| | | | | | | | | | | | | | | | |
|---|---|---|---|---|---|---|---|---|---|---|---|---|---|---|---|
| Met | Glu | Lys | Leu | Glu | Lys | Lys | Tyr | Thr | Ile | Lys | Ser | His | Asp | Cys | Asp |
| 1 | | | | 5 | | | | | 10 | | | | | 15 | |
| Glu | Ser | Gly | Arg | Leu | Lys | Met | Ser | Met | Leu | Ile | Ser | Tyr | Met | Met | Asp |
| | | | 20 | | | | | 25 | | | | | 30 | | |
| Thr | Met | Ser | His | Leu | Leu | Asp | Pro | Cys | Ile | Lys | Ile | Glu | His | Ala | Gly |
| | | 35 | | | | | 40 | | | | | 45 | | | |
| Trp | Val | Val | Asn | Tyr | Gln | Phe | Asp | Ile | Asn | Lys | Leu | Pro | Lys | Phe |
| | 50 | | | | | 55 | | | | | 60 | | | | |
| Asp | Asp | Gln | Ile | Thr | Ile | Lys | Ile | Asp | Leu | Cys | Tyr | Tyr | Asn | Arg | Phe |
| 65 | | | | | 70 | | | | | 75 | | | | | 80 |

```
Phe Ala Tyr Ile Lys Phe Leu Val Lys Asp Leu Gln Glu Asn Glu Leu
                85                  90                  95

Val Thr Ile Asn Ser Gln Trp Ile Leu Phe Asp Leu Leu Ser Arg Arg
            100                 105                 110

Met Ile Glu Leu Asp Ser Ala Lys Val Gly Ile Ser Asp Ala Gln Lys
        115                 120                 125

Ile Ala Lys Leu Pro His Phe Asp Arg Ile Lys Val Leu Ala Gly Gln
    130                 135                 140

Glu Asp Phe Gln Arg Ser Tyr Arg Val Met Tyr Ser Asp Leu Asp Val
145                 150                 155                 160

Asn His His Leu Thr Asn Gly Arg Tyr Phe Asp Trp Ile Val Asn Thr
                165                 170                 175

Ile Pro Arg Asp Phe Leu Asn Ser His Ser Met Val Ala Ala Ser Ile
            180                 185                 190

Gln Phe Arg Lys Glu Ile Leu Tyr Asp Gln Ser Ala Val Val Thr Leu
        195                 200                 205

Thr Trp Asn Ala Asp His Ser Val Ser Tyr His Thr Ile Lys Arg Asp
    210                 215                 220

Glu Gln Ile Leu Thr Val Ala Lys Ile Ser Trp Val Ser Asp Lys
225                 230                 235

<210> SEQ ID NO 83
<211> LENGTH: 139
<212> TYPE: PRT
<213> ORGANISM: Petunia integrifolia

<400> SEQUENCE: 83

Met Asn Glu Phe Tyr Glu Val Glu Leu Lys Val Arg Asp Tyr Glu Leu
1               5                   10                  15

Asp Gln Tyr Gly Val Val Asn Asn Ala Ile Tyr Ala Ser Tyr Cys Gln
            20                  25                  30

His Cys Arg His Glu Leu Leu Glu Lys Ile Gly Val Asn Ala Asp Ala
        35                  40                  45

Val Ala Arg Asn Gly Glu Ala Leu Ala Leu Thr Glu Met Thr Leu Lys
    50                  55                  60

Tyr Leu Ala Pro Leu Arg Ser Gly Asp Arg Phe Ile Val Lys Val Arg
65                  70                  75                  80

Ile Ser Asp Ser Ser Ala Ala Arg Leu Phe Phe Glu His Phe Ile Phe
                85                  90                  95

Lys Leu Pro Asp Gln Glu Pro Ile Leu Glu Ala Arg Gly Thr Ala Val
            100                 105                 110

Trp Leu Asn Lys Ser Tyr Arg Pro Val Arg Ile Pro Ser Glu Phe Arg
        115                 120                 125

Ser Lys Phe Val Gln Phe Leu Arg Gln Glu Ala
    130                 135

<210> SEQ ID NO 84
<211> LENGTH: 245
<212> TYPE: PRT
<213> ORGANISM: Clostridium sp.

<400> SEQUENCE: 84

Met Leu Phe Thr Lys Glu Tyr Glu Ile Lys Tyr Tyr Glu Gln Asn Val
1               5                   10                  15

Asn Gly Asp Leu Lys Glu Ser Ala Leu Leu Asn Phe Leu Gln Asp Ile
            20                  25                  30
```

Ala Thr Leu Ser Ala Glu Ser Leu Gly Phe Gly Pro Ser Phe Val Phe
                35                  40                  45

Ala Asn Asn Tyr Ala Trp Val Val Leu Lys Tyr His Ile Glu Leu Phe
 50                  55                  60

Ala Pro Leu Arg Asn Leu Ser Ser Ile Val Ile Lys Thr Glu Pro Arg
 65                  70                  75                  80

Gly Ile Ala Lys Leu Tyr Ala Tyr Arg Asp Phe Glu Leu Tyr Thr Lys
                 85                  90                  95

Asp Gly Gln Cys Ile Gly Lys Ala Val Ser Thr Trp Val Leu Ile Asp
                100                 105                 110

Ile Cys Thr Arg Lys Leu Leu Asn Thr Gln Lys Ile Leu Ala Asp Phe
                115                 120                 125

Met Ala Pro Tyr Gln Lys Arg Glu Thr Asp Leu Val Tyr Glu Lys Ile
        130                 135                 140

Asp Ser Pro Asp Glu Leu Met Tyr Gln Glu Val Phe Asp Val Arg Phe
145                 150                 155                 160

Asp Asp Ile Asp Val Asn Arg His Ala Asn Asn Ser Asn Tyr Ile Val
                165                 170                 175

Trp Ala Leu Glu Thr Leu Pro Val Asp Phe Arg Leu Lys His Ser Pro
                180                 185                 190

Lys Thr Ile Asp Ile Lys Tyr Lys Lys Glu Ile Gly Ile Asn Ser Arg
        195                 200                 205

Val Leu Ser Glu Ala Gln Gln Ile Leu Thr Asp Gly Asn Val Gln Thr
210                 215                 220

Leu His Val Ile Lys Asp Glu Gln Asn Ala Gln Asp Leu Thr Ser Leu
225                 230                 235                 240

Lys Ile Val Trp Gln
                245

<210> SEQ ID NO 85
<211> LENGTH: 253
<212> TYPE: PRT
<213> ORGANISM: Lactobacillus mucosae

<400> SEQUENCE: 85

Met Ala Leu Lys Ala Pro Leu Val Tyr Glu Thr Lys His His Leu Ser
1               5                   10                  15

Tyr Tyr Glu Cys Asp Ala Thr Gly His Pro Ser Leu Ser Met Leu Ile
                20                  25                  30

Ser Met Ala Val Gln Val Ser Glu Glu His Gly Asn Ser Leu Gly Leu
                35                  40                  45

Asp Thr Ala Thr Ile Gln Ser Tyr Gly Gly Gly Trp Val Ile Thr Ser
 50                  55                  60

Tyr Glu Gly Ser Phe Ala Ala Arg Gln Pro Ile Asn Gly Glu Glu Val
65                  70                  75                  80

Ile Leu Gly Thr Arg Ala Ile Ala Asn Asn Arg Phe Phe Ala Leu Arg
                85                  90                  95

Glu Phe Trp Ile Gln Ser Ala Asp Arg Gln Val Glu Tyr Val Arg Leu
                100                 105                 110

Thr Gly Leu Phe Val Tyr Met Asn Leu Gln Thr Arg His Leu Met Ser
        115                 120                 125

Ile Pro Gln Ala Val Ile Glu Pro Tyr His Gly Pro Glu Lys Lys Arg
        130                 135                 140

Leu Pro Arg Leu Ala Lys Ala Arg Glu Leu Gln Asp Val Arg Cys Lys
145                 150                 155                 160

Asn Asp Tyr His Val Arg Phe Phe Asp Ile Asp Ser Asn Arg His Val
            165                 170                 175

Asn Asn Ala Arg Tyr Phe Asp Trp Met Gln Asp Pro Leu Gly Ala Glu
            180                 185                 190

Phe Leu Thr Arg His Gln Leu Lys His Met Thr Met Arg Tyr Glu Lys
            195                 200                 205

Glu Val Arg Tyr Gly Gln Thr Ile Thr Ser Glu Ile Ser Ser Pro Tyr
210                 215                 220

Arg His Glu Asn Gly Glu Leu Thr Thr Asp His Arg Ile Val Val Asp
225                 230                 235                 240

Gly Gln Leu Ala Ala Ser Thr Met Ile Trp Tyr Glu
            245                 250

<210> SEQ ID NO 86
<211> LENGTH: 252
<212> TYPE: PRT
<213> ORGANISM: Desulfitobacterium metallireducens

<400> SEQUENCE: 86

Met Lys Lys Phe Gln Lys Glu Phe Glu Val His Tyr Tyr Glu Val Asp
1               5                   10                  15

Phe Tyr Gln Glu Leu Thr Pro Leu Ala Leu Leu Asn Phe Leu Glu Glu
            20                  25                  30

Thr Ala Ile Ala His Ser Glu Ala Val Gly Tyr Gly Val Thr Arg Leu
            35                  40                  45

Lys Glu Lys Gly Tyr Gly Trp Val Leu Ser Gln Trp Gln Ile Glu Met
        50                  55                  60

Asp Gln Tyr Pro His Tyr Gly Glu Lys Val Lys Ile Gln Thr Trp Pro
65                  70                  75                  80

Ser His Phe Gln Arg Phe Tyr Gly Asp Arg Glu Phe Leu Val Leu Asn
                85                  90                  95

Ser Gln Asp Lys Val Ile Ala Arg Ala Ser Ser Leu Trp Ile Phe Leu
            100                 105                 110

Asn Leu Glu Lys Arg Arg Pro Thr Arg Ile Pro Gln Glu Val Ser Asp
            115                 120                 125

Ala Tyr His Ile Phe Pro Asp Lys Ala Leu Ser Phe Pro Phe Pro Glu
            130                 135                 140

Leu Lys Met Ser Gln Thr Arg Glu Lys Lys Arg Ser Lys Phe Met Ile
145                 150                 155                 160

Arg Arg Ser Asp Ile Asp Thr Asn Asp His Val Asn Asn Ala Lys Tyr
                165                 170                 175

Ile Glu Trp Val Leu Glu Thr Ile Pro Glu Glu Val Tyr Arg Thr Tyr
            180                 185                 190

Arg Ile Ser Ser Leu Glu Val Val Tyr Lys Lys Glu Ser Thr Tyr Gly
            195                 200                 205

Gln Met Ile Gln Ser Val Thr Glu Glu Gln Arg Val Asp Gln Glu
            210                 215                 220

Ala His Tyr Val His Gln Ile Leu Glu Arg Asp Gly Glu Glu Val
225                 230                 235                 240

Ala Leu Ala Leu Ala Gln Thr Arg Trp Ser Lys Arg
            245                 250

<210> SEQ ID NO 87
<211> LENGTH: 249
<212> TYPE: PRT

<213> ORGANISM: Lactobacillus coleohominis

<400> SEQUENCE: 87

Met Ala Gly Gln Lys Phe Ile Leu Glu His Gln Val Asn Tyr Tyr Glu
1               5                   10                  15

Cys Asp Pro Ser Gly His Leu Ser Leu Ser Met Leu Val Ala Leu Met
            20                  25                  30

Ile Leu Ala Ser Glu Lys Gln Asn Ala Gln Leu Gly Val Asp Glu His
        35                  40                  45

Val Thr Lys Glu Leu Gly Gly Gly Trp Val Ile Ile Asp Tyr Glu Gly
    50                  55                  60

His Phe Gln Arg Glu Trp Pro Lys Glu Asn Gln Ile Lys Phe Glu
65                  70                  75                  80

Thr Ala Ile Val Ala Tyr Asn Lys Tyr Phe Val Val Arg Gln Phe Val
                85                  90                  95

Ile Arg Asp Tyr His Glu Gln Ile Ile Gly Thr Val Asn Gly Leu Phe
            100                 105                 110

Val Tyr Met Asp Leu Ser Lys Arg Arg Met Ala Lys Ile Pro Glu Ala
        115                 120                 125

Ile Met Thr Pro Tyr Glu Ala Ala Ser Thr Leu Arg Leu Pro Lys Val
    130                 135                 140

Ala Arg Pro Asp Lys Val Glu Ala Thr Asp Glu Trp Arg Glu Asn His
145                 150                 155                 160

Tyr Gln Val Arg Tyr Phe Asp Ile Asp Tyr Asn Gly His Val Asn Asn
                165                 170                 175

Ala Arg Tyr Phe Asp Trp Met Leu Asp Thr Leu Asp His Asp Phe Leu
            180                 185                 190

Leu Lys His Gln Ile Met Glu Ile Arg Met Asn Tyr Glu His Glu Val
        195                 200                 205

Arg Pro Gln Thr Glu Val Asn Ser Met Ala Ile Thr Ile Glu Asn Asn
    210                 215                 220

Ala His Glu Trp Thr Thr Gln His Gln Ile Trp Val Gly Thr Gln Lys
225                 230                 235                 240

Cys Ala Thr Ala Thr Ile Lys Trp Arg
                245

<210> SEQ ID NO 88
<211> LENGTH: 259
<212> TYPE: PRT
<213> ORGANISM: Lactobacillus buchneri

<400> SEQUENCE: 88

Met Ser Met Pro Ala His Ser Phe Ser Glu Leu His Thr Ile Pro Phe
1               5                   10                  15

Tyr Glu Cys Asn Val Asn Asn Arg Ile Ser Ile Pro Met Leu Ile Asn
            20                  25                  30

Ile Leu Ile Leu Ala Ser Glu His Gln Asn Glu Asn Leu Gly Leu Asp
        35                  40                  45

Gln Thr Tyr Leu Ile Asp His Tyr Gly Val Gly Trp Val Val Thr Ser
    50                  55                  60

Tyr Ser Ile His Ile Thr His Leu Pro Arg Lys Asp Ser Val Val Lys
65                  70                  75                  80

Met Thr Thr Arg Gly Thr Ser Tyr Asn Arg Tyr Phe Ala Phe Arg Glu
                85                  90                  95

Phe Trp Leu His Asp Gln Ala Gly Asn Glu Leu Val Lys Val Glu Ser

```
            100                 105                 110
Ile Trp Val Leu Met Asn Glu Gln Thr Arg Lys Ile Thr Pro Ile Asp
            115                 120                 125

Glu Thr Ile Ile Ala Pro Tyr Gln Ser Glu Lys Val Lys Arg Val Pro
            130                 135                 140

Arg Leu Ala Arg Pro Glu Arg Ile Glu Ala Thr Asp Asp Val Ser Ala
145                 150                 155                 160

Lys Glu Tyr Gln Val Arg Trp Ser Asp Ile Asp Phe Asn Gly His Val
                165                 170                 175

Asn Asn Ser Arg Tyr Pro Glu Trp Met Leu Asp Ser Leu Pro Met Asp
            180                 185                 190

Phe Leu Asn Gln His Glu Pro Thr Asn Ile Asp Ile Arg Phe Glu Asn
            195                 200                 205

Glu Val Lys Tyr Gly Asn Arg Val Thr Ser Ser Val Leu Val Asp Ser
            210                 215                 220

Ser Asp Asn Ala Lys Ile Lys Thr Val His Glu Ile Lys Ser Asn Asp
225                 230                 235                 240

Val Leu Ser Ala Ser Ala Thr Ile Val Trp Lys Asp Ile Lys Ala Lys
                245                 250                 255

Gly Asn Asp

<210> SEQ ID NO 89
<211> LENGTH: 289
<212> TYPE: PRT
<213> ORGANISM: Triticum aestivum

<400> SEQUENCE: 89

Met Gly Ser Leu Leu Glu Asp Gly Leu Ser Tyr Lys Glu Ser Phe Ile
1               5                   10                  15

Val Arg Cys Tyr Glu Val Gly Ile Asn Lys Thr Ala Thr Val Glu Thr
            20                  25                  30

Ile Ala Asn Leu Leu Gln Glu Val Gly Cys Asn His Ala Gln Ser Val
            35                  40                  45

Gly Phe Ser Thr Asp Gly Phe Ala Thr Thr Thr Thr Met Arg Glu Leu
        50                  55                  60

Gly Leu Ile Trp Val Thr Asn Arg Met His Ile Glu Ile Tyr Lys Tyr
65                  70                  75                  80

Pro Ala Trp Gly Asp Val Val Glu Ile Glu Thr Trp Cys Gln Ala Asp
                85                  90                  95

Gly Lys Ile Gly Thr Arg Arg Asp Trp Ile Leu Lys Asp Leu Ala Asn
            100                 105                 110

Gly Glu Val Ile Gly Arg Ala Thr Ser Lys Trp Val Met Met Asn Gln
            115                 120                 125

Asn Thr Arg Arg Leu Gln Arg Val Ser Asp Glu Val Arg Asp Glu Val
            130                 135                 140

Phe Ile His Cys Pro Lys Ser Pro Arg Leu Ala Phe Pro Glu Glu Asn
145                 150                 155                 160

Asn Gly Ser Leu Lys Lys Ile Pro Val Leu Thr Asp Pro Ala Gln His
                165                 170                 175

Ser Arg Leu Gly Leu Val Pro Arg Arg Ala Asp Leu Asp Met Asn Gln
            180                 185                 190

His Val Asn Asn Val Thr Tyr Ile Gly Trp Val Leu Glu Ser Ile Pro
            195                 200                 205

Gln Asp Ile Ile Asp Thr His Glu Leu Gln Thr Ile Thr Leu Asp Tyr
```

```
                210              215             220
Arg Arg Glu Cys Gln His Asp Ile Val Asp Ser Leu Thr Tyr Ile
225                 230             235                 240

Glu Glu Gly Glu Ile Asn Ser Asn Gly Ser Leu Phe Ser Ala Pro
                245             250             255

His Pro Glu Glu Gln Arg Gln Phe Leu His Cys Leu Arg Phe Ala Gly
            260             265             270

Ala Gly Asp Glu Ile Asn Arg Gly Arg Thr Val Trp Arg Lys Leu Ala
        275             280             285

Arg
```

<210> SEQ ID NO 90
<211> LENGTH: 249
<212> TYPE: PRT
<213> ORGANISM: Cellulosilyticum lentocellum

<400> SEQUENCE: 90

```
Met Asp Asn Thr Phe Ser Lys Lys Tyr Thr Ile Glu Ile Tyr Asp Val
1               5                   10                  15

Asn Ser Asn Tyr Arg Cys Lys Tyr Ser Ser Leu Met Asn Tyr Leu Trp
            20                  25                  30

Asp Val Val Ser Gln Ser Asp Ser Leu Gly Glu Thr Asp Asn Gly
        35                  40                  45

Leu Ile Asn Asn Cys Ala Trp Val Leu Leu Lys Tyr Asp Leu Thr Ile
50                  55                  60

Ile Glu Tyr Pro Lys Phe Arg Asp Thr Ile Thr Val Glu Thr Asp Ile
65                  70                  75                  80

Val Gly Ile Lys Lys Leu Tyr Gly Tyr Arg Ser Phe Thr Ile Lys Thr
                85                  90                  95

Ser Glu Gly Thr Leu Ile Ala Ser Gly Ile Ser Thr Ala Val Leu Ile
            100                 105                 110

Asp Ile Asn Lys Arg Arg Pro Val Arg Ile Ser Pro Glu Gln Cys Lys
        115                 120                 125

Leu Tyr Gly Ile Glu Lys Glu Leu Glu Glu Asn Ile Pro Leu Asp Asp
130                 135                 140

Phe Ile Gln Leu Glu Gly Tyr Lys Tyr Ser Lys Asp Tyr Arg Ala Arg
145                 150                 155                 160

His Ser Asp Ile Asp Ile Asn Gln His Val Asn Asn Val Lys Tyr Leu
                165                 170                 175

Glu Met Ala Val Asp Thr Leu Pro Arg Thr Ile Leu Asn Ala Ser Glu
            180                 185                 190

Ile Ser Asn Ile Lys Val Leu Tyr Lys Lys Glu Ala Leu Asp Glu Ala
        195                 200                 205

Ser Leu His Val Cys Ser Asp Val Ile Glu Asn Glu Lys Gly His Leu
210                 215                 220

Thr Thr Leu His Thr Ile Ile Asp Leu Thr His Asp Lys Leu Leu Thr
225                 230                 235                 240

Lys Leu Glu Leu Lys Trp Arg Lys Ile
                245
```

<210> SEQ ID NO 91
<211> LENGTH: 247
<212> TYPE: PRT
<213> ORGANISM: Enterococcus italicus

<400> SEQUENCE: 91

```
Met Ala Lys Glu Phe Ser Arg Gln His Glu Val Val Tyr Tyr Glu Cys
1               5                   10                  15

Asp Met Asn Gly Asn Met Thr Leu Pro Thr Val Ile Ser Leu Ala Ile
                20                  25                  30

Gln Val Ser Glu Thr Gln Ser Asn Glu Leu Asn Arg Gly Ser Glu Tyr
                35                  40                  45

Ile His Gln His Gly Val Thr Trp Ile Leu Thr Asn Tyr His Leu Glu
    50                  55                  60

Ile Thr Arg Leu Pro Lys Val Asp Glu Gln Ile Ile Val Thr Thr Lys
65                  70                  75                  80

Ala Glu Glu Tyr Asn Lys Tyr Phe Cys Tyr Arg Ser Phe Trp Ile Arg
                85                  90                  95

Thr Leu Ser Gly Glu Glu Leu Val His Ile Gln Ala Val Phe Gly Leu
                100                 105                 110

Met Asn Ile Glu Thr Arg Lys Leu Ser Arg Val Ile Asp Glu Ile Ile
                115                 120                 125

Ala Pro Phe Glu Ser Gln Lys Ile Thr Lys Ile Lys Arg Phe Gly Lys
130                 135                 140

Leu Glu Lys Ile Val Ile Gly Glu Ser Leu Pro Tyr Arg Val Arg Phe
145                 150                 155                 160

Phe Asp Ile Asp Ser Asn Leu His Val Asn Asn Ala Val Tyr Phe His
                165                 170                 175

Trp Ile Leu Asp Val Leu Gly Arg Asp Phe Leu Thr Ser Tyr Val Pro
                180                 185                 190

Lys Thr Ile Thr Ile Arg Tyr Asp Lys Glu Val Glu Tyr Gly Asn Glu
                195                 200                 205

Ile Thr Ser Val Val Glu Lys Ile Asn Gln Asp Gln Val Met Cys Thr
                210                 215                 220

Arg His Ala Ile Met Leu His Glu Glu Thr Cys Cys Glu Ala Leu Ile
225                 230                 235                 240

Glu Trp Lys Glu Leu Ser Lys
                245

<210> SEQ ID NO 92
<211> LENGTH: 247
<212> TYPE: PRT
<213> ORGANISM: Weissella paramesenteroides

<400> SEQUENCE: 92

Met Ala Val Glu Phe Arg Met Pro His Asp Val Tyr Tyr Glu Ala
1               5                   10                  15

Asp Val Thr Gly Lys Leu Ser Leu Pro Met Ile Tyr Asn Leu Ala Ile
                20                  25                  30

Leu Ser Ser Thr Gln Gln Ala Ile Asp Leu Asn Ile Gly Pro Glu Tyr
                35                  40                  45

Thr His Ala Lys Gly Leu Gly Trp Val Val Leu Gln Gln Leu Val Thr
    50                  55                  60

Ile Asn Arg Arg Pro Lys Asp Gly Glu Thr Ile Thr Leu Ala Thr Lys
65                  70                  75                  80

Ala Lys Gln Phe Asn Pro Phe Phe Ala Lys Arg Glu Tyr Arg Leu Ile
                85                  90                  95

Asp Ala Ala Gly Asn Asp Leu Val Ile Met Asp Gly Leu Phe Ser Met
                100                 105                 110

Ile Asp Met Asn Lys Arg Lys Leu Ala Arg Ile Pro Lys Asp Met Ala
```

```
              115                 120                 125
Glu Ala Tyr Gln Pro Glu His Val Arg Lys Ile Pro Arg Ala Pro Glu
130                 135                 140

Val Thr Pro Phe Asp Glu Thr Arg Glu Ala Asp Phe Val Gln Asp Tyr
145                 150                 155                 160

Phe Val Arg Tyr Leu Asp Ile Asp Ser Asn His His Val Asn Asn Ser
                165                 170                 175

Lys Tyr Ala Glu Trp Met Ser Asp Val Leu Pro Val Glu Phe Leu Thr
            180                 185                 190

Ser His Glu Pro Thr Ala Met Asn Ile Lys Tyr Glu His Glu Val Leu
        195                 200                 205

Tyr Gly Asn Lys Ile Lys Ser Glu Val Gln Leu Val Asp Asn Val Thr
    210                 215                 220

Lys His Arg Ile Trp Phe Gly Asp Val Leu Ser Ala Glu Ala Thr Ile
225                 230                 235                 240

Glu Trp Thr Thr Ala Ser Asn
                245

<210> SEQ ID NO 93
<211> LENGTH: 246
<212> TYPE: PRT
<213> ORGANISM: Clostridium perfringens

<400> SEQUENCE: 93

Met Gly Lys Ala Tyr Glu Lys Val Tyr Glu Val Thr Tyr Gly Glu Thr
1               5                   10                  15

Asp Gly Arg Lys Asp Cys Arg Ile Thr Ser Met Met Asn Phe Phe Ser
            20                  25                  30

Asp Cys Cys Leu Ser Gln Glu Glu Lys Asn Ser Met Asn Tyr Ala Asp
        35                  40                  45

Asn Ser Ser Glu Thr Thr Trp Val Phe Phe Asp Tyr Glu Ile Ile Val
    50                  55                  60

Asn Arg Tyr Pro Arg Tyr Arg Glu Lys Ile Lys Val Lys Thr Tyr Val
65                  70                  75                  80

Glu Ser Ile Arg Lys Phe Tyr Ser Asn Arg Val Phe Glu Ala Tyr Asp
                85                  90                  95

Met Asp Gly Ala Leu Val Ala Arg Ala Asp Val Leu Ala Phe Leu Ile
            100                 105                 110

Asn Lys Lys Thr Arg Arg Pro Ala Arg Ile Ser Asp Glu Glu Tyr Glu
        115                 120                 125

Ile His Gly Leu Ser Lys Glu Ser Ser Lys Leu Leu Arg Lys Lys Leu
    130                 135                 140

Asn Phe Glu Lys Phe Asp Lys Glu Asp Leu Asp Met Lys Phe His Ile
145                 150                 155                 160

Arg Tyr Leu Asp Ile Asp Leu Asn Met His Val Ser Asn Ile Lys Tyr
                165                 170                 175

Val Glu Trp Ile Leu Glu Thr Val Pro Val Asp Ile Val Leu Asn Tyr
            180                 185                 190

Lys Met Lys Lys Ile Lys Ile Lys Phe Glu Lys Glu Ile Thr Tyr Gly
        195                 200                 205

His Asn Val Ile Ile Lys Ser Lys Ile Ile Lys Gly Glu Asp Glu Val
    210                 215                 220

Lys Val Leu His Lys Val Glu Asn Glu Glu Gly Glu Ser Ile Thr Leu
225                 230                 235                 240
```

```
Ala Glu Thr Tyr Trp Tyr
            245

<210> SEQ ID NO 94
<211> LENGTH: 370
<212> TYPE: PRT
<213> ORGANISM: Gossypium raimondii

<400> SEQUENCE: 94

Met Leu Lys Phe Ser Tyr Cys Asn Ala Thr Asp Leu Asn Gln Ala Leu
1               5                   10                  15

Val Gln Cys Arg Phe Ala Gly Ser Phe Gly Pro Leu Ser Ser Arg Arg
            20                  25                  30

Arg Ser Pro Arg Ala Ala Val Ser Cys Ser Arg Ser Asn Leu Thr Pro
        35                  40                  45

Ile Gln Ala Val Leu Ser Cys Gln Gln Gln Val Gly Ser Asp Pro Val
    50                  55                  60

Glu Ser Glu Leu Gly Ser Leu Ala Asp Arg Leu Arg Leu Gly Gly Leu
65                  70                  75                  80

Thr Glu Asp Gly Leu Ser Tyr Lys Glu Lys Phe Ile Ile Arg Cys Tyr
                85                  90                  95

Glu Val Gly Ile Asn Lys Thr Ala Thr Ile Glu Thr Ile Ala Asn Leu
            100                 105                 110

Leu Gln Glu Val Gly Gly Asn His Ala Gln Ser Val Gly Phe Ser Arg
        115                 120                 125

Asp Gly Phe Ala Thr Ser Pro Thr Met Arg Lys Leu His Leu Ile Trp
    130                 135                 140

Val Thr Ala Arg Met His Ile Glu Val Tyr Lys Tyr Pro Ala Trp Ser
145                 150                 155                 160

Asp Val Ile Glu Ile Glu Thr Trp Cys Gln Asn Glu Gly Arg Ile Gly
                165                 170                 175

Thr Arg Arg Asp Trp Ile Leu Lys Asp Val Ala Thr Gly Glu Val Ile
            180                 185                 190

Gly Arg Ala Thr Ser Lys Trp Val Met Met Asn Glu Asp Thr Arg Arg
        195                 200                 205

Leu Gln Lys Val Ser Asp Asp Val Lys Glu Glu Tyr Leu Val Phe Cys
    210                 215                 220

Pro Arg Glu Pro Arg Leu Ala Phe Pro Glu Glu Asn Asn Lys Ser Leu
225                 230                 235                 240

Lys Lys Ile Ser Lys Leu Glu Asp Pro Val Gln Tyr Ser Arg Leu Gly
                245                 250                 255

Leu Met Pro Arg Arg Ala Asp Leu Asp Met Asn Gln His Val Asn Asn
            260                 265                 270

Val Thr Tyr Ile Gly Trp Val Leu Glu Ser Met Pro Glu Glu Ile Ile
        275                 280                 285

Asp Thr His Glu Leu Gln Thr Ile Thr Leu Asp Tyr Arg Arg Glu Cys
    290                 295                 300

Gln Arg Asp Asp Val Val Asp Ser Leu Thr Gly Pro Glu Leu Val Glu
305                 310                 315                 320

Gly Ser Lys Ile His Gly Thr Asn Gly Ser Ala Thr Ala Ile Thr Arg
                325                 330                 335

Glu Asp Asp Leu Asp Cys His Gln Phe Leu His Leu Leu Arg Leu Ser
            340                 345                 350

Ser Asp Gly Gln Glu Ile Asn Arg Gly Arg Thr Glu Trp Arg Lys Lys
        355                 360                 365
```

Pro Thr
    370

<210> SEQ ID NO 95
<211> LENGTH: 308
<212> TYPE: PRT
<213> ORGANISM: Physcomitrella patens

<400> SEQUENCE: 95

Val Leu Ala Ala Ile Ala Ser Val Ala Leu Ala Ala Glu Thr Gln Arg
1               5                   10                  15

Arg His Glu Val Phe Ser Gly Lys Thr Arg Val Pro Val Asp Ala Leu
            20                  25                  30

Arg Gln Gly Arg Leu Val Glu Ser Arg Leu Val Tyr Arg Gln Thr Phe
        35                  40                  45

Val Ile Arg Ser Tyr Glu Ile Gly Ala Asp Arg Thr Ala Ser Ile Glu
    50                  55                  60

Thr Met Met Asn His Phe Gln Glu Thr Ala Leu Asn His Val Trp Met
65                  70                  75                  80

Ser Gly Ile Ala Gly Asp Gly Phe Gly Ala Thr Arg Ala Met Ser Cys
                85                  90                  95

Arg Asn Leu Ile Trp Val Val Ser Arg Met Gln Val His Val Glu Gln
            100                 105                 110

Tyr Pro Ala Trp Gly Asp Ala Val Glu Met Asp Thr Trp Val Ala Ala
        115                 120                 125

Ser Gly Lys Asn Gly Met Arg Arg Asp Trp Leu Val Arg Asp Tyr Lys
    130                 135                 140

Thr Gly Gln Ile Leu Ala Arg Ala Thr Ser Thr Trp Val Met Met His
145                 150                 155                 160

Arg Lys Thr Arg Lys Leu Ser Lys Met Pro Glu Glu Val Arg Thr Glu
                165                 170                 175

Ile Ser Pro Tyr Phe Leu Asp Arg Ser Ala Ile Lys His Glu Ser Met
            180                 185                 190

Leu Thr Gln Lys Ile Ile Arg Leu Asp Gly Asn Ala Glu Phe Val Arg
        195                 200                 205

Ser Gly Leu Thr Pro Arg Arg Ser Asp Leu Asp Met Asn Gln His Val
    210                 215                 220

Asn Asn Val Lys Tyr Ile Gly Trp Met Met Glu Ser Val Pro Pro Thr
225                 230                 235                 240

Ile Leu Asp Asn Tyr Glu Leu Val Ser Met Asn Leu Glu Tyr Arg Arg
                245                 250                 255

Glu Cys Gly Gln Ser Asp Val Val Gln Ser Met Ala Ser Leu Glu Pro
            260                 265                 270

Ser Thr Ser Gly Ser Leu Asp Val Gly Phe Leu Gln Phe Val His Leu
        275                 280                 285

Leu Arg Met Glu Ser Asp Gly Ala Glu Ile Val Arg Gly Arg Thr Cys
    290                 295                 300

Trp Arg Pro Lys
305

<210> SEQ ID NO 96
<211> LENGTH: 245
<212> TYPE: PRT
<213> ORGANISM: Leuconostoc citreum

<400> SEQUENCE: 96

Met Asn Ser Phe Glu Ile Lys Arg Arg Val Glu Tyr Tyr Glu Ala Asp
1               5                   10                  15

Val Thr Gly Lys Leu Ala Leu Pro Met Ile Leu Asn Trp Ala Val Leu
            20                  25                  30

Ala Ser Lys Leu Gln Ser Asp Ala Leu Gly Val Gly Gln Ser Thr His
        35                  40                  45

Leu Ala Arg Gly Leu Gly Trp Ile Ile Leu Gln Tyr Glu Val His Ile
50                  55                  60

Thr Arg Arg Pro Ala Val Asn Glu Glu Ile Thr Ile Gln Thr Tyr Ala
65                  70                  75                  80

Ala Lys Tyr Asn Pro Phe Phe Val Arg Arg Pro Phe Ala Phe Phe Asp
                85                  90                  95

Ala Gln Gly Glu Glu Ile Ile Arg Val Asp Ser Ile Trp Thr Met Ile
            100                 105                 110

Asp Ile Asn Asn Arg Arg Met Ala Arg Leu Pro Gln Asp Ile Val Asp
            115                 120                 125

Lys Tyr Gln Ala Glu Arg Val Lys Gln Ile Pro Arg Met Pro Asn Pro
        130                 135                 140

Ile Lys Ile Leu Pro Asn Asp Asp Met Ile Ser Lys Asp Tyr His Val
145                 150                 155                 160

Arg Tyr Leu Asp Ile Asp Ala Asn Gln His Val Asn Asn Ser Lys Tyr
                165                 170                 175

Phe Glu Trp Met Gln Asp Val Val Pro Thr Glu Phe Leu Glu Thr His
            180                 185                 190

Glu Ile Thr Ser Ile Asn Leu Lys Tyr Glu Asn Glu Ile His Leu Gly
        195                 200                 205

His Thr Ile Gln Ser Gln Val Val Leu Gly Asn Gln Ser Ser Lys His
    210                 215                 220

Arg Ile Met Leu Gly Asp Val Val Ser Ala Glu Ala Glu Phe Asn Trp
225                 230                 235                 240

Arg Asn Val Thr Leu
                245

<210> SEQ ID NO 97
<211> LENGTH: 260
<212> TYPE: PRT
<213> ORGANISM: Fibrella aestuarina

<400> SEQUENCE: 97

Met Ala Ala Phe Pro Asn Ala Leu Arg Arg Lys Phe Ala Gly Met Ala
1               5                   10                  15

Phe Ile Gln Thr Asp Ala Tyr Thr Leu Arg Asn Tyr Glu Cys Asp Ala
            20                  25                  30

Ala Gly Arg Leu Ser Ile Pro Ala Leu Met Asn Leu Met Gln Glu Ser
        35                  40                  45

Ala Asn Arg Asn Ala Tyr Asp Tyr Gly Ile Asp Ser Glu Thr Leu Gln
    50                  55                  60

Ala Asn Gly Leu Gly Trp Met Leu Met Arg Phe Gly Leu Val Met His
65                  70                  75                  80

His Tyr Pro Arg Ser Gly Gln Thr Ile Arg Ile Val Thr Tyr Pro Thr
                85                  90                  95

Gly Val Glu Lys Phe Phe Val Tyr Arg Asp Phe Arg Val Tyr Ala Asp
            100                 105                 110

Ala Val Leu Leu Ala Glu Ala Thr Ser Thr Trp Leu Val Phe Asp Ser

```
            115                 120                 125
His Lys Arg Thr Met Val Pro Thr Pro Asp Phe Ile Arg Ser Leu Val
        130                 135                 140

Cys Pro Asp Val Asp Gln Pro Ser Pro Arg Leu Pro Leu Lys Pro Asn
145                 150                 155                 160

Tyr Pro Ser Val Glu Val Ala Glu Glu Ala Gln Ala Val Thr Val Gly
                165                 170                 175

Trp Phe Asp Ile Asp Ser Asn Gln His Val Asn Asn Val Val Tyr Ile
            180                 185                 190

Arg Trp Leu Leu Glu Gln Leu Pro Asp Ala Val Leu Gln Thr Gln Glu
        195                 200                 205

Leu Ala Glu Leu Asp Val Val Tyr Arg Asn Glu Thr His Trp His Glu
    210                 215                 220

Arg Val Leu Val Gln His Gln Ala Asp Asp Ala Gly Thr Phe His His
225                 230                 235                 240

Arg Leu Ala Leu Ala Glu Thr Gly Lys Asp Val Leu Leu Ala Arg Thr
                245                 250                 255

Arg Trp Arg Arg
            260

<210> SEQ ID NO 98
<211> LENGTH: 207
<212> TYPE: PRT
<213> ORGANISM: Yokenella regensburgei

<400> SEQUENCE: 98

Met Asn Phe Lys Tyr Val Phe Arg Trp His Leu Pro Phe Leu Phe Leu
1               5                   10                  15

Ile Leu Leu Thr Phe Arg Thr Ala Ala Ala Asp Thr Leu Leu Val Leu
            20                  25                  30

Gly Asp Ser Leu Ser Ala Gly Tyr Arg Met Ala Ala Ser Ala Ala Trp
        35                  40                  45

Pro Ala Leu Leu Asn Asp Lys Trp Gln Pro Lys Met Thr Val Ile Asn
    50                  55                  60

Ala Ser Ile Ser Gly Asp Thr Ser Gln Gln Gly Leu Ala Arg Leu Pro
65                  70                  75                  80

Ala Leu Leu Lys Gln His Gln Pro Arg Trp Val Leu Val Glu Leu Gly
                85                  90                  95

Gly Asn Asp Gly Leu Arg Gly Phe Pro Pro Gln Gln Thr Glu Gln Thr
            100                 105                 110

Leu Arg Thr Val Leu Gln Gln Leu Glu Ala Ala Lys Val Gln Pro Leu
        115                 120                 125

Leu Met Gln Ile Arg Leu Pro Ala Asn Tyr Gly Arg Arg Tyr Asn Glu
    130                 135                 140

Ala Phe Ser Ala Ile Tyr Pro Lys Leu Ala Gly Glu Phe Asn Ile Pro
145                 150                 155                 160

Leu Leu Pro Phe Phe Met Glu Glu Val Tyr Leu Lys Pro Gln Trp Met
                165                 170                 175

Gln Asp Asp Gly Ile His Pro Asn Arg Asp Ala Gln Pro Phe Ile Ala
            180                 185                 190

Asp Trp Met Ala Thr Arg Leu Ala Pro Leu Val Lys His Asp Ser
        195                 200                 205

<210> SEQ ID NO 99
<211> LENGTH: 247
```

<212> TYPE: PRT
<213> ORGANISM: Clostridium botulinum

<400> SEQUENCE: 99

Met Ser Gly Val Ile Thr Glu Lys Glu Tyr Glu Ile His Tyr Tyr Glu
1               5                   10                  15

Thr His Thr Lys His Gln Ala Thr Thr Asn Ile Ile Asp Phe Phe
            20                  25                  30

Thr Asp Val Ala Thr Phe Gln Ser Glu Lys Leu Gly Val Gly Ile Asp
        35                  40                  45

Phe Met Met Glu Asn Lys Met Ala Trp Met Leu Tyr Lys Trp Asp Ile
    50                  55                  60

Asn Val His Arg Tyr Pro Lys Tyr Arg Glu Lys Ile Ile Val Val Thr
65                  70                  75                  80

Glu Pro Tyr Ala Ile Lys Lys Phe Tyr Ala Tyr Arg Lys Phe Tyr Ile
                85                  90                  95

Leu Asp Glu Asn Arg Asn Val Ile Ala Thr Ala Lys Ser Val Trp Leu
            100                 105                 110

Leu Ile His Ile Glu Lys Arg Lys Pro Leu Lys Ile Ser Ser Glu Ile
        115                 120                 125

Ile Lys Ala Tyr Asn Leu Thr Asp Lys Lys Ser Asp Ile Lys Ile Glu
    130                 135                 140

Lys Leu Gly Lys Leu Pro Glu Glu Tyr Thr Ser Leu Glu Phe Arg Val
145                 150                 155                 160

Arg Tyr Ser Asp Ile Asp Thr Asn Gly His Val Asn Asn Glu Lys Tyr
                165                 170                 175

Ala Ala Trp Met Leu Glu Ser Leu Pro Arg Asn Ile Ile Ser Glu Tyr
            180                 185                 190

Thr Leu Ile Asn Ile Lys Ile Thr Tyr Lys Lys Glu Thr Leu Tyr Gly
        195                 200                 205

Glu Asn Ile Arg Val Leu Thr Gly Ile Lys Glu Ser Glu Asp Lys Leu
    210                 215                 220

Val Phe Ile His Asn Val Ile Arg Glu Asn Gly Glu Leu Leu Thr Glu
225                 230                 235                 240

Gly Glu Thr Val Trp Lys Lys
                245

<210> SEQ ID NO 100
<211> LENGTH: 269
<212> TYPE: PRT
<213> ORGANISM: Microscilla marina

<400> SEQUENCE: 100

Met Cys Asp Leu Ile Ile Glu Asp Ala Lys Asn Ile Tyr Leu Trp Tyr
1               5                   10                  15

Met Glu Lys Asn Gln Thr Thr Gln Leu Pro Lys Ile Trp Leu Asp Phe
            20                  25                  30

Glu Val Arg Ala Tyr Glu Val Asp Ile Tyr Asn Arg Val Ser Pro Val
        35                  40                  45

Thr Ile Ala Asn Tyr Leu Gln Glu Ala Ala Gly Gln His Ala Asp His
    50                  55                  60

Leu Gly Val Gly Val Thr Asp Leu Leu Lys His Arg Leu Thr Trp Val
65                  70                  75                  80

Leu Thr Arg Ile Lys Ile Asp Met Gln Gln Tyr Pro Ser Arg Tyr Glu
                85                  90                  95

```
Pro Val Arg Val Leu Thr Tyr Pro Ile Gly Tyr Asp Lys Tyr Phe Val
             100                 105                 110

Tyr Arg Asn Phe Gln Leu Tyr Asn Ala Gln Gly Lys Gln Ile Gly Gln
        115                 120                 125

Ala Thr Ser Thr Trp Ala Val Met Asp Ile Gln Ala Arg Lys Met Val
    130                 135                 140

Gly Val Pro Gln Leu Ile Thr Ser Leu Pro Ile Pro Asp Asp Glu Asp
145                 150                 155                 160

Phe Ile Thr Arg Thr Lys Gly Lys Ile Ala Lys Val Asn Ala Pro Leu
                165                 170                 175

Ser Glu Thr Leu Phe Arg Val Arg Trp Asn Asp Leu Asp Thr Asn Gln
            180                 185                 190

His Thr Asn Asn Ala Tyr Tyr Leu Gln Trp Ala Ile Glu Ser Leu Pro
        195                 200                 205

Glu Glu Val Leu Lys Ser Arg Gln Leu Ala Ser Ile Asp Leu Leu Tyr
    210                 215                 220

Arg Leu Glu Thr Thr Trp Lys Glu Gly Val Val Ala Arg Thr Glu Gln
225                 230                 235                 240

Thr Ser Thr Gln Pro Leu Ser Phe Ile His Gln Leu Ile Arg Glu Ser
                245                 250                 255

Asp Gln Lys Glu Leu Ala Gln Ala Thr Thr Val Trp Val
            260                 265

<210> SEQ ID NO 101
<211> LENGTH: 220
<212> TYPE: PRT
<213> ORGANISM: Noviherbaspirillum autotrophicum

<400> SEQUENCE: 101

Met Pro Asn Asp Leu Ile Arg Phe Gly Arg Ser Val Arg Ser Leu Gln
1               5                   10                  15

Ile Ile Thr Ala Leu Met Leu Ala Leu Met Thr Asn Trp Ala Tyr Ser
            20                  25                  30

Ala Ser Lys Thr Val Leu Val Leu Gly Asp Ser Leu Ala Ala Glu Tyr
        35                  40                  45

Gly Leu Ala Arg Gly Ser Gly Trp Ala Ala Leu Leu Glu Lys Arg Leu
50                  55                  60

Asn Ala Glu Lys Leu Asp Thr Arg Ile Ile Asn Ala Ser Ile Ser Gly
65                  70                  75                  80

Glu Thr Thr Ser Gly Gly Lys Ala Arg Leu Pro Ala Leu Leu Glu Gln
                85                  90                  95

His Arg Pro Ala Ile Val Ile Glu Leu Gly Ala Asn Asp Gly Leu
            100                 105                 110

Arg Gly Leu Pro Val Ala Ser Ala Lys Ala Asn Leu Arg Thr Met Ile
        115                 120                 125

Ala Ala Val Arg Lys Ala His Ala Gln Pro Leu Leu Val Gly Met Gln
    130                 135                 140

Ile Pro Pro Asn Tyr Gly Arg Gln Tyr Thr Glu Arg Phe Ser Ser Met
145                 150                 155                 160

Tyr Lys Glu Leu Ser Gly Glu Leu Asp Val Pro Leu Val Pro Phe Leu
                165                 170                 175

Leu Asp Gly Val Ala Asp Asn Pro Gln Leu Phe Gln Ala Asp Arg Leu
            180                 185                 190

His Pro Leu Ala Glu Ala Gln Pro Ile Ile Leu Asp Asn Ile Trp Pro
        195                 200                 205
```

His Leu Lys Pro Leu Leu Arg Lys Gln Ala Arg His
    210                 215                 220

<210> SEQ ID NO 102
<211> LENGTH: 201
<212> TYPE: PRT
<213> ORGANISM: Pseudomonas fluorescens

<400> SEQUENCE: 102

Met Arg Met Trp Phe Leu Ser Ala Gly Leu Ala Leu Leu Cys Val Ala
1               5                   10                  15

Gln Ser Ala Ala Ala Gly Thr Ile Leu Ile Val Gly Asp Ser Ile Ser
            20                  25                  30

Ala Gly Phe Gly Leu Asp Thr Arg Lys Gly Trp Val Ala Leu Leu Glu
        35                  40                  45

Gln Arg Leu Lys Lys Glu Gly Phe Asp Asp Lys Val Asn Ala Ser
    50                  55                  60

Ile Ser Gly Asp Thr Ser Ala Gly Gly Leu Ala Arg Leu Pro Ala Ala
65                  70                  75                  80

Leu Ala Glu His Lys Pro Asp Val Val Val Ile Glu Leu Gly Gly Asn
                85                  90                  95

Asp Gly Leu Arg Gly Gln Pro Pro Ala Gln Leu Gln Gln Asn Leu Ala
            100                 105                 110

Ser Met Ile Asp Gln Ser Arg Ala Gly Gly Ala Lys Val Leu Leu Leu
        115                 120                 125

Gly Met Gln Leu Pro Pro Asn Tyr Gly Pro Arg Tyr Thr Lys Ala Phe
    130                 135                 140

Ala Glu Val Phe Gly Thr Leu Ala Lys Glu Lys Asp Ile Pro Leu Val
145                 150                 155                 160

Pro Phe Phe Leu Glu Gly Ile Gly His Pro Glu Leu Met Gln Ala
                165                 170                 175

Asp Gln Leu His Pro Ala Val Ala Ala Gln Gly Lys Leu Leu Glu Asn
            180                 185                 190

Val Trp Pro Ala Leu Lys Pro Leu Leu
    195                 200

<210> SEQ ID NO 103
<211> LENGTH: 257
<212> TYPE: PRT
<213> ORGANISM: Lactobacillus oryzae

<400> SEQUENCE: 103

Met Glu Arg Asn Asp Leu Ala Ala Leu Leu Tyr Thr Glu Asn His Glu
1               5                   10                  15

Val Pro Tyr Tyr Glu Cys Asp Val Thr Asn Arg Met Thr Pro Ala Met
            20                  25                  30

Ile Leu Asn Thr Ile Ile Leu Ile Ser Glu His Gln Asn Ile Glu Leu
        35                  40                  45

Gly Leu Gly Ile Asp Phe Leu Asp Lys Phe Asn Leu Gly Trp Val Val
    50                  55                  60

Val Gln Tyr Glu Ile Asp Ile Glu Arg Met Pro Val Met Asn Glu Thr
65                  70                  75                  80

Ile Ala Ile Ser Thr Gln Ala Thr Ser Tyr Asn Arg Phe Phe Ala Phe
                85                  90                  95

Arg Glu Phe Trp Ile Lys Asp Ser Asn Gly Glu Thr Leu Val His Val
            100                 105                 110

```
Lys Ser Thr Trp Val Thr Met Asp Arg Thr Ala Arg Lys Met Val Ser
        115                 120                 125

Ile Pro Glu Ala Val Ile Leu Pro Tyr Gln Ser Glu Ala Val Lys Arg
    130                 135                 140

Met Pro Arg Leu Lys Arg Pro Thr Asn Ile Asn Glu Ser Asp Asp Leu
145                 150                 155                 160

Ile Lys Lys Pro Tyr Gln Val Arg Tyr Asp Ile Asp Gly Asn Gly
                165                 170                 175

His Val Asn Asn Ala His Tyr Leu Glu Trp Leu Thr Asp Val Leu Pro
                180                 185                 190

Met Asp Phe Leu Thr Thr His Glu Pro Lys Gln Ile Ser Leu Arg Phe
        195                 200                 205

Glu Asn Glu Val Gln Tyr Gly His Met Ile Glu Ser Gln Val Thr Lys
        210                 215                 220

Pro Val Glu Ser Glu Gly Ser Met Val Thr His His Gln Ile Val Val
225                 230                 235                 240

Glu Asp Thr Ile Ser Ala Thr Ala Thr Ile Glu Trp Arg Ser Arg Val
                245                 250                 255

Glu

<210> SEQ ID NO 104
<211> LENGTH: 250
<212> TYPE: PRT
<213> ORGANISM: Clostridium carboxidivorans

<400> SEQUENCE: 104

Met Lys Lys Val Glu Thr Glu Lys Gln Tyr Glu Ile Gln Tyr Tyr Glu
1               5                   10                  15

Ile Asp Cys Asn Lys Lys Leu Leu Leu Thr Ser Leu Met Asn Tyr Leu
            20                  25                  30

Glu Asp Ala Cys Thr Met Gln Ser Glu Asp Ile Gly Ile Gly Leu Asp
        35                  40                  45

Tyr Met Lys Ser Lys Lys Val Ala Trp Val Leu Tyr Lys Trp Asn Ile
50                  55                  60

His Ile Tyr Arg Tyr Pro Leu Tyr Arg Glu Lys Val Lys Val Lys Thr
65                  70                  75                  80

Ile Pro Glu Ser Phe Arg Lys Phe Tyr Ala Tyr Arg Ser Phe Gln Val
                85                  90                  95

Phe Asp Ser Arg Gly Asn Ile Ile Ala Asp Ala Ser Ser Ile Trp Phe
            100                 105                 110

Leu Ile Asn Thr Glu Arg Arg Lys Ala Met Thr Val Thr Glu Asp Met
        115                 120                 125

Tyr Glu Ala Phe Gly Leu Ser Lys Glu Asp Asn Lys Pro Leu Ser Val
        130                 135                 140

Lys Lys Ile Arg Lys Gln Glu Arg Val Asp Ser Glu Lys Val Phe Ser
145                 150                 155                 160

Val Arg Tyr Ser Asp Ile Asp Thr Asn Arg His Val Asn Asn Val Lys
                165                 170                 175

Tyr Val Asp Trp Ala Val Glu Thr Val Pro Leu Asp Ile Val Thr Asn
            180                 185                 190

Cys Lys Ile Val Asp Ile Ile Ala Tyr Glu Lys Glu Thr Thr Tyr
        195                 200                 205

Gly Ala Met Ile Lys Val Leu Thr Gln Ile Asp Lys Lys Glu Glu Gly
        210                 215                 220
```

Phe Val Cys Leu His Lys Ile Val Asp Glu Asp Lys Glu Leu Ala
225                 230                 235                 240

Leu Ile Glu Thr Leu Trp Lys Asn Glu Lys
                245                 250

<210> SEQ ID NO 105
<211> LENGTH: 248
<212> TYPE: PRT
<213> ORGANISM: Lactobacillus curvatus

<400> SEQUENCE: 105

Met Pro Gly Lys Gln Tyr Ser Glu Asn Tyr Gln Ile Pro Tyr Phe Glu
1               5                   10                  15

Thr Asp Ile Lys Gly Glu Leu Thr Leu Ala Ser Leu Val Asn Ile Leu
            20                  25                  30

Ile Leu Ala Ser Glu His Gln Leu Asn Ala Leu Asn Val Gly Glu Ala
        35                  40                  45

Thr Met His Ala Leu Asn Leu Gly Trp Val Val Thr Gln Tyr Gln Met
50                  55                  60

Lys Ile Thr Arg Met Pro Lys Val Asp Glu Lys Val Arg Ile Val Thr
65                  70                  75                  80

Glu Ala Glu Ser Tyr Asn Lys Tyr Phe Cys Tyr Arg Asn Phe Trp Leu
                85                  90                  95

Tyr Asp Glu Ala Gly Asn Glu Cys Val Phe Val Gln Ser Ile Phe Val
            100                 105                 110

Met Met Ser Tyr Glu Thr Arg Ser Met Val Gln Val Val Pro Glu Ile
        115                 120                 125

Met Val Pro Phe Glu Ser Ser Glu Ile Lys Gly Ser Lys Arg Phe Pro
130                 135                 140

Arg Ile Lys Lys Ile Asp Pro Lys Gln Val Thr Thr Lys Glu Tyr Arg
145                 150                 155                 160

Val Arg Tyr Phe Asp Ile Asp Gly Asn Gln His Val Asn Asn Val His
                165                 170                 175

Tyr Phe Glu Trp Met Leu Asp Ala Leu Asp Tyr Asp Phe Leu Thr Thr
            180                 185                 190

His Arg Val Ala Ser Val Asn Ile Arg Tyr Gly His Glu Ile Gln Tyr
        195                 200                 205

Gly Gln Met Thr Gln Ser Met Val Glu Gln Leu Ile Val Asp Asp Ile
210                 215                 220

Ile Thr Thr Arg His Lys Val Ala Val Asp Asp Leu Ser Ala Ala Glu
225                 230                 235                 240

Ala Glu Ile Thr Trp Lys Glu Arg
                245

<210> SEQ ID NO 106
<211> LENGTH: 249
<212> TYPE: PRT
<213> ORGANISM: Proteobacteria bacterium

<400> SEQUENCE: 106

Met Glu Leu Lys Lys Tyr Thr Lys Glu Tyr Thr Ile Arg Ser Tyr Glu
1               5                   10                  15

Cys Asp Arg Asn Asn Asn Leu Arg Ile Val Thr Leu Met Asn Ile Phe
            20                  25                  30

Gln Asp Met Ala Asp Ile Asn Ala Ala Gln Leu Gly Leu Gly Leu Asp
        35                  40                  45

Tyr Val Leu Ser Lys Gly Phe Ala Trp Val Gly Ser Asn Tyr Glu Ile
    50              55                  60

Arg Ile Lys Arg Leu Pro Lys Ile His Glu Lys Val Lys Ile Val Thr
65              70                  75                  80

Trp Pro Ala Val Glu Lys Lys Leu Ala Ala Ile Arg Asp Tyr Glu Val
                85                  90                  95

Tyr Gly Lys Asp Gly Glu Arg Ile Ile Ala Ala Ser Ser Gln Trp Ile
            100                 105                 110

Leu Ile Asn Phe Met Lys Lys Arg Pro Ile Ser Leu Arg Asp Asn Leu
        115                 120                 125

Pro Glu Tyr Gln Ile Ile Asp Asp Arg Ala Ile Glu Thr Glu Phe Glu
    130                 135                 140

Gly Lys Ile Lys Glu Val Glu Arg Ile Asp Glu Gln Thr Lys Phe Arg
145                 150                 155                 160

Val Arg Phe Asp Asp Ile Asp Leu Asn Lys His Val Asn Asn Gly Val
                165                 170                 175

Tyr Ala Leu Trp Ala Ser Glu Ala Val Asn Pro Asp Phe Arg Leu Ser
            180                 185                 190

His Asn Pro Ser Lys Ile Glu Ile Asn Tyr Lys Lys Glu Gly His Ile
        195                 200                 205

Gly Glu Lys Ile Thr Val Leu Thr Glu Cys Asp Gly Leu Val Thr Thr
210                 215                 220

His Ser Ile Gln Thr Tyr Asp Gly Asp Asn Arg Glu Leu Ala Arg Ala
225                 230                 235                 240

Arg Ile Glu Trp Ala Glu Asn Glu Glu
                245

<210> SEQ ID NO 107
<211> LENGTH: 200
<212> TYPE: PRT
<213> ORGANISM: Vibrio vulnificus

<400> SEQUENCE: 107

Met Val Arg Leu Phe Ser Leu Leu Ile Met Phe Phe Leu Ser Asn Val
1               5                   10                  15

Ala His Ala Thr Glu Lys Val Leu Ile Leu Gly Asp Ser Leu Ser Ala
            20                  25                  30

Gly Tyr Asn Met Ser Ala Glu Gln Ala Trp Pro Asn Leu Leu Pro Glu
        35                  40                  45

Ala Leu Asn Thr Tyr Gly Lys Asn Val Glu Val Ile Asn Ala Ser Ile
    50                  55                  60

Ser Gly Asp Thr Thr Gly Asn Gly Leu Ser Arg Leu Pro Glu Leu Leu
65                  70                  75                  80

Lys Thr His Ser Pro Asp Trp Val Leu Ile Glu Leu Gly Ala Asn Asp
                85                  90                  95

Gly Leu Arg Gly Phe Pro His Lys Val Ile Ser Ser Asn Leu Ser Arg
            100                 105                 110

Met Ile Gln Leu Ser Lys Ala Ser Asp Ala Lys Val Ala Leu Met Gln
        115                 120                 125

Ile Arg Val Pro Pro Asn Tyr Gly Lys Arg Tyr Thr Asp Ala Phe Val
    130                 135                 140

Glu Leu Tyr Pro Thr Leu Ala Glu His His Gln Val Pro Leu Phe Pro
145                 150                 155                 160

Phe Phe Leu Glu Glu Val Ile Val Lys Pro Glu Trp Met Met Pro Asp 165                 170                 175
Gly Leu His Pro Met Pro Glu Ala Gln Pro Trp Ile Ala Gln Phe Val
            180                 185                 190
Ala Lys Thr Phe Tyr Lys His Leu
            195                 200

<210> SEQ ID NO 108
<211> LENGTH: 261
<212> TYPE: PRT
<213> ORGANISM: Alistipes sp.

<400> SEQUENCE: 108

Met Glu Lys Ile Asn Val Ser Gly Asn Arg Phe Ser Thr Asp Ile Thr
1               5                   10                  15
Ile Pro Cys Tyr Asp Thr Asp Ala Ser Phe Arg Leu Lys Pro Ala Ala
            20                  25                  30
Phe Met Asp His Ala Gln Glu Met Ala Tyr Leu Ala Ala Gln Ala Leu
        35                  40                  45
His Phe Gly Tyr Asp Asp Leu Gln Arg His His Thr Ala Trp Val Leu
    50                  55                  60
Ser Arg Met Arg Met Asp Phe Leu Asn Pro Pro Lys Trp Thr Asp Glu
65                  70                  75                  80
Thr Thr Leu Tyr Thr Trp His Lys Gly Gln Asp Gly Leu Phe Phe Leu
                85                  90                  95
Arg Asp Phe Glu Leu Arg Arg Lys Gly Asp Thr Asp Phe Ala Asp Lys
            100                 105                 110
Ser Lys Ala Gln Val Leu Cys Thr Ser Ser Trp Ile Val Met Asn Val
        115                 120                 125
Glu Thr Arg Arg Leu Val Arg Ser Asp Glu Val Leu Asn Met Val Pro
    130                 135                 140
Ala Thr Thr Gln Cys Pro Asp Asn Ala Ile Gln Ile Pro Cys Gly Lys
145                 150                 155                 160
Val Val Met Pro Lys Asn Ile Pro Ala Glu Val Gly Cys His Lys
                165                 170                 175
Ala Ala Tyr Ser Asp Ile Asp Val Leu Gly His Thr Asn Asn Ala Arg
            180                 185                 190
Tyr Val Val Trp Ala Met Asp Cys Ile Asp Tyr Glu Glu Val Ala Gly
        195                 200                 205
Asn Pro Ile Arg Ser Ile Ser Ile Asn Phe Ile Lys Glu Thr Lys Pro
    210                 215                 220
Gly Glu Val Val Arg Ile Phe Arg Ser Val Glu Asp Ile Asp Gly Gln
225                 230                 235                 240
Lys Lys Tyr Phe Ile Glu Gly Lys Ile Glu Asp Lys Pro Cys Phe Cys
                245                 250                 255
Ala Arg Ile Asp Phe
            260

<210> SEQ ID NO 109
<211> LENGTH: 252
<212> TYPE: PRT
<213> ORGANISM: Alkalibacterium sp.

<400> SEQUENCE: 109

Met Ser Leu Val Tyr Lys Ser Glu Lys Thr Ile Thr His Tyr Met Cys
1               5                   10                  15
Asp Arg Ser Arg Ser Leu Thr Leu Pro Met Leu Val Asn Leu Leu Leu

```
                    20                  25                  30
Glu Val Ser Glu Glu Gln Ser Ser Glu Leu Ser Arg Asp Glu Ser Tyr
                35                  40                  45

Leu Lys Ala Arg Gly Val Asn Trp Ile Ile Leu Arg Tyr Glu Phe Ser
            50                  55                  60

Val Ser Arg Met Pro Asn Leu Lys Glu Thr Ile Asn Ile Glu Thr Arg
65                  70                  75                  80

Ala Ser Glu Tyr Asn Lys Leu Phe Thr Tyr Arg Glu Phe Val Val Lys
                85                  90                  95

Asp Ser Ser Gly Lys Val Leu Leu Thr Val Asp Thr Thr Phe Ala Leu
            100                 105                 110

Met Asp Leu Ser Thr Arg Lys Met Val Arg Leu Thr Asp Glu Ile Val
        115                 120                 125

Ser Pro Tyr Gln Ala Thr Ala Ser Arg Arg Ile Arg Arg Ser Asp Lys
    130                 135                 140

Pro Lys Glu Leu Thr Asp Phe Asp Asp Cys Lys Gln Arg Thr Phe Asp
145                 150                 155                 160

Val Arg Tyr Phe Asp Ile Asp Gly Asn Gly His Val Asn Asn Ala His
                165                 170                 175

Tyr Ile Ser Trp Leu Leu Asp Ser Leu Pro Ser Asp Phe Leu Lys Ser
            180                 185                 190

His Glu Val Ser Trp Gly Val Ile Ala Phe Asp Lys Glu Val Ser Glu
        195                 200                 205

His Gln Ser Ile Asp Ser Leu Ser Met Arg Arg Lys Glu Arg Gly Thr
    210                 215                 220

Ala Thr Asp His Gln Ile Lys Ser Glu Ala Ala Val His Cys Lys Ala
225                 230                 235                 240

Ser Phe Thr Trp Lys Lys Leu Asn Lys Glu Glu His
                245                 250

<210> SEQ ID NO 110
<211> LENGTH: 397
<212> TYPE: PRT
<213> ORGANISM: Macaca fascicularis

<400> SEQUENCE: 110

Met Ala Arg Pro Gly Leu Ile His Ser Ser Pro Gly Leu Pro Asp Thr
1               5                   10                  15

Cys Ala Leu Leu Gln Pro Pro Ala Ala Ser Ala Ser Ala Ala Pro Ser
                20                  25                  30

Met Ser Gly Pro Asp Val Glu Thr Pro Ser Ala Ile Gln Ile Cys Arg
            35                  40                  45

Ile Met Arg Pro Asp Asp Ala Asn Val Ala Gly Asn Val His Gly Gly
        50                  55                  60

Thr Ile Leu Lys Met Ile Glu Glu Ala Gly Ala Ile Ile Ser Thr Arg
65                  70                  75                  80

His Cys Asn Ser Gln Asn Gly Glu Arg Cys Val Ala Ala Leu Ala Arg
                85                  90                  95

Val Glu Arg Thr Asp Phe Leu Ser Pro Met Cys Ile Gly Glu Val Ala
            100                 105                 110

His Val Ser Ala Glu Ile Thr Tyr Thr Ser Lys His Ser Val Glu Val
        115                 120                 125

Gln Val Asn Val Met Ser Glu Asn Ile Leu Thr Gly Ala Lys Lys Leu
    130                 135                 140
```

Thr Asn Lys Ala Thr Leu Trp Tyr Val Pro Leu Ser Leu Lys Asn Val
145                 150                 155                 160

Asp Lys Val Leu Glu Val Pro Pro Val Val Tyr Ser Arg Gln Glu Gln
                165                 170                 175

Glu Glu Glu Gly Arg Lys Arg Tyr Glu Ala Gln Lys Leu Glu Arg Met
            180                 185                 190

Glu Thr Lys Trp Arg Asn Gly Asp Ile Val Gln Pro Val Leu Asn Pro
        195                 200                 205

Glu Pro Asn Thr Val Ser Tyr Ser Gln Ser Ser Leu Ile His Leu Val
    210                 215                 220

Gly Pro Ser Asp Cys Thr Leu His Gly Phe Val His Gly Val Thr
225                 230                 235                 240

Met Lys Leu Met Asp Glu Val Ala Gly Ile Val Ala Ala Arg His Cys
                245                 250                 255

Lys Thr Asn Ile Val Thr Ala Ser Val Asp Ala Ile Asn Phe His Asp
                260                 265                 270

Lys Ile Arg Lys Gly Cys Val Ile Thr Ile Ser Gly Arg Met Thr Phe
            275                 280                 285

Thr Ser Asn Lys Ser Met Glu Ile Glu Val Leu Val Asp Ala Asp Pro
        290                 295                 300

Val Val Asp Ser Ser Gln Lys Arg Tyr Arg Ala Ala Ser Ala Phe Phe
305                 310                 315                 320

Thr Tyr Val Ser Leu Ser Gln Glu Gly Arg Ser Leu Pro Val Pro Gln
                325                 330                 335

Leu Val Pro Glu Thr Glu Asp Glu Lys Lys Arg Phe Glu Glu Gly Lys
            340                 345                 350

Gly Arg Tyr Leu Gln Met Lys Ala Lys Arg Gln Gly His Thr Glu Pro
        355                 360                 365

Arg Val Ala Met Ala Thr Gly Pro Val Ser Thr Gln Lys Phe Pro Pro
    370                 375                 380

Trp Pro Lys Thr Arg Phe Thr Leu Arg Ala Gly Ile Val
385                 390                 395

<210> SEQ ID NO 111
<211> LENGTH: 418
<212> TYPE: PRT
<213> ORGANISM: Populus trichocarpa

<400> SEQUENCE: 111

Met Val Ala Thr Ala Ala Ser Ser Phe Phe Pro Val Pro Ser Pro
1               5                   10                  15

Ser Gly Asp Ala Lys Ala Ser Lys Phe Gly Ser Val Ser Ala Ser Leu
                20                  25                  30

Gly Gly Ile Lys Thr Lys Ser Ala Ser Ser Gly Ala Leu Gln Val Asn
            35                  40                  45

Thr Asn Gly Gln Ala Pro Pro Lys Ile Asn Gly Pro Val Gly Leu
        50                  55                  60

Ala Ala Ser Val Glu Thr Leu Lys Asn Glu Asp Val Val Ser Ser Pro
65                  70                  75                  80

Ala Pro Arg Thr Phe Ile Asn Gln Leu Pro Asp Trp Ser Met Leu Leu
                85                  90                  95

Ala Ala Ile Thr Thr Met Phe Leu Ala Ala Glu Lys Gln Trp Met Met
            100                 105                 110

Leu Asp Trp Lys Pro Lys Arg Pro Asp Met Leu Ile Asp Pro Phe Gly
        115                 120                 125

Ile Gly Arg Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Lys Thr Ala
            165                 170                 175

Gly Leu Gly Asp Gly Phe Gly Ala Thr Pro Glu Met Ser Lys Arg
            180                 185                 190

Asn Leu Ile Trp Val Val Thr Arg Met Gln Ile Leu Val Asp Arg Tyr
        195                 200                 205

Pro Thr Trp Gly Asp Val Val Gln Val Asp Thr Trp Val Ser Ala Ser
    210                 215                 220

Gly Lys Asn Gly Met Arg Arg Asp Trp Leu Val Arg Asp Ala Lys Thr
225                 230                 235                 240

Gly Glu Thr Leu Thr Arg Ala Ser Ser Val Trp Val Met Met Asn Lys
            245                 250                 255

Val Thr Arg Arg Leu Ala Lys Ile Pro Glu Val Arg Gly Glu Ile
        260                 265                 270

Glu Pro Tyr Phe Leu Thr Ser Asp Pro Val Val Ile Glu Asp Ser Arg
    275                 280                 285

Lys Leu Pro Lys Ile Asp Asp Asn Thr Ala Asp Tyr Ile Cys Glu Ser
290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Ala Pro Pro Ile Met
            325                 330                 335

Glu Ser His Glu Leu Ala Ala Ile Thr Leu Glu Tyr Arg Arg Glu Cys
            340                 345                 350

Gly Arg Asp Ser Val Leu Gln Ser Leu Thr Ala Val Ser Asp Thr Gly
        355                 360                 365

Ile Gly Asn Leu Gly Asn Pro Gly Glu Val Glu Phe Gln His Leu Leu
    370                 375                 380

Arg Phe Glu Glu Gly Ala Glu Ile Val Arg Gly Arg Thr Glu Trp Arg
385                 390                 395                 400

Pro Lys His Ala Asp Asn Phe Gly Ile Met Gly His Ile Pro Ala Glu
            405                 410                 415

Ser Ala

<210> SEQ ID NO 112
<211> LENGTH: 245
<212> TYPE: PRT
<213> ORGANISM: Alkaliphilus oremlandii

<400> SEQUENCE: 112

Met Ala Arg Tyr Thr Glu Glu Phe Val Ile Pro Tyr Tyr Asp Cys Ser
1               5                   10                  15

Gly Asp Arg Phe Val Arg Pro Glu Ser Leu Leu Glu Tyr Met Gly Glu
            20                  25                  30

Ala Ser Leu Leu His Gly Asp Thr Leu Gly Val Gly Gly Ala Asp Leu
        35                  40                  45

Phe Lys Met Gly Phe Ala Trp Met Leu Asn Arg Trp Lys Val Arg Phe
    50                  55                  60

Ile Glu Tyr Pro Lys Ser Arg Thr Thr Ile Thr Val Glu Thr Trp Ser
65                  70                  75                  80

```
Ser Gly Val Asp Arg Phe Tyr Ala Thr Arg Glu Phe Asn Ile Tyr Asp
            85                  90                  95

Ser Asp Arg Lys Leu Leu Val Gln Ala Ser Thr Gln Trp Val Phe Cys
        100                 105                 110

His Ile Leu Lys Arg Lys Pro Ala Arg Val Pro Asp Ile Ile Ser Ala
    115                 120                 125

Val Tyr Asp Ser Glu Asp Glu His Asn Phe Tyr His Phe His Asp Phe
130                 135                 140

Lys Asp Glu Val Gln Ala Asp Glu Ala Ile Glu Phe Arg Val Arg Lys
145                 150                 155                 160

Ser Asp Ile Asp Phe Asn His His Val Asn Asn Val Lys Tyr Leu Asn
                165                 170                 175

Trp Met Leu Glu Val Leu Pro Lys Gln Phe Glu Asp Gln Tyr Leu Tyr
            180                 185                 190

Glu Leu Asp Ile Gln Tyr Lys Lys Gly Ile Lys Gln Gly Ser Leu Ile
        195                 200                 205

Lys Ser Glu Val Ser Met Asp Ile Glu Gly Glu Glu Thr Val Cys Tyr
    210                 215                 220

His Lys Ile Thr Ser Asn Ser Val Leu His Ala Phe Gly Arg Ser Val
225                 230                 235                 240

Trp Lys Asn Arg Lys
                245

<210> SEQ ID NO 113
<211> LENGTH: 380
<212> TYPE: PRT
<213> ORGANISM: Homo sapiens

<400> SEQUENCE: 113

Met Lys Leu Leu Ala Arg Ala Leu Arg Leu Cys Glu Phe Gly Arg Gln
1               5                   10                  15

Ala Ser Ser Arg Arg Leu Val Ala Gly Gln Gly Cys Val Gly Pro Arg
            20                  25                  30

Arg Gly Cys Cys Ala Pro Val Gln Val Val Gly Pro Arg Ala Asp Leu
        35                  40                  45

Pro Pro Cys Gly Ala Cys Ile Thr Gly Arg Ile Met Arg Pro Asp Asp
    50                  55                  60

Ala Asn Val Ala Gly Asn Val His Gly Gly Thr Ile Leu Lys Met Ile
65                  70                  75                  80

Glu Glu Ala Gly Ala Ile Ile Ser Thr Arg His Cys Asn Ser Gln Asn
            85                  90                  95

Gly Glu Arg Cys Val Ala Ala Leu Ala Arg Val Glu Arg Thr Asp Phe
        100                 105                 110

Leu Ser Pro Met Cys Ile Gly Glu Val Ala His Val Ser Ala Glu Ile
    115                 120                 125

Thr Tyr Thr Ser Lys His Ser Val Glu Val Gln Val Asn Val Met Ser
130                 135                 140

Glu Asn Ile Leu Thr Gly Ala Lys Lys Leu Thr Asn Lys Ala Thr Leu
145                 150                 155                 160

Trp Tyr Val Pro Leu Ser Leu Lys Asn Val Asp Lys Val Leu Glu Val
                165                 170                 175

Pro Pro Val Val Tyr Ser Arg Gln Glu Gln Glu Glu Glu Gly Arg Lys
            180                 185                 190

Arg Tyr Glu Ala Gln Lys Leu Glu Arg Met Glu Thr Lys Trp Arg Asn
```

```
        195                 200                 205
Gly Asp Ile Val Gln Pro Val Leu Asn Pro Glu Pro Asn Thr Val Ser
    210                 215                 220

Tyr Ser Gln Ser Ser Leu Ile His Leu Val Gly Pro Ser Asp Cys Thr
225                 230                 235                 240

Leu His Gly Phe Val His Gly Val Thr Met Lys Leu Met Asp Glu
                245                 250                 255

Val Ala Gly Ile Val Ala Arg His Cys Lys Thr Asn Ile Val Thr
            260                 265                 270

Ala Ser Val Asp Ala Ile Asn Phe His Asp Lys Ile Arg Lys Gly Cys
        275                 280                 285

Val Ile Thr Ile Ser Gly Arg Met Thr Phe Thr Ser Asn Lys Ser Met
    290                 295                 300

Glu Ile Glu Val Leu Val Asp Ala Asp Pro Val Val Asp Ser Ser Gln
305                 310                 315                 320

Lys Arg Tyr Arg Ala Ala Ser Ala Phe Phe Thr Tyr Val Ser Leu Ser
                325                 330                 335

Gln Glu Gly Arg Ser Leu Pro Val Pro Gln Leu Val Pro Glu Thr Glu
            340                 345                 350

Asp Glu Lys Lys Arg Phe Glu Glu Gly Lys Gly Arg Tyr Leu Gln Met
        355                 360                 365

Lys Ala Lys Arg Gln Gly His Ala Glu Pro Gln Pro
    370                 375                 380

<210> SEQ ID NO 114
<211> LENGTH: 338
<212> TYPE: PRT
<213> ORGANISM: Bos taurus

<400> SEQUENCE: 114

Met Ser Gly Pro Ala Ala Glu Thr Pro Ser Ala Ile Gln Ile Cys Arg
1               5                   10                  15

Ile Met Arg Pro Asp Asp Ala Asn Val Ala Gly Asn Val His Gly Gly
            20                  25                  30

Thr Val Leu Lys Met Ile Glu Glu Ala Gly Ala Ile Ile Ser Thr Arg
        35                  40                  45

His Cys Asn Ser Gln Asn Gly Glu Arg Cys Val Ala Ala Leu Ala Arg
    50                  55                  60

Val Glu Arg Thr Asp Phe Leu Ser Pro Met Cys Ile Gly Glu Val Ala
65                  70                  75                  80

His Val Ser Ala Glu Ile Thr Tyr Thr Ser Lys His Ser Val Glu Val
                85                  90                  95

Gln Val His Val Met Ser Glu Asn Ile Leu Thr Gly Thr Lys Lys Leu
            100                 105                 110

Thr Asn Lys Ala Thr Leu Trp Tyr Val Pro Leu Ser Leu Lys Asn Val
        115                 120                 125

Asp Lys Val Leu Glu Val Pro Pro Val Val Tyr Ser Arg Gln Glu Gln
    130                 135                 140

Glu Glu Glu Gly Arg Lys Arg Tyr Glu Ala Gln Lys Leu Glu Arg Met
145                 150                 155                 160

Glu Thr Lys Trp Arg Asn Gly Asp Ile Ile Gln Pro Val Leu Asn Pro
                165                 170                 175

Glu Pro Asn Thr Val Ser Tyr Ser Gln Ser Ser Leu Ile His Leu Val
            180                 185                 190
```

```
Gly Pro Ser Asp Cys Thr Leu His Gly Phe Val His Gly Val Thr
            195                 200                 205

Met Lys Leu Met Asp Glu Val Ala Gly Ile Val Ala Ala Arg His Cys
    210                 215                 220

Lys Thr Asn Ile Val Thr Ala Ser Val Asp Ala Ile Asn Phe His Asp
225                 230                 235                 240

Lys Ile Arg Lys Gly Cys Val Ile Thr Ile Ser Gly Arg Met Thr Phe
                245                 250                 255

Thr Ser Asn Lys Ser Met Glu Ile Glu Val Leu Val Asp Ala Asp Pro
            260                 265                 270

Val Val Asn Asn Phe Val Lys Arg Tyr Arg Ala Ala Ser Ala Phe Phe
        275                 280                 285

Thr Tyr Val Ser Leu Ser Pro Glu Gly Lys Ser Leu Pro Val Pro Gln
    290                 295                 300

Leu Val Pro Glu Thr Glu Asp Glu Lys Lys Arg Phe Glu Glu Gly Lys
305                 310                 315                 320

Gly Arg Tyr Leu Gln Met Lys Ala Lys Arg Gln Gly Gln Ala Glu Thr
                325                 330                 335

Gln Ala
```

<210> SEQ ID NO 115
<211> LENGTH: 169
<212> TYPE: PRT
<213> ORGANISM: Caenorhabditis elegans

<400> SEQUENCE: 115

```
Met Val Gly His Ser Glu Ser Ser Thr Asp Ala Val Ile Glu Pro Thr
1               5                   10                  15

Ser Glu Glu Leu Leu Ala Glu Gln Val Arg Val Phe Asn Lys Met Lys
            20                  25                  30

Gly Ser Thr Asn Phe Asn Arg Val Ala Glu Asp Val Tyr Pro Val Glu
        35                  40                  45

Val Thr Lys Ser Lys Leu Val Cys Glu Met Val Val Gln His Gln His
    50                  55                  60

Leu Asn Ser Lys Gly Thr Leu His Gly Gly Gln Thr Ala Thr Leu Thr
65                  70                  75                  80

Asp Val Ile Thr Ala Arg Ala Val Gly Val Thr Val Lys Asp Lys Gly
                85                  90                  95

Met Ala Ser Val Glu Leu Ala Val Ser Tyr Leu Leu Pro Val Lys Val
            100                 105                 110

Gly Asp Val Leu Glu Ile Thr Ala His Val Leu Lys Val Gly Arg Thr
        115                 120                 125

Met Ala Phe Thr Asp Cys Glu Phe Arg Arg Lys Ser Asp Gly Lys Met
    130                 135                 140

Ser Ala Lys Gly Lys His Thr Leu Ala Phe Leu Pro Asn Gln Pro Gly
145                 150                 155                 160

Ile Ser Val Glu Asn Gly Thr Gln Phe
                165
```

<210> SEQ ID NO 116
<211> LENGTH: 238
<212> TYPE: PRT
<213> ORGANISM: Blautia hydrogenotrophica

<400> SEQUENCE: 116

```
Met Gly Tyr Gln Phe Arg Ser Arg Val Arg Tyr Ser Glu Ile Asp Glu
```

```
              1               5                  10                 15
Asp Gly Lys Leu Thr Leu Pro Ala Ile Leu Asn Tyr Phe Gln Asp Cys
                20                  25                  30

Cys Thr Phe His Ser Glu Asp Val Gly Leu Gly Met Lys Lys Leu Arg
                35                  40                  45

Lys Ile His Arg Gly Trp Val Leu Ser Ser Trp Gln Ile Ile Val Glu
 50                  55                  60

Arg Tyr Pro Glu His Gly Glu Glu Leu Thr Val Glu Thr Trp Pro Tyr
 65                  70                  75                  80

Asp Phe Lys Gly Phe Met Gly Met Arg Asn Phe Ile Leu Arg Thr Ser
                85                  90                  95

Gln Gly Glu Ser Leu Cys Lys Ala Asn Thr Leu Trp Ser Phe Met Asn
                100                 105                 110

Thr Asp Ser Gly Met Pro Val Lys Leu Gln Pro Glu Asn Thr Gln Gly
                115                 120                 125

Tyr Gln Leu Glu Pro Lys Leu Glu Met Glu Tyr Ala Pro Arg Lys Ile
                130                 135                 140

Gly Leu Leu Ser Gln Gly Glu Lys Arg Glu Ser Phe Leu Val Gln Lys
145                 150                 155                 160

His His Leu Asp Thr Asn His His Val Asn Asn Ser Gln Tyr Ile Thr
                165                 170                 175

Met Ala Thr Glu Tyr Leu Pro Lys Asp Phe Glu Ile Trp Gln Met Arg
                180                 185                 190

Ala Glu Tyr Lys Met Gln Ala Arg Leu Gly Glu Arg Ile Ile Pro Trp
                195                 200                 205

Val Ser Glu Glu Pro Lys Arg Cys Val Val Ser Leu Asn Gln Glu Thr
                210                 215                 220

Gly Lys Pro Tyr Ala Ile Val Glu Phe Ser Lys Lys Glu Lys
225                 230                 235

<210> SEQ ID NO 117
<211> LENGTH: 253
<212> TYPE: PRT
<213> ORGANISM: Granulicatella elegans

<400> SEQUENCE: 117

Met Thr Val Asp Val Ile Cys Gln Ile Glu Arg Thr Ile Leu Pro Tyr
1               5                   10                  15

Glu Cys Asp Trp Lys Glu Asn Leu Leu Leu Ser Gln Ala Leu Gly Met
                20                  25                  30

Met Met Leu Ala Ser Arg Lys Gln Gln Gln Leu Gln Asn Pro Asn
                35                  40                  45

Leu Ile Tyr Glu Lys Gly Tyr Thr Trp Ile Val Ile Gln His Glu Ile
 50                  55                  60

Glu Ile Gln Arg Met Pro Lys Val Asp Glu Val Ile Ile Glu Thr
 65                  70                  75                  80

Gln Ala Ile Ser Tyr Asn Lys Phe Phe Thr Tyr Arg Glu Tyr Arg Ile
                85                  90                  95

Leu Ser Lys Glu Arg Glu Glu Leu Phe Lys Cys Ile Thr Thr Phe Ala
                100                 105                 110

Met Leu Asp Met Lys Ala Arg Lys Ile Val Ser Ile Asp Glu Glu Val
                115                 120                 125

Val Leu Glu Tyr Pro Leu Ser Ile Gly Lys Glu Met Arg Lys Ala Thr
                130                 135                 140
```

```
Arg Ile Pro Lys Lys Asp Phe Ser Asp Ala Thr Thr Gly Glu Tyr Lys
145                 150                 155                 160

Ile Arg Ile Asn Asp Ile Asp Ala Asn Leu His Val Asn Asn Ala Arg
                165                 170                 175

Tyr Phe Asp Phe Ala Phe Ser Glu Leu Gly Met Glu Phe Ile Glu Asp
            180                 185                 190

His Gln Leu Lys Gln Val Val Ile Lys Tyr Glu Lys Glu Val Leu Pro
        195                 200                 205

Glu Ser Thr Ile Ser Cys Ser Thr Leu Trp Glu Glu Asn Thr Leu Glu
    210                 215                 220

Ser Gln Glu Arg Arg Gln Thr Tyr His Leu Ile Ser Gln Asp Gly Asn
225                 230                 235                 240

Arg Cys Ala Asn Ile Gln Met Lys Trp Glu Glu Ile Val
                245                 250

<210> SEQ ID NO 118
<211> LENGTH: 241
<212> TYPE: PRT
<213> ORGANISM: Firmicutes bacterium

<400> SEQUENCE: 118

Met Glu Pro Ile Phe Gln Gln Asp Phe Pro Val Gln Glu Leu Cys Val
1               5                   10                  15

Asp Arg Tyr Gly Arg Leu Lys Pro Ser Thr Leu Leu Tyr Phe Ala Gln
                20                  25                  30

Glu Ile Ala Gly Arg His Cys Asp Glu Leu Ala Asp Thr Leu Glu Ser
            35                  40                  45

His Arg Leu Phe Trp Ala Val Thr Arg His Arg Val Gln Ile Asn Arg
50                  55                  60

Leu Pro Glu Leu Gly Glu Thr Val His Ile Glu Thr Trp Pro Met Pro
65                  70                  75                  80

Asn Thr His Val Gly Tyr Pro Arg Ser Ile Val Ile Tyr Asp Gln Ala
                85                  90                  95

Gly Asn Glu Cys Ser Arg Ser Ile Ser Leu Trp Val Leu Met Asp Gln
            100                 105                 110

Asp Thr Arg Ser Ser Val Ser Pro Asp Lys Ser Gly Ile Ile Val Pro
        115                 120                 125

Gly Thr Leu Arg Gly Thr Glu Leu Ala Leu Pro Gly Gly Leu Val Pro
    130                 135                 140

Arg Ala Met Glu His Ser Cys Gln Arg Asp Val Cys Phe Thr Asp Leu
145                 150                 155                 160

Asp Arg Asn Gly His Met Asn Asn Thr Arg Tyr Met Asp Trp Ile Asp
                165                 170                 175

Asp Leu Leu Pro Ser Asp Phe His Arg Glu His Pro Val Lys Glu Phe
            180                 185                 190

Ala Val Arg Tyr His Ser Glu Ala Arg Glu Gly Gln Arg Leu Asp Leu
        195                 200                 205

His Trp Asp Phe Val Glu Asp Asn Cys Leu Arg Val Asp Ala Arg Arg
    210                 215                 220

Arg Asn Glu Thr Arg Asp Glu Leu Val Phe Ser Ala Lys Val Leu Phe
225                 230                 235                 240

Asp

<210> SEQ ID NO 119
<211> LENGTH: 247
```

```
<212> TYPE: PRT
<213> ORGANISM: Clostridium sp.

<400> SEQUENCE: 119

Met Lys Leu Glu Asn Ser Ile Phe Glu Glu Thr Tyr Arg Thr Ser Phe
1               5                   10                  15

Ser Gln Thr Gly Ile His Glu Thr Leu Thr Asn Lys Ser Phe Leu Ser
            20                  25                  30

Met Met Glu Asn Leu Ala Gly Ala His Ser Gly Tyr Cys His Tyr Ser
        35                  40                  45

Phe Ala Asn Leu Ala Pro Glu His Lys Thr Trp Ile Ile Leu Asn Trp
    50                  55                  60

Lys Leu Gln Val Phe Arg Arg Pro Tyr Ala Asp Glu Ile Val Thr Leu
65                  70                  75                  80

Lys Thr Trp Gly His Phe Ala Asn Lys Ile Tyr Val Leu Arg Asp Phe
                85                  90                  95

Lys Met Leu Asp Lys Asp Gly Asn Leu Leu Ala Ile Ala Ser Ser Lys
            100                 105                 110

Trp Cys Leu Phe Asp Phe Ser Thr Gly Arg Ile Ala Arg Leu Pro Asp
        115                 120                 125

Asn Leu Glu Glu Ile Tyr Gln Gly Phe Asn Ser Glu Ser Val Phe Asn
    130                 135                 140

Cys Asn Asp Leu Pro Lys Leu Lys Ala Pro Glu Ser Glu Pro Ile Ala
145                 150                 155                 160

Ser Asp Thr Tyr Lys Ile Arg Arg Phe Asp Leu Asp Leu Asn Lys His
                165                 170                 175

Val His Asn Leu Asn Tyr Leu Asn Ile Ala Tyr Glu Leu Leu Pro Leu
            180                 185                 190

Asp Val Tyr Asp Gly Pro Glu Leu Asn Asn Val Glu Ile Val Tyr Lys
        195                 200                 205

Lys Glu Ile Lys Tyr Gly Asp Thr Ile Lys Ser Tyr Leu Tyr Lys Glu
    210                 215                 220

Asn Asp Ser Tyr Ile Ile Val Ile Lys Ser Leu Asp Gly Ser Ile Val
225                 230                 235                 240

His Ser Ile Val Lys Leu Tyr
                245

<210> SEQ ID NO 120
<211> LENGTH: 250
<212> TYPE: PRT
<213> ORGANISM: Streptococcus pyogenes

<400> SEQUENCE: 120

Met Gly Leu Ser Tyr Gln Glu Glu Leu Thr Leu Pro Phe Glu Leu Cys
1               5                   10                  15

Asp Val Lys Ser Asp Ile Lys Leu Pro Leu Leu Leu Asp Tyr Cys Leu
            20                  25                  30

Met Val Ser Gly Arg Gln Ser Ala Gln Leu Gly Arg Ser Asn Asn Asn
        35                  40                  45

Leu Leu Val Asp Tyr Lys Leu Val Trp Ile Val Thr Asp Tyr Glu Ile
    50                  55                  60

Thr Ile His Arg Leu Pro His Phe Gln Glu Thr Ile Thr Ile Glu Thr
65                  70                  75                  80

Lys Ala Leu Ser Tyr Asn Lys Phe Phe Cys Tyr Arg Gln Phe Tyr Ile
                85                  90                  95
```

```
Tyr Asp Gln Glu Gly Cys Leu Leu Val Asp Ile Leu Ala Tyr Phe Ala
            100                 105                 110

Leu Leu Asn Pro Asp Thr Arg Lys Val Ala Thr Ile Pro Glu Asp Leu
        115                 120                 125

Val Ala Pro Phe Lys Thr Asp Phe Val Lys Lys Leu His Arg Ala Pro
130                 135                 140

Lys Met Pro Leu Leu Glu Gln Ser Ile Asp Arg Asp Tyr Tyr Val Arg
145                 150                 155                 160

Tyr Phe Asp Ile Asp Met Asn Gly His Val Asn Asn Ser Lys Tyr Leu
                165                 170                 175

Asp Trp Met Tyr Asp Val Leu Gly Cys Glu Phe Leu Lys Thr His Gln
            180                 185                 190

Pro Leu Lys Met Thr Leu Lys Tyr Val Lys Glu Val Ser Pro Gly Gly
        195                 200                 205

Gln Ile Thr Ser Ser Tyr His Leu Asp Gln Leu Thr Ser Tyr His Gln
    210                 215                 220

Ile Thr Ser Asp Gly Gln Leu Asn Ala Gln Ala Met Ile Glu Trp Arg
225                 230                 235                 240

Ala Ile Lys Gln Thr Glu Ser Glu Thr Asp
                245                 250

<210> SEQ ID NO 121
<211> LENGTH: 249
<212> TYPE: PRT
<213> ORGANISM: Clostridium sp.

<400> SEQUENCE: 121

Met Gly Ile Ser Tyr Glu Lys Met Tyr Glu Ile His Tyr Tyr Glu Cys
1               5                   10                  15

Asp Lys Asn Leu Asn Cys Thr Leu Glu Ser Ile Met Asn Phe Leu Gly
            20                  25                  30

Asp Val Gly Asn Lys His Ala Glu Ser Leu Asn Val Gly Met Glu Tyr
        35                  40                  45

Leu Thr Glu Arg Asn Leu Thr Trp Val Phe Tyr Lys Tyr Asn Ile Lys
    50                  55                  60

Ile Asn Arg Tyr Pro Lys Tyr Glu Glu Lys Ile Lys Val Lys Thr Val
65                  70                  75                  80

Ala Glu Glu Phe Lys Lys Phe Tyr Ala Leu Arg Thr Tyr Glu Ile Tyr
                85                  90                  95

Asp Glu Asn Asn Ile Lys Ile Val Glu Gly Ser Ala Leu Phe Leu Leu
            100                 105                 110

Ile Asp Ile Val Lys Arg Arg Ala Val Lys Ile Thr Asp Asp Gln Tyr
        115                 120                 125

Lys Ala Tyr Asn Val Asp Lys Gly Ser Thr Gly Lys Asn Leu Ile Gly
    130                 135                 140

Arg Leu Glu Arg Leu Glu Lys Val Lys Asn Asn Glu Tyr Val Ser Asn
145                 150                 155                 160

Phe Lys Val Arg Tyr Ser Asp Ile Asp Phe Asn Lys His Val Asn Asn
                165                 170                 175

Val Lys Tyr Val Gln Trp Phe Met Asp Ser Val Pro Gln Glu Ile Arg
            180                 185                 190

Glu Glu Tyr Glu Leu Lys Glu Ile Asp Ile Leu Phe Glu His Glu Cys
        195                 200                 205

Tyr Tyr Asn Asp Glu Ile Lys Cys Val Cys Glu Ile His Lys Asn Glu
    210                 215                 220
```

Asp Asn Leu Leu Val Leu Ser Asn Ile Gln Asp Lys Asp Gly Lys Glu
225                 230                 235                 240

Leu Thr Val Phe Val Ser Lys Trp Glu
                245

<210> SEQ ID NO 122
<211> LENGTH: 243
<212> TYPE: PRT
<213> ORGANISM: Clostridium sp.

<400> SEQUENCE: 122

Met Gly Tyr Phe Glu His Asp Phe Glu Ile Gly Leu Arg Asp Val Glu
1               5                   10                  15

Asn Pro Asn Tyr Leu Ser Asn Lys Ala Ile Leu Ala Phe Phe Glu Asn
                20                  25                  30

Ile Gly Ser Tyr His Ser Asp Ser Ile Asn Phe Gly Leu Asn Glu Ile
            35                  40                  45

Pro Lys Thr Lys Ser Ser Trp Val Leu Gly Trp Lys Val Lys Val
    50                  55                  60

Leu Lys Arg Pro Leu Tyr Gly Asp Lys Leu His Ile Val Thr Trp Ala
65                  70                  75                  80

Arg Asn Thr Glu Lys Phe Ser Thr Tyr Arg Asp Tyr Glu Val Tyr Asn
                85                  90                  95

Gln Asn Asn Glu Leu Val Ile Ile Gly Thr Ser Lys Trp Val Leu Val
                100                 105                 110

Asn Thr Thr Thr Gly Lys Leu Arg Pro Ile Pro Glu Glu Ile Ile Lys
            115                 120                 125

Leu Tyr Cys Pro Asp Thr Lys Thr Ala Phe Pro Pro Glu Glu Ala Leu
130                 135                 140

Leu Thr Lys Leu Thr Asp Ser Glu His Tyr Gly Thr Ala Cys Thr Cys
145                 150                 155                 160

Thr Val Gly Arg Ser Gln Ile Asp Leu Asn Asn His Met His Asn Leu
                165                 170                 175

Tyr Tyr Leu Asp Met Ala Tyr Glu Ala Leu Pro Glu Glu Val Tyr Lys
            180                 185                 190

Asn Asn Thr Phe Asn Phe Phe Glu Ile Thr Tyr Lys Lys Gln Ile Arg
        195                 200                 205

Leu His Asp Ala Val Lys Cys Tyr Tyr Val Phe Glu Glu Asn Thr His
    210                 215                 220

Lys Val Val Ile Lys Ser Leu Asp Asp Lys Lys Thr His Ala Ile Ile
225                 230                 235                 240

Val Phe Lys

<210> SEQ ID NO 123
<211> LENGTH: 218
<212> TYPE: PRT
<213> ORGANISM: Zea mays

<400> SEQUENCE: 123

Met His His Arg Phe Ala Gly Leu Val Pro Thr Ala Arg Pro Ala Leu
1               5                   10                  15

Pro Pro Ile His Gly Gly Val Gly Arg Ser Tyr Pro Pro Val His
                20                  25                  30

Arg Ser Leu Ala Leu Arg Leu Ala Pro Phe Ala Ser Ala Ser Val Arg
            35                  40                  45

Arg Ala Cys Arg Pro Leu Ala Val Ser Ala Gln Ser Thr Ser Leu Arg
    50              55                  60

Pro Glu Lys Phe Phe Glu Val Glu Met Lys Val Arg Asp Tyr Glu Ile
65              70                  75                  80

Asp Gln Tyr Gly Val Val Asn Asn Ala Ile Tyr Ala Ser Tyr Cys Gln
                85                  90                  95

His Gly Arg His Glu Leu Leu Glu Ser Val Gly Ile Ser Ala Asp Ala
            100                 105                 110

Val Ala Arg Ser Gly Glu Ser Leu Ala Leu Ser Glu Leu Asn Leu Lys
            115                 120                 125

Tyr Phe Ala Pro Leu Arg Ser Gly Asp Lys Val Val Lys Val Arg
    130             135                 140

Leu Ala Gly Ile Lys Gly Val Arg Met Ile Phe Asp His Ile Ile Thr
145             150                 155                 160

Lys Leu Pro Asn His Glu Leu Ile Leu Glu Ala Lys Ala Thr Ala Val
                165                 170                 175

Cys Leu Asn Lys Asp Tyr Tyr Pro Thr Arg Ile Pro Arg Glu Leu Leu
            180                 185                 190

Ser Lys Met Gln Leu Phe Leu Pro Val Asp Ser Arg Gly Ser Asn Glu
    195                 200                 205

Asp Val Asn Asn Arg Asn Asn Ser Cys Asn
    210                 215

<210> SEQ ID NO 124
<211> LENGTH: 245
<212> TYPE: PRT
<213> ORGANISM: Mesotoga infera

<400> SEQUENCE: 124

Met Lys Pro Val Val Thr Lys Glu Val Tyr Arg Val Arg Tyr Tyr Glu
1               5                   10                  15

Leu Asp Cys Gln Trp Lys Ala Ser Ile Ser Ser Leu Met Asp Tyr Phe
            20                  25                  30

Asn Asp Val Val Thr Leu Gln Thr Val Glu Met Gly His Gly Val Asp
            35                  40                  45

Val Met Ser Lys Gly Glu Tyr Ala Trp Leu Leu Leu Arg Trp Asp Val
    50              55                  60

Lys Val Asn Arg Tyr Pro Asp Tyr Leu Glu Asn Val Val Gln Thr
65              70                  75                  80

Ile Pro Tyr Ser Met Asp Arg Phe Tyr Ala Tyr Arg Arg Phe Glu Ile
                85                  90                  95

Phe Asp Cys Ser Gly Asn Val Ile Val Asp Ala Asn Ser Gln Trp Ile
            100                 105                 110

Leu Ile Asp Gln Arg Lys Arg Pro Ile Arg Ile Gly Asp Gln Phe
            115                 120                 125

Tyr Glu Leu Tyr Gly Ile Asp Ser Asp Phe His Glu Pro Leu Ser Phe
    130             135                 140

Pro Lys Val Asn Glu Asn Glu Ser Ser Glu Glu Ile Thr Phe Ile
145             150                 155                 160

Val Arg Asn Ser Asp Leu Asp Thr Asn Gly His Ser Asn Asn Val Ala
                165                 170                 175

Tyr Val Arg Trp Ile Met Glu Thr Val Pro Ser Glu Phe Val Lys Arg
            180                 185                 190

Phe Leu Lys Arg Leu Thr Ile Glu Tyr Lys Arg Glu Ser Arg Lys Gly
            195                 200                 205

Asp Val Ile Ser Ile Glu Ser Val Phe Glu Asn Gly Ala Glu Phe Ala
    210                 215                 220

Glu Gly Lys His Lys Ile Thr Ser Ser Gly Arg Val Leu Ser Leu Ala
225                 230                 235                 240

Arg Thr Glu Trp Lys
            245

<210> SEQ ID NO 125
<211> LENGTH: 241
<212> TYPE: PRT
<213> ORGANISM: Opitutus terrae

<400> SEQUENCE: 125

Met Pro Glu Lys Leu Thr Leu Asn Ala Ser Val Leu Tyr Ala Asp Val
1               5                   10                  15

Asp Arg Thr Glu Val Leu Leu Arg Gly Val Phe Lys Phe Leu Gln
            20                  25                  30

Glu Ala Ala Ile Thr His Ala Asn Gln Phe Asp Leu Gly Ser Arg Ala
        35                  40                  45

Met Ala Thr Arg Gly Glu Ser Trp Val Leu Asn Arg Met Ala Val Ala
50                  55                  60

Val His Arg Tyr Pro Arg Tyr Glu Glu Thr Met Arg Ile Glu Thr Trp
65                  70                  75                  80

Ser Arg Gly Ile Lys Gly Phe Lys Gly Tyr Arg Glu Phe Arg Val Phe
                85                  90                  95

Asp Ala Gln Gly Ala Pro Leu Phe Ser Gly Ser Ser Leu Trp Leu Tyr
            100                 105                 110

Val Asn Met Arg Thr Lys Ser Ile Ile Arg Val Pro Ala Glu Leu Ala
        115                 120                 125

Ala Glu Phe Pro Lys Arg Asp Asp Gly Ala Phe Phe Pro Glu Leu Glu
130                 135                 140

Ser Leu Glu Phe Ala Pro Pro Ala Ala Asp Ala Arg Arg Val Pro Ile
145                 150                 155                 160

Ala Ile Arg Tyr Ser Asp Val Asp Val Asn Ala His Val Asn Asn Thr
                165                 170                 175

Ala Tyr Leu Asp Phe Leu Gln Glu Ala Leu Ala Arg Ala Gly Leu Ser
            180                 185                 190

Pro Arg Pro Gln Ser Ile Arg Ile Lys Tyr Ala Arg Ala Ile Pro Ala
        195                 200                 205

Glu Ala Glu Thr Val Arg Val Ala Ile Glu Pro Arg Gly Thr Gly Ala
    210                 215                 220

Ala Phe Ala Ile Glu Asp His Asp Thr Ile Phe Ala Ile Gly Glu Val
225                 230                 235                 240

Asp

<210> SEQ ID NO 126
<211> LENGTH: 286
<212> TYPE: PRT
<213> ORGANISM: Eutrema halophilum

<400> SEQUENCE: 126

Met Val Met Thr His Cys Thr Arg Phe Gln His Leu Leu Gln Pro Lys
1               5                   10                  15

Leu Leu Phe Ser His Ser Arg Val Phe Arg His Pro Ile Arg Ala
            20                  25                  30

```
Arg Thr Pro Leu Arg Ser Ile Met Gly Ser Ser Ser Phe Ser Ser
         35                  40                  45

Lys Leu Leu Phe Arg Gln Leu Phe Glu Lys Glu Ser Ser Thr Tyr Thr
 50                  55                  60

Tyr Leu Leu Ala Asp Val Ser His Pro Asp Lys Pro Ala Leu Leu Ile
 65                  70                  75                  80

Asp Pro Val Asp Lys Thr Val Asp Arg Asp Leu Lys Leu Val Asn Glu
                 85                  90                  95

Leu Gly Leu Lys Leu Ile Tyr Ala Met Asn Thr His Val His Ala Asp
                100                 105                 110

His Val Thr Gly Thr Gly Leu Leu Lys Lys Lys Val Pro Gly Val Lys
            115                 120                 125

Ser Val Ile Ser Lys Ala Ser Gly Ser Lys Ala Asp Met Phe Leu Glu
130                 135                 140

Pro Gly Asp Lys Val Thr Ile Gly Asp Leu Tyr Leu Glu Val Arg Ala
145                 150                 155                 160

Thr Pro Gly His Thr Ala Gly Cys Val Thr Tyr Val Thr Gly Glu Glu
                165                 170                 175

Ala Asp Gln Pro Gln Pro Arg Met Ala Phe Thr Gly Asp Ala Val Leu
            180                 185                 190

Ile Arg Gly Cys Gly Arg Thr Asp Phe Gln Gly Gly Ser Ser Asp Gln
        195                 200                 205

Leu Tyr Glu Ser Val His Ser Gln Ile Phe Thr Leu Pro Lys Asp Thr
    210                 215                 220

Leu Ile Tyr Pro Ala His Asp Tyr Lys Gly Tyr Glu Val Ser Thr Val
225                 230                 235                 240

Gly Glu Glu Met Gln His Asn Pro Arg Leu Thr Lys Asp Lys Glu Thr
                245                 250                 255

Phe Lys Thr Ile Met Ser Asn Leu Asn Leu Ala Tyr Pro Lys Met Ile
            260                 265                 270

Asp Val Ala Val Pro Ala Asn Met Val Cys Gly Leu Gln Glu
        275                 280                 285

<210> SEQ ID NO 127
<211> LENGTH: 207
<212> TYPE: PRT
<213> ORGANISM: Cedecea neteri

<400> SEQUENCE: 127

Met Met Asn Phe Asn Asn Val Phe Arg Trp His Leu Pro Phe Leu Phe
 1               5                  10                  15

Leu Ala Leu Met Thr Phe Arg Ala Ala Ala Ala Asp Thr Leu Leu Ile
                20                  25                  30

Leu Gly Asp Ser Leu Ser Ala Gly Tyr Arg Met Ala Ala Thr Ser Ala
            35                  40                  45

Trp Pro Ala Leu Leu Asp Ala Lys Trp Gln Pro Gln Asn Thr Lys Val
        50                  55                  60

Val Asn Ala Ser Ile Ser Gly Asp Thr Ala Ala Gln Gly Leu Ser Arg
65                  70                  75                  80

Leu Pro Ala Leu Leu Lys Gln His Gln Pro Arg Trp Val Leu Val Glu
                85                  90                  95

Leu Gly Gly Asn Asp Gly Leu Arg Gly Phe Gln Pro Gln Glu Val Glu
                100                 105                 110

Lys Thr Leu Lys Gln Val Ile Thr Asp Val Lys Ala Ala Asn Ala Gln
            115                 120                 125
```

Pro Leu Leu Met Gln Ile Arg Leu Pro Ala Asn Tyr Gly Arg Arg Tyr
            130                 135                 140

Asn Glu Ala Phe Ser Ala Ile Tyr Pro Gln Leu Ala Lys Gln Phe Asp
145                 150                 155                 160

Ile Pro Leu Leu Pro Phe Phe Met Glu Glu Val Tyr Leu Lys Pro Gln
                165                 170                 175

Trp Met Gln Asp Asp Gly Ile His Pro Asn Arg Asp Ala Gln Pro Phe
            180                 185                 190

Ile Ala Asp Trp Met Ala Thr Gln Leu Thr Pro Leu Leu Ser Lys
            195                 200                 205

<210> SEQ ID NO 128
<211> LENGTH: 208
<212> TYPE: PRT
<213> ORGANISM: Klebsiella sp.

<400> SEQUENCE: 128

Met Met Asn Phe Lys Tyr Val Phe Arg Trp His Leu Pro Phe Leu Phe
1               5                   10                  15

Leu Val Leu Phe Thr Cys Arg Ala Met Ala Ala Asp Thr Leu Leu Val
            20                  25                  30

Leu Gly Asp Ser Leu Ser Ala Gly Tyr Arg Met Ala Gly Asn Thr Ala
            35                  40                  45

Trp Pro Ala Leu Leu Asn Asp Lys Trp Gln Thr Lys Thr Pro Val Val
        50                  55                  60

Asn Ala Ser Ile Ser Gly Asp Thr Ser Gln Gln Gly Leu Ala Arg Leu
65                  70                  75                  80

Pro Ala Leu Leu Lys Gln His Gln Pro Arg Trp Val Leu Val Glu Leu
                85                  90                  95

Gly Gly Asn Asp Gly Leu Arg Gly Phe Pro Pro Gln Gln Thr Glu Gln
            100                 105                 110

Thr Leu Arg Thr Ile Ile Glu His Ile Lys Ala Ala Asn Ala Gln Pro
            115                 120                 125

Leu Leu Met Gln Ile Arg Leu Pro Ala Asn Tyr Gly Arg Arg Tyr Asn
            130                 135                 140

Glu Ala Phe Ser Ala Ile Tyr Pro Ala Leu Ala Lys Glu Phe Asp Ile
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gln Pro Phe Ile
            180                 185                 190

Ala Asp Trp Met Ala Thr Arg Leu Ala Pro Leu Val Asn His Asp Ser
            195                 200                 205

<210> SEQ ID NO 129
<211> LENGTH: 257
<212> TYPE: PRT
<213> ORGANISM: Bdellovibrio exovorus

<400> SEQUENCE: 129

Met Ser Thr Ser Ser Glu Thr Thr Glu Lys Arg Ile Trp Glu Glu
1               5                   10                  15

Tyr Lys Ile Thr Ser Tyr Leu Val Asn Leu Arg Gly Arg Ala Gly Leu
            20                  25                  30

Tyr Ala Ile Leu Asn Leu Ile Gln Asp Val Gly Trp Met His Ala Ile
            35                  40                  45

```
Ala Ala Gln Val Arg Leu Pro Ala Asn Leu Ala Trp Val Phe Thr Arg
    50                  55                  60

Gln Lys Leu Val Met Ser Gln Trp Pro Lys Trp Asn Glu Thr Ile Ser
65                  70                  75                  80

Ile Arg Thr Trp Leu Arg Pro Pro Glu Ser Ala Ala Phe Ile Leu Arg
                85                  90                  95

Asp Tyr Glu Ile Ile Leu Asn Gly Gln Val Ile Gly Thr Cys Thr Ser
            100                 105                 110

Thr Phe Ala Val Ile Asp Thr Gln Thr Arg Lys Ile Ala Ala Gln Glu
        115                 120                 125

Trp Ser Glu Tyr Glu Gln Leu Phe Arg Thr Gly Thr Ala Leu Pro His
    130                 135                 140

His Pro Val Lys Ile Pro Tyr Arg Glu Asp Ala Gln Asp Leu Thr Val
145                 150                 155                 160

Phe Glu Val Arg Asn Ser Asp Ile Asp Leu Asn Asn His Val Asn Asn
                165                 170                 175

Thr Lys Tyr Ala Lys Trp Ile Leu Asp Ser Ile Ser Ile Asp Thr Leu
            180                 185                 190

Arg Ala Gly Val Asp Leu Leu Glu Tyr Glu Val Asn Phe Leu Ala Glu
        195                 200                 205

Ala Arg Ser Gly Asp Arg Val Thr Val Gln Ser Cys Ala Glu Glu Lys
    210                 215                 220

Leu Glu Gly Gln Ser Asp Ser Ala Thr Ala Leu Ile Gln Phe Gln Gly
225                 230                 235                 240

Val Arg Val Ser Asp Lys Lys Thr Ile Phe Thr Ala Lys Leu Arg Val
                245                 250                 255

Arg

<210> SEQ ID NO 130
<211> LENGTH: 251
<212> TYPE: PRT
<213> ORGANISM: Clostridium stercorarium

<400> SEQUENCE: 130

Met Ile Pro Glu Leu Val Tyr Arg Asn Ser Tyr Ile Val Gly Tyr Arg
1               5                   10                  15

Asp Val Asp Phe Asn Asn Asp Leu Arg Leu Ser Ser Leu Phe Gly Tyr
                20                  25                  30

Phe Gln Asp Thr Ala Ile Met Asn Val Glu Lys Leu Gly Ile Gly Val
            35                  40                  45

Asn Thr Leu Ser Glu Lys Tyr Ser Val Ser Trp Val Leu Thr Lys Ile
50                  55                  60

Leu Val Glu Ile Asn Arg Ile Pro Lys Trp Asn Glu Lys Ile Thr Val
65                  70                  75                  80

Glu Thr Trp Pro His Arg Pro Lys Lys Phe Glu Phe Asp Arg Asp Phe
                85                  90                  95

Arg Val Arg Asp Asp Asn Gly Asn Ile Ile Ala Ala Ala Ile Ser Asn
            100                 105                 110

Trp Val Leu Leu Asp Leu Lys Thr Arg Glu Ile Arg Lys Ser Glu Ile
        115                 120                 125

Ile Ser Gly Asp Tyr Pro Pro Leu Glu Phe Thr Asp Glu Arg Ala Leu
    130                 135                 140

Glu Gly Arg Leu Arg Lys Leu Arg Pro Ala Gly Glu Pro Glu Val Val
145                 150                 155                 160
```

```
Tyr Lys Arg Val Leu Gly Tyr Ser Asp Thr Asp Ala Asn Gly His Ile
                165                 170                 175

Asn Asn Ala Lys Tyr Ile Asp Phe Ile Met Asp Cys Phe Ser Ile Glu
            180                 185                 190

Glu His Lys Lys His Ser Val Arg Ser Ile Gln Val Asn Tyr Leu Lys
        195                 200                 205

Glu Val Phe Pro Gly Asp Thr Leu Ile Leu Tyr Arg Asp Val Ser Gly
    210                 215                 220

Ala Gly Ser Asn Gln Val Tyr Ile Glu Gly Ile Asn Glu Ala Asp Gln
225                 230                 235                 240

Lys Pro Ala Phe Ser Ala Glu Leu Lys Phe Asp
                245                 250

<210> SEQ ID NO 131
<211> LENGTH: 249
<212> TYPE: PRT
<213> ORGANISM: Clostridium argentinense

<400> SEQUENCE: 131

Met Lys Asn Ile His Arg Glu Asn Tyr Lys Val Lys Phe Asn Glu Thr
1               5                   10                  15

Asp Tyr Ser Thr Lys Ile Lys Met His Ser Leu Ile Asn Tyr Met Gln
            20                  25                  30

Glu Thr Ser Ser Ile His Ala Glu Leu Leu Gly Ala Gly Tyr Glu Glu
        35                  40                  45

Leu Lys Lys His Asn Leu Phe Trp Val Val Ser Arg Leu Lys Ile Asn
50                  55                  60

Met Lys Lys Tyr Val Asn Trp Asn Asp Glu Val Ile Val Glu Thr Trp
65                  70                  75                  80

Pro Ser Gly Val Asp Lys Met Phe Phe Thr Arg Ser Phe Arg Ile Tyr
                85                  90                  95

Asp Arg Glu Glu Asn His Ile Gly Asp Ile Asn Ala Ala Tyr Leu Leu
            100                 105                 110

Val Ala Glu Asp Ser Met Phe Pro Gln Arg Ile Ser Lys Leu Pro Ile
        115                 120                 125

Asn Ile Pro Thr Ile Glu Asn Arg Phe Glu Pro Tyr Glu Arg Leu Glu
    130                 135                 140

Lys Ile Lys Phe Pro Lys Asp Asp Lys Val Leu Val Ala Lys Lys Lys
145                 150                 155                 160

Val Arg Tyr Asn Asp Ile Asp Leu Asn Leu His Val Asn Asn Ala Lys
                165                 170                 175

Tyr Ile Glu Trp Val Glu Asp Cys Phe Pro Leu Glu Met Tyr Lys Asp
            180                 185                 190

Met Arg Ile Glu Thr Leu Gln Leu Asn Phe Ile Lys Glu Ala Lys Cys
        195                 200                 205

Gly Glu Lys Ile Phe Phe Tyr Leu Tyr Asn Asp Leu Glu Asp Glu Asn
    210                 215                 220

Thr Cys Tyr Ile Glu Gly Ile Glu Lys Gln Ser Glu Ser Gln Ile Phe
225                 230                 235                 240

Gln Cys Lys Leu Thr Phe Asn Lys Leu
                245

<210> SEQ ID NO 132
<211> LENGTH: 349
<212> TYPE: PRT
```

<213> ORGANISM: Saccharomyces cerevisiae

<400> SEQUENCE: 132

Met Ser Ala Ser Lys Met Ala Met Ser Asn Leu Glu Lys Ile Leu Glu
1               5                   10                  15

Leu Val Pro Leu Ser Pro Thr Ser Phe Val Thr Lys Tyr Leu Pro Ala
            20                  25                  30

Ala Pro Val Gly Ser Lys Gly Thr Phe Gly Gly Thr Leu Val Ser Gln
        35                  40                  45

Ser Leu Leu Ala Ser Leu His Thr Val Pro Leu Asn Phe Phe Pro Thr
    50                  55                  60

Ser Leu His Ser Tyr Phe Ile Lys Gly Gly Asp Pro Arg Thr Lys Ile
65                  70                  75                  80

Thr Tyr His Val Gln Asn Leu Arg Asn Gly Arg Asn Phe Ile His Lys
                85                  90                  95

Gln Val Ser Ala Tyr Gln His Asp Lys Leu Ile Phe Thr Ser Met Ile
            100                 105                 110

Leu Phe Ala Val Gln Arg Ser Lys Glu His Asp Ser Leu Gln His Trp
        115                 120                 125

Glu Thr Ile Pro Gly Leu Gln Gly Lys Gln Pro Asp Pro His Arg Tyr
    130                 135                 140

Glu Glu Ala Thr Ser Leu Phe Gln Lys Glu Val Leu Asp Pro Gln Lys
145                 150                 155                 160

Leu Ser Arg Tyr Ala Ser Leu Ser Asp Arg Phe Gln Asp Ala Thr Ser
                165                 170                 175

Met Ser Lys Tyr Val Asp Ala Phe Gln Tyr Gly Val Met Glu Tyr Gln
            180                 185                 190

Phe Pro Lys Asp Met Phe Tyr Ser Ala Arg His Thr Asp Glu Leu Asp
        195                 200                 205

Tyr Phe Val Lys Val Arg Pro Pro Ile Thr Thr Val Glu His Ala Gly
    210                 215                 220

Asp Glu Ser Ser Leu His Lys His His Pro Tyr Arg Ile Pro Lys Ser
225                 230                 235                 240

Ile Thr Pro Glu Asn Asp Ala Arg Tyr Asn Tyr Val Ala Phe Ala Tyr
                245                 250                 255

Leu Ser Asp Ser Tyr Leu Leu Leu Thr Ile Pro Tyr Phe His Asn Leu
            260                 265                 270

Pro Leu Tyr Cys His Ser Phe Ser Val Ser Leu Asp His Thr Ile Tyr
        275                 280                 285

Phe His Gln Leu Pro His Val Asn Asn Trp Ile Tyr Leu Lys Ile Ser
    290                 295                 300

Asn Pro Arg Ser His Trp Asp Lys His Leu Val Gln Gly Lys Tyr Phe
305                 310                 315                 320

Asp Thr Gln Ser Gly Arg Ile Met Ala Ser Val Ser Gln Glu Gly Tyr
                325                 330                 335

Val Val Tyr Gly Ser Glu Arg Asp Ile Arg Ala Lys Phe
            340                 345

<210> SEQ ID NO 133
<211> LENGTH: 238
<212> TYPE: PRT
<213> ORGANISM: Eubacterium eligens

<400> SEQUENCE: 133

Met Val Phe Asn Tyr Thr Tyr Arg Ile Gly Leu Glu Asp Cys Gly Arg

```
  1               5                  10                 15
Glu Asn Lys Ala Thr Asn Arg Ala Ile Leu Thr Ile Leu Glu Asp Ile
             20                  25                 30

Ala Gly Leu His Ser Ala Thr Val Gly Leu Gly Leu Asn Glu Ile Asn
             35                  40                 45

Glu Thr Gly Cys Ala Trp Val Val Leu Asn Trp Gln Met Lys Ile Ile
 50                  55                  60

Arg Arg Pro Ala Tyr Asn Asp Glu Leu Thr Val Tyr Thr Trp Ser Thr
 65                  70                  75                 80

Ser Ala Asp Lys Leu Phe Ala Glu Arg Asp Phe Arg Ile Thr Asp Lys
             85                  90                 95

Asn Gly Glu Thr Ile Val Ile Ala Thr Ser Arg Trp Leu Tyr Met Asp
            100                 105                110

Ile Asn Arg Arg Arg Pro Val Arg Ile Thr Pro Glu Ile Met Asp Arg
            115                 120                125

Tyr Glu Ser Glu Pro Glu Ile His Val Phe Thr Glu Lys Val Asn Arg
            130                 135                140

Ile Asp Pro Pro Asp Thr Gly Tyr Ile Glu Ile Pro Tyr Asn Ile Leu
145                 150                 155                160

Arg Arg Asp Val Asp Tyr Leu Gly His Met His Asn Ile Ser Tyr Leu
                165                 170                 175

Asp Ala Ala Tyr Asp Val Met Pro Glu Glu Tyr Phe Asn Gly Pro Gln
            180                 185                190

Phe Asn Phe Val Ser Ile Glu Tyr Arg Lys Glu Leu Leu Arg Asn Asp
            195                 200                205

Glu Val Lys Ala His Phe Tyr Lys Ile Asp Lys Gly Cys Ile Ile Ser
210                 215                 220

Leu Asn Thr Asp Lys Ile Asn Ala Val Ile Met Leu Lys Tyr
225                 230                 235

<210> SEQ ID NO 134
<211> LENGTH: 237
<212> TYPE: PRT
<213> ORGANISM: Terrisporobacter othiniensis

<400> SEQUENCE: 134

Met Ile Tyr Cys Asn Asn Tyr Lys Ile Gly Leu Glu Asp Ile Gly Ile
  1               5                  10                 15

Lys Asn Glu Ala Thr Asn Lys Ala Leu Leu Ala Ile Met Glu Asp Val
             20                  25                 30

Ala Gly Leu His Ser Ala Ser Val Gly Tyr Gly Val Leu Asp Ile Glu
             35                  40                 45

Thr Lys Lys Arg Val Trp Ile Leu Leu Asp Trp Lys Met Lys Val Ile
 50                  55                  60

Lys Arg Pro Lys Tyr Asn Asp Asp Ile Lys Ala Glu Thr Trp Ser Arg
 65                  70                  75                 80

Lys Val Glu Arg Leu Tyr Ala Tyr Arg Asp Phe Gln Leu Lys Asp Lys
             85                  90                 95

Glu Gly Asn Ile Ile Ala Ile Gly Thr Ser Arg Trp Ile Leu Ile Asp
            100                 105                110

Thr Asp Arg Lys Arg Pro Met Lys Leu Thr Ala Asp Ile Ala Asp Leu
            115                 120                125

Tyr Glu Ser Glu Thr Asp Lys Ser Val Phe Pro Glu Gln Ile Glu Asp
            130                 135                140
```

```
Ile Lys Cys Glu Asn Tyr Leu Phe Lys Lys Asp Tyr Tyr Ile Gln Arg
145                 150                 155                 160

Arg Asp Ile Asp Ile Asn Glu His Met His Asn Leu Asn Tyr Leu Asp
                165                 170                 175

Met Ala Tyr Glu Ile Leu Pro Glu Asp Val Tyr Lys Asn Lys Val Phe
            180                 185                 190

Asp Asn Ile Arg Ile Val Tyr Lys Lys Glu Ile Leu Tyr Gly Glu Lys
            195                 200                 205

Val Val Cys Tyr Tyr Glu Glu Gln Gly Asn Lys His Ile Ile Thr Ala
        210                 215                 220

Lys Ser Lys Asp Lys Ile Asn Ala Ile Ile Glu Leu Ser
225                 230                 235
```

<210> SEQ ID NO 135
<211> LENGTH: 244
<212> TYPE: PRT
<213> ORGANISM: Clostridium sulfidigenes

<400> SEQUENCE: 135

```
Met Glu Leu Asn Tyr Lys Glu Gln Phe Thr Ile Lys Phe His Glu Gly
1               5                   10                  15

Asp Phe Met Gly Asn Val Lys Leu Phe Thr Ile Met Asp Tyr Val Gln
            20                  25                  30

Gln Val Ser Glu Gly His Ser Gln Ile Leu Gly Val Asp Phe Gln Ser
        35                  40                  45

Met Met Asn Lys Gly Leu Phe Trp Val Val Ser Arg Val Glu Ile Thr
    50                  55                  60

Met Glu Arg Tyr Pro Lys Val Gly Glu Asp Ile Thr Val Glu Thr Cys
65                  70                  75                  80

Leu Gly Gly Arg Glu Lys Val Phe Met Lys Arg Phe Lys Ile Lys
                85                  90                  95

Asp Lys Asp Gly Gln Val Ile Gly Arg Val Leu Ile Tyr Tyr Leu Ile
            100                 105                 110

Val Asp Ile Glu Thr Arg Leu Pro Gln Lys Pro Ser Met Cys Pro Val
        115                 120                 125

Asp Ile Asn Ile Asn Val Gly Asp Val Ile Asp Asn Lys Leu Asn Lys
    130                 135                 140

Ile Lys Met Pro Gly Glu Ala Ile Glu Thr Val Asn Arg Lys Leu Tyr
145                 150                 155                 160

Tyr Asn Asp Ile Asp Ile Asn Asn His Val Asn Asn Ala Lys Tyr Ile
                165                 170                 175

Ser Phe Ile Glu Asp Phe Phe Ser Leu Asp Trp His Arg Val Lys Lys
            180                 185                 190

Ile Ser Tyr Met Gln Leu Asn Phe Ile Lys Glu Ile Lys Phe Asp Asp
        195                 200                 205

Ser Leu Ile Met Asn Lys Phe Ile Glu Asp Lys Glu Ser Asn Ser Phe
    210                 215                 220

Cys Ile Asn Gly Ile Ser Glu Ile Ser Glu Gln Glu Phe Gln Cys
225                 230                 235                 240

Arg Leu Lys Phe
```

<210> SEQ ID NO 136
<211> LENGTH: 249
<212> TYPE: PRT
<213> ORGANISM: Clostridium tetanomorphum

<400> SEQUENCE: 136

```
Met Glu Gly Leu Val Thr Glu Lys Tyr Glu Ile His Tyr Tyr Glu
1               5                   10                  15

Val Asp Tyr Lys Arg Arg Leu Leu Ile Thr Asn Ile Ile Asn Tyr Phe
            20                  25                  30

Cys Asp Ile Ala Thr Lys Gln Ser Glu Asp Arg Asn Val Gly Leu Asp
        35                  40                  45

Tyr Met Lys Glu Asn Asn Val Ala Trp Val Leu Tyr Lys Trp His Ile
    50                  55                  60

Asn Val His Arg Tyr Pro Leu Tyr Gly Glu Lys Val Ile Val Thr Thr
65                  70                  75                  80

Arg Pro His Ser Phe Arg Lys Phe Tyr Ala Tyr Arg Lys Phe Glu Ile
                85                  90                  95

Ile Asp Glu Lys Gly Lys Ile Ile Ile Glu Ala Asn Ser Ile Trp Phe
            100                 105                 110

Leu Ile Asp Ile Gln Arg Arg Arg Pro Lys Arg Ile Asn Glu His Ile
        115                 120                 125

Glu Glu Ala Tyr Lys Val Ser Lys Asp Asn Asp Glu Arg Ala Ile Leu
    130                 135                 140

Glu Ile Pro Asp Ile Lys Cys Ile Glu Lys Ile His Asn Glu Lys Thr
145                 150                 155                 160

Phe Asn Val Arg Tyr Ser Asp Ile Asp Thr Asn Gly His Val Asn Asn
                165                 170                 175

Ala Lys Tyr Val Ser Trp Ala Ile Glu Thr Val Pro Leu Gly Ile Ile
            180                 185                 190

Lys Ser Tyr Ala Leu Lys Asn Ile Thr Ile Asn Tyr Glu Lys Glu Thr
        195                 200                 205

Lys Tyr Gly Glu Ser Ile Asn Ala Phe Val Glu Val Ile Lys Glu Asp
    210                 215                 220

Lys Met Val Ile Cys Arg His Arg Ile Thr Asp Lys Glu Gly Asn Glu
225                 230                 235                 240

Leu Thr Ile Ala Gln Ser Thr Trp Glu
                245
```

<210> SEQ ID NO 137
<211> LENGTH: 248
<212> TYPE: PRT
<213> ORGANISM: Clostridium sp.

<400> SEQUENCE: 137

```
Met Asp Lys Ile Ile Ser Lys Lys Asp Tyr Asn Ile His Phe Tyr Glu
1               5                   10                  15

Val Asn Tyr Asp Lys Lys Ala Asp Ile Thr Ser Ile Met Ser Tyr Leu
            20                  25                  30

Gly Asp Leu Ala Thr Tyr Gln Ser Glu Glu Leu Gly Val Gly Ile Asp
        35                  40                  45

Tyr Leu Met Arg Asn Lys Met Ala Trp Val Val Tyr Lys Trp Asn Val
    50                  55                  60

His Met Asp Lys Tyr Pro Glu Tyr Asn Asp Thr Ile Thr Val Thr Thr
65                  70                  75                  80

Ile Pro Tyr Ser Ile Arg Lys Phe Tyr Ala Tyr Arg Lys Phe Glu Ile
                85                  90                  95

Phe Asn Lys Gly Glu Lys Ile Gly Glu Ala Thr Ser Leu Trp Phe Leu
            100                 105                 110
```

```
Ile Asn Thr Glu Arg Arg Pro Cys Arg Val Pro Glu Asp Ile Tyr
            115                 120                 125

Arg Ala Tyr Gly Leu Arg Val Glu Asp Gln Gln Leu Glu Phe Glu
        130                 135                 140

Lys Leu Leu Pro Ser Glu Ile Ser Ser Glu Lys Ser Phe Asp Val
145                 150                 155                 160

Arg Tyr Ser Asp Ile Asp Thr Asn Lys His Val Asn Asn Val Lys Tyr
                165                 170                 175

Val Ser Trp Ala Leu Glu Asn Ile Pro Leu Asp Val Val Lys Asn Cys
            180                 185                 190

Ser Val Ser Ser Ile Arg Val Ile Tyr Glu Lys Glu Thr Ser Tyr Gly
            195                 200                 205

Glu Thr Ile Thr Val Gln Thr Gln Met Lys Glu Ile Glu Asp Lys Tyr
        210                 215                 220

Ile Phe Asp His Val Ile Lys Asn Ser Glu Gly Gly Lys Leu Thr Leu
225                 230                 235                 240

Ile Lys Thr Glu Phe Leu Lys Ala
                245

<210> SEQ ID NO 138
<211> LENGTH: 252
<212> TYPE: PRT
<213> ORGANISM: Clostridium cellulolyticum

<400> SEQUENCE: 138

Met Glu Pro Leu Ser Ile Tyr Lys Lys Asn Tyr His Val Asp Tyr Gly
1               5                   10                  15

Asp Ala Asp Phe Tyr Lys Arg Leu Lys Leu Ser Tyr Leu Phe Asn Tyr
                20                  25                  30

Phe Gln Asn Ile Ala Gly Leu His Ser Glu Asn Thr Asn Val Gly Ile
            35                  40                  45

Arg Lys Leu Gln Asn Asp Tyr Gly Ala Ala Trp Val Met Thr Arg Met
        50                  55                  60

Leu Met Asp Ile Asn Arg Met Pro Glu Cys Asn Glu Glu Ile Ser Ile
65                  70                  75                  80

Glu Thr Trp Pro Val Glu Pro Lys Lys Lys Met Ile Asp Arg Asn Phe
                85                  90                  95

Ile Val Arg Asp Met Asp Gly Ser Ile Leu Ala Ser Ala Ile Ser Thr
            100                 105                 110

Trp Val Ile Leu Asp Met Glu Lys Arg Glu Met Val Arg Ile Asp Ser
        115                 120                 125

Val Ile Pro Pro Gln Tyr Pro Glu Phe Leu Lys Ser Lys Ala Ile Asp
130                 135                 140

Arg Lys Phe Asp Lys Leu Lys Pro Ser Gly Gln Leu Gln Pro Ala Tyr
145                 150                 155                 160

Lys Lys Leu Val Gly Phe Ser Asp Ile Asp Ile Asn Gly His Val Asn
                165                 170                 175

Asn Ala Lys Tyr Ile Asp Tyr Ile Leu Asp Cys Phe Thr Val Glu Lys
            180                 185                 190

His Gly Glu Tyr Arg Val Lys Ser Ile Gln Ile Asn Tyr Val Asn Glu
        195                 200                 205

Ala Val Ala Gly Asp Ile Ile Ser Leu Tyr Lys Asp Thr Val Asp Met
    210                 215                 220

Asp Gly Ser Asp Lys Ala Val Tyr Ile Thr Gly Ile Asn Glu Val Asp
225                 230                 235                 240
```

```
Gly Lys Val Asn Phe Glu Ser His Ile Arg Val Gln
                245                 250

<210> SEQ ID NO 139
<211> LENGTH: 152
<212> TYPE: PRT
<213> ORGANISM: Picea sitchensis

<400> SEQUENCE: 139

Met Tyr Asn Met Asp Leu Phe Gly Ala Lys Gly Met Ala Arg Pro Phe
1               5                   10                  15

Glu Leu Glu Leu Lys Val Arg Asp Tyr Glu Leu Asp Gln Tyr Gly Val
            20                  25                  30

Val Asn Asn Ala Thr Tyr Ala Ser Tyr Cys Gln His Cys Arg His Glu
        35                  40                  45

Leu Cys Glu Ala Ile Gly Phe Ser Pro Asp Val Ile Ala Arg Thr Gly
    50                  55                  60

Asn Ala Leu Ala Leu Ser Glu Leu Ser Leu Lys Tyr Leu Ala Pro Leu
65                  70                  75                  80

Arg Ser Gly Asp Ser Phe Val Val Thr Ala Arg Ile Ser Gly Ser Ser
                85                  90                  95

Ala Val Arg Leu Phe Phe Glu His Phe Ile Tyr Lys Leu Pro Asn Arg
            100                 105                 110

Glu Pro Val Leu Glu Ala Lys Ala Thr Ala Val Tyr Leu Asp Lys Ile
        115                 120                 125

Tyr Arg Pro Val Arg Leu Pro Ala Asp Phe Lys Ser Lys Ile Thr Leu
    130                 135                 140

Phe Leu Arg Asn Glu Glu Leu Asn
145                 150

<210> SEQ ID NO 140
<211> LENGTH: 244
<212> TYPE: PRT
<213> ORGANISM: Paenibacillus sp.

<400> SEQUENCE: 140

Met Gly Asn Ile Trp Thr Glu Glu His Leu Ile Tyr Ser Asn Glu Ile
1               5                   10                  15

Asp Tyr Lys Ala Asn Cys Arg Leu Ser Asn Leu Leu Ser Leu Met Gln
            20                  25                  30

Arg Ala Ala Asp Gly Asp Val Glu His Met Gly Gly Thr Arg Asp Gln
        35                  40                  45

Met Val Ala His His Leu Gly Trp Met Leu Thr Thr Ile Asp Leu Ala
    50                  55                  60

Cys Glu Arg Met Pro Ile Phe Asn Glu Thr Leu Lys Ile Thr Thr Trp
65                  70                  75                  80

Asn Lys Gly Thr Lys Gly Pro Leu Trp Leu Arg Asp Phe Arg Ile Phe
                85                  90                  95

Asp Glu Asn Asn Gln Glu Ile Ala Lys Ala Cys Thr Leu Trp Ala Leu
            100                 105                 110

Val Asp Ile Asp Lys Arg Lys Val Leu Arg Pro Ser Ala Tyr Pro Phe
        115                 120                 125

Asn Ile Asn Ser Asn His Glu Asp Ser Val Gly Pro Val Pro Asp Lys
    130                 135                 140

Leu Asn Ile Ser Asp Glu Val Glu Leu Tyr His Ser Tyr Ser Ile Thr
145                 150                 155                 160
```

```
Val Arg Tyr Ser Gly Ile Asp Ser Asn Gly His Leu Asn Asn Ser Arg
                165                 170                 175

Tyr Ala Asp Leu Cys Met Asp Thr Leu Thr Gln Ser Glu Leu Asp Thr
            180                 185                 190

Leu Ser Ile Leu Gly Phe His Ile Thr Tyr Tyr His Glu Val Lys Ser
        195                 200                 205

Ala Glu Gln Ile Gln Val Leu Arg Ser Asp His Leu Glu Gly Tyr Ile
    210                 215                 220

Tyr Phe Arg Gly Gln Ser Leu Glu Asp Glu Arg Tyr Phe Glu Ala Cys
225                 230                 235                 240

Leu His Val Gly
```

<210> SEQ ID NO 141
<211> LENGTH: 134
<212> TYPE: PRT
<213> ORGANISM: Escherichia coli

<400> SEQUENCE: 141

```
Met Asn Thr Thr Leu Phe Arg Trp Pro Val Arg Val Tyr Tyr Glu Asp
1               5                   10                  15

Thr Asp Ala Gly Gly Val Val Tyr His Ala Ser Tyr Val Ala Phe Tyr
            20                  25                  30

Glu Arg Ala Arg Thr Glu Met Leu Arg His His Phe Ser Gln Gln
        35                  40                  45

Ala Leu Met Ala Glu Arg Val Ala Phe Val Val Arg Lys Met Thr Val
    50                  55                  60

Glu Tyr Tyr Ala Pro Ala Arg Leu Asp Asp Met Leu Glu Ile Gln Thr
65                  70                  75                  80

Glu Ile Thr Ser Met Arg Gly Thr Ser Leu Val Phe Thr Gln Arg Ile
                85                  90                  95

Val Asn Ala Glu Asn Thr Leu Leu Asn Glu Ala Glu Val Leu Val Val
            100                 105                 110

Cys Val Asp Pro Leu Lys Met Lys Pro Arg Ala Leu Pro Lys Ser Ile
        115                 120                 125

Val Ala Glu Phe Lys Gln
    130
```

<210> SEQ ID NO 142
<211> LENGTH: 242
<212> TYPE: PRT
<213> ORGANISM: Catabacter hongkongensis

<400> SEQUENCE: 142

```
Met Asn Thr Lys Leu Glu Gln Leu Tyr Thr Ile Arg Ala Phe Asp Val
1               5                   10                  15

Asp Thr Lys Gly Lys Trp Arg Pro Ser Ala Ile Leu Thr Arg Leu Gln
            20                  25                  30

Glu Ile Ala Glu Asp His Ala Ile Ala Val Asn Ala Gly Arg Lys Glu
        35                  40                  45

Leu Val Glu Glu Arg Gly Met Ala Trp Met Leu Thr Arg Leu His Leu
    50                  55                  60

Gln Met Lys Gln Tyr Pro Asp Leu Thr Asp Thr Ile Lys Val Val Thr
65                  70                  75                  80

Trp Pro Gly Lys Pro Thr Lys Leu Phe Phe Val Arg His Ser Met Phe
                85                  90                  95
```

```
Phe Ser Glu Thr Gly Glu Leu Gly Arg Ala Thr Ser Leu Trp Val
                100                 105                 110

Leu Phe Asn Ile Arg Glu Arg Phe Leu Cys Arg Thr Gly Asp Ile Gly
            115                 120                 125

Glu Asn Tyr Pro Tyr Asp Leu Ser His Gly Arg Ala Leu Pro Asp Pro
        130                 135                 140

Gly Lys Ile Lys Leu Pro Asp Glu Met Gln Tyr Met Thr Thr Arg Thr
145                 150                 155                 160

Val Ala Tyr Ser Glu Val Asp Met Asn Gly His Leu Asn Asn Ala Lys
                165                 170                 175

Tyr Ala Asp Trp Ile Cys Glu Leu Phe Asp Ile Ser His Leu Lys Lys
            180                 185                 190

Ala Tyr Met Asp Gln Phe Arg Ile Asn Tyr Ile Ala Glu Ala Tyr Met
        195                 200                 205

Gly Gln Lys Val Asp Leu Tyr Cys Lys Glu Ile Asp Gly Thr Trp Phe
210                 215                 220

Val Cys Gly Lys Thr Gly Asn Lys Thr Val Phe Asp Ala Ser Ile Gln
225                 230                 235                 240

Trp Lys

<210> SEQ ID NO 143
<211> LENGTH: 233
<212> TYPE: PRT
<213> ORGANISM: Firmicutes bacterium

<400> SEQUENCE: 143

Met Asn Tyr Tyr Gln Lys Glu Leu Val Leu Gln Glu Lys Asp Phe Ile
1               5                   10                  15

Asn Asp Glu Leu Ser Pro Tyr Ser Ile Leu Asn Tyr Phe Gln Asp Ile
            20                  25                  30

Ala Gly Ile His Ala Asp Lys Ile Gly Leu Ser His Glu Glu Leu Ile
        35                  40                  45

Lys Asn Asp Leu Val Trp Val Leu Arg Asn Lys Tyr Glu Ile Ile
    50                  55                  60

Lys Met Pro Ser Ile Asn Gln Lys Val Ile Leu Lys Thr Trp Pro His
65                  70                  75                  80

Gln Lys Gly Lys Ile Asp Phe Asp Arg Glu Tyr Ala Ile Tyr Asp Glu
                85                  90                  95

Asn Asn Asn Leu Leu Ile Lys Gly Leu Ser Lys Trp Ile Leu Met Asn
            100                 105                 110

Tyr Lys Thr Arg Arg Ile Ser Met Phe Asn Asn Ile Lys Tyr Ser Phe
        115                 120                 125

Glu Cys Leu Glu Glu Thr Asn Phe Glu Asn Lys Phe Asn Lys Ile Glu
130                 135                 140

Asp Phe Asp Ile Asn Asn Phe Ser Phe Ile Glu Thr Thr Ser Glu
145                 150                 155                 160

Asn Asp Leu Asp Ile Asn Gly His Val Asn Asn Ala Ser Tyr Ala Arg
                165                 170                 175

Ile Val Leu Asn Asn Ile Asp Phe Asp Ile Thr Ile Asn His Phe Glu
            180                 185                 190

Ile Asn Tyr Ile Lys Glu Ile Lys Ala Asn Gln Lys Leu Lys Ile Tyr
        195                 200                 205

Tyr Leu Lys Lys Asp Asn Thr Tyr Tyr Ile Lys Ala Phe Asn Asn Glu
210                 215                 220
```

Glu Val Ile Phe Val Leu Ile Val Tyr
225                 230

<210> SEQ ID NO 144
<211> LENGTH: 244
<212> TYPE: PRT
<213> ORGANISM: Peptoniphilus harei

<400> SEQUENCE: 144

Met Lys Ile Phe Cys Lys Glu Tyr Glu Val Met Asn Phe Leu Ser Ser
1               5                   10                  15

Asp Gly Asp Leu Lys Leu Asn His Leu Val Ser Tyr Leu Ile Glu Thr
            20                  25                  30

Ser Asn Tyr Gln Ser Ile Asp Leu Gly Leu Ser Asn Glu Lys Leu Leu
        35                  40                  45

Asp Met Gly Tyr Thr Trp Met Ile Tyr Lys Trp Lys Ile Lys Ile Asn
    50                  55                  60

Arg Tyr Pro Arg Ser Tyr Glu Lys Ile Lys Lys Thr Trp Ala Ser
65                  70                  75                  80

Gly Phe Lys Asn Ile Asn Ala Phe Arg Glu Phe Glu Val Tyr Cys Gln
                85                  90                  95

Gly Glu Lys Ile Ile Glu Ala Ser Ala Ile Phe Leu Leu Ile Asp Val
            100                 105                 110

Glu Lys Arg Lys Ala Ile Lys Ile Pro Glu Val Leu Ala Glu Ile Tyr
        115                 120                 125

Gly Asn Asn Gly Asn Arg Ile Phe Lys Ser Ile Glu Arg Val Asn Glu
    130                 135                 140

Pro Ser Glu Leu Glu Ile Ala Asn Arg Phe Ser Tyr Lys Ile Leu Arg
145                 150                 155                 160

Arg Asp Leu Asp Phe Asn Asn His Val Asn Asn Ser Val Tyr Leu Glu
                165                 170                 175

Leu Ile Tyr Glu Ala Val Thr Asp Glu Tyr Thr His Val Lys Phe Lys
            180                 185                 190

Asp Ile Asn Val Asn Tyr Ile Asn Glu Leu Lys Leu Gly Asp Glu Ile
        195                 200                 205

Val Ile Asp Phe Tyr Arg Glu Glu Asp Arg Phe Tyr Phe Phe Lys
    210                 215                 220

Ser Lys Asp Gln Ser Gln Ile Tyr Ala Arg Ile Cys Gly Val Ser Glu
225                 230                 235                 240

Thr Pro Ile Ser

<210> SEQ ID NO 145
<211> LENGTH: 246
<212> TYPE: PRT
<213> ORGANISM: Lactobacillus animalis

<400> SEQUENCE: 145

Met Ala Glu Asn Leu Tyr Arg Met Pro His Gln Ile Val Tyr Tyr Glu
1               5                   10                  15

Thr Asp Pro Thr Gly Lys Leu Ser Leu Gly Lys Leu Val Asp Leu Met
            20                  25                  30

Met Leu Ala Ser Tyr Ala Gln Gly Lys Asp Val Gly Met Pro Glu Glu
        35                  40                  45

Lys Leu Asn Ala Gln Gly Tyr Gly Trp Val Ile Thr Gln His Leu Leu
    50                  55                  60

Ser Ile Thr Arg Leu Pro Arg Arg Asp Glu Lys Val Val Ile Glu Thr

```
            65                  70                  75                  80
Lys Ala Thr Ala Tyr Asn Arg Tyr Phe Cys Tyr Arg Asn Phe Tyr Leu
                    85                  90                  95

Arg Asp Glu Gln Gly Glu Leu Leu Ala Lys Met His Thr Ala Phe Val
                100                 105                 110

Leu Leu Asp Leu Glu Thr Arg Lys Ile Thr Arg Ile Thr Ser Asp Val
            115                 120                 125

Ile Ala Pro Phe Gly Pro Glu Pro Ile Arg Ser Ile Glu Arg Ser Ala
        130                 135                 140

Ser Pro Lys Arg Leu Glu Glu Val Met Leu Ala Lys Asp Tyr Arg Val
145                 150                 155                 160

Arg Tyr Phe Asp Ile Asp Ser Asn His His Val Asn Asn Val His Tyr
                    165                 170                 175

Ile Glu Trp Met Leu Asp Val Leu Asp Lys Asp Phe Leu Met Glu His
                180                 185                 190

Glu Pro Val Ala Leu Asn Ile Lys Tyr Glu His Glu Leu Asn Tyr Gly
            195                 200                 205

Gln Thr Cys Thr Ser Lys Val Glu Leu Leu Arg Ser Lys Asp Glu Leu
        210                 215                 220

Thr Thr Leu His Glu Ile Tyr Met Ala Asp Gly Thr Leu Ser Cys Ser
225                 230                 235                 240

Ala Gln Val Thr Trp Lys
                245

<210> SEQ ID NO 146
<211> LENGTH: 211
<212> TYPE: PRT
<213> ORGANISM: Congregibacter litoralis

<400> SEQUENCE: 146

Met Gly Leu Leu Leu Gly Leu Ala Leu Leu Leu Thr Gly Gln Leu Ala
1               5                   10                  15

Arg Ala Glu Ser Thr Ala Gly Glu Arg Pro Arg Ile Leu Val Val Gly
                20                  25                  30

Asp Ser Ile Ser Ala Ala Tyr Gly Met Ser Leu Glu Gln Gly Trp Ala
            35                  40                  45

Ala Leu Leu Glu Arg Arg Leu Gln Thr Arg Trp Pro Gly Ala Gln Val
        50                  55                  60

Ile Asn Ala Ser Ile Ser Gly Asp Thr Ser Ala Gly Gly Ala Arg Arg
65                  70                  75                  80

Leu Pro Lys Leu Leu Ala Glu His Ser Pro Asp Leu Val Val Ile Glu
                85                  90                  95

Leu Gly Gly Asn Asp Gly Leu Arg Gly Tyr Pro Thr Ser Lys Leu Glu
                100                 105                 110

Ala Asn Leu Ser Phe Met Ala Glu Ala Ala Ser Thr Ala Gly Ala Glu
            115                 120                 125

Val Leu Ile Leu Pro Met Glu Ile Pro Pro Asn Tyr Gly Pro Arg Tyr
        130                 135                 140

Thr Arg Ser Phe Arg Glu Ser Phe Glu Arg Ala Thr Asp Thr Gly
145                 150                 155                 160

Ala Thr Leu Gly Pro Phe Leu Leu Asp Gly Ile Ala Thr Glu Glu Gln
                165                 170                 175

Leu Met Gln Gln Asp Gly Ile His Pro Thr Val Glu Ala Gln Pro Met
            180                 185                 190
```

```
Ile Thr Asp Ile Val Gln Pro Val Ile Glu Ala Leu Leu Ala Leu Arg
        195                 200                 205

Glu Ala Ser
    210

<210> SEQ ID NO 147
<211> LENGTH: 249
<212> TYPE: PRT
<213> ORGANISM: Clostridium botulinum

<400> SEQUENCE: 147

Met Gln Pro Val Ile Thr Asp Lys Asn Phe Glu Ile Asn Tyr His Glu
1               5                   10                  15

Ile Asp Phe Lys Lys Arg Val Leu Phe Thr Thr Ile Met Asn Tyr Phe
            20                  25                  30

Glu Asp Ala Ser Leu Glu Gln Ser Glu Lys Leu Gly Val Gly Leu Gln
        35                  40                  45

Tyr Leu Lys Glu Asn Gln Ala Trp Val Leu Tyr Lys Trp Asn Val
    50                  55                  60

Thr Ile Asp Arg Tyr Pro Glu Phe Gly Glu Lys Ile Ile Val Arg Thr
65                  70                  75                  80

Ile Pro Leu Ser Tyr Arg Lys Phe Tyr Ala Tyr Arg Arg Phe Gln Ile
                85                  90                  95

Ile Asp Lys Thr Gly Lys Val Ile Val Thr Gly Asp Ser Ile Trp Phe
            100                 105                 110

Leu Ile Asp Ile Asn Lys Arg Arg Pro Ile Lys Val Thr Glu Asp Met
        115                 120                 125

Gln Asn Ala Tyr Gly Leu Ser Glu Thr Lys Glu Glu Pro Phe Lys Ile
    130                 135                 140

Asp Lys Ile Lys Phe Pro Glu Glu Phe His Tyr Asn Asn Lys Phe Lys
145                 150                 155                 160

Val Arg Tyr Ser Asp Ile Asp Thr Asn Leu His Val Asn Asn Val Lys
                165                 170                 175

Tyr Ile Ser Trp Ala Ile Glu Thr Ile Pro Phe Asp Ile Val Leu Asn
            180                 185                 190

Tyr Thr Leu Lys Asn Phe Val Ile Thr Tyr Glu Lys Glu Val Lys Tyr
        195                 200                 205

Gly Asn Asp Ile Asn Val Tyr Ser Glu Met Val His Asn Asp Asn Asn
    210                 215                 220

Glu Ile Val Phe Val His Lys Val Glu Asn Glu Gly Lys Arg Val
225                 230                 235                 240

Thr Ser Ala Lys Ser Ile Trp Val Lys
                245

<210> SEQ ID NO 148
<211> LENGTH: 271
<212> TYPE: PRT
<213> ORGANISM: Salinispira pacifica

<400> SEQUENCE: 148

Met Glu Arg Asn Met Lys Phe Ser Arg Glu Tyr Glu Val Arg Gly Phe
1               5                   10                  15

Glu Ile Asp Glu Asn Tyr His Leu Lys Pro Tyr His Ile Ala Ser Tyr
            20                  25                  30

Phe Gln Asp Ala Met Ala Gln Asn Phe Ala Asp Asn Met Leu Ala Ala
        35                  40                  45
```

```
Tyr Asp Leu Gln Lys Glu Gly Arg Thr Trp Val Leu Ser Asp Leu Cys
         50                  55                  60

Ile Asp Phe Leu His Gln Met Pro Arg Trp Arg Thr Ser Val Leu Val
 65                  70                  75                  80

Glu Thr Trp Val Ser Ser Ile Arg Gly Phe Arg Leu Thr Ile Asp Phe
                     85                  90                  95

Arg Val Ser Asp Ser Arg Gly Thr Pro Ile Ser Gln Gly Ser Ser Ser
                100                 105                 110

Trp Val Ile Val Lys Lys Pro Gly Asn Arg Pro Glu Lys Ile Glu Pro
            115                 120                 125

Tyr Ala Arg Lys Leu Gly Glu Pro His Ser Pro Leu Tyr Pro Gly Tyr
        130                 135                 140

Arg Phe His Glu Pro Asp Leu Asp Gly Ser Pro Ser Pro Leu Pro Tyr
145                 150                 155                 160

Gly Ala Cys Gly Leu Arg His Pro Trp Glu Glu Asp Gln Lys Ala Trp
                    165                 170                 175

Ser Ile Cys Gln Pro Ile Arg Ser Tyr Asp Ile Asp Phe Asn Gly His
                180                 185                 190

Val Ser Asn Ile Arg Tyr Ile Ala Gly Ala Val Glu Ala Ile Pro Val
            195                 200                 205

Glu Leu Arg Ser Ser Leu Arg Pro Ser Ser Phe Arg Ile Lys Tyr Leu
        210                 215                 220

Arg Glu Ala Val Leu Asp Gln Val Leu Val Ser Glu Val Arg Thr Val
225                 230                 235                 240

His Glu Asp Ser Asp Ala Ile Glu Tyr His His Ile Leu Lys Glu Cys
                    245                 250                 255

Glu Ser Ala Val Glu Phe Ser Arg Met Val Ser Val Trp Lys Arg
                260                 265                 270

<210> SEQ ID NO 149
<211> LENGTH: 248
<212> TYPE: PRT
<213> ORGANISM: Clostridium sp.

<400> SEQUENCE: 149

Met Gly Lys Leu Val Thr Asp Lys Glu Tyr Glu Ile His Phe Tyr Glu
 1               5                  10                  15

Val Asp Tyr Lys Gly Arg Ala Leu Phe Thr Ser Leu Met Asn Tyr Phe
                20                  25                  30

Gly Asp Ile Ser Ser Lys Gln Ser Glu Asp Arg Asn Met Gly Ile Asp
            35                  40                  45

Tyr Leu Lys Lys Val Asn Met Ala Trp Val Leu Tyr Lys Trp Asn Val
 50                  55                  60

Lys Ile His Arg Tyr Pro Thr Tyr Arg Glu Lys Val Ile Ala Arg Thr
 65                  70                  75                  80

Val Pro Tyr Ser Phe Arg Lys Phe Tyr Ala Tyr Arg Lys Phe Tyr Ile
                    85                  90                  95

Leu Asp Ile Glu Gly Asn Val Ile Val Glu Ala Asp Ser Leu Trp Phe
                100                 105                 110

Leu Ile Asp Ile Glu Thr Arg Lys Pro Val Arg Val Gln Glu Glu Met
            115                 120                 125

Tyr Thr Gly Tyr Cys Leu Ser Lys Asp Asp Asn Glu Ile Ile Asp Ile
        130                 135                 140

Pro Lys Ile Thr Ala Pro Asn Glu Ser Asp Phe Cys Lys Thr Phe Asp
145                 150                 155                 160
```

```
Val Arg Tyr Ser Asp Ile Asp Thr Asn Gly His Val Asn Asn Ser Lys
                165                 170                 175

Tyr Ile Ser Trp Ile Leu Glu Ala Val Pro Leu Asn Ile Val Thr Gln
            180                 185                 190

Tyr Ser Leu Ser Asn Leu Ile Ile Thr Tyr Glu Lys Glu Thr Thr Tyr
        195                 200                 205

Gly Glu Val Ile Asp Ser Cys Val Glu Val Arg Glu Val Asp Gly Lys
    210                 215                 220

Ala Val Cys Lys His Lys Ile Val Asp Lys Glu Gly Asn Glu Leu Thr
225                 230                 235                 240

Val Ala Glu Thr Thr Trp Thr Arg
                245

<210> SEQ ID NO 150
<211> LENGTH: 243
<212> TYPE: PRT
<213> ORGANISM: Coraliomargarita sp.

<400> SEQUENCE: 150

Met Lys Phe Ser Arg Ile Tyr Asn Val Arg Ser Glu Ile Thr Pro
1               5                   10                  15

Glu Tyr Lys Leu Lys Glu Phe Tyr Ile Gly Met Tyr Phe Gln Glu Cys
            20                  25                  30

Phe Ala Glu Tyr Met Ala Ser Lys Gly Leu Ala Ala Tyr Asp Leu Ala
        35                  40                  45

Lys Ser Gly Gln Thr Trp Leu Thr Ser Asp Val Gln Ile Asp Tyr Leu
    50                  55                  60

Gln Glu Met Pro Phe Trp Arg Glu Pro Val Glu Met Gln Val Trp Val
65                  70                  75                  80

Arg Gln Ile Ser Ala Ile Arg Ile Tyr Val Asp Phe Glu Ala Ile His
                85                  90                  95

Lys Ser Ser Val Ile Ala Arg Gly Ser Ser Ile Gln Leu Ile Ala Glu
            100                 105                 110

Lys Ser Thr His His Pro Ile Lys Asn Ala Thr Ile Ala Ser Ile Ser
        115                 120                 125

Ser Leu Ser Leu Ile His Glu Ser Ala Leu Pro Gly Val Glu Phe Lys
    130                 135                 140

Lys Ile Asp Pro Phe Gly Gly Glu Tyr Ser Lys Thr Ser Gln Val Val
145                 150                 155                 160

Arg Tyr Asp Asp Leu Asp Phe Asn Met His Leu Asn Asn Val Lys Tyr
                165                 170                 175

Val Pro Arg Ala Leu Glu Ser Ile Pro Gln Glu Phe Arg Asn Ser His
            180                 185                 190

Thr Leu Lys Glu Tyr Arg Ile Lys Phe Met Arg Glu Thr Phe Phe Asn
        195                 200                 205

Asn Thr Val Ser Ser Glu Ala Phe Arg Asp Gly Asn Arg Ile Phe His
    210                 215                 220

Arg Leu Ala Arg Val Glu Asp Gly Val Glu Leu Cys Arg Met Glu Ser
225                 230                 235                 240

Leu Trp Glu

<210> SEQ ID NO 151
<211> LENGTH: 200
<212> TYPE: PRT
<213> ORGANISM: Neptuniibacter caesariensis
```

<400> SEQUENCE: 151

| Met | Arg | Thr | Ala | Ile | Thr | Phe | Leu | Leu | Phe | Val | Phe | Leu | Thr | Leu | Pro |
|---|---|---|---|---|---|---|---|---|---|---|---|---|---|---|---|
| 1 | | | | 5 | | | | | 10 | | | | | 15 | |

Val Gln Ala Arg Ser Leu Ile Val Leu Gly Asp Ser Leu Ser Ala Ala
            20                  25                  30

Tyr Gln Met Ala Pro Glu Glu Gly Trp Val Ala Leu Leu Glu Glu Lys
        35                  40                  45

Met Ala Thr Glu Gly Tyr Ala Tyr Asp Val Ile Asn Ala Ser Val Ser
50                  55                  60

Gly Asp Thr Thr Gln Asn Gly Ile Ala Arg Leu Lys Thr Leu Leu Lys
65                  70                  75                  80

Gln Val Asp Ala Glu Ile Val Ile Glu Leu Gly Gly Asn Asp Gly
                85                  90                  95

Leu Arg Gly Thr Pro Pro Phe Ala Ile Lys Arg Asn Leu Ser Arg Leu
            100                 105                 110

Val Asn Met Ala Lys Asp Ser Gly Ala Gln Val Leu Leu Leu Gly Ile
            115                 120                 125

Gln Leu Pro Ser Asn Tyr Gly Ala Ala Tyr Asn Lys Gln Phe Ser Glu
        130                 135                 140

Ile Tyr Pro Val Ile Ala Glu Asp Glu Asn Val Ala Leu Val Pro Phe
145                 150                 155                 160

Phe Met Glu Gln Val Ala Leu Val Pro Glu Arg Met Gln Asp Asp Gly
                165                 170                 175

Ile His Pro Ser Ala Glu Gly Gln Pro Tyr Leu Leu Asn Thr Val Trp
            180                 185                 190

Pro His Leu Glu Pro Leu Ile Asn
        195                 200

<210> SEQ ID NO 152
<211> LENGTH: 252
<212> TYPE: PRT
<213> ORGANISM: Carboxydothermus hydrogenoformans

<400> SEQUENCE: 152

Met Asn Ser Asn Ile Phe Glu Leu Glu Tyr Arg Ile Pro Tyr Tyr Asp
1               5                   10                  15

Val Asp Tyr Gln Lys Arg Thr Leu Ile Thr Ser Leu Ile Asn Tyr Phe
            20                  25                  30

Asn Asp Ile Ala Phe Val Gln Ser Glu Asn Leu Gly Gly Ile Ala Tyr
        35                  40                  45

Leu Thr Gln Asn Asn Leu Gly Trp Val Leu Met Asn Trp Asp Ile Lys
50                  55                  60

Val Asp Arg Tyr Pro Arg Phe Asn Glu Arg Val Leu Val Arg Thr Ala
65                  70                  75                  80

Pro His Ser Phe Asn Lys Phe Ala Tyr Arg Trp Phe Glu Ile Tyr
                85                  90                  95

Asp Lys Asn Gly Ile Lys Ile Ala Lys Ala Asn Ser Arg Trp Leu Leu
            100                 105                 110

Ile Asn Thr Glu Lys Arg Arg Pro Val Lys Ile Asn Asp Tyr Leu Tyr
            115                 120                 125

Gly Ile Tyr Gly Val Ser Tyr Glu Asn Asn Ile Leu Pro Ile Glu
        130                 135                 140

Glu Pro Gln Lys Leu Leu Ser Ile Asp Ile Glu Lys Gln Phe Glu Val
145                 150                 155                 160

```
Arg Tyr Ser Asp Leu Asp Ser Asn Gly His Val Asn Val Lys Tyr
                165                 170                 175

Val Val Trp Ala Leu Asp Thr Val Pro Leu Glu Ile Ile Ser Asn Tyr
            180                 185                 190

Ser Leu Gln Arg Leu Lys Val Lys Tyr Glu Lys Glu Val Thr Tyr Gly
        195                 200                 205

Lys Thr Val Arg Val Leu Thr Gly Ile Leu Ser Glu Gln Lys Thr Ile
    210                 215                 220

Val Ser Leu His Lys Ile Val Asp Glu Asp Glu Thr Glu Leu Cys Phe
225                 230                 235                 240

Leu Glu Ser Val Trp Phe Leu Asn Glu Lys Leu Ser
                245                 250

<210> SEQ ID NO 153
<211> LENGTH: 132
<212> TYPE: PRT
<213> ORGANISM: Thermus thermophilus

<400> SEQUENCE: 153

Met Glu Ser Val Thr Arg Ile Lys Val Arg Tyr Ala Glu Thr Asp Gln
1               5                   10                  15

Met Gly Val Val His His Ser Val Tyr Ala Val Tyr Leu Glu Ala Ala
            20                  25                  30

Arg Val Asp Phe Leu Glu Arg Ala Gly Leu Pro Tyr His Arg Val Glu
        35                  40                  45

Ala Arg Gly Val Phe Phe Pro Val Val Glu Leu Gly Leu Thr Phe Arg
    50                  55                  60

Ala Pro Ala Arg Phe Gly Glu Val Val Glu Val Arg Thr Arg Leu Ala
65                  70                  75                  80

Glu Leu Ser Ser Arg Ala Leu Leu Phe Arg Tyr Arg Val Glu Arg Glu
                85                  90                  95

Gly Val Leu Leu Ala Glu Gly Phe Thr Arg His Leu Cys Gln Val Gly
            100                 105                 110

Glu Arg Ala Ala Arg Ile Pro Glu Asp Ile Tyr Arg Ala Leu Ser Val
        115                 120                 125

Leu His Leu Lys
    130

<210> SEQ ID NO 154
<211> LENGTH: 197
<212> TYPE: PRT
<213> ORGANISM: Enterobacter lignolyticus

<400> SEQUENCE: 154

Met Pro Phe Leu Phe Leu Val Leu Leu Thr Cys Arg Ala Ala Phe Ala
1               5                   10                  15

Asp Thr Val Leu Val Leu Gly Asp Ser Leu Ser Ala Gly Tyr Arg Met
            20                  25                  30

Ala Ala Asn Ala Ala Trp Pro Ala Leu Leu Asn Ala Lys Trp Gln Pro
        35                  40                  45

Lys Thr Asp Val Ile Asn Ala Ser Ile Ser Gly Asp Thr Ser Gln Gln
    50                  55                  60

Gly Leu Ala Arg Leu Pro Glu Leu Leu Lys Gln His Gln Pro Arg Trp
65                  70                  75                  80

Val Leu Val Glu Leu Gly Gly Asn Asp Gly Leu Arg Gly Phe Pro Pro
                85                  90                  95
```

```
Gln Gln Thr Glu Ala Thr Leu Arg Ala Ile Leu Lys Asp Ile Glu Ala
                100                 105                 110

Ala Asn Ala Lys Pro Leu Leu Met Gln Ile Arg Leu Pro Ala Asn Tyr
            115                 120                 125

Gly Arg Arg Tyr Asn Ala Ser Phe Ser Ala Ile Tyr Pro Lys Leu Ala
        130                 135                 140

Ser Glu Phe Asn Ile Pro Leu Leu Pro Phe Phe Met Glu Glu Val Tyr
145                 150                 155                 160

Leu Lys Pro Gln Trp Met Gln Asp Asp Gly Ile His Pro Asn Arg Asp
                165                 170                 175

Ala Gln Pro Phe Ile Ala Asp Trp Met Ala Thr Arg Leu Ala Pro Leu
            180                 185                 190

Val Asn His Asp Ser
        195

<210> SEQ ID NO 155
<211> LENGTH: 257
<212> TYPE: PRT
<213> ORGANISM: Pseudodesulfovibrio aespoeensis

<400> SEQUENCE: 155

Met Thr Ala His Leu Pro Leu Thr His Asp Arg Leu Tyr Arg Ile Arg
1               5                   10                  15

Ser Tyr Glu Pro Arg Pro Asp Gly Leu Ala Pro Ile Thr Ala Ile Cys
                20                  25                  30

Asn Gln Leu Gln Asp Ile Ala Ser Gly His Ala Asp Ala Leu Gly Phe
            35                  40                  45

Gly Tyr His Asp Leu Glu Thr Gly Gly His Phe Trp Leu Leu Ala Arg
        50                  55                  60

Leu His Val Met Met Asp Arg Leu Pro Ala Tyr Gly Gly Ala Val Arg
65                  70                  75                  80

Val Gln Thr Trp Pro Ser Gly Asn Glu Arg Leu Val Ala Asn Arg Asp
                85                  90                  95

Phe Leu Ile Leu Asp Pro Ala Ala Gln Glu Thr Val Met Gly Arg
            100                 105                 110

Ala Thr Ser Ser Trp Val Thr Met Asn Ala Ser Thr His Arg Pro Glu
        115                 120                 125

Ser Pro Ser Glu Val Leu Ser Thr Arg Phe Ile Pro Asp Arg Glu Arg
130                 135                 140

Ala Leu Thr Phe Pro Ala Lys Ser Ile Thr Arg Leu Lys Asp Gly Glu
145                 150                 155                 160

His Glu Thr Gly Leu Thr Ala Arg Arg Ala Asp Leu Asp Ile Asn Gly
                165                 170                 175

His Val Asn Asn Val Arg Tyr Ala Glu Leu Cys Leu Glu Ala Val Pro
            180                 185                 190

Gln Ala Trp Glu Ala Ala His Arg Cys Leu Gly Leu Asp Ile Gln Phe
        195                 200                 205

Arg Ser Glu Ser Phe Ala Gly Asp Ala Tyr Val Ser Ala Cys Ala Glu
210                 215                 220

Ala Gly Pro Asp Ser Gly Met Arg Thr Leu Leu His Arg Leu Thr Arg
225                 230                 235                 240

Ile Asn Asp Asp Arg Glu Ile Val Arg Met Arg Ser Trp Trp Gln Thr
                245                 250                 255

Gly
```

<210> SEQ ID NO 156
<211> LENGTH: 200
<212> TYPE: PRT
<213> ORGANISM: Vibrio navarrensis

<400> SEQUENCE: 156

```
Met Val Arg Leu Phe Ser Leu Met Met Leu Ile Leu Ser Trp Thr
1               5                   10                  15

Ala Thr Ala Ala Glu Lys Ile Leu Ile Leu Gly Asp Ser Leu Ser Ala
            20                  25                  30

Gly Tyr Asn Met Pro Ala Glu Gln Ala Trp Pro Ser Leu Leu Pro Asp
        35                  40                  45

Val Leu Lys Thr Tyr Gly Lys Asp Val Gln Val Ile Asn Ala Ser Ile
50                  55                  60

Ser Gly Asp Thr Thr Gly Asn Gly Leu Ala Arg Leu Pro Asp Leu Leu
65                  70                  75                  80

Thr Thr His Ser Pro Asp Trp Val Leu Ile Glu Leu Gly Ala Asn Asp
                85                  90                  95

Gly Leu Arg Gly Phe Pro Pro Lys Thr Ile Ala Ala Asn Leu Ser Arg
            100                 105                 110

Met Ile Gln Ile Thr Lys Ala Ala Gly Ala Lys Pro Val Leu Met Gln
        115                 120                 125

Ile Arg Val Pro Pro Asn Tyr Gly Lys Arg Tyr Ser Gln Ala Phe Phe
130                 135                 140

Asp Leu Tyr Pro Thr Leu Ala Glu His Gln Gln Val Pro Leu Leu Pro
145                 150                 155                 160

Phe Phe Leu Glu Gln Val Ile Thr Lys Pro Glu Trp Met Met Gln Asp
                165                 170                 175

Gly Leu His Pro Thr Ala Asp Ala Gln Pro Trp Ile Ala Glu Phe Val
            180                 185                 190

Ala Glu Met Phe Ser Gln His Leu
        195                 200
```

<210> SEQ ID NO 157
<211> LENGTH: 246
<212> TYPE: PRT
<213> ORGANISM: Anaeromyxobacter sp.

<400> SEQUENCE: 157

```
Met Glu Thr Phe Lys Glu Ser Phe Ala Val His Ser Tyr Glu Val Asp
1               5                   10                  15

Ala Phe Gly Thr Leu Ala Pro Pro Ala Leu Thr Gly Phe Leu Met Glu
            20                  25                  30

Ala Ala Gly Leu His Ala Gly Arg Leu Gly Val Gly Ile Asp Ala Leu
        35                  40                  45

Met Glu Lys Gly Leu Thr Trp Val Leu Val Arg Gln Arg Thr Glu Met
    50                  55                  60

Pro Val Pro Ile Val Leu Gly Asp Val Leu Glu Val Glu Thr Trp Pro
65                  70                  75                  80

Val Gly Val Asp Arg Leu Ala Ala Leu Arg Asp Phe Val Arg Arg
            85                  90                  95

Arg Asp Gly Ala Glu Val Ala Arg Gly Thr Thr Gln Trp Phe Val Leu
        100                 105                 110

Asp Val Lys Thr Arg Lys Pro Val Arg Pro Glu Thr Ala Leu Asp Ala
    115                 120                 125
```

Arg Phe Pro Arg Glu Leu Gly Lys Pro Val Ile Asp Val Ala Pro Gly
            130                 135                 140

Lys Leu Pro Glu Leu Arg Thr Trp Glu Phe Gln Lys Arg Phe His Val
145                 150                 155                 160

Arg Tyr Gln Asp Ile Asp Leu Asn Leu His Val Asn Asn Gly Ser Tyr
                165                 170                 175

Val Ala Trp Ala Leu Glu Ala Ile Pro Lys Asp Val Tyr Thr Gly Ser
            180                 185                 190

Arg Val Ala Ala Leu Glu Val Gln Tyr Leu Ala Glu Cys His Tyr Gly
            195                 200                 205

Ser Ala Val Leu Ser Arg Leu Ala Arg Thr Gly Pro Gly Ala Phe Ala
210                 215                 220

His Ala Ile Val Arg Glu Glu Asp Glu Lys Glu Leu Ala Arg Ile Thr
225                 230                 235                 240

Thr Ser Trp Val Pro Arg
                245

<210> SEQ ID NO 158
<211> LENGTH: 204
<212> TYPE: PRT
<213> ORGANISM: Thauera linaloolentis

<400> SEQUENCE: 158

Met Pro Leu Arg Ser Ile Ala Thr Phe Phe Met Leu Leu Phe Val
1               5                   10                  15

Gly Ala Ala His Ala Ala Thr Ile Leu Val Trp Gly Asp Ser Leu Ser
            20                  25                  30

Ala Gly Tyr Gly Leu Glu Pro Gly Arg Ala Trp Pro Thr Leu Leu Gln
        35                  40                  45

Thr Arg Leu Gln Glu Lys Gly Phe Arg His Thr Val Val Asn Ala Ser
    50                  55                  60

Val Ser Gly Glu Thr Ser Ala Gly Gly Arg Ser Arg Leu Pro Ala Ala
65                  70                  75                  80

Leu Glu Arg His Lys Pro Asp Ile Val Ile Leu Glu Leu Gly Ala Asn
                85                  90                  95

Asp Gly Leu Arg Gly Leu Arg Pro Gln Leu Met Ala Glu Asn Leu Glu
            100                 105                 110

Ala Met Ile Ala Ala Ser Arg Asp Ala Gly Ala Gln Ile Leu Leu Val
        115                 120                 125

Gly Met Gln Met Pro Pro Asn Tyr Gly Pro Ala Tyr Thr Arg Arg Phe
    130                 135                 140

Ala Gln Thr Phe Asp Asp Val Ala Lys Ala Gln Gln Val Pro Leu Val
145                 150                 155                 160

Pro Phe Leu Leu Glu Gly Phe Ala Gly Gln Pro Glu Arg Phe Gln Ala
                165                 170                 175

Asp Gly Ile His Pro Thr Ala Asp Ala Gln Pro Leu Val Leu Asp Thr
            180                 185                 190

Val Trp Arg Gly Leu Glu Pro Leu Leu Lys Arg Asn
        195                 200

<210> SEQ ID NO 159
<211> LENGTH: 194
<212> TYPE: PRT
<213> ORGANISM: Shewanella mangrovi

<400> SEQUENCE: 159

Met Leu Val Ile Leu Leu Thr Ala Pro Ala Gln Ala Ala Thr Leu Leu
1               5                   10                  15

Ile Val Gly Asp Ser Leu Gly Ala Ser Tyr Gly Val Asn Glu Lys Asp
                20                  25                  30

Gly Trp Val Glu Gly Leu Arg Asn Ala Leu Pro Gln His Thr Leu Ile
            35                  40                  45

Asn Ala Ser Val Ser Gly Glu Thr Ser Gly Gly Leu Arg Arg Leu
50                  55                  60

Pro Ser Leu Leu Ser Ser Ala Ser Pro Asp Val Val Leu Ile Glu Leu
65                  70                  75                  80

Gly Gly Asn Asp Gly Leu Arg Gly Phe Pro Pro Gln Gln Leu Lys Asn
                85                  90                  95

Asn Leu Thr Lys Met Ile Ala Leu Ala Lys Gln Ala Gly Ala Lys Val
            100                 105                 110

Met Leu Ser Glu Val Met Val Pro Pro Asn Tyr Gly Pro Arg Tyr Glu
            115                 120                 125

Lys Ala Phe Thr Ser Val Tyr Gln Gln Leu Ala Glu Asp Lys Ser Val
            130                 135                 140

Thr Leu Val Pro Phe Phe Met Thr Val Ile Ala Pro His Pro Glu Leu
145                 150                 155                 160

Met Gln Arg Asp Gly Ile His Pro Asn Thr Val Ala Gln Pro Lys Ile
                165                 170                 175

Thr Ala Phe Met Leu Pro Phe Ile Lys His Ala Leu Asp Glu Val Asn
                180                 185                 190

Asn Ser

<210> SEQ ID NO 160
<211> LENGTH: 276
<212> TYPE: PRT
<213> ORGANISM: Physcomitrella patens

<400> SEQUENCE: 160

Gly Gly Phe Val Asp Asn Ser Leu Met Tyr Arg Gln Ile Phe Val Val
1               5                   10                  15

Arg Ser Tyr Glu Val Gly Pro Asp Arg Leu Met Ser Ile Arg Glu Ile
                20                  25                  30

Phe Ser Leu Phe Gln Glu Thr Ala Leu Asn His Val Gln Leu Leu Gly
            35                  40                  45

Ile Ala Gly Asp Gly Phe Gly Ala Thr Arg Ala Met Asn Arg Leu Gly
50                  55                  60

Leu Ile Trp Val Val Thr Lys Met Lys Val Glu Val Asn Arg Tyr Pro
65                  70                  75                  80

Val Trp Pro Glu Val Val Glu Ile Asp Thr Trp Val Ala His Ala Gly
                85                  90                  95

Lys Asn Gly Met Gln Arg Asp Trp Ile Met Arg Ser Tyr Gln Thr Asp
            100                 105                 110

Glu Val Leu Ala Arg Ala Thr Ser Thr Trp Cys Met Met Asp Gly Val
            115                 120                 125

Thr Arg Arg Leu Ser Lys Ile Pro Asp Glu Val Arg Ala Glu Ile Val
            130                 135                 140

Pro Cys Phe Met Asp Asp Tyr Pro Ser Ser Phe Arg Glu Asp Glu Glu
145                 150                 155                 160

Ser Pro Arg Ile Thr Lys Leu Asp Asn Thr Thr Ala Glu Asn Arg Arg
                165                 170                 175

```
Ser His Leu Lys Ser Thr Thr Ala Asp Leu Asp Met Asn Gln His Val
            180                 185                 190

Asn Asn Leu Lys Tyr Ile Asn Trp Val Leu Asp Ser Val Pro Val Glu
            195                 200                 205

His Met Glu Lys His Val Leu Ala Ser Ile Ser Leu Glu Tyr Arg Arg
210                 215                 220

Glu Cys His Ser Thr Asp Val Val Glu Ser Leu Thr Asn Ser Lys Met
225                 230                 235                 240

Asp Ile Gln Gly Asn Asp Ser Asp Pro Ser Arg Pro Cys Glu Tyr Val
            245                 250                 255

His Leu Leu Arg Lys Gln Asp Ser Ser Asn Gln Glu Ile Leu Arg Gly
            260                 265                 270

Met Thr Lys Trp
            275

<210> SEQ ID NO 161
<211> LENGTH: 199
<212> TYPE: PRT
<213> ORGANISM: Photobacterium gaetbulicola

<400> SEQUENCE: 161

Met Met Arg Phe Leu Ser Val Ile Phe Phe Leu Val Phe Thr Gln His
1               5                   10                  15

Ala Leu Ala Ala Lys Leu Met Val Leu Gly Asp Ser Leu Ser Ala Gly
            20                  25                  30

Tyr Gln Met Gln Ala Glu Gln Ser Trp Pro Asn Leu Leu Asp Ala Glu
        35                  40                  45

Leu Glu Lys Tyr Gly His Glu Val Thr Val Val Asn Ala Ser Ile Ser
    50                  55                  60

Gly Asp Thr Thr Gly Asn Gly Met Ala Arg Leu Pro Arg Leu Leu Glu
65                  70                  75                  80

Gln His Gln Pro Asp Phe Val Leu Ile Glu Leu Gly Ala Asn Asp Gly
                85                  90                  95

Leu Arg Gly Phe Pro Pro Thr Thr Ile Arg Asn Asn Leu Gly Glu Met
            100                 105                 110

Ile Thr Gln Ile Glu Gln Ala Gly Ala Tyr Pro Leu Leu Met Gln Ile
        115                 120                 125

Val Val Pro Pro Asn Tyr Gly Lys Arg Tyr Ser Asp Gln Phe Ala Lys
    130                 135                 140

Val Tyr Gln Glu Ile Ser Asn Thr Leu Asp Ile Pro Leu Leu Pro Phe
145                 150                 155                 160

Phe Leu Glu His Ile Ile Leu Lys Gln Glu Trp Met Met Glu Asp Gly
                165                 170                 175

Leu His Pro Lys Pro Asp Ala Gln Pro Trp Ile Ala Asn Phe Met Ala
            180                 185                 190

Asn Glu Ile Ala Pro His Leu
        195

<210> SEQ ID NO 162
<211> LENGTH: 438
<212> TYPE: PRT
<213> ORGANISM: Arabidopsis thaliana

<400> SEQUENCE: 162

Met Asn Ser Pro Arg Pro Ile Ser Val Val Ser Thr Phe Ala Ser Pro
1               5                   10                  15
```

```
Ser Ser Thr Ser Asp Pro Thr Arg Lys Pro Leu Ser Leu Trp Pro Gly
        20                  25                  30

Met Tyr His Ser Pro Val Thr Thr Ala Leu Trp Glu Ala Arg Ser Lys
            35                  40                  45

Ile Phe Glu Ser Leu Leu Asp Pro Pro Lys Asp Ala Pro Pro Gln Ser
 50                  55                  60

Gln Leu Leu Thr Arg Thr Pro Ser His Ser Arg Thr Thr Ile Phe Tyr
 65                  70                  75                  80

Pro Phe Ser Thr Asp Phe Ile Leu Arg Glu Gln Tyr Arg Asp Pro Trp
                85                  90                  95

Asn Glu Val Arg Ile Gly Ile Leu Leu Glu Asp Leu Asp Ala Leu Ala
                100                 105                 110

Gly Thr Ile Ser Val Lys His Cys Ser Asp Asp Ser Thr Thr Arg
                115                 120                 125

Pro Leu Leu Leu Val Thr Ala Ser Val His Lys Ile Val Leu Lys Lys
    130                 135                 140

Pro Ile Cys Val Asp Ile Asp Leu Lys Ile Val Ala Ser Val Ile Trp
145                 150                 155                 160

Val Gly Arg Ser Ser Ile Glu Ile Gln Leu Glu Val Met Gln Ser Glu
                165                 170                 175

Leu Lys Asp Val Lys Ala Ser Ser Asp Ser Val Ala Leu Thr Ala Asn
                180                 185                 190

Phe Ile Phe Val Ala Arg Asp Ser Lys Thr Gly Lys Ala Ala Pro Ile
                195                 200                 205

Asn Arg Leu Ser Pro Glu Thr Glu Val Glu Lys Leu Leu Phe Glu Glu
                210                 215                 220

Ala Glu Ala Arg Asn Asn Leu Arg Lys Lys Lys Arg Gly Gly Asp Arg
225                 230                 235                 240

Arg Glu Phe Asp His Gly Glu Cys Lys Lys Leu Glu Ala Trp Leu Ala
                245                 250                 255

Glu Gly Arg Ile Phe Ser Asp Met Pro Ala Leu Ala Asp Arg Asn Ser
                260                 265                 270

Ile Leu Leu Lys Asp Thr Arg Leu Glu Asn Ser Leu Ile Cys Gln Pro
                275                 280                 285

Gln Gln Arg Asn Ile His Gly Arg Ile Phe Gly Gly Phe Leu Met His
    290                 295                 300

Arg Ala Phe Glu Leu Ala Phe Ser Thr Ala Tyr Thr Phe Ala Gly Leu
305                 310                 315                 320

Val Pro Tyr Phe Leu Glu Val Asp His Val Asp Phe Leu Arg Pro Val
                325                 330                 335

Asp Val Gly Asp Phe Leu Arg Phe Lys Ser Cys Val Leu Tyr Thr Gln
                340                 345                 350

Leu Asp Lys Gln Asp Cys Pro Leu Ile Asn Ile Glu Val Val Ala His
                355                 360                 365

Val Thr Ser Pro Glu Ile Arg Ser Ser Glu Val Ser Asn Thr Phe Tyr
                370                 375                 380

Phe Lys Phe Thr Val Arg Pro Glu Ala Lys Arg Asn Asn Gly Phe
385                 390                 395                 400

Lys Leu Arg Asn Val Val Pro Ala Thr Glu Glu Ala Arg His Ile
                405                 410                 415

Leu Glu Arg Met Asp Ala Glu Ala Leu Lys Ser Ser Lys Gln Gln Cys
                420                 425                 430
```

Val Gly Thr Ile Leu Gln
        435

<210> SEQ ID NO 163
<211> LENGTH: 308
<212> TYPE: PRT
<213> ORGANISM: Ostreococcus tauri

<400> SEQUENCE: 163

Met Ile Ala Arg Ala Ser Gly Ala Ser Asp Val Ala Ser Ala Asp Arg
1               5                   10                  15

Ser Val Ala Lys Pro Thr Ala Asn Gly Glu Lys Ser Phe Ser Gly Met
            20                  25                  30

Asp Gly Thr Glu Trp Phe Ser Arg Asn Phe Ser Glu Gln Gly Arg Lys
        35                  40                  45

Phe Ser Glu Val Phe Pro Val Arg Tyr Ala Glu Thr Gly Pro Asn Gly
    50                  55                  60

Glu Ala Thr Met Val Thr Ile Ala Asp Leu Ile Gln Glu Cys Ala Cys
65                  70                  75                  80

Asn His Ala Gln Gly Ile Trp Gly Val Gly Gln Ser Met Pro Ala Glu
                85                  90                  95

Met Ala Lys Gly His Leu Ala Trp Val Cys Thr Arg Leu His Leu Cys
            100                 105                 110

Val Arg Lys Tyr Pro Lys Trp Gly Glu Lys Met Glu Val Ser Thr Trp
        115                 120                 125

Phe Glu Pro Gln Gly Lys Ile Ala Ala Arg Arg Asp Tyr Ser Ile Thr
    130                 135                 140

Asp Glu Ser Gly Val Gln Ile Gly Glu Ala Thr Ser Gln Trp Val Val
145                 150                 155                 160

Leu Asn Leu Asn Thr Arg Arg Met Ala Arg Ile Pro Asn Ser Val Leu
                165                 170                 175

Glu Asp Phe Lys Tyr Gln Ala Leu Glu Arg Gln Val Met Glu Glu Gly
            180                 185                 190

Tyr Ala Ser Asp Lys Leu Ala Asp Val Thr Glu Ile Ala Ala Asn Gln
        195                 200                 205

Cys Val Ser Pro Ile Thr His His Val Arg Arg Asn Asp Met Asp Met
    210                 215                 220

Asn Gly His Val Asn Asn Val Val Tyr Val Gln Trp Ile Leu Glu Ser
225                 230                 235                 240

Val Pro Gln Glu Thr Trp Asn Gly Arg Ala Leu Gln Glu Ile Ile Leu
                245                 250                 255

Glu Tyr Arg Ser Glu Cys Asn Phe Gly Glu Cys Ile Thr Ala Thr Cys
            260                 265                 270

Cys Glu Val Glu Glu Gln Ser Asp Ser Tyr Val Leu Leu His Lys Leu
        275                 280                 285

Ala Arg Gly Asp Asp Glu Ile Val Arg Ala Lys Thr Val Trp Thr Lys
    290                 295                 300

Gln Lys Thr Ser
305

<210> SEQ ID NO 164
<211> LENGTH: 286
<212> TYPE: PRT
<213> ORGANISM: Escherichia coli

<400> SEQUENCE: 164

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
                35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
                115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
                180                 185                 190

Arg Val His Gln Tyr Leu Leu Gly Tyr Ala Ser Asp Leu Asn Phe Leu
                195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
                260                 265                 270

Val Ala Ser Thr Val Gln Glu Gly Val Met Arg Asn His Asn
        275                 280                 285

<210> SEQ ID NO 165
<211> LENGTH: 308
<212> TYPE: PRT
<213> ORGANISM: Bos taurus

<400> SEQUENCE: 165

Met Val Leu Gly Arg Gly Leu Leu Gly Arg Trp Ser Val Ala Glu Leu
1               5                   10                  15

Gly Ala Val Cys Ala Arg Leu Gly Leu Gly Pro Ala Leu Leu Gly Ser
            20                  25                  30

Leu His His Leu Gly Leu Arg Lys Ser Leu Thr Val Asp Gln Gly Thr
                35                  40                  45

Met Lys Val Glu Leu Leu Pro Ala Leu Thr Asp Asn Tyr Met Tyr Leu
    50                  55                  60

Leu Ile Asp Glu Asp Thr Lys Glu Ala Ala Ile Val Asp Pro Val Gln
65                  70                  75                  80

Pro Gln Lys Val Val Glu Thr Ala Arg Lys His Gly Val Lys Leu Thr
            85                  90                  95

```
Thr Val Leu Thr Thr His His His Trp Asp His Ala Gly Gly Asn Glu
            100                 105                 110

Lys Leu Val Lys Leu Glu Pro Gly Leu Lys Val Tyr Gly Gly Asp Asp
            115                 120                 125

Arg Ile Gly Ala Leu Thr His Lys Val Thr His Leu Ser Thr Leu Gln
            130                 135                 140

Val Gly Ser Leu His Val Lys Cys Leu Ser Thr Pro Cys His Thr Ser
145                 150                 155                 160

Gly His Ile Cys Tyr Phe Val Thr Lys Pro Asn Ser Pro Glu Pro Pro
                165                 170                 175

Ala Val Phe Thr Gly Asp Thr Leu Phe Val Ala Gly Cys Gly Lys Phe
            180                 185                 190

Tyr Glu Gly Thr Ala Asp Glu Met Tyr Lys Ala Leu Leu Glu Val Leu
            195                 200                 205

Gly Arg Leu Pro Ala Asp Thr Arg Val Tyr Cys Gly His Glu Tyr Thr
            210                 215                 220

Ile Asn Asn Leu Lys Phe Ala Arg His Val Glu Pro Asp Asn Thr Ala
225                 230                 235                 240

Val Arg Glu Lys Leu Ala Trp Ala Lys Glu Lys Tyr Ser Ile Gly Glu
                245                 250                 255

Pro Thr Val Pro Ser Thr Ile Ala Glu Glu Phe Thr Tyr Asn Pro Phe
            260                 265                 270

Met Arg Val Arg Glu Lys Thr Val Gln Gln His Ala Gly Glu Thr Glu
            275                 280                 285

Pro Val Ala Thr Met Arg Ala Ile Arg Lys Glu Lys Asp Gln Phe Lys
            290                 295                 300

Met Pro Arg Asp
305

<210> SEQ ID NO 166
<211> LENGTH: 161
<212> TYPE: PRT
<213> ORGANISM: Medicago truncatula

<400> SEQUENCE: 166

Met Pro Ser Trp Phe Asp Ile His Glu Ile Pro Val Thr Ala Asn Ser
1               5                   10                  15

Pro Asn Asp Glu Ser Ser Leu Leu Lys Ala Val Gln Asn Val His Ala
            20                  25                  30

Thr Ile Asp Lys Glu Ile Ala Ala Gly Thr Asn Pro Asn Asn Ile Phe
            35                  40                  45

Ile Cys Gly Phe Ser Gln Gly Gly Ala Leu Thr Leu Ala Ser Val Leu
        50                  55                  60

Leu Tyr Pro Lys Thr Leu Gly Gly Ala Val Phe Ser Gly Trp Val
65              70                  75                  80

Pro Phe Asn Ser Ser Val Ile Glu Gln Ile Thr Pro Glu Ala Lys Arg
                85                  90                  95

Thr Pro Ile Leu Trp Ser His Gly Leu Ser Asp Lys Thr Val Leu Phe
            100                 105                 110

Glu Ala Arg Gln Ala Ala Pro Pro Phe Leu Glu Lys Ile Gly Val Ser
            115                 120                 125

Cys Glu Phe Lys Ala Tyr Pro Gly Leu Ala His Ser Ile Asn Asn Glu
            130                 135                 140

Glu Leu Lys His Leu Glu Ser Trp Ile Lys Ala Arg Leu Gln Ser Ser
```

145             150             155             160

Ser

<210> SEQ ID NO 167
<211> LENGTH: 431
<212> TYPE: PRT
<213> ORGANISM: Eutrema halophilum

<400> SEQUENCE: 167

Met Glu Ser Ala Met Asn Thr Glu Ser Val Phe Glu Phe Leu Gly Asn
1               5                   10                  15

Val Pro Leu Leu Gln Lys Leu Pro Ser Ser Leu Lys Lys Ile Ala
            20                  25                  30

Gln Val Val Leu Lys Arg Tyr Gly Lys Gly Asp Tyr Val Ile Arg
        35                  40                  45

Glu Asp Gln Ala Trp Asp Gly Cys Tyr Phe Ile Phe Ala Gly Glu Ala
    50                  55                  60

Gln Val Ser Gly Pro Ala Glu Glu Asn Arg Ser Glu Phe Leu Leu
65                  70                  75                  80

Lys Lys Tyr Asp Tyr Phe Gly His Gly Ile Ser Ala His Val His Ser
                85                  90                  95

Ala Asp Ile Ile Ala Thr Ser Glu Leu Thr Cys Leu Val Leu Pro Arg
            100                 105                 110

Asp His Cys Arg Leu Leu Glu Thr Asn Ser Ile Trp Gln Ser Asp Lys
        115                 120                 125

Glu Val Gln Lys Cys Ser Leu Val Glu Arg Ile Leu His Leu Asp Pro
    130                 135                 140

Leu Glu Leu Asn Ile Phe Arg Gly Ile Thr Leu Pro Asp Ala Pro Lys
145                 150                 155                 160

Phe Gly Lys Val Phe Gly Gly Gln Phe Met Gly Gln Ala Leu Ala Ala
                165                 170                 175

Ala Ser Lys Thr Val Asp Phe Leu Lys Ile Val His Ser Leu His Ser
            180                 185                 190

Tyr Phe Leu Leu Val Gly Asp Ile Asp Ile Pro Ile Ile Tyr Gln Val
        195                 200                 205

His Arg Ile Arg Asp Gly Asn Asn Phe Ala Thr Arg Arg Val Asp Ala
    210                 215                 220

Ile Gln Lys Gly Asn Ile Ile Phe Ile Leu Leu Ala Ser Phe Gln Lys
225                 230                 235                 240

Glu Gln Gln Gly Phe Asp His Gln Glu Ser Thr Met Pro Ser Ala Pro
                245                 250                 255

Asp Pro Asp Thr Leu Leu Ser Leu Glu Glu Leu Arg Glu Arg Ile
            260                 265                 270

Thr Asp Pro His Leu Pro Arg Ser Tyr Arg Asn Lys Val Ala Thr Ala
        275                 280                 285

Asn Phe Val Pro Trp Pro Ile Asp Ile Arg Phe Cys Asp Pro Ser Asn
    290                 295                 300

Ser Thr Asn Gln Thr Lys Ser Pro Pro Arg Leu Arg Tyr Trp Phe Arg
305                 310                 315                 320

Ala Lys Gly Lys Leu Ser Asp Asp Gln Ala Leu His Arg Cys Val Val
                325                 330                 335

Ala Phe Ala Ser Asp Leu Ile Phe Ala Ser Val Ser Leu Asn Pro His
            340                 345                 350

Arg Arg Lys Gly Leu Arg Ser Ala Ala Leu Ser Leu Asp His Ala Met

```
                    355                 360                 365
Trp Phe His Arg Pro Leu Arg Ala Asp Asp Trp Leu Leu Phe Val Ile
    370                 375                 380

Val Ser Pro Thr Ala His Met Thr Arg Gly Phe Val Ser Gly Gln Met
385                 390                 395                 400

Phe Asn Arg Lys Gly Glu Leu Val Val Ser Leu Thr Gln Glu Ala Leu
                405                 410                 415

Leu Arg Glu Ala Arg Pro Pro Lys Pro Ser Val Thr Ser Lys Leu
                420                 425                 430

<210> SEQ ID NO 168
<211> LENGTH: 396
<212> TYPE: PRT
<213> ORGANISM: Picea sitchensis

<400> SEQUENCE: 168

Met Tyr His Ser Pro Val Thr Asn Ala Leu Trp His Ala Arg Ser Ser
1               5                   10                  15

Ile Phe Glu Arg Leu Leu Asp Pro Ser Val Asp Ala Pro Pro Gln Ser
                20                  25                  30

Gln Leu Leu Ser Lys Thr Pro Ser Gln Ser Arg Thr Ser Ile Leu Tyr
            35                  40                  45

Asn Phe Ser Ser Asp Tyr Ile Leu Arg Glu Gln Tyr Arg Asp Pro Trp
    50                  55                  60

Asn Glu Val Arg Ile Gly Lys Leu Leu Glu Asp Leu Asp Ala Leu Ala
65              70                  75                  80

Gly Thr Ile Ala Val Lys His Cys Ser Asp Asp Ser Thr Thr Arg
                85                  90                  95

Pro Leu Leu Leu Val Thr Ala Ser Val Asp Lys Met Val Leu Lys Lys
                100                 105                 110

Pro Ile Arg Val Asp Thr Asp Leu Lys Val Ala Gly Ala Val Thr Trp
            115                 120                 125

Val Gly Arg Ser Ser Leu Glu Ile Gln Met Val Ile Thr Gln Pro Pro
    130                 135                 140

Glu Gly Glu Thr Glu Thr Gly Asp Ser Val Ala Leu Thr Ala Asn Phe
145                 150                 155                 160

Met Phe Val Ala Arg Asp Ser Lys Thr Gly Lys Ser Ala Leu Ile Asn
                165                 170                 175

Arg Leu Leu Pro Gln Thr Glu Gln Glu Lys Ala Leu Leu Ala Glu Gly
            180                 185                 190

Glu Ala Arg Asp Met Arg Arg Lys Glu Arg Gln Arg Gln Gly Lys
            195                 200                 205

Glu Phe Glu Glu Gly His Arg Leu His Gly Asp Gly Asp Arg Leu Lys
    210                 215                 220

Ala Leu Leu Arg Glu Gly Arg Val Leu Cys Asp Met Pro Ala Leu Ala
225                 230                 235                 240

Asp Arg Asp Ser Met Leu Ile Lys Asp Thr Arg Leu Glu Asn Ala Leu
                245                 250                 255

Ile Cys Gln Pro Gln Gln Arg Asn Leu His Gly Arg Ile Phe Gly Gly
            260                 265                 270

Phe Leu Met His Arg Ala Ser Glu Leu Ala Phe Ser Thr Cys Tyr Ala
            275                 280                 285

Phe Val Gly His Thr Pro Leu Phe Leu Glu Val Asp His Val Asp Phe
    290                 295                 300
```

```
Leu Arg Pro Val Asp Val Gly Asp Phe Leu Arg Phe Lys Ser Cys Val
305                 310                 315                 320

Leu Phe Thr Gln Val Asp Asp Pro Lys Arg Pro Leu Ile Asp Ile Glu
                325                 330                 335

Val Val Ala His Val Thr Arg Pro Glu Leu Arg Ser Ser Glu Val Ser
            340                 345                 350

Asn Thr Phe Tyr Phe Thr Phe Thr Val His Pro Val Ala Leu Glu Gly
        355                 360                 365

Gly Leu Lys Ile Arg Lys Val Leu Pro Ala Thr Glu Glu Glu Ala Arg
    370                 375                 380

His Val Leu Glu Arg Ile Asp Ala Glu Asn Leu Asn
385                 390                 395

<210> SEQ ID NO 169
<211> LENGTH: 250
<212> TYPE: PRT
<213> ORGANISM: Clostridium ultunense

<400> SEQUENCE: 169

Met Lys Ala Thr Pro Leu Tyr Ile Lys Asp Tyr Lys Val Glu Ile Asn
1               5                   10                  15

His Val Asp Phe Lys Gly Asp Leu Lys Leu Ser Ser Leu Phe Thr Tyr
            20                  25                  30

Cys Gln Asp Ile Ala Gly Leu His Ala Glu Asn Leu Gly Met Gly Arg
        35                  40                  45

Glu Val Leu Tyr Thr Gln His Arg Val Ile Trp Val Leu Val Arg Val
    50                  55                  60

Arg Val Asp Ile Ile Lys Tyr Pro Lys Trp Lys Asp Ile Leu Thr Leu
65                  70                  75                  80

Glu Thr Trp Pro Gln Glu Pro Ser Arg Met Gly Phe Asp Arg Asp Phe
                85                  90                  95

Leu Ile Lys Asp Lys Lys Gly Asn Ile Leu Ala Lys Ala Val Ser Thr
            100                 105                 110

Trp Val Val Ile Asp Val Glu Ser Arg Lys Leu Val Arg Thr Lys Ser
        115                 120                 125

Val Tyr Thr Gly Tyr Pro Leu Val Val Glu Lys Arg Ala Ile Asp Cys
    130                 135                 140

Lys Leu Gly Asn Leu Lys Ser Ser Gly Glu Leu Glu Thr Ala Tyr Glu
145                 150                 155                 160

Arg Thr Val Arg Tyr Ser Asp Ile Asp Val Asn Glu His Leu Asn Asn
                165                 170                 175

Ala Lys Tyr Leu Asp Phe Ile Met Asp Ser Phe Ser Phe Glu Glu His
            180                 185                 190

Arg Arg Phe Asn Val Lys Ser Val Glu Ile Ser Tyr Ser Asn Glu Ala
        195                 200                 205

Leu Leu Gly Glu Thr Ile Lys Ile Tyr Glu Asp Arg Ser Arg Ile Asp
    210                 215                 220

Ser Asn Ile Ile Tyr Met Glu Gly Ile Arg Glu Gly Lys Asp Leu Val
225                 230                 235                 240

Phe Lys Ser Gln Ile Glu Ile Glu Glu Lys
                245                 250

<210> SEQ ID NO 170
<211> LENGTH: 240
<212> TYPE: PRT
<213> ORGANISM: Clostridium sp.
```

<400> SEQUENCE: 170

```
Met Ala Ile Ile Glu Asn Lys Tyr His Ile Gly Ile Lys Tyr Val Asp
1               5                   10                  15

Lys Asp Arg Leu Leu Ser Leu Arg Gly Ile Ile Leu Leu Phe Glu Asp
            20                  25                  30

Ile Ala Cys Arg His Ser Asp Met Val Gly Tyr Gly Ile Asn Asp Val
        35                  40                  45

Thr Lys Thr His Phe Ser Trp Val Leu Leu Asn Trp Lys Ile Lys Val
50                  55                  60

Leu Ser Arg Ile Asn Tyr Gly Ser Ile Val Thr Val Lys Thr Trp Ser
65                  70                  75                  80

Arg Glu Thr Ser Lys Leu Tyr Thr Tyr Arg Asp Phe Glu Ile Tyr Asp
                85                  90                  95

Glu Asn Asn Asn Leu Ile Cys Ile Ala Ser Ser Lys Trp Val Leu Leu
            100                 105                 110

Ser Thr Glu Thr Gly His Ile Ile His Ile Thr Glu Gly Ile Lys Asn
        115                 120                 125

Ala Tyr Leu Ala Glu Asn Lys Thr Val Phe Asn Glu Ser Asp Leu His
    130                 135                 140

Lys Ile Val Glu Pro Asp Asn Ala Glu Lys Thr Phe Ser Phe Thr Val
145                 150                 155                 160

Arg Arg Arg Asp Ile Asp Ile Asn Asn His Met Asn Asn Leu Tyr Tyr
                165                 170                 175

Leu Asp Tyr Ala Leu Glu Ala Leu Pro Glu Glu Val Tyr Ser Lys Phe
            180                 185                 190

Phe Asn Asn Val Glu Ile Met Tyr Lys Tyr Ser Ala Lys Leu Gly Glu
        195                 200                 205

Thr Ile Asn Cys Phe Tyr Lys Glu Glu Glu Asp Gly Tyr Tyr Val Met
    210                 215                 220

Met Lys Ser Ala Thr Asp Asn Ile Leu His Ala Leu Val Lys Leu Tyr
225                 230                 235                 240
```

<210> SEQ ID NO 171
<211> LENGTH: 242
<212> TYPE: PRT
<213> ORGANISM: Roseburia sp.

<400> SEQUENCE: 171

```
Met Tyr Gln Phe Lys Ser Arg Val Arg Phe Ser Glu Val Asp Ser Gln
1               5                   10                  15

Leu His Met Thr Leu Pro Ser Ile Ile Asn Tyr Phe Gln Asp Cys Ser
            20                  25                  30

Thr Phe His Ser Asp Ser Ile Gly Tyr Gly Ile Glu Val Met Met Glu
        35                  40                  45

Gln Gly Tyr Ala Trp Ile Leu Ser Ser Trp Gln Ile Ile Ile Asn Arg
    50                  55                  60

Tyr Pro Lys Phe Gly Glu Glu Ile Thr Val Ser Thr Trp Ala His Gly
65                  70                  75                  80

Trp Lys Ala Phe Phe Gly Tyr Arg Asn Phe Lys Leu Glu Asp Thr Glu
                85                  90                  95

Gly Asn Leu Leu Ala Tyr Ala Asn Thr Asn Trp Ile Tyr Met Asn Ile
            100                 105                 110

Arg Thr Gly His Pro Glu Arg Ile Pro Lys Glu Ile Cys Asp Leu Tyr
        115                 120                 125
```

Lys Cys Glu Pro Ala Leu Pro Met Glu Glu Ser Ser Arg Lys Ile Thr
130                 135                 140

Pro Pro Ala Lys Gly Thr Gly Ile Thr Pro Ile Gln Val His Arg Tyr
145                 150                 155                 160

Asp Ile Asp Ser Asn Asn His Val Asn Asn Glu Arg Tyr Val Pro Met
                165                 170                 175

Ala Met Glu Cys Leu Pro Glu Gly Ala Gln Ile Arg Gln Leu Arg Val
                180                 185                 190

Glu Tyr Arg Asn Ser Ala Val Tyr Gly Asp Thr Ile Tyr Pro Val Tyr
            195                 200                 205

His Gln Glu Glu Asp Leu Leu Lys Val Ser Leu Asn Asp Ser Asp Gly
            210                 215                 220

Lys Pro Tyr Ala Ile Val Glu Phe Gln Leu Ala Pro Leu Ser Asp Gln
225                 230                 235                 240

Ala Asp

<210> SEQ ID NO 172
<211> LENGTH: 242
<212> TYPE: PRT
<213> ORGANISM: Pseudoramibacter alactolyticus

<400> SEQUENCE: 172

Met Gly Lys Ile Phe Glu Arg Pro Gln Ala Ile Ala Thr Tyr Asp Cys
1               5                   10                  15

Leu Glu Asp His His Leu Ser Pro Val Ala Val Met Asn Tyr Phe Gln
                20                  25                  30

Gln Ile Ser Leu Glu His Ser Ala Ser Leu Lys Ala Gly Pro Tyr Glu
            35                  40                  45

Leu Ser Ala Leu Asp Leu Thr Trp Ile Val Val Lys Tyr His Val Asp
50                  55                  60

Phe Trp Gln Met Pro Arg Phe Leu Asp Gln Leu Gln Leu Gly Thr Trp
65                  70                  75                  80

Ala Ser Ala Phe Lys Gly Phe Thr Ala His Arg Gly Phe Phe Leu Lys
                85                  90                  95

Asn Gln Ser Gly Glu His Met Val Asp Gly Gln Ser His Trp Met Met
                100                 105                 110

Val Asp Arg Arg Gln Asn His Ile Val Arg Val Asn Glu Val Pro Ile
            115                 120                 125

Asn Ala Val Tyr Asp Val Glu Asp Gln Gly Pro Arg Phe Lys Met Pro
130                 135                 140

Arg Leu Ala Arg Ile Lys Asp Trp Glu Asn Val Arg Gln Phe Ser Val
145                 150                 155                 160

Arg Tyr Leu Asp Ile Asp Tyr Asn Gly His Val Asn Asn Val Cys Tyr
                165                 170                 175

Leu Ala Trp Ala Leu Ala Cys Leu Pro Ala Val Val Leu Gln Thr Arg
                180                 185                 190

Thr Leu Lys Thr Leu Asp Ile Val Phe Lys Glu Gln Ala Leu Tyr Gly
            195                 200                 205

Asp Val Val Thr Val Lys Asp Arg Glu Ile Ala Pro Asn Cys Tyr Arg
210                 215                 220

Val Asp Ile Phe Asn Ala Asn Glu Thr Leu Leu Thr Gln Leu Gln Leu
225                 230                 235                 240

Gln Phe

MATERIALS AND METHODS FOR BIOSYNTHETIC MANUFACTURE AND UTILIZATION OF SYNTHETIC POLYPEPTIDES, AND PRODUCTS THEREFROM

CROSS REFERENCE TO RELATED APPLICATION

The present application claims the benefit of U.S. Provisional Patent Application No. 62/650,629 filed Mar. 30, 2018, which is incorporated herein by reference for all purposes.

SEQUENCE LISTING

The instant application contains a Sequence Listing which has been filed electronically in ASCII format and is hereby incorporated by reference in its entirety. Said ASCII copy, created on Jul. 24, 2019, is named 061646-1131147_(00601US)_SL.txt and is 366,159 bytes in size.

FIELD

The teachings in the present disclosure relate to novel, synthetic polypeptides having, for example, acyl-acyl carrier protein (ACP) thioesterase (TE) activity, including polypeptides that convert pimeloyl-ACP to pimelic acid. In some aspects of the present disclosure, the synthetic polypeptides have advantageous enzymatic activity and/or improved substrate specificity relative to a wild type acyl-ACP TE.

BACKGROUND

Biochemical pathways are utilized to produce products useful for an organism. See, for example, LEHNINGER, A. L., NELSON, D. L., & COX, M. M. (2000). Lehninger principles of biochemistry. New York, Worth Publishers. A biochemical pathway for the production of 7-Aminoheptanoic acid (7-AHA) utilizes the biotin biosynthesis pathway in E. coli (Lin et al., "Biotin Synthesis Beings by Hijacking the Fatty Acid Synthesis Pathway," Nat. Chem. Biol. 6(9): 682-688 2010). The first committed step in biotin biosynthesis is the methylation of malonyl-ACP by BioC. The malonyl-ACP methyl ester thus generated then serves as a starter unit for the fatty acid biosynthesis pathway.

Two rounds of fatty acid elongation and reduction then occur to generate pimeloyl-ACP methyl ester. Pimeloyl-ACP is then generated by the removal of the methyl group by the esterase BioH (FIG. 1). Pimeloyl-ACP is then acted upon by a thioesterase enzyme to produce pimelic acid. Thioesterases (TE) therefore play a crucial role in the production of 7-AHA using the biotin synthesis pathway (FIG. 2).

Polyamides, such as nylons, can be synthesized by the condensation polymerisation of a diamine with a dicarboxylic acid or alternatively by the condensation polymerisation of lactams. Nylon 6,6 is a ubiquitous nylon produced by the reaction of hexamethylenediamine (HMD) and adipic acid. Nylon 6 is produced by a ring opening polymerisation of caprolactam. Nylon 7 represents a novel polyamide with value-added characteristics compared to Nylon 6 and Nylon 6,6. The key intermediate for the synthesis of Nylon 7 is 7-AHA. However, no economically favorable petrochemical routes exist to produce 7-AHA.

BRIEF SUMMARY

Synthetic biology is exploited for the design and construction of new biological parts, devices, and systems, and the re-design of existing, natural biological systems for useful purposes. In one aspect, synthetic polypeptides, having an acyl-ACP TE activity, useful for the production of 7-AHA, via biosynthetic routes, are taught.

The present disclosure, in one embodiment, provides various polypeptides having acyl-ACP TE activity. In another aspect, the polypeptides having acyl-ACP TE activity comprise one or more amino acid substitution(s) relative to a wild-type acyl-ACP TE, wherein the one or more amino acid substitution(s) are at amino acid(s) that occupy position(s) corresponding to position(s) 5, 32, 33, 35, 36, 38, 40, 45, 59, 64, 90, 111, 128, 175, and 241 of SEQ ID NO: 1, or a functional fragment thereof.

In some embodiments, the wild-type acyl-ACP TE is classified under EC 3.1.2.-. In some embodiments, the wild-type acyl-ACP TE is classified under EC 3.1.2.14.

In some embodiments, the amino acid corresponding to position 5 is substituted with tyrosine (Y) or an equivalent amino acid. In some embodiments, the amino acid corresponding to position 35 is substituted with serine (S) or an equivalent amino acid. In some embodiments, the amino acid corresponding to position 38 is substituted with glutamine (Q) or an equivalent amino acid. In some embodiments, the amino acid corresponding to position 64 is substituted with valine (V) or an equivalent amino acid. In some embodiments, the amino acid corresponding to position 241 is substituted with glutamic acid (E) or an equivalent amino acid. In some embodiments, the amino acid corresponding to position 45 is substituted with methionine or isoleucine (I) or an equivalent amino acid. In some embodiments, the amino acid corresponding to position 128 is substituted with tyrosine (Y) or an equivalent amino acid. In some embodiments, the amino acid corresponding to position 175 is substituted with serine (S) or an equivalent amino acid. In some embodiments, the amino acid corresponding to position 33 is substituted with aspartic acid (D) or an equivalent amino acid, and the amino acid corresponding to position 128 is substituted with tyrosine (Y) or an equivalent amino acid. In some embodiments, the amino acid corresponding to position 59 is substituted with valine (V) or an equivalent amino acid, and the amino acid corresponding to position 90 is substituted with phenylalanine (F) or an equivalent amino acid. In some embodiments, the amino acid corresponding to position 40 is substituted with glutamic acid (E) or an equivalent amino acid, and the amino acid corresponding to position 111 is substituted with tryptophan (W) or an equivalent amino acid. In some embodiments, the amino acid corresponding to position 36 is substituted with glycine (G) or an equivalent amino acid, and the amino acid corresponding to position 128 is substituted with tyrosine (Y) or an equivalent amino acid. In some embodiments, the amino acid corresponding to position 32 is substituted with glutamine (Q) or an equivalent amino acid, and the amino acid corresponding to position 40 is substituted with glutamic acid (E) or an equivalent amino acid.

In some embodiments, the amino acid sequence of the polypeptide having an acyl-ACP TE activity has at least 50% amino acid sequence identity with the amino acid sequence of the wild-type acyl-ACP TE.

In some embodiments, the polypeptide having an acyl-ACP TE activity has increased enzymatic activity and/or improved substrate specificity relative to the wild-type acyl-ACP TE. In certain embodiments the the polypeptide having an acyl-ACP TE activity has improved substrate specificity for pimeloyl-ACP relative to the wild-type acyl-ACP TE. In certain embodiments, the the polypeptide having an acyl- ACP TE activity has an increase in enzymatic activity of at least 10% relative to the wild-type acyl-ACP TE.

The present disclosure provides, in another embodiment, a nucleic acid encoding a polypeptide having an acyl-ACP TE activity. In some embodiments, the nucleic acid encodes a polypeptide having an acyl-ACP TE activity, wherein the polypeptide comprises one or more amino acid substitution(s) relative to a wild-type acyl-ACP TE, wherein the one or more amino acid substitution(s) are at amino acid(s) that occupy position(s) corresponding to position(s) 5, 32, 33, 35, 36, 38, 40, 45, 59, 64, 90, 111, 128, 175, and 241 of SEQ ID NO: 1, or a functional fragment thereof. Also provided, in another embodiment, is a vector comprising a nucleic acid encoding a polypeptide having acyl-ACP TE activity. In some embodiments, the vector comprises a nucleic acid encoding a polypeptide having an acyl-ACP TE activity, wherein the polypeptide comprises one or more amino acid substitution(s) relative to a wild-type acyl-ACP TE, wherein the one or more amino acid substitution(s) are at amino acid(s) that occupy position(s) corresponding to position(s) 5, 32, 33, 35, 36, 38, 40, 45, 59, 64, 90, 111, 128, 175, and 241 of SEQ ID NO: 1.

Further provided, in another embodiment, is a metabolically engineered organism or a host cell comprising any of the vectors provided herein. In some embodiments, the host cell is a prokaryotic cell.

Also provided, in another embodiment, is a composition comprising any of the polypeptides described herein. In some embodiments, the composition further comprises pimeloyl-ACP.

Further provided, in another embodiment, is a method for producing pimelic acid, pimelate semialdehyde or 7-AHA, the method comprising the step of converting pimeloyl-ACP to pimelic acid in the presence of any one of the polypeptides provided herein. Also, provided, in another embodiment, is a method for producing pimelic acid, pimelate semialdehyde or 7-AHA, the method comprising the steps of culturing a host cell comprising a vector encoding any of the polypeptides described herein in a suitable medium and recovering the pimelic acid, pimelate semialdehyde or 7-AHA.

Also provided, in another embodiment is a bioderived pimelic acid, pimelate semialdehyde or 7-AHA, that is produced by any of the methods provided herein. Further provided, in another embodiment, is a product comprising a chemical produced from any of the bioderived products provided herein, wherein the product comprises a pharmaceutical, a biofuel, a fragrance, a nylon intermediate, a polyester, or a food additive.

Also provided is a bio-based or fermentation-derived product, wherein said product comprises: (i) a composition comprising at least one bio-derived, bio-based or fermentation-derived compound, or salts thereof, produced in the presence any of the polypeptides described herein, or produced from the product of a reaction catalyzed by any of the polypeptides described herein, or any combination thereof; (ii) a bio-derived, bio-based or fermentation-derived polymer comprising the bio-derived, bio-based or fermentation-derived composition or compound of (i), or any combination thereof (iii) a bio-derived, bio-based or fermentation-derived resin comprising the bio-derived, bio-based or fermentation-derived compound or bio-derived, bio-based or fermentation-derived composition of (i), or any combination thereof or the bio-derived, bio-based or fermentation-derived polymer of (ii), or any combination thereof (iv) a substance obtained by molding the bio-derived, bio-based or fermentation-derived polymer of (ii), or the bio-derived, bio-based or fermentation-derived resin of (iii), or any combination thereof (v) a bio-derived, bio-based or fermentation-derived formulation comprising the bio-derived, bio-based or fermentation-derived composition of (i), bio-derived, bio-based or fermentation-derived compound of (i), bio-derived, bio-based or fermentation-derived polymer of (ii), bio-derived, bio-based or fermentation-derived resin of (iii), or bio-derived, bio-based or fermentation-derived substance of (iv), or any combination thereof, or; (vi) a bio-derived, bio-based or fermentation-derived semi-solid or a non-semi-solid stream, comprising the bio-derived, bio-based or fermentation-derived composition of (i), bio-derived, bio-based or fermentation-derived compound of (i), bio-derived, bio-based or fermentation-derived polymer of (ii), bio-derived, bio-based or fermentation-derived resin of (iii), bio-derived, bio-based or fermentation-derived formulation of (v), bio-derived, bio-based or fermentation-derived molded substance of (iv), or any combination thereof.

BRIEF DESCRIPTION OF THE FIGURES

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 5 shows the correlated residues at the substrate binding site for higher activity of Acyl-ACP-TEs. The degree of correlation is plotted as a heat-map (left panel) and the top 5 correlated residues are shown in the table (center panel). The correlated residues indicate that these two positions are coupled, and favours a residue at position two when a specific residue is present at position one. Spatial occupancy of the correlated residues is shown as a sphere in the 3D model of the enzyme (right panel).

DETAILED DESCRIPTION

Figure 1:
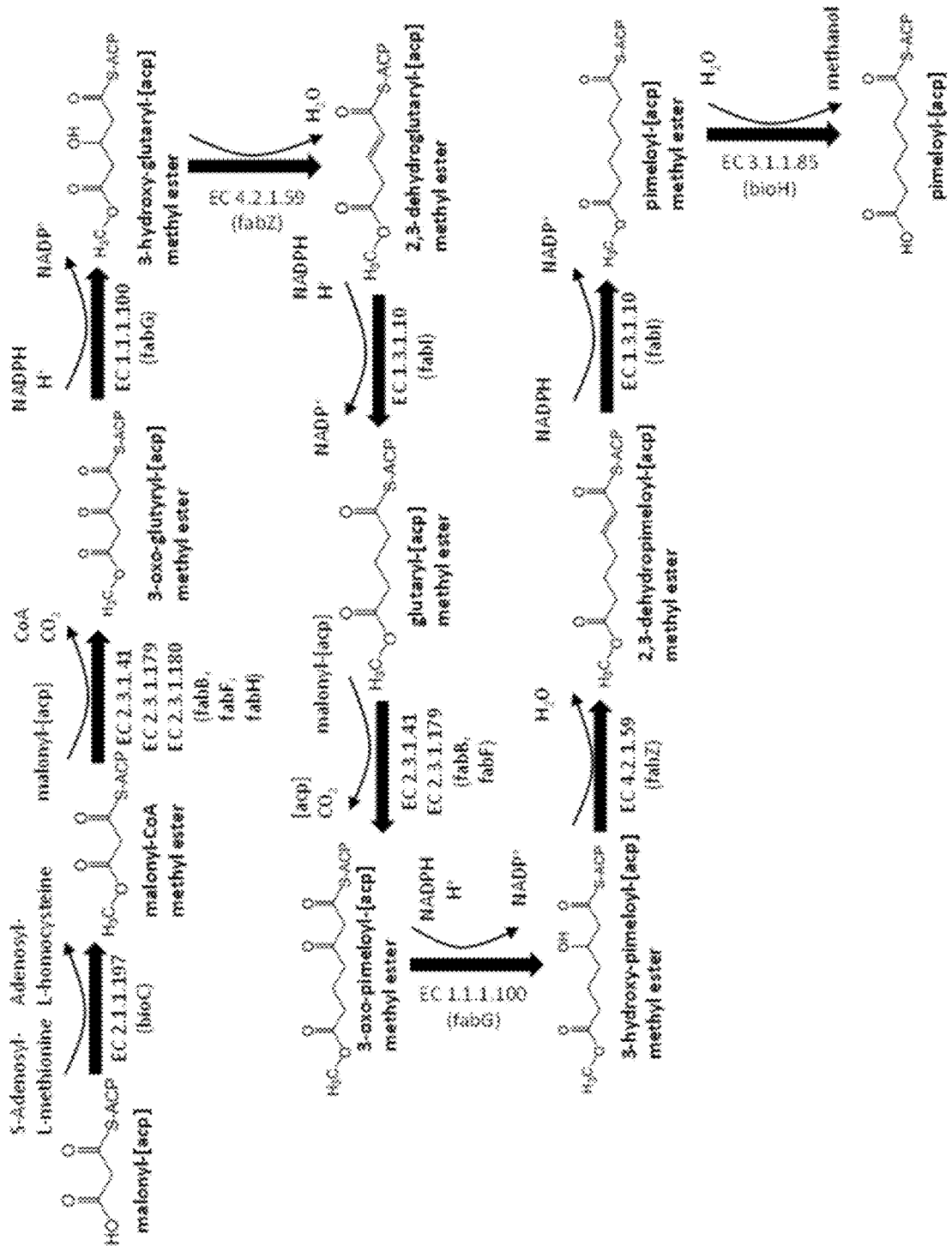
FIG. 1 is a schematic of a biochemical pathway for the production of pimeloyl-ACP from malonyl-ACP.

All references cited herein and the material for which they are cited are hereby specifically incorporated by reference in their entireties.

Many modifications and other embodiments of the disclosures set forth herein will come to mind to one skilled in the art to which these disclosures pertain having the benefit of the teachings presented in the foregoing and following descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In the present description and claims, the conventional one-letter and three-letter codes for amino acid residues are used. All of the numbering, including the numbering of the substitutions is with reference to corresponding amino acid residues in the amino acid sequence set forth herein as SEQ ID NO: 1. SEQ ID NO: 1 is the full-length amino acid sequence for an *Eggerthella* sp. acyl-ACP TE deposited under Uniprot ID No. R5FQ35. In the present description and claims, the activity of the claimed polypeptide is measured relative to that of a wild-type acyl-ACP TE, unless otherwise specified.

"Correspondence" to another sequence (e.g., regions, fragments, nucleotide or amino acid positions, or the like), for example, SEQ ID NO: 1, is based on the convention of numbering according to nucleotide or amino acid position number and then aligning the sequences in a manner that maximizes the percentage of sequence identity. Because not all positions within a given "corresponding region" need be identical, non-matching positions within a corresponding region may be regarded as "corresponding positions."

Definitions

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The practice of the present disclosure will employ, unless otherwise indicated, conventional techniques of microbiology, tissue culture, molecular biology, chemistry, biochemistry and recombinant DNA technology, which are within the skill of the art. The materials, methods and examples are illustrative only and not limiting. The following is presented by way of illustration and is not intended to limit the scope of the disclosure.

In some embodiments, numbers expressing quantities of reagents, properties, reaction conditions and results, and so forth, used to describe and claim certain embodiments of the present disclosure are to be understood as being modified in some instances by the term "about," In some embodiments, the numerical parameters set forth in the specification (into which the claims are incorporated in their entirety) are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practical. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

As used in this specification and the appended claims, the singular forms "a," "an," and "the" include plural reference unless the context clearly dictates otherwise.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). The structures of these twenty natural amino acids are shown in, e.g., Stryer et al., *Biochemistry*, 5$^{th}$ ed., Freeman and Company (2002). The term "amino acid" also includes unnatural amino acids, modified amino acids (e.g., having modified side chains and/or backbones), and amino acid analogs.

As used herein, the term "bioderived" means derived from or synthesized by a biological organism and can be considered a renewable resource since it can be generated by a biological organism. Such a biological organism, in particular the microbial organisms disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the disclosure. A biobased or bioderived product is in contrast to a petroleum derived product, wherein such a product is derived from or synthesized from petroleum or a petrochemical feedstock.

For compounds containing carboxylic acid groups such as organic monoacids, hydroxyacids, amino acids and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. The salt can be isolated as is from the system as the salt or converted to the free acid by reducing the pH to below the pKa through addition of acid or treatment with an acidic ion exchange resin.

For compounds containing amine groups such as but not limited to organic amines, amino acids and diamine, these compounds may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid. Acceptable inorganic bases are known in the art and include aluminum hydroxide, calcium hydroxide, potassium hydroxide, sodium carbonate, sodium hydroxide, and the like. The salt can be isolated as is from the system as a salt or converted to the free amine by raising the pH to above the pKb through addition of base or treatment with a basic ion exchange resin For compounds containing both amine groups and carboxylic acid groups such as but not limited to amino acids, these compounds may be formed or converted to their ionic salt form by either 1) forming acid addition salts with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-acid), carboxylic acid, glucoheptonic acid, 4,4'-methylenebis-(3-hydroxy-2-ene-1-carboxylic 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid. Acceptable inorganic bases include aluminum hydroxide, calcium hydroxide, potassium hydroxide, sodium carbonate, sodium hydroxide, and the like or 2) replacing an acidic proton present in the parent compound with a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate, sodium hydroxide, and the like. The salt can be isolated as is from the system or converted to the free acid by reducing the pH to below the pKa through addition of acid or treatment with an acidic ion exchange resin.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition that "comprises," "has" or "includes" one or more features is not limited to possessing only those one or more features and can cover other unlisted features. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element as essential to the practice of the present disclosure.

As used herein, "consisting essentially of" means the inclusion of additional sequences in a polynucleotide or polypeptide sequence provided herein where the additional sequences do not materially affect the basic function of the claimed polynucleotide or polypeptide sequences. With regard to compositions in general, the term "consisting essentially of" refers to those elements required for a given embodiment and additionally permits the presence of elements that do not materially affect the basic and novel or functional characteristic(s) of that embodiment of the disclosure.

As used herein, the term "consisting of" refers to compositions, methods, and respective components thereof as described herein, which are exclusive of any element not recited in that description of the embodiment.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon (Ishizuka, et al., (1993) *J. Gen, Microbiol.* 139:425-32) can be modified to yield a functionally identical molecule. Accordingly, each silent variation of a nucleic acid, which encodes a polypeptide of the present disclosure, is implicit in each described polypeptide sequence and incorporated herein by reference.

As to amino acid sequences, one of skill will recognize that individual substitutions, deletions or additions to a nucleic acid, peptide, polypeptide or protein sequence which alters, adds, or deletes a single amino acid or a small percentage of amino acids in the encoded sequence is a "conservatively modified variant" when the alteration results in the substitution of an amino acid with a chemically similar amino acid. Thus, any number of amino acid residues can be so altered. Conservatively modified variants typically provide equivalent biological activity as the unmodified polypeptide sequence from which they are derived. Conservative substitution tables providing functionally similar amino acids, also referred herein as "equivalent amino acids" are well known in the art.

As used herein, "codon optimization" is the process of modifying a nucleotide sequence in a manner that improves its expression, G/C content, RNA secondary structure, and translation in eukaryotic cells, without altering the amino acid sequence it encodes. Altered codon usage is often employed to alter translational efficiency and/or to optimize the coding sequence for expression in a desired host or to optimize the codon usage in a heterologous sequence for expression in a particular host. Codon usage in the coding regions of the polynucleotides of the present disclosure can be analyzed statistically using commercially available software packages such as "Codon Preference" available from the University of Wisconsin Genetics Computer Group. See, Devereaux, et al., (1984) *Nucleic Acids Res.* 12:387-395) or MacVector 4.1 (Eastman Kodak Co., New Haven, Conn.). Thus, the present disclosure provides a codon usage frequency characteristic of the coding region of at least one of the polynucleotides of the present disclosure. The number of polynucleotides (3 nucleotides per amino acid) that can be used to determine a codon usage frequency can be any integer from 3 to the number of polynucleotides of the present disclosure as provided herein. Optionally, the polynucleotides will be full-length sequences. An exemplary number of sequences for statistical analysis can be at least 1, 5, 10, 20, 50 or 100.

The term "derived" encompasses the terms "originated from", "obtained" or "obtainable from", and "isolated from".

"Equivalent amino acids" can be determined either on the basis of their structural homology with the amino acids for which they are substituted or on the results of comparative tests of biological activity between the various variants likely to be generated. As a non-limiting example, the list below summarizes possible substitutions often likely to be carried out without resulting in a significant modification of the biological activity of the corresponding variant:

1) Alanine (A), Serine (S), Threonine (T), Valine (V), Glycine (G), and Proline (P);
2) Aspartic acid (D), Glutamic acid (E);
3) Asparagine (N), Glutamine (Q);
4) Arginine (R), Lysine (K), Histidine (H);
5) Isoleucine (I), Leucine (L), Methionine (M), Valine (V) and
6) Phenylalanine (F), Tyrosine (Y), Tryptophan (W).

See also, Creighton, Proteins, W.H. Freeman and Co. (1984).

In making such changes/substitutions, the hydropathic index of amino acids may also be considered. The importance of the hydropathic amino acid index in conferring interactive biologic function on a protein is generally understood in the art (Kyte and Doolittle; (1982) *J Mol Biol.* 157(1):105-32). It is accepted that the relative hydropathic character of the amino acid contributes to the secondary structure of the resultant protein, which in turn defines the interaction of the protein with other molecules, for example, enzymes, substrates, receptors; DNA, antibodies, antigens and the like.

It is known in the art that certain amino acids may be substituted by other amino acids having a similar hydropathic index or score and still result in a protein with similar biological activity, i.e., still obtain a biological functionally equivalent protein. Each amino acid has been assigned a hydropathic index on the basis of its hydrophobicity and charge characteristics (Kyte and Doolittle, ibid). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (−4.5). In making such changes, the substitution of amino acids whose hydropathic indices are within +2 is preferred; those which are within +1 are particularly preferred and those within +0.5 are even more particularly preferred.

It is also understood in the art that the substitution of like amino acids can be made effectively on the basis of hydrophilicity. U.S. Pat. No. 4,554,101, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues; arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

"Endogenous" with reference to a polynucleotide or protein refers to a polynucleotide or protein that occurs naturally in the host cell.

As used herein, Enzyme Classification (EC) Numbers (EC numbers) are established by the Nomenclature Committee of the International Union of Biochemistry and Molecular Biology (IUBMB), description of which is available on the IUBMB Enzyme Nomenclature website on the World Wide Web. EC numbers classify enzymes according to the reaction catalyzed. For example, enzymes classified under EC 3.1.2.- or EC 3.1.2.14 are acyl-ACP hydrolases that cleave the thioester bonds from acyl-carrier proteins in the presence of water. On some embodiments, the enzyme is an acyl-ACP TE classified under EC 3.1.2.-. In some embodiments, the enzyme is an acyl-ACP TE classified under EC 3.1.2.14. An exemplary sequence classified under EC 3.1.2.14 is the sequence set forth under UniProt ID No. B1MVT0 from *Leuconostoc citreum*, hereby incorporated in its entirety by this reference. In other embodiments, the enzyme is an acyl-ACP TE classified under EC 3.1.1.1, EC 3.1.1.2, or EC 3.1.1.5. In specific embodiments, the acyl-ACP TE catalyzes the conversion of pimeloyl-ACP to pimelic acid.

As used herein, "expression" refers to the process by which a polypeptide is produced based on the nucleic acid sequence of a gene. The process includes both transcription and translation.

An "expression vector" as used herein means a DNA construct comprising a DNA sequence which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

Examples of routinely used "expression systems" include recombinant baculovirus, lentivirus, protozoa (e.g., eukaryotic parasite *Leishmania tarentolae*), microbial expression systems, including yeast-based (e.g. *Pichia pastoris, Saccharomyces cerevisiae, Yarrowia lipolytica, Hansenula polymorpha, Aspergillus* and *Trichoderma* Fungi) and bacterial-based (e.g. *E. coli, Pseudomonas fluorescens, Lactobacillus, Lactococcus, Bacillus megaterium, Bacillus subtilis, Brevibacillus, Corynebacterium glutamicum*), Chinese hamster ovary (CHO) cells, CHOK1SVNSO (Lonza, Basel, Switzerland), baby hamster kidney (BHK) cells, PerC.6 or Per.C6 cells (e.g. Percivia, Cambridge, Mass.; Crucell, Leiden, Netherlands), different cell lines of HEK 293, Expi293F™ cells (Life Technologies, Carlsbad, Calif.), GenScript's YeastHIGH™ Technology (GenScript, Piscataway, N.J.), human neuronal precursor cell line AGE1.HN (Probiogen (Berlin Germany) and other mammalian cells, plants (e.g., corn, alfalfa, and tobacco), insect cells, avian eggs, algae, and transgenic animals (e.g., mice, rats, goats, sheep, pigs, cows). The advantages and disadvantages of these various systems have been reviewed in the literature and are known to one of ordinary skill in the art.

A "gene" refers to a DNA segment that is involved in producing a polypeptide and includes regions preceding and following the coding regions as well as intervening sequences (introns) between individual coding segments (exons).

"Host strain" or "host cell" means a suitable host for an expression vector or DNA construct comprising a polynucleotide encoding a polypeptide according to the disclosure. Specifically, host strains may be bacterial cells, mammalian cells, insect cells, and other cloning or "expression systems." In an embodiment of the disclosure, "host cell" means both the cells and protoplasts created from the cells of a microbial strain. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Heterologous" with reference to a polynucleotide or protein refers to a polynucleotide or protein/polypeptide that does not naturally occur in a host cell. In some embodiments, the protein is a commercially important industrial protein. It is intended that the term encompass proteins that are encoded by naturally occurring genes, mutated genes, and/or synthetic genes.

The terms "identical" or percent "identity," in the context of two or more nucleic acids or polypeptide sequences, refer to two or more sequences or subsequences that are the same or have a specified percentage of nucleotides or amino acid residues that are the same (e.g., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Sequences are "substantially identical" to each other if they are at least 20%, at least 25%, at least 30%, at least 35%, at least 40%, at least 45%, at least 50%, or at least 55% identical. Optionally, the identity exists over a region that is at least about 50 nucleotides in length, or more typically over a region that is 100 to 500 or 1000 or more nucleotides in length.

As used herein, "percentage of sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution and this process results in "sequence homology" of, e.g., at least 90%, 91%, 92%, 93%, 94%, 95%, 96%, 97%, 98%, or 99%. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.* 4:11-17, e.g., as implemented in the program PC/GENE (Intelligenetics, Mountain View, Calif., USA).

"Introduced" in the context of inserting a nucleic acid sequence into a cell, includes "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA). The term can also refer to the translocation of the nucleic acid sequence from outside a cell to inside a cell. In some cases, introducing refers to translocation of a nucleic acid from outside the cell to inside the nucleus of the cell.

With regard to enzymatic activity, "$K_{cat}$ ($s^{-1}$)" is the overall catalytic rate of the enzyme, or the maximum number of enzymatic reactions catalyzed per second. This constant is also referred to as the "turnover number" of the enzyme or the number of substrate molecules each enzyme site converts to product per unit time. "$K_m$" is the substrate concentration required for the enzymatic reaction to occur at one-half $V_{max}$, or one-half its maximal rate.

As used herein, a metabolically engineered microorganism is an organism produced via the introduction of genetic material into a host or parental microorganism of choice thereby modifying or altering the cellular physiology and biochemistry of the microorganism.

The term "mutant," refers to both polypeptides and nucleic acids. The term "mutant" may be used interchangeably with the term "variant" or "synthetic". Mutants or variants include alterations, insertions, substitutions, transversions, truncations, and/or inversions at one or more locations in the amino acid or nucleotide sequence, respectively, of a parent sequence. In the context of the synthetic acyl-ACP TEs of the present disclosure, a mutant acyl-ACP TE means a polypeptide, typically recombinant, that comprises one or more amino acid modifications, for example, one or more substitutions, relative to a corresponding, acyl-ACP TE, for example, a wild-type Acyl-ACP TE. In some embodiments, the mutant acyl-ACP TEs of the present disclosure are non-naturally occurring.

As used herein, "nucleotide sequence" or "nucleic acid sequence" refers to an oligonucleotide sequence or polynucleotide sequence and variants, homologues, fragments and derivatives thereof. The nucleotide sequence may be of genomic, synthetic or recombinant origin and may be double-stranded or single-stranded, whether representing the sense or anti-sense strand. As used herein, the term "nucleotide sequence" includes genomic DNA, cDNA, synthetic DNA, and RNA.

The term "nucleic acid" encompasses DNA, cDNA, RNA, heteroduplexes, and synthetic molecules capable of encoding a polypeptide. RNA includes mRNA, RNA, RNAi, siRNA, cRNA and autocatalytic RNA. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. A nucleic acid comprises a nucleotide sequence which typically includes nucleotides that comprise an A, G, C, T or U base. However, nucleotide sequences may include other bases such as, without limitation inosine, methylycytosine, methylinosine, methyladenosine and/or thiouridine, although without limitation thereto. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. A nucleic acid can be or can include, e.g., a chromosome or chromosomal segment, a vector (e.g., an expression vector), an expression cassette, a naked DNA or RNA polymer, or the product of a polymerase chain reaction (PCR), an oligonucleotide, a probe, and a primer. Unless otherwise indicated, a particular nucleic acid sequence optionally comprises or encodes complementary sequences, in addition to any sequence explicitly indicated.

The term "operably linked" and its variants refer to chemical fusion or bonding or association of sufficient stability to withstand conditions encountered in the nucleotide incorporation methods utilized, between a combination of different compounds; molecules or other entities such as, but not limited to: between a protein and a reporter moiety (e.g., fluorescent dye or nanoparticle); between a nucleotide and a reporter moiety (e.g., fluorescent dye); or between a promoter and a coding sequence, if it controls the transcription of the sequence.

A "promoter" is a regulatory sequence that is involved in binding RNA polymerase to initiate transcription of a gene. The promoter may be an inducible promoter or a constitutive promoter. An exemplary promoter used herein is a T7 promoter, which is an inducible promoter.

A "periplasmic tag" or "periplasmic leader sequence" is a sequence of amino acids which, when attached to/present at the N-terminus of a protein/peptide, directs the protein/peptide to the bacterial periplasm, where the sequence is often removed by a signal peptidase. Protein/peptide secretion into the periplasm can increase the stability of recombinantly-expressed proteins/peptides. An example of a periplasmic tag is a PelB leader sequence derived from an *Erwinia carotovora* pectate lyase gene, disclosed herein as SEQ ID NO: 2 (MKYLLPTAAAGLLLLAAQPAMAMG).

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

"Recombinant" when used in reference to a cell, nucleic acid, protein or vector indicates that the cell, nucleic acid, protein or vector has been modified by the introduction of a "heterologous nucleic acid" or protein, or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. A recombinant nucleic acid can be originally formed in vitro, in general, by the manipulation of a nucleic acid by endonucleases, in a form not normally found in nature. Thus an isolated, mutant acyl-ACP TE nucleic acid, in a linear form, or an expression vector formed in vitro by ligating DNA molecules that are not normally joined, are both considered recombinant for the purposes of this disclosure. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the disclosure. A recombinant protein can be made using recombinant techniques, i.e., through the expression of a recombinant nucleic acid as depicted above. A recombinant protein is typically distinguished from a naturally occurring protein by at least one or more characteristics.

A "signal sequence" or "signal peptide" means a sequence of amino acids bound to the N-terminal portion of a protein, which facilitates the secretion of the mature form of the protein outside the cell. The definition of a signal sequence is a functional one. The mature form of the extracellular protein lacks the signal sequence which is cleaved off during the secretion process.

"Selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

"Substrate" refers to a molecule that an enzyme binds to and converts to a product. Pimeloyl-ACP is an example of a substrate that is converted to pimelic acid by a polypeptide described herein.

"Under transcriptional control" is a term well understood in the art that indicates that transcription of a polynucleotide sequence, usually a DNA sequence, depends on its being operably linked to an element which contributes to the initiation of, or promotes transcription.

"Under translational control" is a term well understood in the art that indicates a regulatory process that occurs after mRNA has been formed.

As used herein, "transformed cell" includes cells that have been transformed or transduced by use of recombinant DNA techniques. Transformation typically occurs by insertion of one or more nucleotide sequences into a cell. The inserted nucleotide sequence may be a "heterologous nucleotide sequence," i.e., is a sequence that is not natural to the cell that is to be transformed, such as a fusion protein.

As used herein, "transformed", "stably transformed", "transduced," and "transgenic" used in reference to a cell means the cell has a non-native (e.g., heterologous) nucleic acid sequence integrated into its genome or as an episomal plasmid that is maintained through multiple generations.

The term "vector", as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the claimed embodiments are intended to include such other forms of expression vectors, such as viral vectors (e.g., replication defective retroviruses, adenoviruses and adeno-associated viruses), which serve equivalent functions. Vectors also include cloning vectors, shuttle vectors, plasmids, phage particles, cassettes and the like.

The term "wild-type," in the context of a nucleotide sequence or polypeptide sequence, refers to the major or most common allele of the sequence as it occurs in nature. A wild-type sequence can also be referred to as a naturally occurring typical or normal sequence without modifications.

Synthetic Polypeptides

It has been discovered that altering amino acid residues at specific positions in a polypeptide having an acyl-ACP thioesterase activity could improve enzymatic activity and/or substrate specificity, for example substrate specificity for pimeloyl-ACP.

The present disclosure provides polypeptides having an acyl-acyl carrier protein (ACP) thioesterase (TE) activity. In some embodiments, the polypeptide having an acyl-ACP TE activity is a polypeptide comprising one or more amino acid substitution(s) relative to a wild-type acyl-ACP TE, wherein the one or more amino acid substitution(s) are at amino acid(s) that occupy position(s) corresponding to position(s) 5, 32, 33, 35, 36, 38, 40, 45, 59, 64, 90, 111, 128, 175, and 241 of SEQ ID NO: 1, or a functional fragment thereof.

Also provided are polypeptides comprising, consisting essentially of, or consisting of a mutant acyl-ACP TE or a functional fragment thereof. In some embodiments, the mutant acyl-ACP TE comprises one or more amino acid substitution(s) relative to a wild-type acyl-ACP TE, wherein the one or more amino acid substitution(s) are at amino acid(s) that occupy position(s) corresponding to position(s) 5, 32, 33, 35, 36, 38, 40, 45, 59, 64, 90, 111, 128, 175, and 241 of SEQ ID NO: 1. SEQ ID NO: 1 is the polypeptide sequence of a wild-type acyl-ACP TE from *Eggerthella* sp. CAG:1427 (Uniprot ID No. R5FQ35). In some embodiments, the enzyme is an acyl-ACP TE classified under EC 3.1.2.-. In some embodiments, the wild-type acyl-ACP TE is classified under EC 3.1.2.14. In other embodiments, the wild-type acyl-ACP TE is classified under EC 3.1.1.1, 3.1.1.2, or 3.1.1.5. Examples of wild-type acyl-ACP TEs include, but are not limited to, the wild-type acyl-ACP TEs set forth in Table 1.

TABLE 1

| Uniprot ID No | Organism | Amino acid sequence | SEQ ID NO: |
|---|---|---|---|
| R5FQ35 | *Eggerthella* sp. CAG: 1427 | MTIGYEQTYQLRTGDFDRYAHLLPSSILDVFQDVAGVNAEQVPGMTWKELTDAG LFWVVTRIKYEVIETPHLHEQVIARTWPLAPTRLGFQREYTMRKLDGTPLVKCSS DWILMDYKTRSFASARDFYNGPQDFSEEKVFEKKLRKIKTFEPEDTGETFQVHFV DIDINGHVNNSKYPNFVMNSLDLGEDETIKTFQIDYRHELRAGSTVRIHSKRDGN VITSMGISTEGDTAGECMFATQIELA (SEQ ID NO: 1) | 1 |
| Q07792 | *Vibrio mimicus* | MIRLLSLVLFFCLSAASQASEKLLVLGDSLSAGYQMPIEKSWPSLLPDALLEHGQD VTVINGSISGDTTGNGLARLPQLLDQHTPDLVLIELGANDGLRGFPPKVITSNLSK MISLIKDSGANVVMMQIRVPPNYGKRYSDMFYDIYPKLAEHQQVQLMPFFLEHVI TKPEWMMDDGLHPKPEAQPWIAEFVAQELVKHL | 3 |

TABLE 1-continued

| Uniprot ID No | Organism | Amino acid sequence | SEQ ID NO: |
|---|---|---|---|
| A0A0F7J XA5 | Sedimenticola thiotaurini | MKKLFLLLIFAMSNVPAAEPVILVLGDSLSAAYGIERSRGWVSLLQSRLQQAGYP HRVVNASISGDTTAGGLARLPRALEQFQPDILIIELGNDGLRGLGNRQTRDHLD QMITLARASHSRPLLLGMMLPPNFGKAFTEKFLQIYRDLAEQRNVPLVPFFLAGV ADRPEWMQSDGIHPTAEGQPLMLEHVWEQLQPMLEETSVHSDKSLK | 4 |
| K5D7V3 | Bacteroides finegoldii CL09T03 C10 | MSESNKIGTYKFVAEPFHVDFNGRLTMGVLGNHLLNCAGFHASDRGFGIASLNE DNYTWVLSRLAIELDEMPYQYEDFSVQTWVENVYRLFTDRNFAIMNKEGKKIGY ARSVWAMISLNTRKPADLLALHGGSIVDYICDEPCPIEKPSRIKVTNTQPLATLTA KYSDIDINGHVNSIRYIEHILDLFPIDLYKTKRIRRFEMAYVAESYFGDELIFFCDE ANENEFHVEVKKNGSEVVCRSKVIFE | 5 |
| A0A0M9 UHQ1 | Pseudo- altromonas sp. SW0106-04 | MSASILRVPIVLLLVTKPLFAWADNQILVLGDSLSAAYGLKQHQGWVQLLQDTY EQQNTPTTLINASISGETTGGALRRLDAILKEHTPTHVLIELGNDGLRGFPVTKM KANLHALIDKSREAGAEVALMQIRIPPNYGRRYTELFEQSFVDVAKEKQVTLMPF FVEQVATNGELMQNDNIHPNAEAQPILRDIMKTQISNWLTK | 6 |
| A0A0F9W 7B7 | marine sediment metagenome | MTVKALTTRLPAPGPQVRYFSALRSAVLCVFLLAAGFCASTSAESDDGVLLVFGD SLSAAYRMDERDGWVALLQQQLREESTALQVVNGSVSGETTAGGLARLPAMLD AHQPDIVMLELGGNDGLRGLPVTSIRQNLERMIQMSQQAGARVILAGIQIPPNYGP RYTAPFYAQYQELADEYGLVLIPFLLEGIADNPALMQDDGIHPTAAAQPMIVDTV WPVLQGVLTATDRP | 7 |
| A0A0C3E BX5 | Vibrio mytili | MIRLLSLFLFFSLSTLAHANEKLLVLGDSLSAGYQMPIEKSWPSLLSNALLEHDQD VTVINGSISGDTTGNGLARLPQLLDQHTPDFVILELGANDGLRGFPPKLITANLSK MITMIKNSGAKVFMMQIRVPPNYGKRYSDMFYDIYPKLAEHQQVTLLPFFLEHV VTKPEWMMDDGLHPKPEAQPWIAEFVAQELIKHL | 8 |
| A6D1N2 | Vibrio shilonii AK1 | MIRQLSYFVLIVISLASFHAKAATLLILGDSLSAGYNMRAEQSWPTMLSDELSSGD EPMKVINGSVSGDTTSNGLAKLPGLLKQHSPDYVLIELGANDGLRGFQPSIIKNNL ASLIEMSQQAGSKVLLMQIRIPPNYGKRYASMFEGIYPALAQESGVPLLPFFLEQVI IKPEWMMEDGLHPKPEAQPFIAQFVAESMQPHL | 9 |
| A0A0B7D FD2 | Pseudomonas fluorescens | MRVWFLSAGLALMCMAQNAAAGTVLIVGDSISAGFGLDTRLGWVSLLEQRLEQ EGFDDKVVNASISGDTSAGGQARLPALLAEHKPDLVILELGGNDGLRGMPPTQLQ QNLAAMIDSSRQSGAKVLLLGMQLPPNYGKRYTDAFAEVYGKLADDKKIPLVPF FLDGVGGHPDLMQADGLHPAAGAQGKLLENVWPTLKPLL | 10 |
| A0A0B4Y 4H4 | Thalassospira xiamenensis M-5 = DSM 17429 | MTIQWDEIAKPALPANCGWRGTYRVRYSEIGDNGLAMLPALADYMQDAAGWG ARILKLAYDDTVDKGMAWVLARMVIHVRRYPGNGEDIIVETWPSGVARRVATR DFRLIDSSGDVIAVAQSFWVMFDLLERRAASWPDWIEEERLPKPPGPKLIEPPFRPPF TTDPLPEIDSIKARPSDLDLYGHVNNVRLMQWVLGATGADSKPDFHPESIDIQFRT ECRVQERVTVRQKDGFAAITRDGDGVDLVRAHVVPKNRTALA | 11 |
| A4VL40 | Pseudomonas stutzeri (strain A1501) | MRRWLKCGALALLCWTQGALAGTVLVVGDSISAAFGLETSQGWVHLLQERLVE GDESWRVVNASISGDTTAGGLARLDPLLEEHTPEVVILELGGNDGLRGQSPVQLK QNLADMIDRSREAGAEVLLLGMRMPPNLGQRYTRAFADAFDSLAQEKSVAYVPF LLEGVGGVAGMMQADGIHPTAEAQSQLLETVWPALEPLL | 12 |
| E1WY53 | Halo- bacteriovorax marinus (strain ATCC BAA-682/ DSM 15412/ SJ) (Bacterio vorax marinus) | MKSPVFKKKYQVSISNVNINKRLGLFGLLGYLQDIATLHAEIAGFGLDEMISSNSF WVLVRQEIRMNKFPKWNDEIEIQTWSRTPQGMYAFREFEFFLNDEKVGSCSTAW MILSGDTRRIKKPDFPIEKINPRLDSLLDYCAERIKVLDNFELVNEIKVRISDLDLN MHVNNTKYTQWVLDSIPIELHKSAKLRNYQINFLKEAHLGDEIDIYRASSAKDES AHDTQFKGIRRSDQSTIFYVNIIADT | 13 |
| F7Z1I0 | Bacillus coagulans (strain 2-6) | MANGSSLYKGQYHIELRDVDFTKKLKLSALFSLFQDIASLAAEDLGYGIETLEKK YKVAWILTRIRVDILRHPTWDENITIETWPLQPSKIDFDRDFLVKDHTGAVIIKAAS KWVVMGLNDRKIKRTESINIHYPENRTERAIEGKFGKFKDFGGLEPAYQKVIGYS DIDFNGHLNNSKYVDYIMDCFLPDFHKRHPIHTIEINFNQEALPGDSITLYKDISKM DEHELYVEGVNQTDHHTIFKSHITIH | 14 |
| E1SPF5 | Ferrimonas balearica (strain DSM 9799/ CCM 4581/ PAT) | MVRRSLLILMLCLYQPGAWADQPSILILGDSLASYGMSEAAEGWVKKLQQNLPD AQIINASVSGETSGGGLRRLPGLLQQHQPDWVFELGGNDGLRGFQPTITENNIEQ LITLSKASGAQVLLSEVMVPPNYGRRYAERFQQIYHGLAKEHEVELVPFFMTEIA TDPNLMQADGIHPNREAQGRIAAFLLPWFEQAIAE | 15 |

TABLE 1-continued

| Uniprot ID No | Organism | Amino acid sequence | SEQ ID NO: |
|---|---|---|---|
| A0A067A754 | Pseudomonas sp. P482 | MSAGLALMCMAQGAAAGTVLIVGDSISAAFGLDTREGWVALLEQRLKREGFDA KVVNASISGDTSAGGQARLPALLAEHKPELVVLELGGNDGLRGQLPTQLQQNLA SMIDKSRAAGAKVLLLGMRLPPNYGKRYNEAFAKVYENLATEKQVPLVPFFLEG VGGVPELMQADGIHPGQGAQARLLENAWPQLKPLL | 16 |
| F2JLT2 | Cellulosilyticum lentocellum (strain ATCC 49066/ DSM 5427 / NCIMB 11756/ RHM5) (Clostridium lentocellum) | MSRLKENYQVDFDVVDFTGKLSINGLCSYMQTVAAKHATKLGINFYKNGEKPTY YWILSRVKYEIDTYPRWEDLVSLETYPGGYEKLFAVRLFDLTDEKGELIGRITGDY LLMDAEKGRPVRIKGATGPLSVLDFPYEGRKIDKIEVPEVVLREQIRKAYYSELDL NGHMNNAHYIRWTVDMLPLEVLKENEIVSLQINYNASITYGVETKLIIGKNEAGN YLVAGNSLDDSVNYFTSEIILRKNK | 17 |
| L1M6X0 | Pseudomonas putida CSV86 | MRVWLLSAGLALLCMAQNAAAGTVLIVGDSISAAFGLDTRQGWVALLEKRLKD EGFDDKVINASISGDTSAGGQARLPALLSAHKPSLVVLELGGNDGLRGQLPAQLQ QNLASMIDKSRAAGAKVLLLGMQLPPNYGARYTKAFAQVYSDLAVQKNVPLVP FFLEGVGGHPELMQADGIHPAQGAQGRLLENAWPAIKPLL | 18 |
| L8M832 | Pseudomonas pseudo-alcaligenes KF707 = NBRC 110670 | MRAWLLGGCLSLLLLAQEAMAGTVLVVGDSISAALGLESSQGWVSLLEKRLVEK GYDKQVVNASISGDTSAGGLSRLPALLAEHKPELVIILELGGNDGLRGQPPAQLQQ NLAGMIDSSRAQGAAVLLLGMRLPPNYGARYTSAFAKVYSDLAEQKQVPLVPFF LEGVGGVPELMQPDGIHPQANAQPRLLENVWPTLEPLL | 19 |
| G8Q1V9 | Pseudomonas fluorescens F113 | MRVWFLSAGLALMCMAQNAAAGTVLIVGDSISAAFGLDTRQGWVSLLEQRLKA EGFDDKVVNASISGDTSAGGQARLPALLAAHKPDLVILELGGNDGLRGQPPTQLQ QNLAAMIDSARASGAKVLLLGMQLPPNYGRRYTEAFARVYSTVAEEKKVPLVPF FLKDVGGIPTMMQGDGLHPSVAAQGQLLENVWPTLKPLL | 20 |
| A0A075P0V4 | Alteromonas australica | MFYSLRNIAFVFLLLIPTFAQSDQHDSDEKEPNAKLLILGDSLSAAYGLRQEEGWV SLLQNTWRDENIPIDIVNAAVSGETTDGGLARLPRLLTQHQPSHVLIELGGNDGLQ GHNVKKIRSNLVALVKIAQSADAVKFLQDMQIPTNYGKRYTNMFGESFDRVGEE LNVPVIPFFLQNIALDTSLMQRDGIHPNAEAQALIAEFMHRQLMPLFDN | 21 |
| K1LL76 | Cecembia lonarensis LW9 | MKESSNKPFQFQKTFEILSFQIDPSGKLRWAALADLLQEVAWKHADSREFGQVLF DKGFMWVLSRFDIQVHAMPSWGETIHIETAGRGINKLFALREFRVTDSSGTVLAT AMSAWLLLDIKTKRPQRPSLVLPSELFETEPSDYAPPEKISVPEKGHTGKTFHVNH SDLDMNNHVNNVSYIRWIEDFCLEQGFTFDKISINYLNEALLGENIEILFSLDAQK MLVSGRSGERDVFTSWVEKLNG | 22 |
| A0A0F7M706 | Spongiibacter sp. IMCC21906 | MTHFIQFLPGRISPRRALALLLVLLLQGALPRIVLADTILLLGDSLSAAYKIPVESS WPALLQDSIDEEHSLKNASVSGETTAGGLARLPALLAKNNTDILIIELGGNDGLRG YPLVRIRENIEKMIKLGQKKGAVVLLGMHIPPNYGRRYADGFHNIYLSLAEENN TALLPFLLDGVAKQPRLMQGDGIHPTAEAQPIILQNVLSVLRPLLDSTN | 23 |
| G7LRH3 | Brenneria sp. EniD312 | MAADTLLILGDSLSAGYRMPAASAWPALLDQKWQTRPDGVKVVNASISGDTAG QGLARLPALLKQHQPRWVLIELGGNDGLRGFPPNNIEQDLSKIITLVEQAQAPLL MQIRLPTNYGRRYNESFSDVYPRLAKQFSIPLVPFFMEQVYLKPEWILEDGIHPAR DAQPFIADWMAQQLESLYPIDFELQEGGN | 24 |
| H7FRY9 | Flavobacterium frigoris PS1 | MPIASNFTSVLSKDWEINFTQCMPNGYLKYTDLCNILQLTAAAHSDMGGISFSDM QEFNQAWVLSRMRVEIAALPKWRDIVTVKTWINTLENSRSVRALEMYVNGEKIV GSETFWAVFNTERRRPEGLALPYEHFELYPELKATKESFSKININSEKEDVFEKSIY LSDLDIVNHVNNVKYLEWCLDHLEVDLILSQKIRSFEMNFLKELSLYDKVIIHENY SEDSILFSITKENKNCYALQLNL | 25 |
| H2FZ27 | Oceanimonas sp. (strain GK1) | MLRILVLLLCLVSPTVLADTLLILGDSLSAGYRMRSDQAWPHLLAEQWRREGRQ VTVINASVSGDTTQGGLQRLPPLLQRHQPSLVLLELGGNDGLRGLPPGLIERNLER LIALAGDAGARVILTDIQLPPNYGRRYLQQFEQVFSRLASQHQLPLLPFFVAPLMG EQGMMMDDGIHPTVKAQPLIARQVGEFLTPYLTP | 26 |
| I2BBI6 | Shimwellia blattae (strain ATCC 29907/ DSM 4481/ JCM 1650/ | MMHFKNMLRWHLPFLLLVLLMCRTAAADTLLVLGDSLSAGYRMPAEEAWPAL LDKQWEKRQIRVINASISGDTAAQGLARLPTLLAEHKPRWVVIELGGNDGLRGFP PAGIAATLSQIISQVKAARARPILVQIHLPANYGRRYNESFGAIYATLAASNDIPLL PFFMEEVYLKPQWMQDDGIHPNASAQPFIADWMAQHLNPLVNHDS | 27 |

TABLE 1-continued

| Uniprot ID No | Organism | Amino acid sequence | SEQ ID NO: |
|---|---|---|---|
| | NBRC 105725/ CDC 9005-74) (Escherichia blattae) | | |
| M1WJV0 | Pseudode sulfovibrio piezophilus (strain DSM 21447/ JCm 15486/ CITLV30) (Desulfo- vibrio piezophilus) | MVSLHPFPSQLHKIVMTTNIDLAFEHLYPVQSYEPRMDGRIAIPSVCNYLQDIASR HADTLGFGYHDLEKCGHFWMLARLHVTMERLPRFGESCRIETWPSGNERLVALR DFLLHDEKGLIGKATTSWVTVNTTTHKPDNPETVLNRRFIPKRDRATIFPTKAIKR LKGGEHDIRLVARRSDMDINNHVNNVHYVEFCLEAIPRSWEEKNRCLGIDIQFRS ESHAGDEYVSACAPADPDGPHATFLHSLTRLSDGREVVRMRSWWIQA | 28 |
| J3H5M3 | Pseudomonas sp. GM67 | MRVWFLSAGLALMCMAQNAAAGTVLIVGDSISAGFGLDTREGWVSLLEQRLKR EGFDDKVVNASISGDTSAGGRARLPALLAEHKPELVILELGGNDGLRGMLPTQLQ QNLAAMINSSKASGAKVLLLGMQLPPNYGARYNKVFAEAFSNVAAEKKIPLVPF FLEGVGGHPELMQSDGLHPAAGAQDKLLENVWPTLKPLL | 29 |
| E6W9H0 | Pantoea sp. (strain At-9b) | MLSLTDGLSKMMNFNNVFRWHYSFLLLLLLVSRLAAADTLLVLGDSLSAGYR MSANVAWPYLLDKEWQQQPKVINASISGDTAGQGLARLPALLKQHQPRWVLIEL GGNDGLRGFPPQNIAQDLSKIIDDVKAANAQPLLMQIRLPANYGRRYTQAFSAIY PQLAQQYNIPLVPFFMEQVYLKPEWMQQDGIHPNPDAQPFIASVMAKELAPLVK HD | 30 |
| T0CHD7 | Bacterio- vorax sp. BAL6)X | MKDKVFKKTYQVSINSVNINKKLGLFGILGYLQDIATVHAEVMGFGLEDMIRDQS FWVLVRQKLRMTKFPVWNESVEIQTWSRPPEGMYAFREFEIFLDGEKIGDCSTV WMILDGVIRKVKKPDFSMERINPRTDYHLDYIAHKVEVRDNFEKVNTITVRNSD LDLNMHVNNTKYSQWILDSIPIELHKTATLNEFEINFMAETHLGDEIDIYRARNVE GEFKHDITYKGVRHSDGKTCFLAKLLAD | 31 |
| A0A0C4 WQF1 | Azotobacter chroococcum NCIMB 8003 | MLGGALASLLFWAQGALAGTVLVVGDSISAALGVETSQGWVALLERRLVDQGL THRVVNASISGDTSAGGLARLPTLLATHRPELVIIELGGNDGLRGQPPQQLQQNLA AMIDSSHSSGAQVVLLGMQLPPNYGPRYNQAFSRVYATLAEEKQVPLVPFFLDG VGGVPGMMQADGIHPTAKAQPKMLDNLWPTLEPLL | 32 |
| D2TLW8 | Citrobacter rodentium (strain ICC168) (Citrobacter freundii biotype 4280) | MVNFNNVFRWHLPFLFLILFTCRSVAADTLLILGDSLSAGYRMSASAAWPALLND KWHSKTTIVNASISGDTSGQALARLPALLKQHQPRWVLVELGGNDGLRGFSPAQ TEQTLRTILQNVKAASAEPLLMQIRLPANYGRRYNETFSAIYPKLASEFDIPLLPFF MEEVYLKPQWMQDDGIHPNRDAQPFIADWMAKQLSPLVKYES | 33 |
| K5YG62 | Pseudomonas sp. Chol1 | MRSWLKGGVLLLVMWAQGALAGTVLVVGDSISAAFGLETSQGWVHLLQQRLA EQARPRSVVNASISGDTSAGGLARLPTLAEHRPEVVILELGGNDGLRGQSPAQL KQNLAAMIEQSQQADAKVLLLGMRLPPNYGRRYTEAFARVYHELADERDVALV PFVLEGVAGEPGMMQGDGVHPTASAQAQLLENVWPALAPLLAPQR | 34 |
| E1RAP4 | Sediminis pirochaeta smaragdinae (strain DSM 11293/ JCM 15392/ SEBR 4228) (Spirochaeta smaragdinae) | MKQVSRYTTEHTVMYSETDARGVLSLPSFFALFQEAALLHAEELGFGETYSKQE NLMWVLSRLLLEIDAFPKHRDRIRLSTWPKQPQGFAIRDYILESEEGTVCARATS SWLLLKLDTMRPIRPQTIFANLSMEGIGLAVEGTAPKISEIDNDSKQEMEVTARYS DLDQNNHVNNTRYVRWFLDCYTPEEITTSGNLHFAINYLQAASYSDKLLLRRYD TESDSSVYGYLEDGTPSFSARIERKSD | 35 |
| A3DJY9 | Clostridium thermocellum (strain ATCC 27405/ DSM 1237/ NBRC | MQKKRFSKKYEVHYYEINSMQEATLLSLLNYMEDCAISHSTSAGYGVNELLAAD AGWVLYRWLIKIDRLPKLGETITVQTWASSFERFYGNREFIVLDGRDNPIVKASSV WIYPNIKKRKPMRIPLEMGDAYGIDETRALEEPTDFDFDFEPKVIEEFTVKRSDID TNSHVNNKKYVDWIMETVPQQIYDNYKVTSLQIIYKKESSLGSGIKAGCVIDEQN TDNPRLLHKIWDKNTGLELVSAETIWQKIQS | 36 |

TABLE 1-continued

| Uniprot ID No | Organism | Amino acid sequence | SEQ ID NO: |
|---|---|---|---|
| | 103400/ NCIMB 10682/ NRRL B-4536/ VPI 7372) (Rumini-clostridium thermocellum) | | |
| A0A0F2P667 | Gamma-proteobacteria bacterium BRH_c0 | MLLIILLSCYFGTFSSASLANTILVLGDSISAAYRIPVESGWVSLLQERLDEHRPGH YTVVNASISGDTTAGALNRLPPLLEKHRPDQVIVELGGNDGLRGLPLKGMRDNL QAIIDLSRQQGADVVLVSIDLPTSYGSHFNQRFTQVYDELEESNKLPRVSLGFKLL NDRNLIQEDGIHPTEEAQPLLLDVVWPLIAPGVEREG | 37 |
| A0A0B3WUQ1 | Terri-sporobacter othiniensis | MERVFTKEYEVTYRDTDARGECFLTSYMNFMADCGLSQDEKYGFVIADMVKEN HTWMLVDYEITIYKYVKYEKLRAITYIEGMNKFYAVRYFKIYNDKDDLILEGKT LVILVDSKKRRPLSIPDEHYKAYGVEEKTPTIGRNKLKLSKCKNVDYKKEFNVRY SDIDLNLHVGNVTYLGWILETIPFEIMTDYKIYSVKIKYQKELTYGDKVSVKTEME YNDNNISAYHEIINESEEVVALLETHWNEI | 38 |
| A3D613 | Shewanella baltica (strain OS155/ ATCC BAA-1091) | MAKTLGAFILLSVLTVTPAHAAKVLILGDSLGASYGMAEQSGWVALLQKNLPEH QFTNGSVSGETTAGGLRRLPALLDSVAPDLVVVELGGNDGLRGFPPTQLENNLIQI ITLAKDSGAKVLLTEIMVPPNYGPRYTQKFTQVYQDISKTQDIVLIPFFMQDIAPHP ELMQRDGIHPNEKAQAQIATWMQPWIEDALTQ | 39 |
| A3QFM1 | Shewanella loihica (strain ATCC BAA-1088/ PV-4) | MQAACLLVFFLIPQAHANPILILGDSLSASYGMEQDKGWVHLLQQQSPEVTIINGS VSGETSAGGLRRLPALLDSTKAKRVFIELGGNDGLRGFSPKQLKNNLTKMILLAK DSGAEVLLSEVMVPPNYGPRYAKQFTQVYQELSSEQGVTLVPFFMTEIAIHPELM QADGIHPNEQAQPQIVSFIRPWLIDTQQPSE | 40 |
| A0A0C1Q9A5 | Lactobacillus brevis | MAANEFSETHRVVYYEADDTGQLTAMLINLFVLVSEDQNDALGLSTAFVQSHG VGWVVTQYHLHIDELPRTGAQVTIKTRATAYNRYFAYREYWLLDDAGQVLAYG EGIWVTMSYATRKITTIPAEVMAPYHSEEQTRLPRLPRPDHFDEAVNQTLKPYTV RYFDIDGNGHVNNAHYFDWMLDVLPATFLRAHHPTDVKIRFENEVQYGHQVTS ELSQAAALTTQHMIKVGDLTAVKATIQWDNR | 41 |
| A0A0K8QXH4 | Bacteroidales bacterium 6E | MVPLKHVHHLKAKSYHINRFGEVSTPFLFWYMQEIAWEHAHKLGFGFEHLKEDQ LFWVLSRLLVKIDHRPRWTDEFTLETWSRGTDGFFAYRDYRFLDQNGNEFIKATS SWLVLDLESRRIQRLSQFKNFPVYQESVLGNNAGKVDTPETLGDLSFFPVLFNEID INQHFNTGRYLERINNSYSFDFHENHTLSELEVNFIKEGMADDSLAVCQQRLSEGE HLCSVIRQRDGSELIKARLVWEQKKKI | 42 |
| A1WYS0 | Halor-hodospira halophila (strain DSM 244/ SL1) (Ectothio-rhodospira halophila (strain DSM 244/ SL1)) | MAGSSCFSLSLRRALCAAALALLLGPSAATAERPTILIFGDSLSTAYGFDRDEAWP VLLEARLDEADRPHRVANVSRSGETTSGGTRRLPDALEEHEPEIVLLQLGGNDGL RGQPPERIRSNLQQMIEQARAVDSRVLLIGIRIPPNYGRTYTEQFAAIYPELADEQD VPVIPFLLEGVWDRDGMMQDDGVHPTAKAQPEIAETVWETLREMLDGPS | 43 |
| P44886 | Haemophdus influenzae (strain ATCC 51907/ DSM 11121/ KW20/ Rd) | MSANFTDKNGRQSKGVLLLRTLAMPSDTNANGDIFGGWIMSQMDMGGAILAKEI AHGRVVTVAVESMNFIKPISVGDVVCCYGQCLKVGRSSIKIKVEVWVKKVASEPI GERYCVTDAVFTFVAVDNNGRSRTIPRENNQELEKALALISEQPL | 44 |

TABLE 1-continued

| Uniprot ID No | Organism | Amino acid sequence | SEQ ID NO: |
|---|---|---|---|
| D6E2B1 | [Eubacterium] rectale DSM 17629 | MAFSFDSRIRYSEVDSSCRLSLTGLTNYFQDCSVFHSQSHDVGIRFLADNHIAWVL SSWQICINRLPLLNEQVKISTWAYGMKAFYGYRNFTLEDAGGSTLAYANSVWVL VDTRTGRPVKVPQEFADTYGLEPQLEMECAKRKLHIPDDMEKKGEIEVPQFFIDS NHHMNNEKYVMLAQQLLPNDFEISELRVEYRKEAKLGDTVISYVKYTSKSVTVV LADTDKKPYSVVEFLSKPVPGK | 45 |
| Q69MT1 | Oryza sativa subsp. japonica (Rice) | MAATRSTATAALALSRTLARRPAASSSSRRISLELSAPRGTNPFQSAAFSSTTTGDP PPPTMDSPIKVVSHIGGSGGDGGGGAIDAGRSARKPLSLWPGMYHSPVTNALWE ARSSIFERMIDAGAAGKQQQQPPQTELLTKTPAGSRTSIVYKFATDDILREQYRDP WNEVRIGKLLEDLDALAGTIAVKHCSDEDSTTRPLLLVTASVDKMELKKPICVDT DLKIAGAVTYVGRSSIDIQIEVTQVDQDSDMQSDPIALTANFTFVARDSMTGKSAP VNRLSPETEKEKQLFAEREARDKLRKRKREEQKGVFENGINKLHVEAERLNSLLA EGRVFSDLPALADRDSILLKDTRLENSLICQPQQRNLHGRIFGGFLMHRAFELAFS TAYAFVGQRPCFLEVDHVDFLKPVDVGDFLRFKSCVLYTQLDNAEQPLVNVEVV AHVTRPELRKSEVSNTFHFTFTVCSDALKNGLKIRHVVPSTEEEARRILERMDAEG LFD | 46 |
| A0A0K6I SB1 | Marinomonas fungiae | MMSKVCVVLLCFLSLLTNAHANTLLVFGDSLSAAYNLRQQQGWVSLLSQQLNR SHPDVNVVNASISGETTQGGLSRLPKLLETHQPKWVVLELGANDLRGYPLNQM KQNLAHMIDQSQQTGAKVLLVGNHLPSNYGRTYTTQFFNVYSELAKEYQLAYVP FMLENVALDSTLMQNDGLHPNADGQPVVLENIAPTLLPLLNLP | 47 |
| A4Y830 | Shewanella putrefaciens (strain CN-32/ ATCC BAA-453) | MAKTLGAFILLSMLMATPVHAAKVLILGDSLGASYGMSEQLGWVAMLQKNLPE HQFINGSVSGETTAGGLRRLPALLDSVSPDLVVVELGGNDGLRGFPPTQLENNLIQ IITLAQKSGAKVLLTEIMVPPNYGPRYTQKFTQVYQDISKTQNIELIPFFMQEIAPY PDLMQRDGIHPNEKAQAKIAAWMQPWIEKALNQ | 48 |
| K1J0J2 | Aeromonas veronii AMC35 | MVRILFALFVGLGSLLSSAQAQTLLVLGDSLSAGYQMVEQSWPALLNQKWQEE GSKHTLLLNASISGETTQGALARLPALLKEHKPDWLLIELGGNDGLRGFAPTITRQN LASMIALAKEQQTRVVLTQIQLPRNYGARYLRQFEQIFPELAQANDLPLLPFFMD DIALRPELMMNDIHPTAAQPQIRDKVARFMEPLLSQ | 49 |
| D8QRX8 | Selaginella moellend orffii (Spikemoss) | DTLKQGRLVERVVYRQTFVVRSYEVGPDKTATLDTFLNLFQETALNHVLISGLAG NGFGTTHEMIRNNLIWVVTRMQVQVERYPAWGNALEIDTWVGASGKNGMRRD WLVRDYKTGSILARATSTWVMMHKDTRRLSKMPDLVRAEISPWFLSRTAFIPEES CSKIEKLDNSNTRYIRSNLTPRHSDLDMNQHVNNVKYLTWMMESLPQNILESHH LVGITLEYRRECKSDMVESLTHPERGGHLAINGAAAAAAAAAAAPPSQLDFIHL LRMQTGGSEIVRARTSWKSRH | 50 |
| A0A085A ET1 | Trabulsiella guamensis ATCC 49490 | MDFKYIFRWHLPFLLLVLFAFRAAAADTVLVLGDSLSAGYRMAANAAWPALLN EKWQPQTRVINASISGDTAQQGLARLPALLKQHQPDWVLVELGGNDGLRGFQPQ QTEQTLRTILQDIKAANARPVLMQIRLPANYGRRYNEAFSAIYPKLAGEFSVPLLP FFMEEVYLKPQWMQDDGIHPNRDAQPFIADWMAARLAPLVNHDS | 51 |
| F0P329 | Weeksella virosa (strain ATCC 43766/ DSM 16922/ JCM 21250/ NBRC 16016/ NCTC 11634/ CL345/78) | MNPVDYYTEKFYIDYSRVYPNRKIKYPELANILQITAANHADFCGLGFDDLQHNK QAWVMNRIRIEIDTLPELNDEVTIDWLELLRVPKSIRNLEIKKEGKKLVGVSSLW AVFNTERRRPEALKIDADHLKIFTDLHATSLENNKIETPESFQKVAEYQVKLSDLD VVNHVNNIQYLTWCDLTSLSKEEVLERSIAVLEMNFLKELSYQKIIHIEQYRQEHEL YLRIRDEQFIYFVARITYQ | 52 |
| F3BKQ8 | Pseudo alteromonas haloplanktis ANT/505 | MTHSILRLVFILFLVIKPLSAAADNTILILGDSLSAAYGLQQEEGWVKLLQDKYDD EQADIELINASISGETSGGALRRLDALLEQYEPTHVLIELGANDGLRGFPVKKMQT NLTSLIQKSQAANAMTALMEIYIPPNYGPRYSKMFTDTFSRVSEETNAHLMNFFM LDIASQSDLMQNDSLHPNKKAQPLIRDEMYDSIKKWLNKD | 53 |
| P0ADA2 | Escherichia coli O6:H1 (strain CFT073/ ATCC 700928/ UPEC) | MMNFNNVFRWHLPFLFLVLLTFRAAAADTLILGDSLSAGYRMSASAAWPALLN DKWQSKTSVVNASISGDTSQQGLARLPALLKQHQPRWVLVELGGNDGLRGFQP QQTEQTLRQILQDVKAANAEPPLLMQIRLPANYGRRYNEAFSAIYPKLAKEFDVPL LPFFMEEVYLKPQWMDDGIHPNRDAQPFIADWMAKQLQPLVNHDS | 54 |

TABLE 1-continued

| Uniprot ID No | Organism | Amino acid sequence | SEQ ID NO: |
|---|---|---|---|
| A0A0F4L189 | Lactobacillus mellis | MGQQYQETKVIPFYSTNATSEINISALFNEMLLVSEHQLHAVGIDSQQMVAQGIG WVVTKYHLEIKRLPRINEKVTIVTEANSYNKFFCYRTFTLYDSQGQQLLHLLSNW VMMDIKKRSMIEVIPETMAKIGCEYSTDIWRFPRIQRFKYSQSPQIYRTRFFDIDVN GHVNNSIYLDWMLDSLGKDFLMQHQLQTLDIKYDREVAYGQSVQSFVQLEDNLI SHHQILTDNKVNAQAQMQWQQRQK | 55 |
| Q74KZ2 | Lactobacillus johnsonii (strain CNCM1-12250/ La1/ NCC 533) | MEKIFKEEHQVSYGDCDETGKIQLPHLIEHFMQVSNDQLTAGGAGIHDLLKQNLG WVVVEYHLDIDRLPEAGEKITVTTNGSGYNRFFEYRDFGIIDSTNKKIVGVKSQW VILDLKNRKITEADDQMMQKFGNPYLKHMPRFKRLRPLKEYRSSKKYTVRYYDL DTNHHLTNSIYFDWMIDTLPREFLNSHTVKSIDISFKKEVQYGDQALAEVELDQD TLTSYHLISNQGEASALAEINWKEN | 56 |
| G7V8P3 | Thermovirga lienii (strain ATCC BAA-1197/ DSM 17291/ Cas60314) | MYEHNFRISYSQAGALGRLKLTGAMNLCQDIADDHAERVGVSVADLLKQSKTW VLHRFKMTIQTMPQRGDLVTIKTWYRPEKNLYSLRNFEMLDCNGKKLLSVQTSW VVVDMNRGRPLRLDRVMPEAYDKNKDENLEVSFQELLLPEKVDVKKTIQVAVT DLDMNFHVNNVHYLRWALDTIPVEILKEYKPKGVEIAFKRPAFYGDSVISEVGID KNSCSILCRHHIYGEKDGQSMAVISTEWEKISREER | 57 |
| C7ML86 | Crypto-bacterium curtum (strain ATCC 700683/ DSM 15641/ 12-3) | MTISASLFLEKDYRLRTGDFDRYRRLHPTAVLDLFQDIGGLQAEMMGIGYDAMA AQDVFWAVVRTAYQVEHTPAEHEVVKVSTWPHSPSRYSFQRDYALRSTDGSLL VRGTSEWVLMDMNTRSLTSVLDYYHGSLDFIDERMFAKKLRKIRDFTEEGSGLSI TPRYSDVDQNGHVNNARYASFVLDALDPSAAGSIASFQIDFRHEVIEGTPLVVFTQ VEGKDIQAKGLDSNGEIKFACKITAQA | 58 |
| F5YIQ3 | Treponema primitia (strain ATCC BAA-887/ DSM 12427/ ZAS-2) | MDVWKESYPVGFTAVDESEGLTLAAAFDYFQEAARRHAEVLGVGQEPMVQAG QGWVLSRISVLVERRPRQGELITVSTWPRGWEKLFALRDFDIRDESDKPIVRARSC WLIVNIEKRRPLRPQATMEKLPLNEGRDALPGGGVGLAPLENLLKAGDRVAAYS DIDYNGHVNNARYVQWVQDIADPTALVQAKTLRLDINYLSEVKIHEPIELWTEPL PAESDAVYTLGVEGRRNGGAVFRAELRIKD | 59 |
| F7R2D3 | Lactobacillus ruminis SPM0211 | MESKGFSEKHRVTYYETDMNGTVGLGRLVDLMMLSCNDQSDAVGLSSEKVNQ MGLGWIVTQNMIDIKRLPRRNETIYITTHAKSYNRYFCYRDFWIHDIRKQELAHM HTVFALMDQNERKIVRIPENLIEPYHSEYATKIERLPLPKELERIDRQKEYEVRFW DIDINQHVNNVHYFEWMLDALDLDFLIKYQPVSMNIEYKKEIRYGQKAVSQAQIT MTGVETVTTFHEIKVNDELSCRAVCDWKLRKEEWIM | 60 |
| I7K130 | Lactococcus raffinolactis 4877 | MLTYKKKYTVPYYETDANGNMKLPSLFNIALQLSGEQHSLGISDDWLKETYNY AWVVVEYDVTIQRLPRFSEIITMSTFAKSYNKFFCYRDFVFYAENGDTLLTINSTF VLIDTTSRKVAHVEDDIVAPYQSEKISKIVRGHKSTALSDTPLEKSYHVRFNDIDQ NGHVNNSKYFDWMTDVLGYDFLSSHVPSRIHLKYSKEVLYGATVTSRVDLVGV QSFHEIVSEGKHAQAEMTWREK | 61 |
| D4YGM6 | Aerococcus viridans ATCC 11563 = CCUG 311 | MINIRHYQGGKRMGLLYQESVKVRHYHCNALGEMTLPAILDIMLIASNNQEATIP EAKEGFRQEGWAWIITQNQIDINRLPRYDEDIIAETEATTYNKFFSKRHYALKTRD GLVLAQAETTFALIDLNQRSIVRIPEIVAEWYQVEKEERPSRRKRLNKEIAVESKL DRFEVKFLDIDLNNHVNNTIYLRWITNSLGMEWFEKYTPTSFTVAYEKEMYLHQ EGAVHSDISTVSEDLKSGDTFNSQHVIDSEDKAHCLTEITWQVK | 62 |
| U2CXE7 | Clostridiales bacterium oral taxon 876 str. F0540 | MPGFVYEKEYEIHYYEIDYKRRALITSLVDFFGDIATVQSEQLGIGIEYLKENNLA WVLYKWNIDVVKYPLHGEKIIVKTCPYSMKKFYAYRTFEVLNSEGEVIATADSIW FLINIERRRPVRINEDVYRLYGLDYNDQNTLEIEDIKKPDKADLEKIFNVRYSDIDT NQHVNNAKYIAWAIETVPMEVVLNYTIKNLKVIYEKETTYGEIVKVITEIIHNDNT VICIHKIIDKEEKELTLIKTTWEKNF | 63 |
| A0PXB0 | Clostridium novyi (strain NT) | MSGIITEKQYEIHYYEAHLKQQATITNIIDFFTDVSTFQSEELGVGINYMMENNMA WILYKWDINVERYPRYREKILAVTEPYSIKKFYAYRKFYILDENRNIIASAKSTWL LIDTKKRRPLRISKEMVKAFGLENKEETLEIENVHKLPEENTEINFKVRYSDIDTNG HVNNEKYVAWMIESIPRDIILNYTLKNTKITYKKETMYGESIKVITGKIKEDEDKV KFVHNILRENGELLTEGETLWEKNK | 64 |

TABLE 1-continued

| Uniprot ID No | Organism | Amino acid sequence | SEQ ID NO: |
|---|---|---|---|
| P44679 | Haemophdus influenzae (strain ATCC 51907/ DSM 11121/ KW20/ Rd) | MLDNGFSFPVRVYYEDTDAGGVVYHARYLHFFERARTEYLRTLNFTQQTLLEEQ QLAFVVKTLAIDYCVAAKLDDLLMVETEVSEVKGATILFEQRLMRNTLMLSKAT VKVACVDLGKMKPVAFPKEVKAAFHHLK | 65 |
| J0YTE5 | Streptococcus infantis SPAR10 | MGLTYQMKMKIPFDMADMNGHIKLPDVILLSLQVSGMQSINLGVSDKDVLEQY NLVWIITDYDIDVVRLPQFDEEITIETEALTYNRLFCYRRFTIYDEDGQEIIRMVATF VLMDRDSRKVHPVVPEIVAPYQSEFSKKLVRGPKYTELENAINKDYHVRFYDLD MNGHVNNSKYLDWIFEVMGADFLTNHIPKKINLKYVKEVRPGGMITSSYELNQL ESNHQVTSDGDINAQAKIIWQEINTD | 66 |
| I2F781 | Mesotoga prima MesG1.Ag.4.2 | MKPVITKEVYKVRYYELDCHWKASVSTLMDYFNDIVTLQTVEIGHGVDIMSKGE YAWLLLRWDVNVRYPDYMENVVVQTIPYSMDRFYAYRRFEIFDRSDNLIVDA NSQWILIDQRKRRPIRIGDQFYALYGIDSDFHQPLSFPQVNDNDSYGEEITFRVRSS DLDTNGHSNNVSYVRWIMETVPDEFAKRSLRRLTIEYKRESREGDEISVESVFEN GDEFAEGKHKIISSGRVLSLARTEWK | 67 |
| R5BH39 | Bacteroides sp. CAG: 1060 | MGKYCEKDIITCYRSDSHHKMRSEAFLDFAQQLAVKGAQLLSFNDTALSQLGCI WVLARMHVRFERDVAFDEKVDLSTWHKGQSGLYFLRDYQLCDRHGAAVNATS SWIVMNAETRHISRDEKVLELLSVGPQSEDHAIKEASPKITVPKDCTLEVIGEHTV RYSDVDYNNHANNVKYTVWALDHLPDNIAMTRRLKELSINFNKETLLGETVTLY HCITPEGEHIVEGRSGDIQVFIEKLLFE | 68 |
| E3GJ26 | Eubacterium limosum (strain KIST612) | MGIIYEKKQKINGYECTYNYQLQPTAALNYFQQTSQEQSEQLGVGPEVLDEMGL AWFLVKYKLQFHEYPKFNDEVMVETEMAFDKFAAHRRFAIKSLDGRMMVEGD TEWMLQNRKENRLERLSNVPELDVYESGHENHFKLKRVAKVEEWTESKNFQVR YLDIDFNSHVNHVKYLAWALETLPLEKVKAGEIETAKIIYKNQGFYGDMITVKSA EIDENTYRMDIENQEGILLCQIEMTMRIRED | 69 |
| F4LT66 | Tepidanaerobacter acetatoxydans (strain DSM 21804/ JCM 16047/ Re1) | MSGSNILEKEYRIHYYEVNAKGRVLIASLMRYFDDIATQQSRELGVGINYLKEHN VAWMLYQWDIKINKYPRYGETIKVRTAPYSFRKFYAYRWFDVLNKDGETLVNA NSVWLFVDTDKRRPLKIPDVMYEAYQVTSDEPLEIGEITELSSCDIEKKFQVRYSD IDTNSHVNNVYVTWALEALPYDIISNYELRNLKVTYKQETTYGMIIRSQAQVIKS DDEVITRHSILSEEGKKLCLLEGRWIKNS | 70 |
| D5XAN2 | Thermincola potens (strain JR) | MEPYQTSIPVHYYEINNHRQASPVAILNYLEEAAIRHSESVGWGIEKLLANSRGW LLTRWSLHMQKYPQWGETVNIETWPYKFERFYATREFRISDREGRVLGAATTLW VFFDLRRKRPVRIPPDIYDAYGTGAERMVADEFADLPVVDEPEIKLEFVRLSDID TNDHVNNTKYVEWLLETVPLSVHNGFLLSSVEIAYKKETSYGSTVLCGIKETEAG ERQTTFLHIILDKDSGTELARARTVWQKRSKI | 71 |
| Q8XH69 | Clostridium perfringens (strain 13/Type A) | MSENKFMKKYDVLYYDSDVNENIRMVPLMKIFGDVSAIHEEELAYEGIKYLKDH ELSWIIYSYSIDIKKPIPYKSSINVETYLEGIKKFYACRVYKVYNEKNELVAEGKII F LLIDLEKRRAVRIPKEYCELINMSDTGEVELKSTKVEKLIREDLESNISVRRSDIDF NKHVNNTKYLEWTMEATPECILDEYSLISAKIKYEKEVRLGDDVNIICQWDEIEE GYKCLYKIVNNRLGEVSASIETIWKKEF | 72 |
| B5B3P5 | Solanum lycopersicum (Tomato) (Lycopersicon esculentum) | MAEFHEVELKVRDYELDQYGVVNNAIYASYCQHGRHELLERIGISADEVARSGD ALALTELSLKYLAPLRSGDRFVVKARISDSSAARLFFEHFIFKLPDQEPILEARGIA VWLNKSYRPVRIPAEFRSKFVQFLRQEASN | 73 |
| D4KXX4 | Roseburia intestinalis XB6B4 | MYSFSNRVRYSEVNSEKELTLPSLLDYLQDCCTFESEDFGVGVDYLAKEQVAWIL SSWEIKVYRYPQMGQHIKVSTWPYAFRGFYGYRNFCIEGEDGEIFAEANSVWVF MDTEKMRPARVSERMQEVYIPEIRDEIPGEWADRKISLPDEAVQKSVEKEPVRVS RFYIDTNHHMNNGKYILVAEEYLPEQVFVCGLRAEYRKAAMLGDMLYPVVTIEE KQITVTLADEKGASYAIICFQIKKKERQS | 74 |
| R7L7B6 | Coraliomargarita sp. CAG: 312 | MLDNIHRTSYKVRISDADQNGTLKCNALLQMLQEAATEHATILGVDFKALKPLN LGWAVSKFVIDVKRLPQWGERINVTTWASDKERVATYREFVVTDSSGTELVSAR SQWVLFDTRERKIAKMEKIQDWSRLENKYANASNFEPLKQPKTTTSSAICAARND DIDLNMHVNNAVYLIWAAESLPQNFTSVPKQIRINFLEEVMPHTNVEVLCHIDGK NSYHTLINMNTNRECARINIFWQ | 75 |
| H1X5Q2 | Weissella confusa | MAEVYSMQHEVLYYEADVTGKLSLPMIFNLAVLSSTQQSVDLGVGPDYAHANG VGWIILQHVVDIKRRPKIGEKVALETLAKEFNPFFAKRLYIRIVDEAGNELVSIDAL | 76 |

TABLE 1-continued

| Uniprot ID No | Organism | Amino acid sequence | SEQ ID NO: |
|---|---|---|---|
| | LBAE C39-2 | YAMIDMEKRKMARIPQEMVDAYAPERVKKIPRQPEPDHMIGDIPVDVDQQYAVR YLDIDSNRHVNNSKYFDWMQDVLGPAFLEAHEPTHLNIKYEHEILLGDTVRSEAQ IMEDKTIHRIWSGDTLSAEAHIDWTKSEN | |
| J6HI88 | Peptoanaerobacter stomatis | MLKTYSENYIVDFRDVDRYYDIKIPQLLEIMGTVSTKEITNELGFDPFYLIRQGLA WILYEWKVDIEKTKLYAQTIKIETFAVDRKGMYFIRYFGIYDKDDKLIGRAAAKW VVINTTQRKIVKLPQEILEAAKINIEELNENQKYIYDMPEKPLRLEKRQDDFIQTIFP IRFYDIDSNHHANNVKYVDWAIESLHQHEDFLKKYKVSHLSITYKKETGEDGDIIC KTYIDNLRTYHEIYSSDNSLLTVLEFKWAERPQ | 77 |
| U2MZJ9 | Clostridium intestinale URNW | MGRVFEKQYEINYYNLDNSLKCKITSILDFFCDIGMQQSEELGVGVDSLTGRNLT WVFYKYNINMKRYPRYGEKIRIITDPIGFKKFYAFRDYTILDEGNKVIGEGKSLFFL IDLAKRRPTRIPRDLYEAYGCADEIKDNPTIVDPEKLEEEQYFREFYVRRSDIDSNK HVNNTKYVEWALEVIPDEIVDEYELDNISIVYSKEITYGHMVKTKCSVHNEDNGII KIRHLIQDDVGRDITLNTFWRKN | 78 |
| F6B7F0 | Desulfotomaculum nigrificans (strain 14880/ VKM B-2319/ CO-1-SRS) (Desulfotomaculum carboxydivorans) | MLNRKYRKEFEVHYYEINQFEEATPVAVLNYLEETAVAHSESVGVGISKLKSQG VAWMLNRWHIKMEKYPLWNEKIVIETWPSRFERFYATREFNIRDSYDHIIGRASS LWVFLNIEKKRPLRIPDKIKDAYGTDPHRAIDEPFGELYNLDDSVEKKEFRVRRSD IDTNNHVNNAKYVDWVLETIPAEIYHNYTLASLEVLYRKEVAFGATIWAGCQGI DSMGKGLNPVYAHSIMNQDGNLALARTMWQRRNKNLHTN | 79 |
| A7H762 | Anaeromyxobacter sp. (strain Fw 109-5) | MEKHRQTFGVHTYEVDAFGTVAIAALSGYLQEVAGQHAAALGVGLEVLMPRGL TWVLARQRIENPVPIVLGDRLEIETWPAGIDRLAALRDFVVRRADGTEVARATTQ WFVLDLESRRPVKPAEVLDPRFQRELLPPILPLAPGKLPELRSWEFQKRFHVRYGD IDVNMHVTNTSYPTWAQEVVPREVFRGQRLASVEVHFLAEAHYGSAILSRLAST GEGAFAHAIVREEDEKELARLATRWVPRAAPAVPGAR | 80 |
| F8F2E5 | Treponema caldarium (strain ATCC 51460/ DSM 7334/ H1) (Spirochaeta caldaria) | MKALWTEQFTVRTWDVDRNNRLSPSSLFNYFQEVAGNHATELGVGKDALLRGN QAWILSRMTTLLYRRPGWGETIVTRTWPRGTEKLFAIRDYDIIDGFGSTIAQGRSA WLLLVDVEKLRPLRPQSLTENLPTNTDPMPAIPDGAQALTALPELQAAGTRTAAYSD IDYNGHVNNARYIEWIQDILDASILEQTNHFRIDINYLAEIRPQETISLWKEPLPNQ DAGTEEHAGERPPPFTPFEVTELWAFEGKHIDSGQSSFRAELRCGA | 81 |
| C8PCP7 | Lactobacillus iners DSM 13335 | MEKLEKKYTIKSHDCDESGRLKMSMLISYMMDTMSHLLDPCIKIEHAGWVVVN YQFDINKLPKFDDQITIKIDLCYYNRFFAYIKFLVKDLQENELVTINSQWILFDLLS RRMIELDSAKVGISDAQKIAKLPHFDRIKVLAGQEDFQRSYRVMYSDLDVNHHLT NGRYFDWIVNTIPRDFLNSHSMVAASIQFRKEILYDQSAVVTLTWNADHSVSYHT IKRDEQILTVAKISWVSDK | 82 |
| Q6PUQ2 | Petunia integrifolia subsp. inflata | MNEFYEVELKVRDYELDQYGVVNNAIYASYCQHCRHELLEKIGVNADAVARNG EALALTEMTLKYLAPLRSGDRFIVKVRISDSSAARLFFEHFIFKLPDQEPILEARGT AVWLNKSYRPVRIPSEFRSKFVQFLRQEA | 83 |
| R6Q7V8 | Clostridium sp. CAG: 306 | MLFTKEYEIKYYEQNVNGDLKESALLNFLQDIATLSAESLGFGPSFVFANNYAWV VLKYHIELFAPLRNLSSIVIKTEPRGIAKLYAYRDFELYTKDGQCIGKAVSTWVLID ICTRKLLNTQKILADFMAPYQKRETDLVYEKIDSPDELMYQEVFDVRFDDIDVNR HANNSNYIVWALETLPVDFRLKHSPKTIDIKYKKEIGINSRVLSEAQQILTDGNVQ TLHVIKDEQNAQDLTSLKIVWQ | 84 |
| A0A099Y BD8 | Lactobacillus mucosae | MALKAPLVYETKEHLSYYECDATGHPSLSMLISMAVQVSEEHGNSLGLDTATIQS YGGGWVITSYEGSFAARQPINGEEVILGTRAIANNRFFALREFWIQSADRQVEYV RLTGLFVYMNLQTRHLMSIPQAVIEPYHGPEKKRLPRLAKARELQDVRCKNDYH VRFFDIDSNRHVNNARYFDWMQDPLGAEFLTRHQLKHMTMRYEKEVRYGQTIT SEISSPYRHENGELTTDHRIVVDGQLAAASTMIWYE | 85 |
| W0ED98 | Desulfitobacterium metallireducens DSM 15288 | MKKFQKEFEVHYYEVDFYQELTPLALLNFLEETAIAHSEAVGYGVTRLKEKGYG WVLSQWQIEMDQYPHYGEKVKIQTWPSHFQRFYGDREFLVLNSQDKVIARASSL WIFLNLEKRRPTRIPQEVSDAYHIFPDKALSFPFPELKMSQTREKKRSKFMIRRSDI DTNDHVNNAKYIEWVLETIPEEVYRTYRISSLEVVYKKESTYGMQIQSVTEEQQR VDQEAHYVHQILERDGEEEVALALAQTRWSKR | 86 |

TABLE 1-continued

| Uniprot ID No | Organism | Amino acid sequence | SEQ ID NO: |
|---|---|---|---|
| C7XWA4 | Lactobacillus coleohominis 101-4-CHN | MAGQKFILEHQVNYYECDPSGHLSLSMLVALMILASEKQNAQLGVDEHVTKELG GGWVIIDYEGHFQREWPKENEQIKFETAIVAYNKYFVVRQFVIRDYHEQIIGTVN GLFVYMDLSKRRMAKIPEAIMTPYEAASTLRLPKVARPDKVEATDEWRENHYQV RYFDIDYNGHVNNARYFDWMLDTLDHDFLLKHQIMEIRMNYEHEVRPQTEVNS MAITIENNAHEWTTQHQIWVGTQKCATATIKWR | 87 |
| J9W2E3 | Lactobacillus buchneri CD034 | MSMPAHSFSELHTIPFYECNVNNRISIPMLINILILASEHQNENLGLDQTYLIDHYG VGWVVTSYSIHITHLPRKDSVVKMTTRGTSYNRYFAFREFWLHDQAGNELVKVE SIWVLMNEQTRKITPIDETIIAPYQSEKVKRVPRLARPERIEATDDVSAKEYQVRW SDIDFNGHVNNSRYPEWMLDSLPMDFLNQHEPTNIDIRFENEVKYGNRVTSSVLV DSSDNAKIKTVHEIKSNDVLSASATIVWKDIKAKGND | 88 |
| Q8L6B 1 | Triticum aestivum (Wheat) | MGSLLEDGLSYKESFIVRCYEVGINKTATVETIANLLQEVGCNHAQSVGFSTDGF ATTTTMRELGLIWVTVNRMHIEIYKYPAWGDVVEIETWCQADGKIGTRRDWILKD LANGEVIGRATSKWVMMNQNTRRLQRVSDEVRDEVFIHCPKSPRLAFPEENNGS LKKIPVLTDPAQHSRLGLVPRRADLDMNQHVNNVTYIGWVLESIPQDIIDTHELQ TITLDYRRECQHDDIVDSLTYIEEGEEINSNGSLFSAPHPEEQRQFLHCLRFAGAGD EINRGRTVWRKLAR | 89 |
| F2JL78 | Cellulosilyticum lentocellum (strain ATCC 49066/ DSM 5427/ NCIMB 11756/ RHM5) (Clostridium lentocellum) | MDNTFSKKYTIEIYDVNSNYRCKYSSLMNYLWDVVVSQSDSLGETDNGLINNCA WVLLKYDLTIIEYPKFRDTITVETDIVGIKKLYGYRSFTIKTSEGTLIASGISTAVLID INKRRPVRISPEQCKLYGIEKELEENIPLDDFIQLEGYKYSKDYRARHSDIDINQHV NNVKYLEMAVDTLPRTILNASEISNIKVLYKKEALDEASLHVCSDVIENEKGHLTT LHTIIDLTHDKLLTKLELKWRKI | 90 |
| E6LHJ1 | Enterococcus italicus DSM 15952 | MAKEFSRQHEVVYYECDMNGNMTLPTVISLAIQVSETQSNELNRGSEYIHQHGV TWILTNYHLEITRLPKVDEQIIVTTKAEEYNKYFCYRSFWIRTLSGEELVHIQAVFG LMNIETRKLSRVIDEIIAPFESQKITKIKRFGKLEKIVIGESLPYRVRFFDIDSNLHVN NAVYFHWILDVLGRDFLTSYVPKTITIRYDKEVEYGNEITSVVEKINQDQVMCTR HAIMLHEETCCEALIEWKELSK | 91 |
| C5R921 | Weissella paramesenteroides ATCC 33313 | MAVEFRMPHDVVYYEADVTGKLSLPMIYNLAILSSTQQAIDLNIGPEYTHAKGLG WVVLQQLVTINRRPKDGETITLATKAKQFNPFFAKREYRLIDAAGNDLVIMDGLF SMIDMNKRKLARIPKDMAEAYQPEHVRKIPRAPEVTPFDETREADFVQDYFVRYL DIDSNHHVNNSKYAEWMSDVLPVEFLTSHEPTAMNIKYEHEVLYGNKIKSEVQL VDNVTKHRIWFGDVLSAEATIEWTTASN | 92 |
| Q8XH68 | Clostridium perfringens (strain 13/Type A) | MGKAYEKVYEVTYGETDGRKDCRITSMMNFFSDCCLSQEEKNSMNYADNSSET TWVFFDYEIIVNRYPRYREKIKVKTYVESIRKFYSNRVFEAYDMDGALVARADVL AFLINKKTRRPARISDEEYEIHGLSKESSKLLRKKLNFEKFDKEDLDMKFHIRYLDI DLNMHVSNIKYVEWILETVPVDIVLNYKMKKIKIKFEKEITYGHNVIIKSKIIKGED EVKVLHKVENEEGESITLAETYWY | 93 |
| A0A0D2S 4B4 | Gossypium raimondii (New World cotton) | MLKFSYCNATDLNQALVQCRFAGSFGPLSSRRRSPRAAVSCSRSNLTPIQAVLSC QQQVGSDPVESELGSLADRLRLGGLTEDGLSYKEKFIIRCYEVGINKTATIETIANL LQEVGGNHAQSVGFSRDGFATSPTMRKLHLIWVTARMHIEVYKYPAWSDVIEIET WCQNEGRIGTRRDWILKDVATGEVIGRATSKWVMMNEWIRRLQKVSDDVKEEY LVFCPREPRLAFPEENNKSLKKISKLEDPVQYSRLGLMPRRADLDMNQHVNNVT YIGWVLESMPEEIIDTHELQTITLDYRRECQRDDVVDSLTGPELVEGSKIHGTNGS ATAITREDDLDCHQFLHLLRLSSDGQEINRGRTEWRKKPT | 94 |
| A9RDN5 | Physcomitrella patens subsp. patens (Moss) | VLAAIASVALAAETQRRHEVFSGKTRVPVDALRQGRLVESRLVYRQTFVIRSYEI GADRTASIETMMNHFQETALNHVWMSGIAGDGFGATRAMSCRNLIWVVSRMQV HVEQYPAWGDAVEMDTWVAASGKNGMRRDWLVRDYKTGQILARATSTWVM MHRKTRKLSKMPEEVRTEISPYFLDRSAIKHESMLTQKIIRLDGNAEFVRSGLTPR RSDLDMNQHVNNKYIGWMMESVPPTILDTNYELVSMNLEYRRECGQSDVVQSM ASLEPSTSGSLDVGFLQFVHLLRMESDGAEIVRGRTCWRPK | 95 |
| B1MVT0 | Leuconostoc citreum (strain KM20) | MNSFEIKRRVEYYEADVTGKLALPMILNWAVLASKLQSDALGVGQSTHLARGLG WIILQYEVHITRRPAVNEEITIQTYAAKYNPFFVRRPFAFFDAQGEEIIRVDSIWTMI DINNRRMARLPQDIVDKYQAERVKQIPRMPNPIKILPNDDMISKDYHVRYLDIDA NQHVNNSKYFEWMQDVVPTEFLETHEITSINLKYENEIHLGHTIQSQVVLGNQSS KHRIMLGDVVSAEAEFNWRNVTL | 96 |
| I0K660 | Fibrella aestuarina BUZ 2 | MAAFPNALRRKFAGMAFIQTDAYTLRNYECDAAGRLSIPALMNLMQESANRNA YDYGIDSETLQANGLGWMLRFGLVMHHYPRSGQTIRIVTYPTGVEKPFVYRDF RVYADAVLLAEATSWLVFDSHKRTMVPTPDFIRSLVCPDVDQPSPRLPLKPNYP SVEVAEEAQAVTGWFDIDSNQHVNNVYIRWLLEQLPDAVLQTQELAELDVV YRNETHWHERVLVQHQADDAGTFHHRLALAETGKDVLLARTRWRR | 97 |

TABLE 1-continued

| Uniprot ID No | Organism | Amino acid sequence | SEQ ID NO: |
|---|---|---|---|
| G9Z4R4 | Yokenella regensburgei ATCC 43003 | MNFKYVFRWHLPFLFLILLTFRTAAADTLLVLGDSLSAGYRMAAASAWPALLND KWQPKMTVINASISGDTSQQGLARLPALLKQHQPRWVLVELGGNDGLRGFPPQQ TEQTLRTVLQQLEAAKVQPLLMQIRLPANYGRRYNEAFSAIYPKLAGEFNIPLLPF FMEEVYLKPQWMQDDGIHPNRDAQPFIADWMATRLAPLVKHDS | 98 |
| C5VPS2 | Clostridium botulinum D str. 1873 | MSGVITEKEYEIHYYETHTKHQATITNIIDFFTDVATFQSEKLGVGIDFMMENKMA WMLYKWDINVHRYPKYREKIIVVTEPYAIKKFYAYRKFYILDENRNVIATAKSV WLLIHIEKRKPLKISSEIIKAYNLTDKKSDIKIEKLGKLPEEYTSLEFRVRYSDIDTN GHVNNEKYAAWMLESLPRNIISEYTLINIKITYKKETLYGENIRVLTGIKESEDKLV FIHNVIRENGELLTEGETVWKK | 99 |
| A1ZMT4 | Alicroscilla marina ATCC 23134 | MCDLIIEDAKNIYLWYMEKNQTTQLPKIWLDFEVRAYEVDIYNRVSPVTIANYLQ EAAGQHADHLGVGVTDLLKHRLTWVLTRIKIDMQQYPSRYEPVRVLTYPIGYDK YFVYRNFQLYNAQGKQIGQATSTWAVMDIQARKMVGVPQLITSLPIPDDEDFITR TKGKIAKVNAPLSETLFRVRWNDLDTNQHTNNAYYLQWAIESLPEEVLKSRQLA SIDLLYRLETTWKEGVVARTEQTSTQPLSFIHQLIRESDQKELAQATTVWV | 100 |
| A0A0C1Y HD1 | Noviherb aspirillum autotrophicum | MPNDLIRFGRSVRSLQIITALMLALMTNWAYSASKTVLVLGDSLAAEYGLARGS GWAALLEKRLNAEKLDTRIINASISGETTSGGKARLPALLEQHRPAIVIIELGANDG LRGLPVASAKANLRTMIAAVRKAHQPLLVGMQIPPNYGRQYTERFSSMYKELS GELDVPLVPFLLDGVADNPQLFQADRLHPLAEAQPIILDNIWPHLKPLLRKQARH | 101 |
| E2XNS9 | Pseudomonas fluorescens WH6 | MRMWFLSAGLALLCVAQSAAAGTILIVGDSISAGFGLDTRKGWVALLEQRLKKE GFDDKVVNASISGDTSAGGLARLPAALAEHKPDVVVIELGGNDGLRGQPPAQLQ QNLASMIDQSRAGGAKVLLLGMQLPPNYGPRYTKAFAEVFGTLAKEKDIPLVPFF LEGIGGHPELMQADQLHPAVAAQGKLLENVWPALKPLL | 102 |
| A0A081B K12 | Lactobacillus oryzae KM 18671 | MERNDLAALLYTENHEVPYYECDVTNRMTPAMILNTIILISEHQNIELGLGIDFLD KFNLGWVVVQYEIDIERMEPVMNETIAISTQATSYNRFFAFREFWIKDSNGETLVH VKSTWVTMDRTARKMVSIPEAVILPYQSEAVKRMPRLKRPTNINESDDLIKKPYQ VRYYDIDGNGHVNNAHYLEWLTDVLPMDFLTTHEPKQISLRFENEVQYGHMIES QVTKPVESEGSMVTHHQIVVEDTISATATIEWRSRVE | 103 |
| C6Q1L2 | Clostridium carboxidivorans P7 | MKKVETEKQYEIQYYEIDCNKKLLLTSLMNYLEDACTMQSEDIGIGLDYMKSKK VAWVLYKWNIHIYRYPLYREKVKVKTIPESFRKFYAYRSFQVFDSRGNIIADASSI WFLINTERRKAMTVTEDMYEAFGLSKEDNKPLSVKKIRKQERVDSEKVFSVRYS DIDTNRHVNNVKYVDWAVETVPLDIVTNCKIVDIIIAYEKETTYGAMIKVLTQIDK KEEGFVCLHKIVDEEDKELALIETLWKNEK | 104 |
| G6CEI8 | Lactobacillus curvatus CRL 705 | MPGKQYSENYQIPYFETDIKGELTLASLVNILILASEHQLNALNVGEATMHALNL GWVVTQYQMKITRMPKVDEKVRIVTEAESYNKYFCYRNFWLYDEAGNECVFVQ SIFVMMSYETRSMVQVVPEIMVPFESSEIKGSKRFPRIKKIDPKQVTTKEYRVRYF DIDGNQHVNNHYFEWMLDALDYDFLTTHRVASVNIRYGHEIQYGMQTQSMVE QLIVDDIITTRHKVAVDDLSAAEAEITWKER | 105 |
| R5RBT8 | Proteobacteria bacterium CAG: 495 | MELKKYTKEYTIRSYECDRNNNLRIVTLMNIFQDMADINAAQLGLGLDYVLSKG FAWVGSNYEIRIKRLPKIHEKVKIVTWPAVEKKLAAIRDYEVYGKDGERIIAASSQ WILINFMKKRPISLRDNLPEYQIIDDRAIETEFEGKIKEVERIDEQTKFRVRFDDIDL NKHVNNGVYALWASEAVNPDFRLSHNPSKIEINYKKEGHIGEKITVLTECDGLVT THSIQTYDGDNRELARARIEWAENEE | 106 |
| A0A0871 QH8 | Vibrio vulnificus | MVRLFSLLIMFFLSNVAHATEKVLILGDSLSAGYNMSAEQAWPNLLPEALNTYG KNVEVINASISGDTTGNGLSRLPELLKTHSPDWVLIELGANDGLRGFPHKVISSNL SRMIQLSKASDAKVALMQIRVPPNYGKRYTDAFVELYPTLAEHHQVPLFPFFLEE VIVKPEWMMPDGLHPMPEAQPWIAQFVAKTFYKHL | 107 |
| R6XTQ7 | Alistipes sp. CAG: 435 | MEKINVSGNRFSTDITIPCYDTDASFRLKPAAFMDHAQEMAYLAAQALHFGYDD LQRHHTAWVLSRMRMDFLNPPKWTDETTLYTWHKGQDGLFFLSRLRDFELRRKGDT DFADKSKAQVLCTSSWIVMNVETRRLVRSDEVLNMVPATTQCPDNAIQIPCGKV VMPKNIPAEEVGCHKAAYSDIDVLGHTNNARYVVWAMDCIDYEEVAGNIPIRSISI NFIKETKPGEVVRIFRSVEDIDGQKKYFIEGKIEDKPCFCARIDF | 108 |
| A0A011R NY4 | Alkalibacterium sp. AK22 | MSLVYKSEKTITHYMCDRSRSLTLPMLVNLLLEVSEEQSSELSRDESYLKARGVN WIILRYEFSVSRMPNLKETINIETRASEYNKLFTYREFVVKDSSGKVLLTVDTTFAL MDLSTRKMVRLTDEIVSPYQATASRRIRRSDKPKELTDFDDCKQRTFDVRYFDID GNGHVNNAHYISWLLDSLPSDFLKSHEVSWGVIAFDKEVSEHQSIDSLSMRRKER GTATDHQIKSEAAVHCKASFTWKKLNKEEH | 109 |
| Q4R7D6 | Macaca fascicularis (Crab-eating macaque) (Cynomolgus monkey) | MARPGLIHSSPGLPDTCALLQPPAASASAAPSMSGPDVETPSAIQICRIMRPDDAN VAGNVHGGTILKMIEEAGAIISTRHCNSQNGERCVAALARVERTDFLSPMCIGEV AHVSAEITYTSKHSVEVQVNVMSENILTGAKKLTNKATLWYVPLSLKNVDKVLE VPPVVYSRQEQEEEGRKRYEAQKLERMETKWRNGDIVQPVLNPEPNTVSYSQSS LIHLVGPSDCTLHGFVHGGVTMKLMDEVAGIVAARHCKTNIVTASVDAINFHDKI RKGCVITISGRMTFTSNKSMEIEVLVDADPVVDSSQKRYRAASAFFTYVSLSQEG RSLPVPQLVPETEDEKKRFEEGKGRYLQMKAKRQGHTEPRVAMATGPVSTQKFP PWPKTRFTLRAGIV | 110 |

TABLE 1-continued

| Uniprot ID No | Organism | Amino acid sequence | SEQ ID NO: |
|---|---|---|---|
| A9PJK8 | Populus trichocarpax Populus deltoides | MVATAAASSFFPVPSPSGDAKASKFGSVSASLGGIKTKSASSGALQVNTNGQAPP KINGPPVGLAASVETLKNEDVVSSPAPRTFINQLPDWSMLLAAITTMFLAAEKQW MMLDWKPKRPDMLIDPFGIGRIVQDGLVFRQNFSIRSYEIGADRTASIETLMNHLQ ETALNHVKTAGLLGDGFGATPEMSKRNLIWVVTRMQILVDRYPTWGDVVQVDT WVSASGKNGMRRDWLVRDAKTGETLTRASSVWVMMNKVTRRLAKIPEEVRGEI EPYFLTSDPVVIEDSRKLPKIDDNTADYICESLTPRWNDLDVNQHVNNVKYIGWIL ESAPPPIMESHELAAITLEYRRECGRDSVLQSLTAVSDTGIGNLGNPGEVEFQHLL RFEEGAEIVRGRTEWRPKHADNFGIMGHIPAESA | 111 |
| A8MEW2 | Alkaliphilus oremlandii (strain OhILAs) (Clostridium oremlandii (strain OhILAs)) | MARYTEEFVIPYYDCSGDRFVRPESLLEYMGEASLLHGDTLGVGGADLFKMGFA WMLNRWKVRFIEYPKSRTTITVETWSSGVDRFYATREFNIYDSDRKLLVQASTQ WVFCHILKRKPARVPDIISAVYDSEDEHNFYHFHDFKDEVQADEAIEFRVRKSDID FNHHVNNVKYLNWMLEVLPKQFEDQYLYELDIQYKKEIKQGSLIKSEVSMDIEG EETVCYHKITSNSVLHAFGRSVWKNRK | 112 |
| O00154 | Homo sapiens (Human) | MKLLARALRLCEFGRQASSRRLVAGQGCVGPRRGCCAPVQVVGPRADLPPCGA CITGRIMRPDDANVAGNVHGGTILKMIEEAGAIISTRHCNSQNGERCVAALARVE RTDFLSPMCIGEVAHVSAEITYTSKHSVEVQVNVMSENILTGAKKLTNKATLWY VPLSLKNVDKVLEVPPVVYSRQEQEEEGRKRYEAQKLERMETKWRNGDIVQPVL NPEPNTVSYSQSSLIHLVGPSDCTLHGFVHGGVTMKLMDEVAGIVAARHCKTNIV TASVDAINFHDKIRKGCVITISGRMTFTSNKSMEIEVLVDADPVVDSSQKRYRAAS AFFTYVSLSQEGRSLPVPQLVPETEDEKKRFEEGKGRYLQMKAKRQGHAEPQP | 113 |
| Q14814 | Bos taurus (Bovine) | MSGPAAETPSAIQICRIMRPDDANVAGNVHGGTVLKMIEEAGAIISTRHCNSQNG ERCVAALARVERTDFLSPMCIGEVAHVSAEITYTSKHSVEVQVHVMSENILTGTK KLTNKATLWYVPLSLKNVDKVLEVPPVVYSRQEQEEEGRKRYEAQKLERMETK WRNGDIIQPVLNPEPNTVSYSQSSLIHLVGPSDCTLHGFVHGGVTMKLMDEVAGI VAARHCKTNIVTASVDAINFHDKIRKGCVITISGRMTFTSNKSMEIEVLVDADPVV NNFVKRYRAASAFFTYVSLSPEGKSLPVPQLVPETEDEKKRFEEGKGRYLQMKA KRQGQAETQA | 114 |
| P34419 | Caenorhabditis elegans | MVGHSESSTDAVIEPTSEELLAEQVRVFNKMKGSTNFNRVAEDVYPVEVTKSKL VCEMVVQHQHLNSKGTLHGGQTATLTDVITARAVGVTVKDKGMASVELAVSYL LPVKVGDVLEITAHVLKVGRTMAFTDCEFRRKSDGKMSAKGKEITLAFLPNQPGI SVENGTQF | 115 |
| R5BT85 | Blautia hydrogenotrophica CAG: 147 | MGYQFRSRVRYSEIDEDGKLTLPAILNYFQDCCTFHSEDVGLGMKKLRKIHRGW VLSSWQIIVERYPEHGEELTVETWPYDFKGFMGMRNFILRTSQGESLCKANTLWS FMNTDSGMPVKLQPENTQGYQLEPKLEMEYAPRKIGLLSQGEKRESFLVQKHHL DTNHHVNNSQYITMATEYLPKDFEIWQMRAEYKMQARLGERIIPWVSEEPKRCV VSLNQETGKPYAIVEFSKKEK | 116 |
| D0BKN0 | Granulicatella elegans ATCC 700633 | MTVDVICQIERTILPYECDWKENLLLSQALGMMMLASRKQQQQLQNPNLIYEKG YTWIVIQHEIEIQRMPKVDEEVIIETQAISYNKFFTYREYRILSKEREELFKCITTFA MLDMKARKIVSIDEEVVLEYPLSIGKEMRKATRIPKKDFSDATTGEYKIRINDIDA NLHVNNARYFDFAFSELGMEFIEDHQLKQVVIKYEKEVLPESTISCSTLWEENTLE SQERRQTYHLISQDGNRCANIQMKWEEIV | 117 |
| R5EEV3 | Firmicutes bacterium CAG: 110 | MEPIFQQDFPVQELCVDRYGRLKPSTLLYFAQEIAGRHCDELADTLESHRLFWAV TRHRVQINRLPELGETVHIETWPMPNTHVGYPRSIVIYDQAGNECSRSISLWVLM DQDTRSSVSPDKSGIIVPGTLRGTELALPGGLVPRAMEHSCQRDVCFTDLDRNGH MNNTRYMDWIDDLLPSDFHREHPVKEFAVRYHSEAREGQRLDLHWDFVEDNCL RVDARRRNETRDELVFSAKVLFD | 118 |
| R5NTL8 | Clostridium sp. CAG: 793 | MKLENSIFEETYRTSFSQTGIHETLTNKSFLSMMENLAGAHSGYCHYSFANLAPE HKTWIILNWKLQVFRRPYADEIVTLKTWGHFANKIYVLRDFKMLDKDGNLLAIA SSKWCLFDFSTGRIARLPDNLEEIYQGFNSESVFNCNDLPKLKAPESEPIASDTYKI RRFDLDLNKHVHNLNYLNIAYELLPLDVYDGPELNNVEIVYKKEIKYGDTIKSYL YKENDSYIIVIKSLDGSIVHSIVKLY | 119 |
| Q1J6W5 | Streptococcus pyogenes serotype M4 (strain MGAS10750) | MGLSYQEELTLPFELCDVKSDIKLPLLLDYCLMVSGRQSAQLGRSNNNLLVDYKL VWIVTDYEITIHRLPHFQETITIETKALSYNKFFCYRQFYIYDQEGCLLVDILAYFA LLNPDTRKVATIPEDLVAPFKTDFVKKLHRAPKMPLLEQSIDRDYVVRYFDIDMN GHVNNSKYLDWMYDVLGCEFLKTHQPLKMTLKYVKEVSPGGQITSSYHLDQLT SYHQITSDGQLNAQAMIEWRAIKQTESETD | 120 |
| R6FXC3 | Clostridium sp. CAG: 221 | MGISYEKMYEIHYYECDKNLNCTLESIMNFLGDVGNKHAESLNVGMEYLTERNL TWVFPYKYNIKINRYPKYEEKIKVKTVAEEFKKFYALRTYEIYDENNIKIVEGSALF LLIDIVKRRAVKITDDQYKAYNVDKGSTGKNLIGRLERLEKVKNNEYVSNFKVR YSDIDFNKHVNNVKYVQWFMDSVPQEIREEYELKEIDILFEHECYYNDEIKCVCEI HKNEDNLLVLSNIQDKDGKELTVFVSKWE | 121 |

TABLE 1-continued

| Uniprot ID No | Organism | Amino acid sequence | SEQ ID NO: |
|---|---|---|---|
| R7F611 | Clostridium sp. CAG:354 | MGYFEHDFEIGLRDVENPNYLSNKAILAFFENIGSYHSDSINFGLNEIPKTKSSWVL LGWKVKVLKRPLYGDKLHIVTWARNTEKFSTYRDYEVYNQNNELVIIGTSKWVL VNTTTGKLRPIPEEIIKLYCPDTKTAFPPEEALLTKLTDSEHYGTACTCTVGRSQID LNNHMHNLYYLDMAYEALPEEVYKNNTFNFFEITYKKQIRLHDAVKCYYVFEEN THKVVIKSLDDKKTHAIIVFK | 122 |
| C4JAL9 | Zea mays (Maize) | MHHRFAGLVPTARPALPPIHGGVVGRSYPPVHRSLALRLAPFASASVRRACRPLA VSAQSTSLRPEKFFEVEMKVRDYEIDQYGVVNNAIYASYCQHGRHELLESVGISA DAVARSGESLALSELNLKYFAPLRSGDKFVVKVRLAGIKGVRMIFDHIITKLPNHE LILEAKATAVCLNKDYYPTRIPRELLSKMQLFLPVDSRGSNEDVNNRNNSCN | 123 |
| N1JPQ7 | Mesotoga infera | MKPVVTKEVYRVRYYELDCQWKASISSLMDYFNDVVTLQTVEMGHGVDVMSK GEYAWLLLRWDVKVNRYPDYLENVVVQTIPYSMDRFYAYRRFEIFDCSGNVIVD ANSQWILIDQRKRRPIRIGDQFYELYGIDSDFHEPLSFPKVNENESSSEEITFIVRNS DLDTNGHSNNVAYVRWIMETVPSEFVKRFLKRLTIEYKRESRKGDVISIESVFENG AEFAEGKHKITSSGRVLSLARTEWK | 124 |
| B1ZXQ1 | Opitutus terrae (strain DSM 11246/ JCM 15787/ PB90-1) | MPEKLTLNASVLYADVDRTEVLLLRGVFKFLQEAAITHANQFDLGSRAMATRGE SWVLNRMAVAVHRYPRYEETMRIETWSRGIKGFKGYREFRVFDAQGAPLFSGSS LWLYVNMRTKSIIRVPAELAAEFPKRDDGAFFPELESLEFAPPAADARRVPIAIRY SDVDVNAHVNNTAYLDFLQEALARAGLSPRPQSIRIKYARAIPAEAETVRVAIEPR GTGAAFAIEDHDTIFAIGEVD | 125 |
| E4MXK9 | Eutrema halophilum (Salt cress) (Sisymbrium halophilum) | MVMTHCTRFQHLLQPKLLFSHSRVFRHPHIRARTPLRSIMGSSSSFSSKLLFRQLFE KESSTYTYLLADVSHPDKPALLIDPVDKTVDRDLKLVNELGLKLIYAMNTHVHA DHVTGTGLLKKKVPGVKSVISKASGSKADMFLEPGDKVTIGDLYLEVRATPGHT AGCVTYVTGEEADQPQPRMAFTGDAVLIRGCGRTDFQGGSSDQLYESVHSQIFTL PKDTLIYPAHDYKGYEVSTVGEEMQHNPRLTKDKETFKTIMSNLNLAYPKMIDV AVPANMVCGLQE | 126 |
| A0A089R LX5 | Cedecea neteri | MMNFNNVFRWHLPFLFLALMTFRAAAADTLLILGDSLSAGYRMAATSAWPALL DAKWQPQNTKVVNASISGDTAAQGLSRLPALLKQHPRWVLVELGGNDGLRGF QPPQEVEKTLKQVITDVKAANAQPLLMQIRLPANYGRRYNEAFSAIYPQLAKQFDI PLLPFFMEEVYLKPQWMQDDGIHPNRDAQPFIADWMATQLTPLLSK | 127 |
| J5XTZ9 | Klebsiella sp. OBRC7 | MMNFKYVFRWHLPFLFLVLFTCRAMAADTLLVLGDSLSAGYRMAGNTAWPALL NDKWQTKTPVVNASISGDTSQQGLARLPALLKQHPRWVLVELGGNDGLRGFPP QQTEQTLRTIIEHIKAANAQPLLMQIRLPANYGRRYNEAFSAIYPALAKEFDIPLLP FFMEEVYLKPQWMQDDGIHPNRDAQPFIADWMATRLAPLVNHDS | 128 |
| M4VN84 | Bdello- vibrio exovorus JSS | MSTSSETTEKRIWEEEYKITSYLVNLRGRAGLYAILNLIQDVGWMHAIAAQVRLP ANLAWVFTRQKLVMSQWPKWNETISIRTWLRPPESAAFILRDYEIILNGQVIGTCT STFAVIDTQTRKIAAQEWSEYEQLFRTGTALPHHPVKIPYREDAQDLTVFEVRNSD IDLNNHVNNTKYAKWILDSISIDTLRAGVDLLEYEVNFLAEARSGDRVTVQSCAE EKLEGQSDSATALIQFQGVRVSDKKTIFTAKLRVR | 129 |
| L7VMU3 | Clostridium stercorarium subsp. stercorarium (strain ATCC 35414/ DSM 8532/ NCIMB 11754) | MIPELVYRNSYIVGYRDVDFNNDLRLSSLFGYFQDTAIMNVEKLGIGVNTLSEKY SVSWVLTKILVEINRIPKWNEKITVETWPHRPKKFEFDRDFRVRDDNGNIIAAAIS NWVLLDLKTREIRKSEIISGDYPPLEFTDERALEGRLRKLRPAGEPEVVYKRVLGY SDTDANGHINNAKYIDFIMDCFSIEEHKKHSVRSIQVNYLKEVFPGDTLILYRDVS GAGSNQVYIEGINEADQKPAFSAELKFD | 130 |
| A0A0C1Q ZB7 | Clostridium argentinense CDC 2741 | MKNIHRENYKVKFNETDYSTKIKMHSLINYMQETSSIHAELLGAGYEELKKHNLF WVVSRLKINMKKYVNWNDEVIVETWPSGVDKMFFTRSFRIYDREENHIGDINAA YLLVAEDSMFPQRISKLPINIPTIENRFEPYERLEKIKFPKDDKVLVAKKKVRYNDI DLNLHVNNAKYIEWVEDCFPLEMYKDMRIETLQLNFIKEAKCGEKIFFYKYNDLE DENTCYIEGIEKQSESQIFQCKLTFNKL | 131 |
| P41903 | Saccharomyces cerevisiae (strain ATCC 204508/ S288c) (Baker's yeast) | MSASKMAMSNLEKILELVPLSPTSFVTKYLPAAPVGSKGTFGGTLVSQSLLASLH TVPLNFFPTSLHSYFIKGGDPRTKITYHVQNLRNGRNFIHKQVSAYQHDKLIFTSMI LFAVQRSKEHDSLQHWETIPGLQGKQPDPHRYEEATSLFQKEVLDPQKLSRYASL SDRFQDATSMSKYVDAPQYGVMEYQFPKDMFYSARHTDELDYFVKVRPPITTVE HAGDESSLHKEIHPYRIPKSITPENDARYNYVAFAYLSDSYLLLTIPYFHNLPLYCH SFSVSLDHTIYFHQLPHVNNWIYLKISNPRSHWDKHLVQGKYFDTQSGRIMASVS QEGYVVYGSERDIRAKF | 132 |

TABLE 1-continued

| Uniprot ID No | Organism | Amino acid sequence | SEQ ID NO: |
|---|---|---|---|
| C4Z694 | Eubacterium eligens (strain ATCC 27750 / VPI C15-48) | MVFNYTYRIGLEDCGRENKATNRAILTILEDIAGLHSATVGLGLNEINETGCAWV VLNWQMKIIRRPAYNDELTVYTWSTSADKLFAERDFRITDKNGETIVIATSRWLY MDINRRRPVRITPEIMDRYESEPEIHVFTEKVNRIDPPDTGYIEIPYNILRRDVDYLG HMHNISYLDAAYDVMPEEYFNGPQFNFVSIEYRKELLRNDEVKAHFYKIDKGCII SLNTDKINAVIMLKY | 133 |
| A0A0B3V S79 | Terrisporobacter othiniensis | MIYCNNYKIGLEDIGIKNEATNKALLAIMEDVAGLHSASVGYGVLDIETKKRVWI LLDDWKMKVIKRPKYNDDIKAETWSRKVERLYAYRDFQLKDKEGNIIAIGTSRWIL IDTDRKRPMKLTADIADLYESETDKSVFPEQIEDIKCENYLFKKDYYIQRRDIDINE HMHNLNYLDMAYEILPEDVYKNKVFDNIRIVYKKEILYGEKVVCYYEEQGNKHII TAKSKDKINAIIELS | 134 |
| A0A084J BW2 | Clostridium sulfidigenes | MELNYKEQFTIKPHEGDFMGNVKLFTIMDYVQQVSEGHSQILGVDFQSMMNKGL FWVVSRVEITMERYPKVGEDITVETCLGGREKVFMKRRFKIKDKDGQVIGRVLIY YLIVDIETRLPQKPSMCPVDININVGDVIDNKLNKIKMPGEAIETVNRKLYYNDIDI NNHVNNAKYISFIEDFFSLDWHRVKKISYMQLNFIKEIKFDDSLIMNKFIEDKESNS FCINGISEISEQEFFQCRLKF | 135 |
| A0A037Z 4L7 | Clostridium tetanomorphum DSM 665 | MEGLVTEKEYEIHYYEVDYKRRLLITNIINYFCDIATKQSEDRNVGLDYMKENNV AWVLYKWHINVHRYPLYGEKVIVTTRPHSFRKFYAYRKFEIIDEKGKIIIEANSIW FLIDIQRRRPKRINEHIEEAYKVSKDNDERAILEIPDIKCIEKIHNEKTFNVRYSDIDT NGHVNNAKYVSWAIETVPLEIIKSYALKNITINYEKETKYGESINAFVEVIKEDKM VICRHRITDKEGNELTIAQSTWE | 136 |
| A0A0L8E W05 | Clostridium sp. DMHC 10 | MDKIISKKDYNIHFYEVNYDKKADITSIMSYLGDLATYQSEELGVGIDYLMRNKM AWVVYKWNVHMDKYPEYNDTITVTTIPYSIRKFYAYRKFEIFNKGEKIGEATSLW FLINTERRRPCRVPEDIYRAYGLRVEDDQQLEFEKLLLPSEISSEKSFDVRYSDIDT NKHVNNVKYVSWALENIPLDVVKNCSVSSIRVIYEKETSYGETITVQTQMKEIED KYIFDHVIKNSEGEKLTLIKTEFLKA | 137 |
| B8I625 | Clostridium cellulolyticum (strain ATCC 35319/ DSM 5812/ JCM 6584/ H10) | MEPLSIYKKNYHVDYGDADFYKRLKLSYLFNYFQNIAGLHSENTNVGIRKLQND YGAAWVMTRMLMDINRMPECNEEISIETWPVEPKKKMIDRNFIVRDMDGSILAS AISTWVILDMEKREMVRIDSVIPPQYPEFLKSKAIDRKFDKLKPSGQLQPAYKKLV GFSDIDINGHVNNAKYIDYILDCFTVEKHGEYRVKSIQINYVNEAVAGDIISLYKD TVDMDGSDKAVYITGINEVDGKVNFESHIRVQ | 138 |
| D5ADX2 | Picea sitchensis (Sitka spruce) (Pinus sitchensis) | MYNMDLFGAKGMARPFELELKVRDYELDQYGVVNNATYASYCQHCRHELCEAI GFSPDVIARTGNALALSELSLKYLAPLRSGDSFVVTARISGSSAVRLFFEHFIYKLP NREPVLEAKATAVYLDKIYRPVRLPADFKSKITLFLRNEELN | 139 |
| A0A0D3V 4E9 | Paenibacillus sp. IHBB 10380 | MGNIWTEEHLIYSNEIDYKANCRLSNLLSLMQRAADGDVEHMGGTRDQMVAHH LGWMLTTIDLACERMPIFNETLKITTWNKGTKGPLWLRDFRIFDENNQEIAKACT LWALVDIDKRKVLRPSAYPFNINSNHEDSVGPVPDKLNISDEVELYHSYSITVRYS GIDSNGHLNNSRYADLCMDTLTQSELDTLSILGFHITYYHEVKSAEQIQVLRSDHL EGYIYFRGQSLEDERYFEACLHVG | 140 |
| P0A8Z3 | Escherichia coli (strain K12) | MNTTLFRWPVRVYYEDTDAGGVVYHASVAFYERARTEMLRHHHFSQQALMA ERVAFVVRKMTVEYYAPARLDDMLEIQTEITSMRGTSLVFTQRIVNAENTLLNEA EVLVVCVDPLKMKPRALPKSIVAEFKQ | 141 |
| A0A0M2 NEM6 | Catabacter hongkongensis | MNTKLEQLYTIRAFDVDTKGKWRPSAILTRLQEIAEDHAIAVNAGRKELVEERG MAWMLTRLHLQMKQYPDLTDTIKVVTWPGKPTKLFFVRHSMFFSETGEELGRA TSLWVLFNIRERFLCRTGDIGENYPYDLSHGRALPDPGKIKLPDEMQYMTTRTVA YSEVDMNGHLNNAKYADWICELFDISHLKKAYMDQFRINYIAEAYMGQKVDLY CKEIDGTWPVCGKTGNKTVFDASIQWK | 142 |
| R6RDZ9 | Firmicutes bacterium CAG: 449 | MNYYQKELVLVQEKDFINDELSPYSILNYFQDIAGIHADKIGLSHEELIKNDLVWVV LRNKYEIIKMPSINQKVILKTWPHQKGKIDFDREYAIYDENNNLLIKGLSKWILMN YKTRRISMFNNIKYSFECLEETNFENKFNKIEDFDINNFSIETTTSENDLDINGHVN NASYARIVLNNIDFDITINHFEINYIKEIKANQKLKIYYLKKDNTYYIKAFNNEEVIF VLIVY | 143 |
| E4L0C9 | Peptoniphilus hardi | MKIFCKEYEVMNFLSSDGDLKLNHLVSYLIETSNYQSIDLGLSNEKLLDMGYTW MIYKWKIKINRYPRSYEKIKIKTWASGFKNINAFREFEVYCQGEKIIEASAIFLLIDV EKRKAIKIPEVLAEIYGNNGNRIFKSIERVNEPSELEIANRFSYKILRRDLDFNNHV | 144 |

TABLE 1-continued

| Uniprot ID No | Organism | Amino acid sequence | SEQ ID NO: |
|---|---|---|---|
| | ACS-146-V-Sch2b | NNSVYLELIYEAVTDEYTHVKFKDINVNYINELKLGDEIVIDFYREEDRFYFFFKS KDQSQIYARICGVSETPIS | |
| A0A062X 6R3 | Lactobacillus animalis | MAENLYRMPHQIVYYETDPTGKLSLGKLVDLMMLASYAQGKDVGMPEEKLNA QGYGWVITQHLLSITRLPRRDEKVVIETKATAYNRYFCYRNFYLRDEQGELLAK MHTAFVLLDLETRKITRITSDVIAPFGPEPIRSIERSASPKRLEEVMLAKDYRVRYF DIDSNHHVNNVHYIEWMLDVLDKDFLMEHEPVALNIKYEHELNYGQTCTSKVEL LRSKDELTTLHEIYMADGTLSCSAQVTWK | 145 |
| A4A3N9 | *Congregi-bacter litoralis* KT71 | MGLLLGLALLLTGQLARAESTAGERPRILVVGDSISAAYGMSLEQGWAALLERR LQTRWPGAQVINASISGDTSAGGARRLPKLLAEHSPDLVVIELGGNDGLRGYPTS KLEANLSFMAEAASTAGAEVLILPMEIPPNYGPRYTRSFRESFERAATDTGATLGP FLLDGIATEEQLMQQDGIHPTVEAQPMITDIVQPVIEALLALREAS | 146 |
| B1IHP0 | *Clostridium botulinum* (strain Okra/ Type B1) | MQPVITDKNFEINYHEIDFKKRVLFTTIMNYFEDASLEQSEKLGVGLQYLKENEQ AWVLYKWNVTIDRYPEFGEKIIVRTIPLSYRKFYAYRRFQIIDKTGKVIVTGDSIWF LIDINKRRPIKVTEDMQNAYGLSETKEEPFKIDKIKFPEEFHYNNKFKVRYSDIDTN LHVNNVKYISWAIETIPFDIVLNYTLKNFVITYEKEVKYGNDINVYSEMVHNDNN EIVFVHKVENEEGKRVTSAKSIWVK | 147 |
| V5WGX9 | *Salinispira pacifica* | MERNMKFSREYEVRGFEIDENYHLKPYHIASYFQDAMAQNFADNMLAAYDLQK EGRTWVLSDLCIDFLHQMPRWRTSVLVETWVSSIRGFRLTIDFRVSDSRGTPISQG SSSWVIVKKPGNRPEKIEPYARKLGEPHSPLYPGYRFHEPDLDGSPSPLPYGACGL RHPWEEDQKAWSICQPIRSYDIDFNGHVSNIRYIAGAVEAIPVELRSSLRPSSFRIK YLREAVLDQVLVSEVRTVHEDSDAIEYHHILKECESAVEFSRMVSVWKR | 148 |
| A0A099R RK7 | *Clostridium* sp. HMP27 | MGKLVTDKEYEIHFYEVDYKGRALFTSLMNYFGDISSKQSEDRNMGIDYLKKVN MAWVLYKWNVKIHRYPTYREKVIARTVPYSFRKFYAYRKFYILDIEGNVIVEADS LWFLIDIETRKPVRVQEEMYTGYCLSKDDNEIIDIPKITAPNESDFCKTFDVRYSDI DTNGHVNNSKYISWILEAVPLNIVTQYSLSNLIITYEKETTYGEVIDSCVEVREVD GKAVCKHKIVDKEGNELTVAETTWTR | 149 |
| R7LAU3 | *Coraliom argarita* sp. CAG: 312 | MKFSRIYNVRSSEITPEYKLKEFYIGMYFQECFAEYMASKGLAAYDLAKSGQTWL TSDVQIDYLQEMPFWREPVEMQVWVRQISAIRIYVDFEAIHKSSVIARGSSIQLIAE KSTHHPIKNATIASISSLSLIHESALPGVEFKKIDPFGGEYSKTSQVVRYDDLDFNM HLNNVKYVPRALESIPQEFRNSHTLKEYRIKFMRETFFNNTVSSEAFRDGNRIFHR LARVEDGVELCRMESLWE | 150 |
| Q2BL39 | *Neptunii-bacter caesariensis* | MRTAITFLLFVFLTLPVQARSLIVLGDSLSAAYQMAPEEGWVALLEEKMATEGYA YDVINASVSGDTTQNGIARLKTLLKQVDAEIVIIELGGNDGLRGTPPFAIKRNLSRL VNMAKDSGAQVLLLGIQLPSNYGAAYNKQFSEIYPVIAEDENVALVPFFMEQVA LVPERMQDDGIHPSAEGQPYLLNTVWPHLEPLIN | 151 |
| Q3ADW4 | *Carboxy-dothermus hydrogen oformans* (strain ATCC BAA-161/ DSM 6008/Z-2901) | MNSNIFELEYRIPYYDVDYQKRTLITSLINYFNDIAFVQSENLGGIAYLTQNNLGW VLMNWDIKVDRYPRFNERVLVRTAPHSFNKFFAYRWFEIYDKNGIKIAKANSRW LLINTEKRRPVKINDYLYGIYGVSYENNNILPIEEPQKLLSIDIEKQFEVRYSDLDSN GHVNNVKYVVWALDTVPLEIISNYSLQRLKVKYEKEVTYGKTVRVLTGILSEQK TIVSLHKIVDEDETELCFLESVWFLNEKLS | 152 |
| Q5SJV0 | *Thermus thermophilus* (strain HB8/ ATCC 27634/ DSM 579) | MESVTRIKVRYAETDQMGVVHHSVYAVYLEAARVDFLERAGLPYHRVEARGVF FPVVELGLTFRAPARFGEVVEVRTRLAELSSRALLFRYRVEREGVLLAEGFTRHL CQVGERAARIPEDIYRALSVLHLK | 153 |
| E3G686 | *Enterobacter lignolyticus* (strain SCF1) | MPFLFLVLLTCRAAFADTVLVLGDSLSAGYRMAANAAWPALLNAKWQPKTDVI NASISGDTSQQGLARLPELLKQHQPRWVLVELGGNDGLRGFPPQQTEATLRAILK DIEAANAKPLLMQIRLPANYGRRYNASFSAIYPKLASEFNIPLLPFFMEEVYLKPQ WMQDDGIHPNRDAQPFIADWMATRLAPLVNHDS | 154 |
| E6VY45 | *Pseudo-desulfovibrio* aespoeen*sis* (strain ATCC 700646/ DSM 10631 / Aspo-2) | MTAHLPLTHDRLYRIRSYEPRPDGLAPITAICNQLQDIASGHADALGFGYHDLETG GHFWLLARLHVMMDRLPAYGGAVRVQTWPSGNERLVANRDFLILDPAAAQETV MGRATSSWVTMNASTHRPESPSEVLSTRFIPDRERALTFPAKSITRLKDGEHETGL TARRADLDINGHVNNVRYAELCLEAVPQAWEAAHRCLGLDIQFRSESFAGDAYV SACAEAGPDSGMRTLLHRLTRINDDREIVRMRSWWQTG | 155 |

TABLE 1-continued

| Uniprot ID No | Organism | Amino acid sequence | SEQ ID NO: |
|---|---|---|---|
| | (Desulfovibrio aespoeensis) | | |
| A0A099LW85 | Vibrio navarrensis | MVRLFSLMLMLILSWTATAAEKILILGDSLSAGYNMPAEQAWPSLLPDVLKTYG KDVQVINASISGDTTGNGLARLPDLLTTHSPDWVLIELGANDGLRGFPPPKTIAANL SRMIQITKAAGAKPVLMQIRVPPNYGKRYSQAFFDLYPTLAEHQQVPLLPFFLEQ VITKPEWMMQDGLHPTADAQPWIAEFVAEMFSQHL | 156 |
| A0A0D6QP57 | Anaeromyxobacter sp. PSR-1 | METFKESFAVHSYEVDAFGTLAPPALTGFLMEAAGLHAGRLGVGIDALMEKGLT WVLVRQRTEMPVPIVLGDVLEVETWPVGVDRLAALRDFVVRRRDGAEVARGTT QWFVLDVKIRKPVRPETALDARFPRELGKPVIDVAPGKLPELRTWEFQKRFHVR YQDIDLNLHVNNGSYVAWALEAIPKDVYTGSRVAALEVQYLAECHYGSAVLSRL ARTGPGAFAHAIVREEDEKELARITTSWVPR | 157 |
| N6Z483 | Thauera linaloolentis 47Lol = DSM 12138 | MPLRSIATFFFMLLFVGAAHAATILVWGDSLSAGYGLEPGRAWPTLLQTRLQEKG FRHTVVNASVSGETSAGGRSRLPAALERHKPDIVILELGANDGLRGLRPQLMAEN LEAMIAASRDAGAQILLVGMQMPPNYGPAYTRRFAQTFDDVAKAQQVPLVPFLL EGFAGQPERFQADGIHPTADAQPLVLDTVWRGLEPLLKRN | 158 |
| A0A094JFG0 | Shewanella mangrovi | MLVILLTAPAQAATLLIVGDSLGASYGVNEKDGWVEGLRNALPQHTLINASVSGE TSGGGLRRLPSLLSSASPDVVLIELGGNDGLRGFPPQQLKNNLTKMIALAKQAGA KVMLSEVMVPPNYGPRYEKAFTSVYQQLAEDKSVTLVPFFMTVIAPHPELMQRD GIHPNTVAQPKITAFMLPFIKHALDEVNNS | 159 |
| A9SDT6 | Physcomitrella patens subsp. patens (Moss) | GGFVDNSLMYRQIFVVRSYEVGPDRLMSIREIFSLFQETALNHVQLLGIAGDGFGA TRAMNRLGLIWVVIKMKVEVNRYPVWPEVVEIDTWVAHAGKNGMQRDWIMR SYQTDEVLARATSTWCMMDGVTRRLSKIPDEVRAEIVPCFMDDYPSSFREDEESP RITKLDNTTAENRRSHLKSTTADLDMNQHVNNLKYINWVLDSVPVEHMEKHVL ASISLEYRRECHSTDVVESLTNSKMDIQGNDSDPSRPCEYVHLLRKQDSSNQEILR GMTKW | 160 |
| A0A0B9GJL1 | Photobacterium gaetbulicola | MMRFLSVIFFLVFTQHALAAKLMVLGDSLSAGYQMQAEQSWPNLLDAELEKYG HEVTVVNASISGDTTGNGMARLPRLLEQHQPDFVLIELGANDGLRGFPPTTIRNNL GEMITQIEQAGAYPLLMQIVVPPNYGKRYSDQFAKVYQEISNTLDIPLLPFFLEHII LKQEWMMEDGLHPKPDAQPWIANFMANEIAPHL | 161 |
| Q9LK77 | Arabidopsis thaliana (Mouse-ear cress) | MNSPRPISVVSTFASPSSTSDPIRKPLSLWPGMYHSPVTTALWEARSKIFESLLDPP KDAPPQSQLLTRTPSHSRTTIFYPFSTDFILREQYRDPWNEVRIGILLEDLDALAGTI SVKHCSDDDSTTRPLLLVTASVHKIVLLKKPICVDIDLKIVASVIWVGRSSIEIQLEV MQSELKDVKASSDSVALTANFIFVARDSKTGKAAPINRLSPETEVEKLLFEEAEAR NNLRKKKRGGDRREFDHGECKKLEAWLAEGRIFSDMPALADRNSILLKDTRLEN SLICQPQQRNIHGRIFGGFLMHRAFELAFSTAYTFAGLVPYFLEVDHVDFLRPVDV GDFLRFKSCVLYTQLDKQDCPLINIEVVAHVTSPEIRSSEVSNTFYFKFTVRPEAKA RNNGFKLRNVVPATEEEARHILERMDAEALKSSKQQCVGTILQ | 162 |
| Q01FC4 | Ostreococcus tauri | MIARASGASDVASADRSVAKPTANGEKSFSGMDGTEWFSRNFSEQGRKFSEVFP VRYAETGPNGEATMVTIADLIQECACNHAQGIWVGVGQSMPAEMAKGHLAWVCT RLHLCVRKYPKWGEKMEVSTWFEPQGKIAARRDYSITDESGVQIGEATSQWVVL NLNTRRMARIPNSVLEDFKYQALERQVMEEGYASDKLADVTEIAANQCVSPITH HVRRNDMDMNGHVNNVVYVQWILESVPQETWNGRALQEIILEYRSECNFGECIT ATCCEVEEQSDSYVLLHKLARGDDEIVRAKTVWTKQKTS | 163 |
| P0AGG2 | Escherichia coli (strain K12) | MSQALKNLLTLLNLEKIEEGLFRGQSEDLGLRQVFGGQVVGQALYAAKETVPEE RLVHSFHSYFLRPGDSKKPIIYDVETLRDGNSFSARRVAAIQNGKPIFYMTASFQA PEAGFEHQKTMPSAPAPDGLPSETQIAQSLAHLLPPVLKDKFICDRPLEVRPVEFH NPLKGHVAEPHRQVWIRANGSVPDDLRVHQYLLGYASDLNFLPVALQPHGIGFL EPGIQIATIDHSMWFHRPFNLNEWLLYSVESTSASSARGFVRGEFYTQDGVLVAST VQEGVMRNHN | 164 |
| Q3B7M2 | Bos taurus (Bovine) | MVLGRGLLGRWSVAELGAVCARLGLGPALLGSLHHLGLRKSLTVDQGTMKVEL LPALTDNYMYLLIDEDTKEAAIVDPVQPQKVVETARKHGVKLTTVLTTHHWD HAGGNEKLVKLEPGLKVYGGDDRIGALTHKVTHLSTLQVGSLHVKCLSTPCHTS GHICYFVTKPNSPEPPAVFTGDTLFVAGCGKFYEGTADEMYKALLEVLGRLPADT RVYCGHEYTINNLKFARHVEPDNTAVREKLAWAKEKYSIGEPTVPSTIAEEFTYN PFMRVREKTVQQHAGETEPVATMRAIRKEKDQFKMPRD | 165 |
| I3S4A5 | Aledicago truncatula (Barrel medic) (Nledicago tribuloides) | MPSWFDIHEIPVTANSPNDESSLLKAVQNVHATIDKEIAAGTNPNNIFICGFSQGG ALTLASVLLYPKTLGGGAVFSGWVPFNSSVIEQITPEAKRTPILWSHGLSDKTVLF EARQAAPPFLEKIGVSCEFKAYPGLAHSINNEELKHLESWIKARLQSSS | 166 |
| E4MWI3 | Eutrema halophilum | MESAMNTESVFEFLGNVPLLQKLPSSSLKKIAQVVVLKRYGKGDYVIREDQAWD GCYFIFAGEAQVSGPAEEENRSEFLLKKYDYFGHGISAHVHSADIIATSELTCLVLP | 167 |

TABLE 1-continued

| Uniprot ID No | Organism | Amino acid sequence | SEQ ID NO: |
|---|---|---|---|
| | (Salt cress) (Sisymbrium halophilum) | RDHCRLLETNSIWQSDKEVQKCSLVERILHLDPLELNIFRGITLPDAPKFGKVFGG QFMGQALAAASKTVDFLKIVHSLHSYFLLVGDIDIPIIYQVHRIRDGNNFATRRVD AIQKGNIIFILLASFQKEQQGFDHQESTMPSAPDPDTLLSLEELRERRITDPHLPRSY RNKVATANFVPWPIDIRFCDPSNSTNQTKSPPRLRYWFRAKGKLSDDQALHRCV VAFASDLIFASVSLNPHRRKGLRSAALSLDHAMWFHRPLRADDWLLFVIVSPTAH MTRGFVSGQMFNRKGELVVSLTQEALLREARPPKPSVTSKL | |
| A9NV70 | Picea sitchensis (Sitka spruce) (Pinus sitchensis) | MYHSPVTNALWHARSSIFERLLDPSVDAPPQSQLLSKTPSQSRTSILYNFSSDYILR EQYRDPWNEVRIGKLLEDLDALAGTIAVKHCSDDDSTTRPLLLVTASVDKMVLK KPIRVDTDLKVAGAVTWVGRSSLEIQMVITQPPEGETETGDSVALTANFMFVARD SKTGKSALINRLLPQTEQEKALLAEGEARDMRRKKERQRQGKEFEEGHRLHGDG DRLKALLREGRVLCDMPALADRDSMLIKDTRLENALICQPQQRNLHGRIFGGFL MHRASELAFSTCYAFVGHTPLFLEVDHVDFLRPVDVGDFLRFKSCVLFTQVDDPK RPLIDIEVVAHVIRPELRSSEVSNTFYFTFTVHPVALEGGLKIRKVLPATEEEARHV LERIDAENLN | 168 |
| M1Z1V0 | [Clostridium] ultunense Esp | MKATPLYIKDYKVEINHVDFKGDLKLSSLFTYCQDIAGLHAENLGMGREVLYTQ HRVIWVLVRVRVDIIKYPKWKDILTLETWPQEPSRMGFDRDFLIKDKKGNILAKA VSTWVVIDVESRKLVRTKSVYTGYPLVVEKRAIDCKLGNLKSSGELETAYERTVR YSDIDVNEHLNNAKYLDFIMDSFSFEEHRRFNVKSVEISYSNEALLGETIKIYEDRS RIDSNIIYMEGIREGKDLVFKSQIEIEEK | 169 |
| R6XLC3 | Clostridium sp. CAG: 798 | MAIIENKYHIGIKYVDKDRLLSLRGIILLFEDIACRHSDMVGYGINDVTKTHFSWV LLNWKIKVLSRINYGSIVTVKTWSRETSKLYTYRDFEIYDENNNLICIASSKWVLL STETGHIIHITEEIKNAYLAENKTVFNESDLHKIVEPDNAEKTFSFTVRRRDIDINNH MNNLYYLDYALEALPEEVYSKFFNNVEIMYKYSAKLGETINCFYKEEEDGYYVM MKSATDNILHALVKLY | 170 |
| R5TEH3 | Roseburia sp. CAG: 50 | MYQFKSRVRFSEVDSQLHMTLPSIINYFQDCSTFHSDSIGYGIEVMMEQGYAWILS SWQIIINRYPKFGEEITVSTWAHGWKAFFGYRNFKLEDTEGNLLAYANTNWIYM NIRTGHPERIPKEICDLYKCEPALPMEESSRKITPPAKGTGITPIQVHRYDIDSNNHV NNERYVPMAMECLPEGAQIRQLRVEYRNSAVYGDTIYPVYHQEEDLLKVSLNDS DGKPYAIVEFQLAPLSDQAD | 171 |
| E6MF99 | Pseudora mibacter alactolyticus ATCC 23263 | MGKIFERPQAIATYDCLEDHHLSPVAVMNYFQQISLEHSASLKAGPYELSALDLT WIVVKYHVDFWQMPRFLDQLQLGTWASAFKGFTAHRGFFLKNQSGEHMVDGQ SHWMMVDRRQNHIVRVNEVPINAVYDVEDQGPRFKMPRLARIKDWENVRQFSV RYLDIDYNGHVNNVCYLAWALACLPAVVLQTRTLKTLDIVFKEQALYGDVVTV KDREIAPNCYRVDIFNANETLLTQLQLQF | 172 |

In some embodiments, the amino acid corresponding to position 5 is substituted with tyrosine (Y) or an equivalent amino acid. In some embodiments, the amino acid corresponding to position 35 is substituted with serine (S) or an equivalent amino acid. In some embodiments, the amino acid corresponding to position 38 is substituted with glutamine (Q) or an equivalent amino acid. In some embodiments, the amino acid corresponding to position 64 is substituted with valine (V) or an equivalent amino acid. In some embodiments, the amino acid corresponding to position 241 is substituted with glutamic acid (E) or an equivalent amino acid. In some embodiments, the amino acid corresponding to position 45 is substituted with methionine or isoleucine (I) or an equivalent amino acid. In some embodiments, the amino acid corresponding to position 128 is substituted with tyrosine (Y) or an equivalent amino acid. In some embodiments, the amino acid corresponding to position 175 is substituted with serine (S) or an equivalent amino acid. In some embodiments, the amino acid corresponding to position 33 is substituted with aspartic acid (D) or an equivalent amino acid, and the amino acid corresponding to position 128 is substituted with tyrosine (Y) or an equivalent amino acid. In some embodiments, the amino acid corresponding to position 59 is substituted with valine (V) or an equivalent amino acid, and the amino acid corresponding to position 90 is substituted with phenylalanine (F) or an equivalent amino acid. In some embodiments, the amino acid corresponding to position 40 is substituted with glutamic acid (E) or an equivalent amino acid, and the amino acid corresponding to position 111 is substituted with tryptophan (W) or an equivalent amino acid. In some embodiments, the amino acid corresponding to position 36 is substituted with glycine (G) or an equivalent amino acid, and the amino acid corresponding to position 128 is substituted with tyrosine (Y) or an equivalent amino acid. In some embodiments, the amino acid corresponding to position 32 is substituted with glutamine (Q) or an equivalent amino acid, and the amino acid corresponding to position 40 is substituted with glutamic acid (E) or an equivalent amino acid.

In some embodiments substitution of one or more amino acid(s) corresponding to position(s) 5, 35, 38, 64 and 241, as described above, increases enzymatic activity and/or improves substrate specificity. In some embodiments, substitution of one or more amino acid(s) in the substrate binding site, for example, one or more amino acid(s) corresponding to position(s) 45, 128, and 175, as described above, increases enzymatic activity and/or improves substrate specificity. In some embodiments, substitution of pairs of amino acid residues at the substrate binding site, for example, one or more amino acid(s) corresponding to positions 33 and 128; positions 59 and 90; positions 40 and 111; positions 36 and 128; positions 32 and 40; as described above, increases enzymatic activity and/or improves substrate specificity.

It is understood that any wild-type acyl-ACP TE can be mutated with any combination of the amino acid substitutions described to obtain a polypeptide with increase enzymatic activity and/or improved substrate specificity. In some embodiments, the mutant acyl-ACP TE comprises two or more, three or more, four or more, five or more, six or more, seven or more, eight or more, nine or more or ten or more substitutions at amino acid(s) that occupy position(s) corresponding to position(s) 5, 32, 33, 35, 36, 38, 40, 45, 59, 64, 90, 111, 128, 175, and 241 of SEQ ID NO: 1.

As set forth above, the mutant acyl-ACP TE can have one or more amino acid substitutions described above, relative to a wild-type acyl-ACP TE, for example, and not to be limiting, relative to a wild-type acyl-ACP TE classified under EC 3.1.2.- or EC 3.1.2.14. In some embodiments, the mutant acyl-ACP TE has one or more additional modifications. Protein modifications include amino acid sequence modifications. Modifications in amino acid sequence may arise naturally as allelic variations (e.g., due to genetic polymorphism), may arise due to environmental influence (e.g., by exposure to ultraviolet light), or may be produced by human intervention (e.g., by mutagenesis of cloned DNA sequences), such as induced point, deletion, insertion, and substitution mutants. Modifications in a nucleic acid encoding an acyl-ACP TE can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about 1 to 10 amino acid residues; and deletions will range from about 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. Substitutional modifications are those in which at least one residue has been removed and a different residues inserted in its place. In some embodiments, conservative or equivalent substitutions are made. A conservative substitution results in substitution of an amino acid with a chemically and/or functionally similar amino acid. Modifications, including specific amino acid substitutions, are made by known methods.

By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example, PCR mutagenesis, primer extension or inverse PCR mutagenesis.

Fusion polypeptides comprising any of the polypeptides described herein are also provided. The polypeptides can be fused to heterologous sequences, for example, and not to be limiting, tags or sequences designed to facilitate expression, purification and/or detection of recombinantly-expressed proteins. Non-limiting examples include a periplasmic tag, a poly-histidine tag, a maltose binding protein (MBP), Protein A, glutathione S-transferase (GST), fluorescent protein sequences (e.g. GFP), and epitope tags such as myc, FLAG, and haemagglutinin tags.

In some embodiments, the amino acid sequence of the polypeptide having an acyl-ACP TE activity, for example, a mutant acyl-ACP TE has at least 50%, 55% 60%, 65%, 70%, 75%, 80%, 85%, 90%, 95%, or 99% amino acid sequence identity with the amino acid sequence of the wild-type acyl-ACP TE, and has enzymatic activity. In certain embodiments, the amino acid sequence of the polypeptide having an acyl-ACP TE activity, for example, a mutant acyl-ACP TE has at least 90%, 95%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, or 99.9% sequence identity to the wild-type acyl-ACP TE and has enzymatic activity. In certain embodiments, the enzymatic activity is specific for pimeloyl-ACP.

Also provided herein are fragments of the polypeptides described herein. These fragments preferably include at least 20 contiguous amino acids, more preferably at least 25, 30, 35, 40, 45, 50, 60, 70, 80, 90, 100 or more contiguous amino acids. In some embodiments, the polypeptide comprises a fragment of a mutant acyl-ACP TE described herein.

Derivatives of any of the mutant polypeptides described herein also provided. In some embodiments, derivative polypeptides are polypeptides that have been further altered, for example by conjugation or complexing with other chemical moieties, by post-translational modification (e.g. phosphorylation, acetylation and the like), modification of glycosylation (e.g. adding, removing or altering glycosylation), and/or inclusion/substitution of additional amino acid sequences as would be understood in the art. Derivatives also include fusion proteins, as described above. Other derivatives contemplated by the embodiments include, but are not limited to, modification to side chains, incorporation of unnatural amino acids and/or their derivatives during peptide, or protein synthesis and the use of crosslinkers and other methods which impose conformational constraints on the polypeptides and fragments thereof.

Nucleic Acids and Vectors

In another embodiment, a nucleic acid encoding any of the polypeptides having an acyl-ACP TE activity described herein is provided. In some embodiments, the nucleic acid encodes a polypeptide having an acyl-ACP TE activity, wherein the polypeptide comprises one or more amino acid substitution(s) relative to a wild-type acyl-ACP TE, wherein the one or more amino acid substitution(s) are at amino acid(s) that occupy position(s) corresponding to position(s) 5, 32, 33, 35, 36, 38, 40, 45, 59, 64, 90, 111, 128, 175, and 241 of SEQ ID NO: 1. In some embodiments, the nucleic acid encodes a polypeptide comprising a mutant acyl-ACP TE or a functional fragment thereof. In some embodiments, the nucleic acid encodes a polypeptide comprising a mutant acyl-ACP TE, wherein the mutant acyl-ACP TE comprises one or more amino acid substitution(s) relative to a wild-type acyl-ACP TE, wherein the one or more amino acid substitution(s) are at amino acid(s) that occupy position(s) corresponding to position(s) 5, 32, 33, 35, 36, 38, 40, 45, 59, 64, 90, 111, 128, 175, and 241 of SEQ ID NO: 1, or a functional fragment thereof. In some embodiments, the enzyme is an acyl-ACP TE classified under EC 3.1.2.-. In some embodiments, the wild-type acyl-ACP TE is classified under EC 3.1.2.14. Vectors or genetic constructs, including expression vectors, comprising any of the nucleic acid sequences disclosed herein are also provided.

In some embodiments, the nucleic acid encoding the polypeptide having an acyl-ACP-TE activity, for example, a mutant acyl-ACP TE has at least 50%, 55%, 60%, 65%, 70%, 75%, 80%, 85%, 90%, 95%, or 99% sequence identity with the nucleic acid sequence encoding the wild-type acyl-ACP TE. In certain embodiments, the nucleic acid sequence encoding the polypeptide having an acyl-ACP-TE activity, for example, a mutant acyl-ACP TE, has at least 90%, 95%, 98%, 98.1, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, or 99.9% sequence identity to the nucleic acid encoding a wild-type acyl-ACP TE.

Nucleic acid molecules that are fragments of these nucleic acid sequences encoding polypeptides are also encompassed by the embodiments. By "fragment" is intended a portion of the nucleic acid sequence encoding a portion of a polypeptide. In some embodiments, the nucleic acid has been codon optimized for expression of any one of the polypeptides described herein.

Some embodiments relate to nucleic acids consisting essentially of or consisting of a nucleic acid sequence encoding a polypeptide as described above and elsewhere herein. In some embodiments, the nucleic acid sequence is a DNA sequence, for example, a cDNA sequence. In other embodiments, the nucleic acid sequence is an RNA sequence. In some embodiments, the nucleic acid is a cDNA encoding any of the polypeptides described herein. The nucleotide sequences encoding the polypeptide may be prepared by any suitable technologies well known to those skilled in the art, including, but not limited to, recombinant DNA technology and chemical synthesis. Synthetic polynucleotides may be prepared using commercially available automated polynucleotide synthesizers.

In some embodiments, the polynucleotide comprises a sequence encoding any one of the polypeptides described herein operably linked to a sequence encoding another protein, which can be a fusion protein or another protein separated by a linker. In some embodiments, the linker has a protease cleavage site, such as a cleavage site for Factor Xa or thrombin, which allow the relevant protease to partially digest the fusion polypeptide described herein and thereby liberate the recombinant polypeptide therefrom. The liberated polypeptide can then be isolated from the fusion partner by, for example, subsequent chromatographic separation.

Some embodiments provide genetic constructs in the form of, or comprising genetic components of, a plasmid, bacteriophage, a cosmid, a yeast or bacterial artificial chromosome, as are well understood in the art. Genetic constructs may be suitable for maintenance and propagation of the isolated nucleic acid in bacteria or other host cells, for manipulation by recombinant DNA technology and/or expression (expression vectors) of the nucleic acid or an encoded polypeptide as described herein.

Some embodiments relate to recombinant expression vectors comprising a DNA sequence encoding one or more of the polypeptides described herein. In some embodiments, the expression vector comprises one or more of said DNA sequences operably linked to a promoter. Suitably, the expression vector comprises the nucleic acid encoding one of the polypeptides described herein operably linked to one or more additional sequences. In some embodiments, the expression vector may be either a self-replicating extrachromosomal vector such as a plasmid, or a vector that integrates into a host genome. Non-limiting examples of viral expression vectors include adenovirus vectors, adeno-associated virus vectors, herpes viral vectors, retroviral vectors, lentiviral vectors, and the like. For example, adenovirus vectors can be first, second, third, and/or fourth generation adenoviral vectors or gutless adenoviral vectors. Adenovirus vectors can be generated to very high titers of infectious particles, infect a great variety of cells, efficiently transfer genes to cells that are not dividing, and are seldom integrated in the host genome, which avoids the risk of cellular transformation by insertional mutagenesis. The vector may further include sequences flanking the polynucleotide giving rise to RNA which comprise sequences homologous to eukaryotic genomic sequences or viral genomic sequences. This will allow the introduction of the polynucleotides described herein into the genome of a host cell.

An integrative cloning vector may integrate at random or at a predetermined target locus in the chromosome(s) of the host cell into which it is to be integrated.

Expression of the Polypeptides

Any of the polypeptides disclosed herein, including mutant or variant polypeptides, can be expressed using conventional methods known to those of skill in the art. Generally, for production of acyl-ACP TEs in *E. coli* the T7 expression system can be used. Genes for acyl-ACP TEs can be cloned into a vector under the control of the T7 promoter and transformed into a BL21[DE3] *E. coli* host. Expression can then be induced by the addition of 1 mM IPTG to the culture media. In some embodiments, a nucleic acid sequence encoding any of the polypeptides disclosed herein, for example, a DNA sequence, can be expressed, using an expression vector, which typically includes control sequences encoding a promoter, operator, ribosome binding site, translation initiation signal, and, optionally, a repressor gene or various activator genes. In some embodiments, the expression vector optionally comprises a suitable transcription terminator. In some embodiments, polyadenylation sequences operably connected to the DNA sequence encoding the polypeptide are used for expression in eukaryotic cells. Termination and polyadenylation sequences may suitably be derived from the same sources as the promoter or not. One of skill in the art would know which combination of an expression vector, including specific elements of the vector, can be used with one or more host cells to produce the desired polypeptide. In some embodiments, the vector comprises a selectable marker. Selectable markers are well known in the art and will vary with the host cell used. Suitable selection markers can include, for example, genes coding for ampicillin and/or tetracycline resistance, which enable cells transformed with these vectors to grow in the presence of these antibiotics.

In some embodiments, a host cell comprising a vector described herein is cultured. After reaching a desired cell density or titer of the polypeptide, the culture is stopped and the polypeptide is recovered using known procedures. Alternatively, the host cell is used directly (e.g., pellet, suspension), i.e., without isolation of the recombinant protein.

The recombinant expression vector carrying the DNA sequence encoding a polypeptide as described herein may be any vector, which may conveniently be subjected to recombinant DNA procedures, and the choice of vector will often depend on the host cell into which it is to be introduced. Thus, the vector may be an autonomously replicating vector, i.e., a vector that exists as an extrachromosomal entity, e.g., a plasmid, a bacteriophage or an extrachromosomal element, minichromosome, or an artificial chromosome, the replication of which is independent of chromosomal replication. Alternatively, the vector may be one which, when introduced into a host cell, is integrated into the host cell genome and replicated together with the chromosome(s) into which it has been integrated.

In the vector, the DNA sequence typically is operably connected to a suitable promoter sequence. The promoter may be any DNA sequence that shows transcriptional activity in the host cell of choice and may be derived from genes encoding proteins either homologous or heterologous to the host cell. Examples of suitable promoters for directing the transcription of the DNA sequence encoding a polypeptide as described herein, especially in a bacterial host, are the promoter of the lac operon of *E. coli*, the *Streptomyces coelicolor* agarase gene dagA promoters, the promoters of the *Castellaniella defragrans*, and others. For transcription in a fungal host, examples of useful promoters are those derived from the gene encoding *A. oryzae* TAKA amylase, *Rhizomucor miehei* aspartic proteinase, *A. niger* neutral LDH, *A. niger* acid stable LDH, *A. niger* glucoamylase, *Rhizomucor miehei* lipase, *A. oryzae* alkaline protease, *A. oryzae* triose phosphate isomerase or *A. nidulans* acetamidase. The promoters can be selected based on the desired outcome. The nucleic acids can be combined with constitutive, tissue-preferred, inducible, or other promoters for expression in the host cell or organism. The above list of promoters is not meant to be limiting. Any appropriate promoter can be used in the embodiments.

In some embodiments, the expression vector described may also comprise a suitable transcription terminator and, in eukaryotes, polyadenylation sequences operably connected to the DNA sequence encoding the polypeptide as described herein. Termination and polyadenylation sequences may suitably be derived from the same sources as the promoter or not.

In some embodiments, the vector may further comprise a DNA sequence enabling the vector to replicate in the host cell in question. Examples of such sequences are the origins of replication of plasmids pUC19, pACYC177, pUB110, pE194, pAMB1 and pIJ702. The above list of origins of replication is not meant to be limiting. Any appropriate origins of replication can be used in the embodiments In some embodiments, the vector may also comprise a selectable marker. Selectable marker genes are utilized for the selection of transformed cells or tissues, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation. The above list of selectable marker genes is not meant to be limiting. Any selectable marker gene can be used in the embodiments.

Appropriate culture mediums and conditions for the above-described host cells are known in the art. While intracellular expression may be advantageous in some respects, e.g., when using certain bacteria as host cells, it might be preferred that the expression is extracellular or periplasmic.

Enzymatic Activity and Substrate Specificity

In some embodiments, any of the polypeptides described herein has increased enzymatic activity and/or improved substrate specificity as compared to a wild-type acyl-ACP TE. In some embodiments, any of the polypeptides described herein comprises, consists essentially of or consists of a mutant acyl-ACP that has increased enzymatic activity and/or improved substrate specificity relative to the wild-type acyl-ACP TE. In some embodiments, any of the polypeptide described herein comprises, consists essentially of or consists of a mutant acyl-ACP that has increased enzymatic activity relative to the wild-type acyl-ACP TE. In some embodiments, any of the polypeptides described herein comprises, consists essentially of or consists of a mutant acyl-ACP TE that has improved substrate specificity relative to the wild-type acyl-ACP TE. In some embodiments, any of the polypeptides described herein comprises, consists essentially of or consists of a mutant acyl-ACP that has increased enzymatic activity and/or improved substrate specificity for pimeloyl-ACP relative to the wild-type acyl-ACP TE.

In some embodiments, a polypeptide, for example, a polypeptide comprising a mutant acyl-ACP TE has an increase in enzymatic activity of at least 5%, 10%, 20%, 30%, 40%, 50%, 60%, 70%, 80%, 90%, 100%, 200%, 300%, 400%, or at least 500% relative to the activity of the wild-type acyl-ACP TE. In certain embodiments, enzymatic activity is specific activity, i.e., enzymatic activity for reaction of the mutant acyl-ACP TE with a specific substrate, for example, pimeloyl-ACP. In some embodiments, the increase in enzymatic activity results in an increase in the production of 7-AHA when the polypeptide is expressed in a host cell or organism, as described herein.

In some embodiments, the improved substrate specificity of the polypeptide, for example, a mutant acyl-ACP TE, relative to the substrate specificity of the wild-type acyl-ACP TE results in a polypeptide that can convert at least one substrate into at least one product at a $k_{cat}$ ($s^{-1}$) greater than that of the wild-type acyl-ACP TE.

In some embodiments, the improved substrate specificity of the polypeptide, for example, a mutant acyl-ACP TE, relative to the activity of the wild-type acyl-ACP TE results in a polypeptide that can convert at least one substrate into at least one product at a $K_m$ lower than that of the wild-type acyl-ACP TE. In some embodiments, the improved substrate specificity is improved substrate specificity for pimeloyl-ACP.

Host Cells and Organisms

Any of the nucleic acids disclosed herein can be stably or transiently introduced into an organism, such as a host cell, using established techniques, including, but not limited to, electroporation, calcium phosphate precipitation, liposome-mediated transfection, contact with nanowires or nanotubes, spheroplasting, PEG 1000-mediated transformation, biolistics, lithium acetate transformation, lithium chloride transformation, and the like.

For stable transformation, a subject nucleic acid will generally further include a selectable marker, e.g., any of several well-known selectable markers such as neomycin resistance, and the like. Some embodiments relate to host cells comprising an exogenous DNA molecule (i.e., a molecule not otherwise present in the wild-type counterpart cell) encoding a polypeptide as described herein. In some embodiments, these host cells can be described as expression systems. Suitable host cells for expression may be prokaryotic or eukaryotic. Without limitation, suitable host cells may be mammalian cells (e.g. HeLa, HEK293T, Jurkat cells), yeast cells (e.g. *Saccharomyces cerevisiae*), insect cells (e.g. Sf9, *Trichoplusia ni*) used with or without a baculovirus expression system, or bacterial cells, such as *E. coli* (Origami2(DE3), BL21(DE3)), or a vaccinia virus host. Introduction of genetic constructs into host cells (whether prokaryotic or eukaryotic) is well known in the art, for example, as described in Current Protocols in Molecular Biology Eds. Ausubel et al., (John Wiley & Sons, Inc. current update Jul. 2, 2014).

A further embodiment relates to a transformed or transduced organism or microorganism (i.e., an engineered organism), such as an organism selected from plant cells, insect cells, bacteria, yeast, baculovirus, protozoa, nematodes, algae, and transgenic mammals (e.g., mice, rats, pigs). The microorganisms include prokaryotic and eukaryotic microbial species from the domains Archaea, Bacteria and Eucarya, the latter including yeast and filamentous fungi, protozoa, algae, or higher Protista. The terms "microbial cells" and "microbes" are used interchangeably with the term microorganism. The transformed organism comprises a DNA molecule of the embodiments, an expression cassette comprising the DNA molecule or a vector comprising the expression cassette of the disclosed embodiments, which may be stably incorporated or not stably incorporated into the genome of the transformed organism. Other suitable organisms also include synthetic cells or cells produced by synthetic genomes as described in Venter et al. US Pat. Pub. No. 2007/0264688, and cell-like systems or synthetic cells as described in Glass et al. US Pat. Pub. No. 2007/0269862.

In certain embodiments, the host is a prokaryote selected from the group consisting of *Escherichia; Clostridia; Corynebacteria; Cupriavidus; Pseudomonas; Delftia; Bacillus; Lactobacillus; Lactococcus*; and *Rhodococcus*, or a eukaryote selected from the group consisting of *Aspergillus, Saccharomyces, Pichia, Yarrowia, Issatchenkia, Debaryomyces, Arxula,* and *Kluyveromyces.*

In some embodiments, the host microorganism is a prokaryote. For example, the prokaryote can be from the bacterial genus *Escherichia* such as *Escherichia coli*; from the bacterial genus Clostridia, such as *Clostridium ljungdahlii, Clostridium autoethanogenum* or *Clostridium kluyveri*; from the bacterial genus *Corynebacteria*, such as *Corynebacterium glutamicum*; from the bacterial genus *Cupriavidus*, such as *Cupriavidus necator* or *Cupriavidus metallidurans*; from the bacterial genus *Pseudomonas*, such as *Pseudomonas fluorescens, Pseudomonas putida* or *Pseudomonas oleavorans*; from the bacterial genus *Delftia* such as *Delftia acidovorans*; from the bacterial genus *Bacillus* such as *Bacillus subtillis*; from the bacterial genus *Lactobacillus*, such as *Lactobacillus delbrueckii*; or from the bacterial genus *Lactococcus*, such as *Lactococcus lactis.*

In some embodiments, the host microorganism is a eukaryote (e.g., a fungus such as a yeast). For example, the eukaryote can be from the fungus genus *Aspergillus* such as *Aspergillus niger*; from the yeast genus *Saccharomyces*, such as *Saccharomyces cerevisiae*; from the yeast genus *Pichia* such as *Pichia pastoris*; from the yeast genus *Yarrowia* such as *Yarrowia hpolytica*; from the yeast genus *Issatchenkia*, such as *Issathenkia orientalis*; from the yeast genus *Debaryomyces* such as *Debaryomyces hansenii*; from the yeast genus *Arxula* such as *Arxula adenoinivorans*; or from the yeast genus *Kluyveromyces* such as *Kluyveromyces lactis.*

Exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica,* and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Another embodiment of the disclosure comprises a method of making a polypeptide from a recombinant nucleic acid sequence disclosed herein comprising: a) providing a population of host cells or organisms; and b) growing the population of cells or organisms under conditions whereby the polypeptide encoded by the nucleic acid of the disclosure is expressed; and c) isolating the resulting polypeptide.

The host cells can be fermented to produce a polypeptide having acyl-ACP TE activity described herein or to catalyze the reactions that are catalyzed by the polypeptides described herein. Fermentation broadly refers to the conversion of organic materials into target substances by host cells, for example, the conversion of a carbon source by recombinant host cells into fatty acids or derivatives thereof by propagating a culture of the recombinant host cells in a media comprising the carbon source. As used herein, conditions permissive for the production means any conditions that allow a host cell to produce a desired product, such as a fatty acid or a fatty acid derivative. Similarly, conditions in which the polynucleotide sequence of a vector is expressed means any conditions that allow a host cell to synthesize a polypeptide. Suitable conditions include, for example, fermentation conditions. Fermentation conditions can comprise many parameters, including but not limited to temperature ranges, levels of aeration, feed rates and media composition. Each of these conditions, individually and in combination, allows the host cell to grow. Fermentation can be aerobic, anaerobic, or variations thereof (such as microaerobic). Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source. For small scale production, the engineered host cells can be grown in batches of, for example, about 100 mL, 500 mL, 1 L, 2 L, 5 L, or 10 L; fermented; and induced to express a desired polynucleotide sequence, such as a polynucleotide sequence encoding a polypeptide comprising a mutant acyl-ACP TE disclosed herein. For large scale production, the engineered host cells can be grown in batches of about 10 L, 100 L, 1000 L, 10,000 L, 100,000 L, 1,000,000 L or larger; fermented; and induced to express a desired polynucleotide sequence. Alternatively, large scale fed-batch fermentation may be carried out.

Methods

The polypeptides, nucleotides, and cells/organisms described herein are useful for many different applications.

Figure 2:
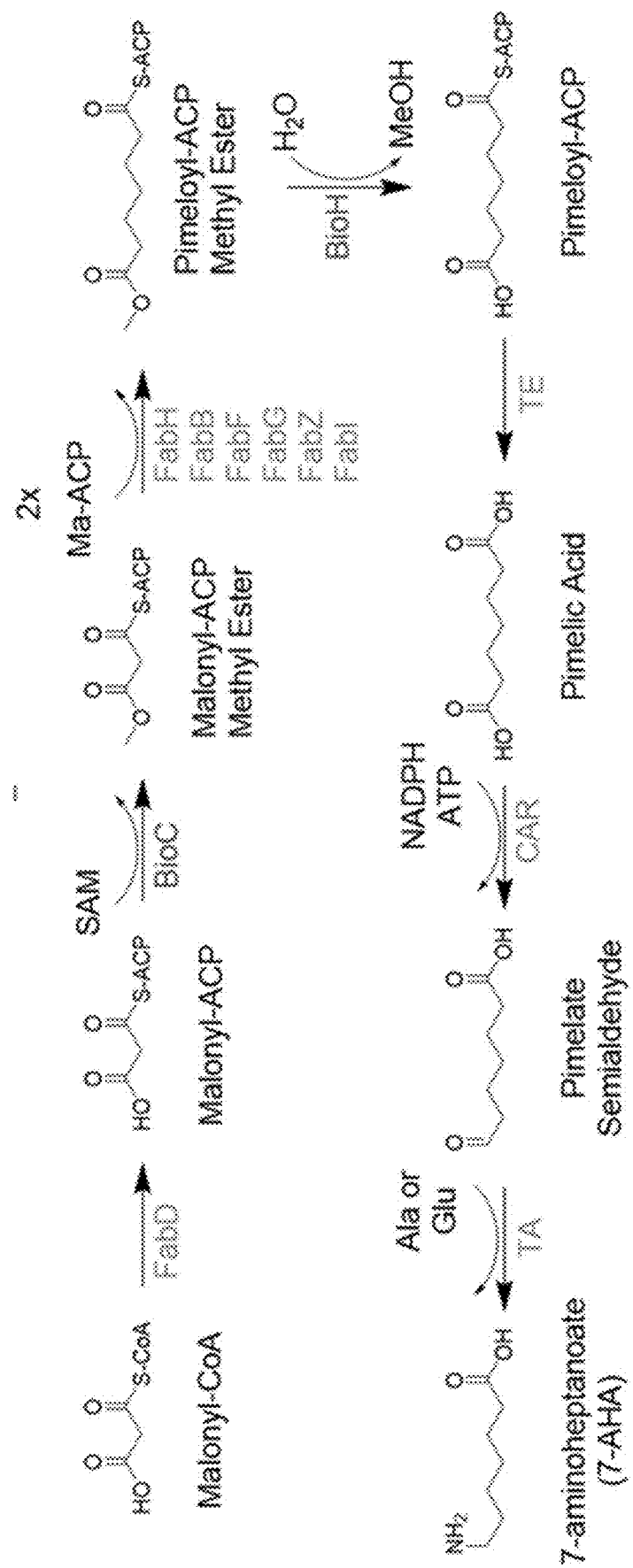
FIG. 2 is a schematic of a biochemical pathway for producing 7-AHA from malonyl-CoA.

Provided herein, in one embodiment, is a method for producing pimelic acid, pimelate semialdehyde or 7-AHA or any product of FIG. 2, comprising the step of enzymatically converting pimeloyl-ACP to pimelic acid in the presence of any one of the polypeptides described herein.

In a related embodiment, also provided is a method for producing pimelic acid, pimelate semialdehyde or 7-AHA or any product of FIG. 2, comprising the steps of culturing a host cell comprising a nucleic acid sequence encoding a mutant polypeptide of the disclosure in a suitable medium and recovering the pimelic acid, pimelate semialdehyde or 7-AHA. In some embodiments, the host cell can further comprise a nucleic acid encoding an enzyme that catalyzes a different reaction in a biosynthetic pathway for 7-AHA, for example, an enzyme that catalyzes a reaction in the pathway for the production of 7-AHA, shown in FIG. 2. Exemplary recombinant enzymes that can be used include, but are not limited to, a pimeloyl-ACP methyl ester esterase (bioH) that catalyzes the conversion of pimeloyl-ACP methyl ester to pimeloyl-ACP, a carboxlic acid reductase (CAR) that catalyzes the conversion of pimelic acid to pimelate semialdehyde and a transaminase that converts pimelate semialdehyde to 7-AHA.

Another embodiment relates to the use of the polypeptides described herein to produce intermediates, for example, 7-AHA, in the production of synthetic polymers. In some embodiments, the polypeptides described herein are used to produce intermediates in the production of nylon. In certain embodiments, the polypeptides described herein are used to produce intermediates in the production of Nylon 7.

Products

Other embodiments relate to bioderived or fermentation derived products produced by the methods disclosed herein, for example, bioderived pimelic acid, pimelate semialdehyde and 7-amino heptanoate or any product of FIG. 2. In related embodiments, products comprising a chemical produced from any of the bioderived products produced using the methods disclosed herein are also provided. In some embodiments, the product comprises a nylon intermediate, a polyester, a pharmaceutical, a biofuel, a fragrance or a food additive.

Other embodiments include a bio-based or fermentation-derived product, wherein said product comprises: (i) a composition comprising at least one bio-derived, bio-based or fermentation-derived compound, or salts thereof, produced in the presence any of the polypeptides described herein, or produced from the product of a reaction catalyzed by the any of the polypeptides described herein, or any combination thereof; (ii) a bio-derived, bio-based or fermentation-derived polymer comprising the bio-derived, bio-based or fermentation-derived composition or compound of (i), or any combination thereof; (iii) a bio-derived, bio-based or fermentation-derived resin comprising the bio-derived, bio-based or fermentation-derived compound or bio-derived, bio-based or fermentation-derived composition of (i), or any combination thereof, or the bio-derived, bio-based or fermentation-derived polymer of (ii), or any combination thereof; (iv) a substance obtained by molding the bio-derived, bio-based or fermentation-derived polymer of (ii), or the bio-derived, bio-based or fermentation-derived resin of (iii), or any combination thereof; (v) a bio-derived, bio-based or fermentation-derived formulation comprising the bio-derived, bio-based or fermentation-derived composition of (i), bio-derived, bio-based or fermentation-derived compound of (i), bio-derived, bio-based or fermentation-derived polymer of (ii), bio-derived, bio-based or fermentation-derived resin of (iii), or bio-derived, bio-based or fermentation-derived substance of (iv), or any combination thereof, or; (vi) a bio-derived, bio-based or fermentation-derived semi-solid or a non-semi-solid stream, comprising the bio-derived, bio-based or fermentation-derived composition of (i), bio-derived, bio-based or fermentation-derived compound of (i), bio-derived, bio-based or fermentation-derived polymer of (ii), bio-derived, bio-based or fermentation-derived resin of (iii), bio-derived, bio-based or fermentation-derived formulation of (v), or bio-derived, bio-based or fermentation-derived molded substance of (iv), or any combination thereof.

Compositions

Some embodiments relate to compositions comprising one or more disclosed polypeptides or nucleotides, alone or in combination, including in combination with wild-type acyl-ACP TEs. In some embodiments, the composition comprises one or more disclosed polypeptides with improved enzymatic activity and/or substrate specificity. In some embodiments, the composition comprises one or more polypeptides with improved specific activity for the conversion of pimeloyl-ACP to pimelic acid. In some embodiments, the composition comprises pimeloyl-ACP and one or more polypeptides described herein.

In some embodiments the composition is composed of one or more disclosed polypeptides, from (1) commercial suppliers; (2) cloned genes expressing said polypeptides; (3) complex broth (such as that resulting from growth of a microbial strain or any other host cell in media, wherein the strains/host cells secrete the disclosed polypeptides into the media; (4) cell lysates of strains/host cells grown as in (3); and/or (5) any other host cell material expressing the disclosed polypeptide. Different disclosed polypeptides in a composition may be obtained from different sources.

EMBODIMENTS

The following embodiments are contemplated. All combinations of features and embodiment are contemplated.

Embodiment 1

A polypeptide having an acyl-acyl carrier protein (ACP) thioesterase (TE) activity, wherein the polypeptide having acyl-ACP TE activity comprises one or more amino acid substitution(s) relative to a wild-type acyl-ACP TE, wherein the one or more amino acid substitution(s) are at amino acid(s) that occupy position(s) corresponding to position(s) 5, 32, 33, 35, 36, 38, 40, 45, 59, 64, 90, 111, 128, 175, and 241 of SEQ ID NO: 1, or a functional fragment thereof.

Embodiment 2

An embodiment of embodiment 1, wherein the wild-type acyl-ACP TE is an acyl-ACP TE classified under EC 3.1.2.-.

Embodiment 3

An embodiment of embodiment 1 or 2, wherein the wild-type acyl-ACP TE is an acyl-ACP TE classified under EC 3.1.2.14.

Embodiment 4

An embodiment of any of the embodiments of embodiment 1-3, wherein the amino acid corresponding to position 5 is substituted with tyrosine (Y) or an equivalent amino acid.

Embodiment 5

An embodiment of any of the embodiments of embodiment 1-4, wherein the amino acid at position 35 is substituted with serine (S) or an equivalent amino acid.

Embodiment 6

An embodiment of any of the embodiments of embodiment 1-5, wherein the amino acid at position 38 is substituted with glutamine (Q) or an equivalent amino acid.

Embodiment 7

An embodiment of any of the embodiments of embodiment 1-6, wherein the amino acid at position 64 is substituted with valine (V) or an equivalent amino acid.

Embodiment 8

An embodiment of any of the embodiments of embodiment 1-7, wherein the amino acid at position 241 is substituted with glutamic acid (E) or an equivalent amino acid.

Embodiment 9

An embodiment of any of the embodiments of embodiment 1-8, wherein the amino acid at position 45 is substituted with methionine or isoleucine (I) or an equivalent amino acid.

Embodiment 10

An embodiment of any of the embodiments of embodiment 1-9, wherein the amino acid at position 128 is substituted with tyrosine (Y) or an equivalent amino acid.

Embodiment 11

An embodiment of any of the embodiments of embodiment 1-10, wherein the amino acid at position 175 is substituted with serine (S) or an equivalent amino acid.

Embodiment 12

An embodiment of any of the embodiments of embodiment 1-11, wherein the amino acid at position 33 is substituted with aspartic acid (D) or an equivalent amino acid, and the amino acid at position 128 is substituted with tyrosine (Y) or an equivalent amino acid.

Embodiment 13

An embodiment of any of the embodiments of embodiment 1-11, wherein the amino acid at position 59 is substituted with valine (V) or an equivalent amino acid, and the amino acid at position 90 is substituted with phenylalanine (F) or an equivalent amino acid.

Embodiment 14

An embodiment of any of the embodiments of embodiment 1-11, wherein the amino acid at position 40 is substituted with glutamic acid (E) or an equivalent amino acid, and the amino acid at position 111 is substituted with tryptophan (W) or an equivalent amino acid.

Embodiment 15

An embodiment of any of the embodiments of embodiment 1-11, wherein the amino acid at position 36 is substituted with glycine (G) or an equivalent amino acid and the amino acid at position 128 is substituted with tyrosine (Y) or an equivalent amino acid

Embodiment 16

An embodiment of any of the embodiments of embodiment 1-11, wherein the amino acid at position 32 is substituted with glutamine (Q) or an equivalent amino acid, and the amino acid at position 40 is substituted with glutamic acid (E) or an equivalent amino acid.

Embodiment 17

An embodiment of any of the embodiments of embodiment 1-16, wherein the amino acid sequence of the polypeptide has at least 50% amino acid sequence identity with the amino acid sequence of the wild-type acyl-ACP TE.

Embodiment 18

An embodiment of any of the embodiments of embodiment 1-17, wherein the polypeptide has increased enzymatic activity and/or improved substrate specificity relative to the wild-type acyl-ACP TE.

Embodiment 19

An embodiment of embodiment 18, wherein the polypeptide has improved substrate specificity for pimeloyl-ACP relative to the wild-type acyl-ACP TE.

Embodiment 20

An embodiment of embodiment 18, wherein the polypeptide has an increase in enzymatic activity of at least 10% relative to the wild-type acyl-ACP TE.

Embodiment 21

A nucleic acid sequence encoding the polypeptide of an embodiment of any of the embodiments of embodiment 1-20.

Embodiment 22

A vector or genetic construct comprising the nucleic acid sequence of embodiment 21.

Embodiment 23

An organism or a host cell comprising the vector or genetic construct of embodiment 22, or a functional fragment thereof.

Embodiment 24

The host of embodiment 23, wherein the host is a prokaryotic cell.

Embodiment 25

A composition comprising the polypeptide or functional fragment thereof of an embodiment of any of the embodiments of embodiment 1-20, or the nucleic acid sequence or functional fragment thereof encoding the polypeptide of an embodiment of any of the embodiments of embodiment 1-20, or the vector or genetic construct comprising the nucleic acid sequence of embodiment 21, or the organism or a host comprising the vector or genetic construct of embodiment 22.

Embodiment 26

An embodiment of embodiment 25, further comprising pimeloyl-ACP.

Embodiment 27

A method for producing pimelic acid, pimelate semialdehyde or 7-aminoheptanoate (7-AHA) or any product of FIG. 2, comprising the step of enzymatically converting pimeloyl-ACP to pimelic acid in the presence of any one of the polypeptides or functional fragments thereof of an embodiment of any of the embodiments of embodiment 1-20.

Embodiment 28

A method for producing pimelic acid, pimelate semialdehyde or 7-AHA or any product of FIG. 2, comprising the steps of culturing the host cell of embodiment 23 in a suitable medium and recovering the pimelic acid, pimelate semialdehyde or 7-AHA or other product of FIG. 2.

Embodiment 29

A bio-derived pimelic acid, pimelate semialdehyde or 7-AHA or other product of FIG. 2, that is produced by the method of embodiment 27 or 28.

Embodiment 30

A product comprising a chemical produced from the bio-derived product of embodiment 29, wherein the product comprises a nylon intermediate, a polyester, a pharmaceutical, a biofuel, a fragrance or a food additive.

Embodiment 31

A bio-derived, bio-based or fermentation-derived product, wherein said product comprises: i. a composition comprising at least one bio-derived, bio-based or fermentation-derived compound, or salts thereof, produced in the presence of the polypeptide according to an embodiment of any of the embodiments of embodiment 1-20, or produced from the product of a reaction catalyzed by the polypeptide according to an embodiment of any of the embodiments of embodiment 1-20, or any combination thereof; ii. a bio-derived, bio-based or fermentation-derived polymer comprising the bio-derived, bio-based or fermentation-derived composition or compound of i., or any combination thereof; iii. a bio-derived, bio-based or fermentation-derived resin comprising the bio-derived, bio-based or fermentation-derived compound or bio-derived, bio-based or fermentation-derived composition of i. or any combination thereof or the bio-derived, bio-based or fermentation-derived polymer of ii. or any combination thereof; iv. a substance obtained by molding the bio-derived, bio-based or fermentation-derived polymer of ii. or the bio-derived, bio-based or fermentation-derived resin of iii., or any combination thereof; v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, bio-based or fermentation-derived substance of iv, or any combination thereof; or vi. a bio-derived, bio-based or fermentation-derived semi-solid or a non-semi-solid stream, comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

While the disclosure has been described in detail, modifications within the spirit and scope of the disclosure will be readily apparent to those of skill in the art. It should be understood that aspects of the disclosure and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the disclosure. All US patents and publications cited herein are incorporated by reference in their entirety.

Examples

The following examples are provided by way of illustration only and not by way of limitation. Those of skill in the art will readily recognize a variety of non-critical parameters that could be changed or modified to yield essentially the same or similar results.

Acyl-acyl carrier protein (ACP) thioesterases (TE) play a crucial role in controlling the metabolic flux through the FAS pathway. In particular, acyl-ACP TEs hydrolyze the thioester bonds of acyl-ACPs to release free fatty acids and thereby play essential roles in controlling the amount and composition of fatty acids produced by the fatty acid synthesis (FAS) pathway. This family of enzymes has also received significant interest with regards to metabolic engineering and recently, acyl-ACP TE has attracted even more attention because of increasing interest in producing fatty acids as biofuels or biorenewable chemicals.

Figure 3:
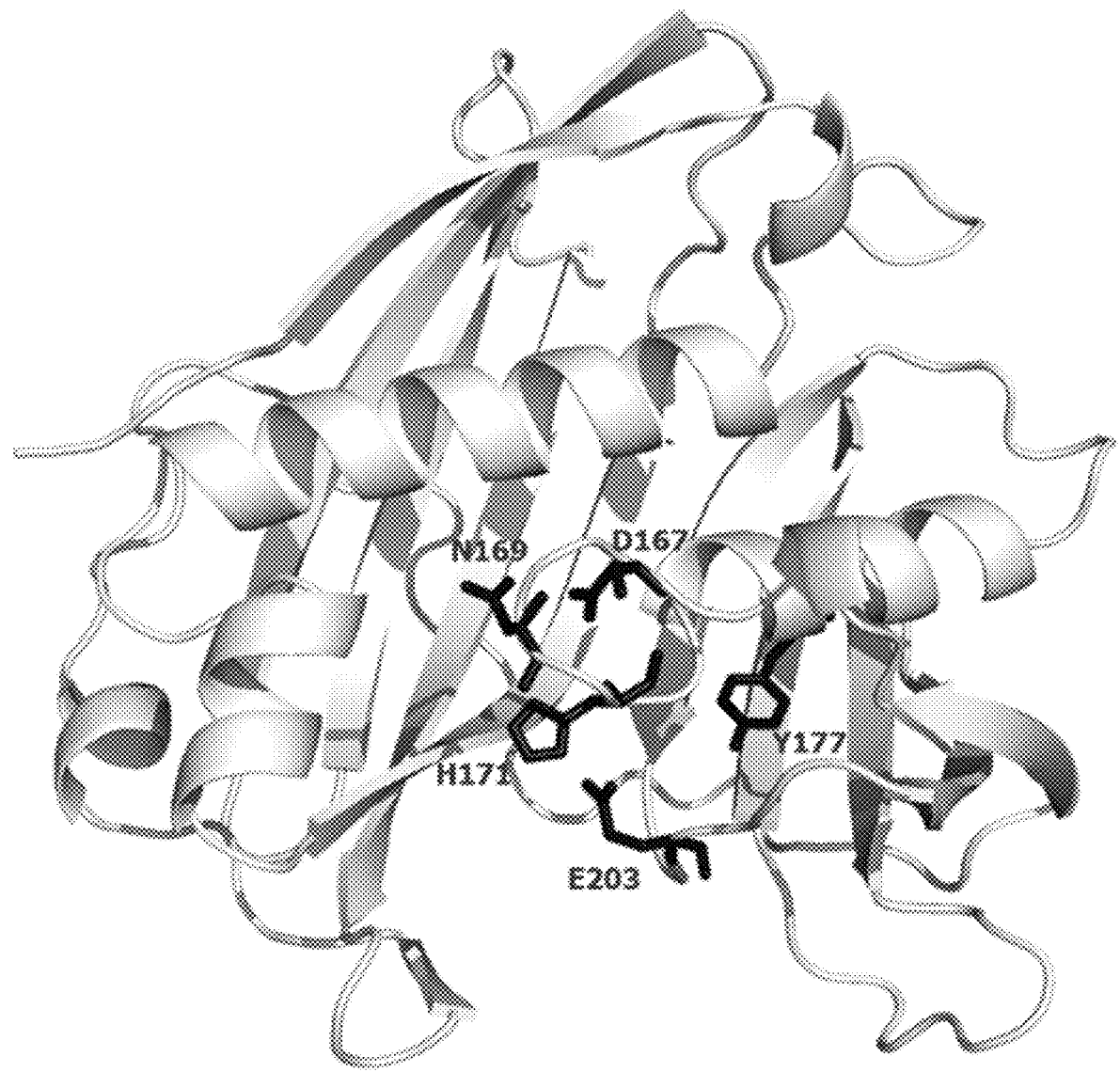
FIG. 3 depicts a three-dimensional model of the Acyl-ACP TE obtained from Uniprot ID No. R5FQ35 highlighting catalytic residues.

Acyl-ACP TEs were previously proposed to utilize a papain-like protease catalytic triad consisting of Cys, His, and Asn. However, the catalytically active Cys residue was not found near the active site of the studied TEs. Crystallographic study of the Oleoyl-ACP-TE (Pdb 2OWN) indicates that residues Asp173, Asn175, His177, and Glu211 play a crucial role for thioesterase activity. These residues correspond to the Asp167, Asn169, His171, and Glu203 in SEQ ID NO: 1 (Uniprot ID No. R5FQ35) one of the top ranked TEs studied. In addition, the Tyr177 was also considered as one of the catalytic residues due to its presence near the proposed catalytic residues. Multiple sequence analyses of the active and inactive Acyl-ACP-TEs indicated that Asp167 and His171 are highly conserved. A three-dimensional model of the Acyl-ACP-TE obtained from Uniport Id No. R5FQ35 shows the catalytic residues (FIG. 3). Analyses also showed that Tyr177 is conserved and substitution of this residue with an aliphatic hydrophobic residue causes substantial loss of enzyme function. Glu203 on the other hand has less of an impact on the catalytic activity of the enzyme. Most surprisingly, the three sequences (Uniprot Nos. B 1ZXQ1, D4KXX4, and H7FRY9) show an activity profile that is restrictive for defining the catalytic residues. This result suggested that, in addition to these residues, other residues could play important roles in catalysis. As described below, the studies described herein identified specific residues and distributions of specific residues in acyl-ACP TEs that can increase enzyme activity and/or affect substrate specificity.

Testing of Thioesterase Enzymes

171 TEs were tested for 7-AHA synthesis in this study. Methods for in vitro and in vivo screening of thioesterase activity are described in U.S. Patent Application Publication No. 20180023103. 54% of the tested enzymes were found to be active. The TE enzymes were ranked based on their activity and subjected to multiple sequence alignment (MSA). The phylogenetic tree constructed from the MSA shows the distribution of the TE over the sequence space. The top 3 TE (from in vitro data) were segregated into 3 clusters. Based on this clustering, it was difficult to identify definite parameters for higher activity. However, the analysis revealed that 63% of the total active TEs are Acyl-ACP-TEs (FIG. 4) that belong to the class of Acyl-ACP hydrolases, or more specifically Oleoyl-ACP TEs (EC 3.1.2.14). This family of enzymes can cleave the thioester bonds from acyl-carrier proteins in the presence of water.

Figure 4B:
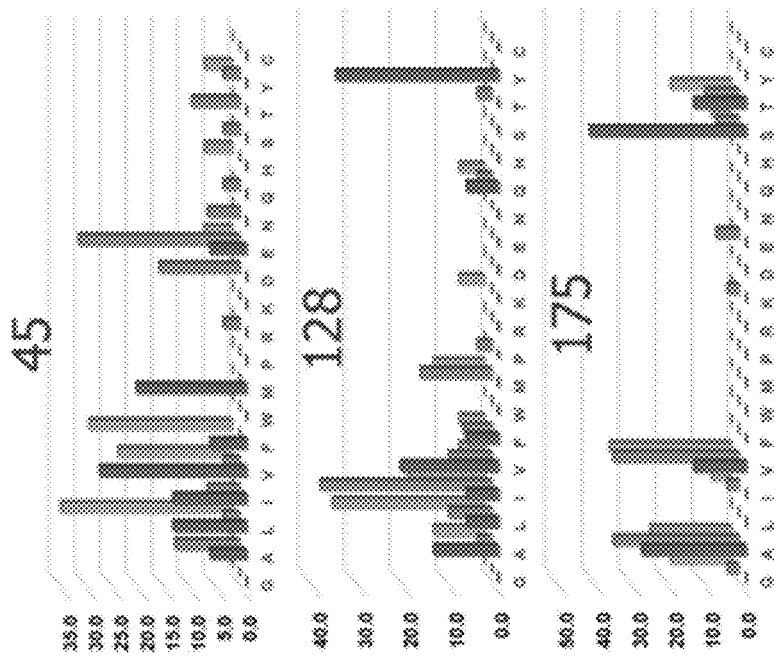
FIG. 4B shows the major contribution of amino acid residues 45, 128 and 175 at the binding site. Residue numbering used in this study was obtained from the sequence with Uniprot ID R5FQ35.
Figure 4A:
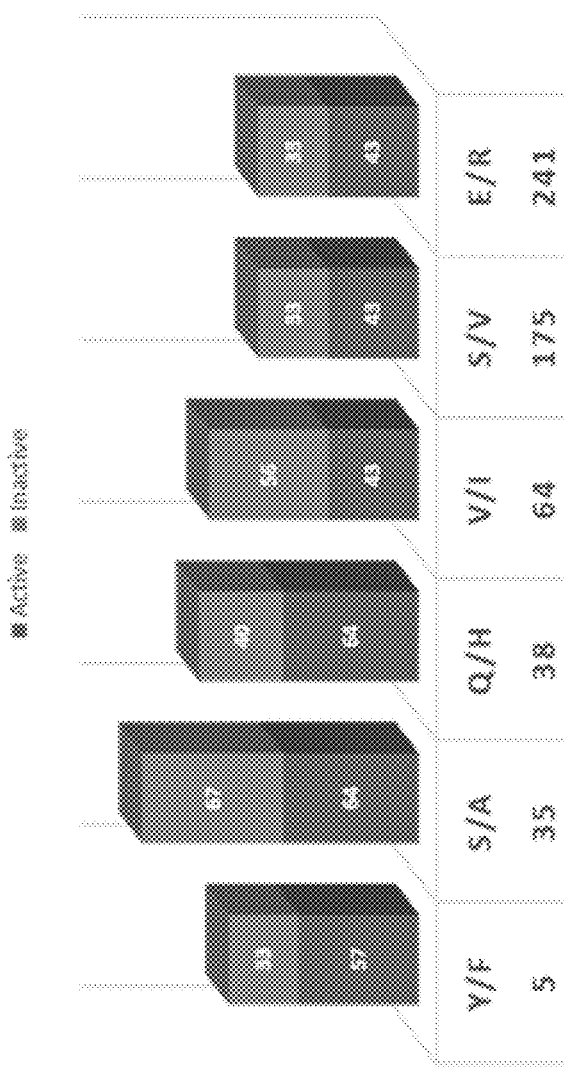
FIG. 4A shows site-specific distribution of residues in the acyl-ACP TEs. A population of more than 40% was considered.

Site specific amino acid distributions were calculated for the active and inactive acyl-ACP-TEs. All acyl-ACP-TEs were subjected to MSA, and distributions of every single residue at each position were calculated. Amino acid population indicated that residue numbers 5, 35, 38, 64, 175, and 241 may play a crucial role in the selectivity and activity of the TEs. The distribution profile indicates a preference for more polar residues at positions 5, 35, and 175 for active enzymes as compared to the inactive enzymes. Interestingly the amino acid at position 241 with a charge in the active enzyme that is the opposite the charge at this position in the inactive enzyme can have significant impact on enzyme activity (FIG. 4A).

Distribution of residues within the substrate binding site showed that three residues can significantly contribute to the activity of the enzyme. Residues Met and Ile at position 45, as well as Tyr and Ser at positions 128 and 175, respectively could play important roles in determining thioesterase activity (FIG. 4B). In addition to the distribution of residues within the binding site, the degree of correlation of the among these positions was calculated.

Statistical coupling analysis (SCA) provides correlation between mutually coupled elements. This method was used to identify the degree of correlation between two residues that are mutually evolved during evolution. See, for example, Shulman et al. "Structural determinants of allosteric ligand activation in RXR heterodimers," Cell 2004; 116:417-429. In addition, this method provided the statistical distribution of an amino acid for a particular position within the sequence. Given an MSA, the algorithm identifies correlated residues observed within a protein molecule. The SCA method calculates a score for two positions x and y by selecting the most dominant residue at position y and defines a sub-alignment consisting of only sequences having that specific amino acid at position y. The score is calculated using the difference between the amino acids (aa) distribution in full alignment and the subset.

$$\Delta G = G_I - G_{II}$$

$$\text{Score} = \Sigma_{x=1}^{20} \Sigma_{y=1}^{20} \Delta G^* F$$

$G_I = N_x/N_y$ (aa fraction at position $x$ in presence of specific aa at $y$)

Figure 5:
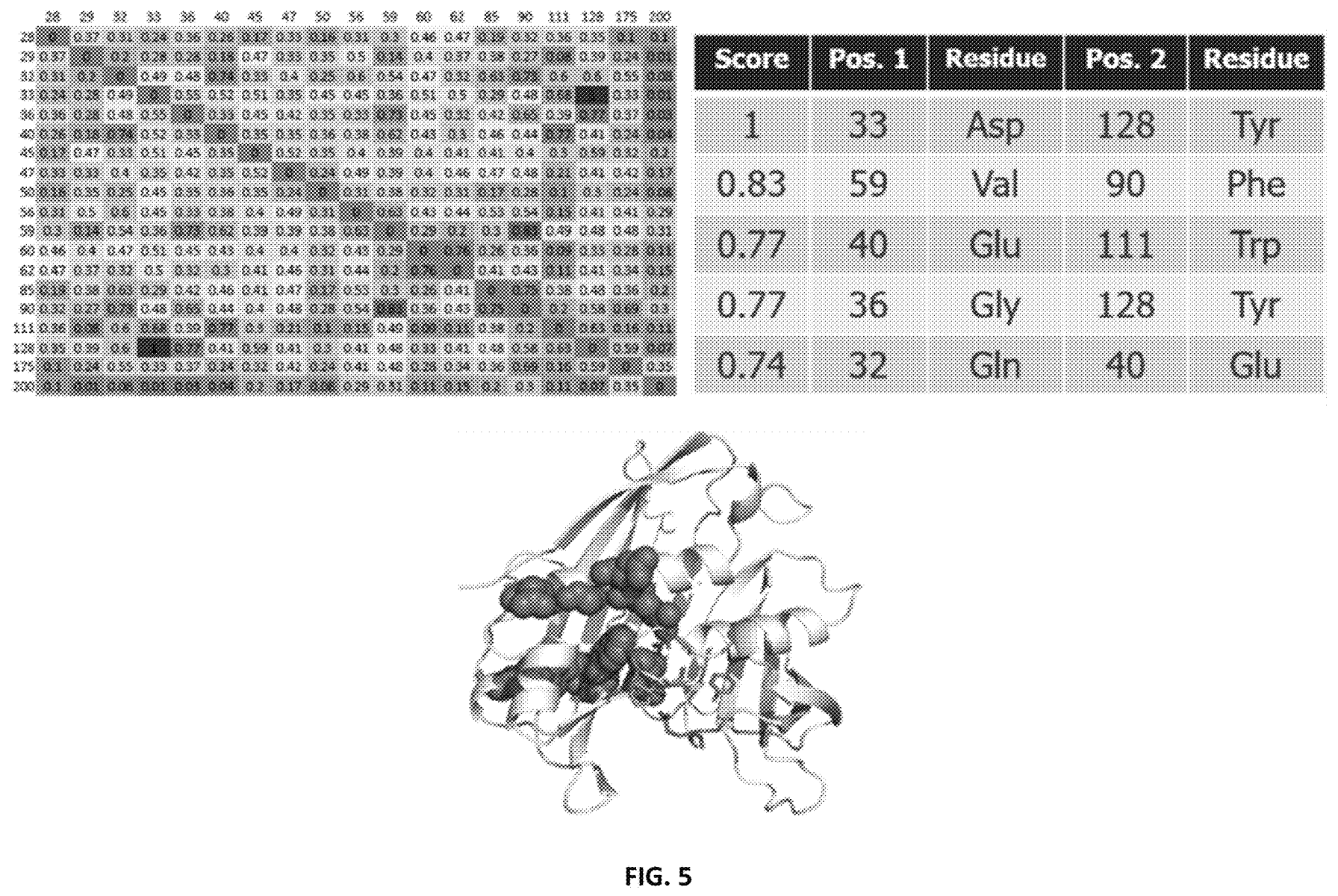

$G_{II} = N_x/N_{(total-MSA)}$ (fraction of aa at position $x$); $F$=Observed frequency of each aa pair To calculate the correlation between substrate binding residues, the acyl-ACP-TEs were divided into three segments: highly active (>100), medium active (>0 and <100), and inactive (below 0). Selecting the top 5 correlated residues from the high, medium, and inactive TEs showed that correlated residues are significantly different for each system (FIG. 5). However, when the correlated residues from highly active enzymes were compared with the other two systems, a better picture was obtained. First of all, these residues were found to have lower correlation in medium active enzymes, and a significant loss in correlation was observed for these residues in the inactive enzymes. In particular, in highly active enzymes, residues Asp33 and Tyr128 are highly correlated, but in the medium active enzymes Tyr128 is changed to Met. Further, these two positions are occupied by two different amino acids (Glu33 and Leu128) in the inactive enzymes (FIG. 5). These results clearly indicate that the residue correlation in the binding site of the enzyme can play an important role in the activity of the enzyme. Considering the potential of the positional correlation for higher activity, the residue pairs shown in the Table 3 could play an important role in increasing enzymatic activity and/or improving substrate specificity of Acyl-ACP TEs.

In summary, residue distribution in the active and inactive TEs suggested that amino acids at positions 5, 35, 38, 64, 175, and 241, along with substrate binding residues at positions 45 and 128 could potentially impact the activity of the Acyl-ACP TEs. Met45, Tyr128, and Ser175 are important residues for substrate specificity and activity. Moreover, the active enzymes were found to have a high degree of correlation among a few residues, which were able to differentiate between the active and the inactive enzymes. Residue pairs Asp33-Tyr128, Val59-Phe90, Glu40-Trp111, Gly36-Tyr128, and Gln32-Glu40 could have an impact on substrate specificity and catalytic activity of the TEs studied for the biosynthesis of 7-AHA.

Therefore, given a wild-type Acyl-ACP-TE, alteration of residues at one or more specific positions could lead to a highly active enzyme for a specific substrate, for example, pimeloyl-ACP.

This is based on the following findings. Higher occurrences of a specific residue at a particular position can have a significant impact on enzyme activity. A specific residue at a given position can also influence the enzymatic activity, for example, increase enzymatic activity. A summary of preferable residues at particular positions is provided in Table 2.

TABLE 2

| Position | Preferable residue |
|---|---|
| 5 | Tyr |
| 35 | Ser |
| 38 | Gln |
| 64 | Val |
| 241 | Glu |

Substrate binding also has a significant preference for residues at particular positions, as provided in Table 3.

TABLE 3

| Position | Preferable residue |
|---|---|
| 45 | Met/Ile |
| 128 | Tyr |
| 175 | Ser |

Correlated residues at the substrate binding site were also identified. The pairs of residues provided in Table 4, were found to be highly correlated. This suggests that the presence of one residue at a position can preferentially favor another specific residue at a different site. The top 5 highly correlated residues were considered. For the inactive enzymes, the degree of correlation among these residues were found to be drastically reduced.

TABLE 4

| Pos. 1 | Res. at Pos. 1 | Pos. 2 | Res. at Pos. 2 |
|---|---|---|---|
| 33 | Asp | 128 | Tyr |
| 59 | Val | 90 | Phe |

TABLE 4-continued

| Pos. 1 | Res. at Pos. 1 | Pos. 2 | Res. at Pos. 2 |
|---|---|---|---|
| 40 | Glu | 111 | Trp |
| 36 | Gly | 128 | Tyr |
| 32 | Gln | 40 | Glu |

Alteration of residues at one or more specific positions can be made using methods for site-directed mutagenesis that are available to those of skill in the art.

What is claimed is:

1. A polypeptide having an acyl-acyl carrier protein (ACP) thioesterase (TE) activity, wherein the polypeptide having acyl-ACP TE activity:
   (a) has at least 90% sequence identity to the polypeptide of SEQ ID NO: 1, and comprises seven or more amino acid substitutions at positions corresponding to positions in the polypeptide of SEQ ID NO: 1 selected from the group consisting of positions 5, 32, 33, 35, 36, 38, 40, 45, 59, 64, 90, 111, 128, 175, and 241, or
   (b) is a fragment of a polypeptide that consists of all of SEQ ID NO: 1 except for seven to fifteen amino acid substitutions at positions corresponding to positions in the polypeptide of SEQ ID NO: 1 selected from the group consisting of positions 5, 32, 33, 35, 36, 38, 40, 45, 59, 64, 90, 111, 128, 175, and 241, wherein said fragment has acyl-ACP TE activity, and wherein said fragment comprises the seven to fifteen amino acid substitutions at positions corresponding to positions in the polypeptide of SEQ ID NO: 1 selected from the group consisting of positions 5, 32, 33, 35, 36, 38, 40, 45, 59, 64, 90, 111, 128, 175, and 241.

2. The polypeptide of claim 1, wherein the amino acid corresponding to position 5 is substituted with tyrosine (Y), phenylalanine (F), or tryptophan (W)an equivalent amino.

3. The polypeptide of claim 1, wherein the amino acid at position 35 is serine (S), alanine (A), threonine (T), valine (V), glycine (G), or proline (P).

4. The polypeptide of claim 1, wherein the amino acid at position 38 is glutamine (Q) or asparagine (N).

5. The polypeptide of claim 1, wherein the amino acid at position 64 is valine (V), isoleucine (I), leucine (L), or methionine (M).

6. The polypeptide of claim 1, wherein the amino acid at position 241 isglutamic acid (E) or aspartic acid (D).

7. The polypeptide of claim 1, wherein the amino acid at position 45 is methionine (M), valine (V), or isoleucine (I).

8. The polypeptide of claim 1, wherein the amino acid at position 128 is tyrosine (Y), phenylalanine (F), or tryptophan (W).

9. The polypeptide of claim 1, wherein the amino acid at position 175 is serine (S), alanine (A), threonine (T), valine (V), glycine (G), or proline (P).

10. The polypeptide of claim 1, wherein the amino acid at position 33 is aspartic acid (D) or glutamic acid (E) and the amino acid at position 128 is tyrosine (Y), phenylalanine (F), or tryptophan (W).

11. The polypeptide of claim 1, wherein the amino acid at position 59 is valine (V), isoleucine (I), leucine (L), or methionine (M) and the amino acid at position 90 is phenylalanine (F), tyrosine (Y), or tryptophan (W).

12. The polypeptide of claim 1, wherein the amino acid at position 40 is glutamic acid (E) or aspartic acid (D), and the amino acid at position 111 tryptophan (W), phenylalanine (F), or tyrosine (Y).

13. The polypeptide of claim 1, wherein the amino acid at position 36 is glycine (G), alanine (A), serine (S), threonine (T), valine (V), or proline (P) and the amino acid at position 128 tyrosine (Y), phenylalanine (F), or tryptophan (W).

14. The polypeptide of claim 1, wherein the amino acid at position 32 is glutamine (Q) or asparagine (N) and the amino acid at position 40 is glutamic acid (E) or aspartic acid (D).

15. The polypeptide of claim 1, wherein the polypeptide having acyl-ACP TE activity allows for improved conversion of pimeloyl-ACP to pimelic acid when compared to the polypeptide of SEQ ID NO: 1.

16. A method for producing pimelic acid, pimelate semialdehyde or 7-aminoheptanoate (7-AHA), comprising the step of enzymatically converting pimeloyl-ACP to pimelic acid in the presence of the polypeptide of claim 1.

* * * * *